(12) United States Patent
Shelton, IV et al.

(10) Patent No.: US 12,232,735 B2
(45) Date of Patent: Feb. 25, 2025

(54) METHOD OF USING MULTIPLE RFID CHIPS WITH A SURGICAL ASSEMBLY

(71) Applicant: Cilag GmbH International, Zug (CH)

(72) Inventors: Frederick E. Shelton, IV, Hillsboro, OH (US); Shane R. Adams, Lebanon, OH (US); Kevin M. Fiebig, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/415,181

(22) Filed: Jan. 17, 2024

(65) Prior Publication Data

US 2024/0197325 A1 Jun. 20, 2024

Related U.S. Application Data

(63) Continuation of application No. 18/127,164, filed on Mar. 28, 2023, now abandoned, which is a
(Continued)

(51) Int. Cl.
*A61B 17/064* (2006.01)
*A61B 17/072* (2006.01)
(Continued)

(52) U.S. Cl.
CPC ........ *A61B 17/1155* (2013.01); *A61B 17/072* (2013.01); *A61B 17/07207* (2013.01); *A61B 17/115* (2013.01); *A61B 90/96* (2016.02); *A61B 90/98* (2016.02); *G06K 7/10366* (2013.01); *G06K 19/07758* (2013.01); *A61B 2017/00039* (2013.01); *A61B 2017/00115* (2013.01); *A61B 2017/00119* (2013.01); *A61B 2017/00221* (2013.01); *A61B 2017/00367* (2013.01); *A61B 2017/00398* (2013.01); *A61B 2017/00477* (2013.01); *A61B 2017/00734* (2013.01);
(Continued)

(58) Field of Classification Search
CPC ............................................ A61B 2017/00734
See application file for complete search history.

(56) References Cited

U.S. PATENT DOCUMENTS 5,205,459 A 4/1993 Brinkerhoff et al.
5,271,544 A 12/1993 Fox et al.
(Continued)

OTHER PUBLICATIONS

"ATM-MPLS Network Interworking Version 2.0, af-aic-0178.001" ATM Standard, The ATM Forum Technical Committee, published Aug. 2003.
(Continued)

*Primary Examiner* — Eyamindae C Jallow

(57) ABSTRACT

A method of operating a surgical assembly is disclosed. The method includes receiving a first input from a first RFID scanner indicative of a first information stored in a first RFID chip of a first modular component of the surgical assembly, receiving a second input from a second RFID scanner indicative of a second information stored in a second RFID chip of a second modular component of the surgical assembly, determining an operational parameter of a motor of the surgical assembly based on the first input and the second input, and causing the motor to effect a tissue treatment motion of the first modular component.

20 Claims, 95 Drawing Sheets

Related U.S. Application Data continuation of application No. 17/361,574, filed on Jun. 29, 2021, now Pat. No. 11,684,369, which is a continuation of application No. 16/458,107, filed on Jun. 30, 2019, now Pat. No. 11,241,235.

(60) Provisional application No. 62/868,457, filed on Jun. 28, 2019.

(51) Int. Cl.

| | |
|---|---|
| *A61B 17/115* | (2006.01) |
| *A61B 90/96* | (2016.01) |
| *A61B 90/98* | (2016.01) |
| *G06K 7/10* | (2006.01) |
| *G06K 19/077* | (2006.01) |
| *A61B 17/00* | (2006.01) |

(52) U.S. Cl.
CPC ............ *A61B 2017/07228* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01)

(56) References Cited

U.S. PATENT DOCUMENTS

| | | | |
|---|---|---|---|
| 5,275,322 | A | 1/1994 | Brinkerhoff et al. |
| 5,285,945 | A | 2/1994 | Brinkerhoff et al. |
| 5,292,053 | A | 3/1994 | Bilotti et al. |
| 5,333,773 | A | 8/1994 | Main et al. |
| 5,350,104 | A | 9/1994 | Main et al. |
| 5,403,312 | A | 4/1995 | Yates et al. |
| 5,533,661 | A | 7/1996 | Main et al. |
| 6,978,921 | B2 | 12/2005 | Shelton, IV et al. |
| 6,988,649 | B2 | 1/2006 | Shelton, IV et al. |
| 7,000,818 | B2 | 2/2006 | Shelton, IV et al. |
| 7,044,352 | B2 | 5/2006 | Shelton, IV et al. |
| 7,143,923 | B2 | 12/2006 | Shelton, IV et al. |
| 7,422,139 | B2 | 9/2008 | Shelton, IV et al. |
| 7,464,849 | B2 | 12/2008 | Shelton, IV et al. |
| 7,670,334 | B2 | 3/2010 | Hueil et al. |
| 7,753,245 | B2 | 7/2010 | Boudreaux et al. |
| 7,900,805 | B2 * | 3/2011 | Shelton, IV ..... A61B 17/07207 227/176.1 |
| 7,922,063 | B2 | 4/2011 | Zemlok et al. |
| 7,959,050 | B2 | 6/2011 | Smith et al. |
| 8,910,847 | B2 | 12/2014 | Nalagatla et al. |
| 9,005,230 | B2 | 4/2015 | Yates et al. |
| 9,171,244 | B2 | 10/2015 | Endou et al. |
| 9,179,912 | B2 | 11/2015 | Yates et al. |
| 9,398,905 | B2 | 7/2016 | Martin |
| 9,468,438 | B2 | 10/2016 | Baber et al. |
| 9,504,520 | B2 | 11/2016 | Worrell et al. |
| 9,629,629 | B2 | 4/2017 | Leimbach et al. |
| 9,888,914 | B2 | 2/2018 | Martin et al. |
| 10,022,120 | B2 | 7/2018 | Martin et al. |
| 10,238,385 | B2 | 3/2019 | Yates et al. |
| 10,405,859 | B2 * | 9/2019 | Harris ............ A61B 17/07207 |
| 10,426,468 | B2 | 10/2019 | Contini et al. |
| 10,456,137 | B2 | 10/2019 | Vendely et al. |
| 10,736,616 | B2 | 8/2020 | Scheib et al. |
| 10,772,651 | B2 | 9/2020 | Shelton, IV et al. |
| 10,842,473 | B2 | 11/2020 | Scheib et al. |
| 10,905,415 | B2 | 2/2021 | DiNardo et al. |
| 10,932,804 | B2 | 3/2021 | Scheib et al. |
| 10,932,806 | B2 | 3/2021 | Shelton, IV et al. |
| 10,952,708 | B2 | 3/2021 | Scheib et al. |
| 10,959,744 | B2 | 3/2021 | Shelton, IV et al. |
| 10,980,560 | B2 | 4/2021 | Shelton, IV et al. |
| 11,026,687 | B2 | 6/2021 | Shelton, IV et al. |
| 11,026,712 | B2 | 6/2021 | Shelton, IV et al. |
| 11,026,713 | B2 | 6/2021 | Stokes et al. |
| 11,045,197 | B2 | 6/2021 | Shelton, IV et al. |
| 11,051,836 | B2 | 7/2021 | Shelton, IV et al. |
| 11,071,560 | B2 | 7/2021 | Deck et al. |
| 11,103,268 | B2 | 8/2021 | Shelton, IV et al. |
| 11,109,866 | B2 | 9/2021 | Shelton, IV et al. |
| 11,109,878 | B2 | 9/2021 | Shelton, IV et al. |
| 11,116,485 | B2 | 9/2021 | Scheib et al. |
| 11,123,070 | B2 | 9/2021 | Shelton, IV et al. |
| 11,129,634 | B2 | 9/2021 | Scheib et al. |
| 11,129,636 | B2 | 9/2021 | Shelton, IV et al. |
| 11,141,160 | B2 | 10/2021 | Shelton, IV et al. |
| 11,207,090 | B2 | 12/2021 | Shelton, IV et al. |
| 11,224,497 | B2 | 1/2022 | Shelton, IV et al. |
| 11,229,436 | B2 | 1/2022 | Shelton, IV et al. |
| 11,229,437 | B2 | 1/2022 | Shelton, IV et al. |
| 11,241,235 | B2 | 2/2022 | Shelton, IV et al. |
| 11,246,678 | B2 | 2/2022 | Shelton, IV et al. |
| 11,259,803 | B2 | 3/2022 | Shelton, IV et al. |
| 11,291,451 | B2 | 4/2022 | Shelton, IV |
| 11,291,465 | B2 | 4/2022 | Parihar et al. |
| 11,298,127 | B2 | 4/2022 | Shelton, IV |
| 11,304,699 | B2 | 4/2022 | Shelton, IV et al. |
| 11,317,919 | B2 | 5/2022 | Shelton, IV et al. |
| 11,350,938 | B2 | 6/2022 | Shelton, IV et al. |
| 11,361,176 | B2 | 6/2022 | Shelton, IV et al. |
| 11,376,098 | B2 | 7/2022 | Shelton, IV et al. |
| 11,389,164 | B2 | 7/2022 | Yates et al. |
| 11,399,837 | B2 | 8/2022 | Shelton, IV et al. |
| 11,406,390 | B2 | 8/2022 | Shelton, IV et al. |
| 11,413,042 | B2 | 8/2022 | Shelton, IV et al. |
| 11,426,167 | B2 | 8/2022 | Shelton, IV et al. |
| 11,464,601 | B2 | 10/2022 | Shelton, IV et al. |
| 11,553,971 | B2 | 1/2023 | Shelton, IV et al. |
| 11,559,307 | B2 | 1/2023 | Shelton, IV et al. |
| 11,559,308 | B2 | 1/2023 | Yates et al. |
| 11,564,703 | B2 | 1/2023 | Shelton, IV et al. |
| 11,576,677 | B2 | 2/2023 | Shelton, IV et al. |
| 11,589,888 | B2 | 2/2023 | Shelton, IV et al. |
| 11,602,366 | B2 | 3/2023 | Shelton, IV et al. |
| 11,638,587 | B2 | 5/2023 | Shelton, IV et al. |
| 11,648,022 | B2 | 5/2023 | Shelton, IV |
| 11,659,023 | B2 | 5/2023 | Shelton, IV et al. |
| 11,660,163 | B2 | 5/2023 | Shelton, IV et al. |
| 11,684,369 | B2 | 6/2023 | Shelton, IV et al. |
| 11,684,434 | B2 | 6/2023 | Shelton, IV |
| 11,696,778 | B2 | 7/2023 | Shelton, IV et al. |
| 11,759,224 | B2 | 9/2023 | Shelton, IV et al. |
| 11,771,419 | B2 | 10/2023 | Shelton, IV et al. |
| 11,793,537 | B2 | 10/2023 | Shelton, IV et al. |
| 11,819,231 | B2 | 11/2023 | Shelton, IV et al. |
| 11,853,835 | B2 | 12/2023 | Shelton, IV |
| 11,871,901 | B2 | 1/2024 | Shelton, IV et al. |
| 2007/0175955 | A1 | 8/2007 | Shelton et al. |
| 2009/0108048 | A1 * | 4/2009 | Zemlok .............. G16Z 99/00 227/176.1 |
| 2011/0288573 | A1 * | 11/2011 | Yates ................ A61B 50/36 227/175.1 |
| 2013/0126581 | A1 * | 5/2013 | Yates ............ A61B 17/1155 227/175.1 |
| 2014/0246479 | A1 * | 9/2014 | Baber ........... A61B 17/07207 227/180.1 |
| 2015/0053737 | A1 * | 2/2015 | Leimbach ........ A61B 90/90 227/175.1 |
| 2015/0053743 | A1 | 2/2015 | Yates et al. |
| 2015/0196347 | A1 * | 7/2015 | Yates ............... A61B 17/068 227/180.1 |
| 2016/0310134 | A1 * | 10/2016 | Contini ........... A61B 17/0686 |
| 2017/0296189 | A1 * | 10/2017 | Vendely .......... A61B 17/105 |
| 2019/0125320 | A1 | 5/2019 | Shelton, IV et al. |
| 2019/0125336 | A1 | 5/2019 | Deck et al. |
| 2019/0125361 | A1 | 5/2019 | Shelton, IV et al. |
| 2019/0125432 | A1 | 5/2019 | Shelton, IV et al. |
| 2019/0125476 | A1 | 5/2019 | Shelton, IV et al. |
| 2019/0200844 | A1 | 7/2019 | Shelton, IV et al. |
| 2019/0200981 | A1 | 7/2019 | Harris et al. |
| 2019/0201045 | A1 | 7/2019 | Yates et al. |
| 2019/0201594 | A1 | 7/2019 | Shelton, IV et al. |
| 2019/0206564 | A1 | 7/2019 | Shelton, IV et al. |

(56) References Cited

U.S. PATENT DOCUMENTS

| | | |
|---|---|---|
| 2019/0206569 A1 | 7/2019 | Shelton, IV et al. |
| 2020/0405302 A1 | 12/2020 | Shelton, IV et al. |
| 2023/0414219 A1 | 12/2023 | Shelton, IV et al. |

OTHER PUBLICATIONS

IEEE Std 802.Mar. 2012 (Revision of IEEE Std 802.3-2008, published Dec. 28, 2012.

* cited by examiner

| RFID TAG | HOUSING ASSEMBLY | BATTERY | MOTOR/ GEARBOX | SHAFT | CARTRIDGE |
|---|---|---|---|---|---|
| Identifies: | ● Device ID$_{tag}$ | ● Battery ID$_{tag}$ | ● Motor ID$_{tag}$ | ● Shaft ID$_{tag}$ ● Length(STD) ● Type:single-axis artic. | ● Cartridge ID$_{tag}$ ● Length=60mm ● Color=blue ● Smart GST |
| Defines: | ● Capabilities ● Mfg & date ● Communication capabilities & protocol ● Encryption methods | ● Type of battery (e.g. recharge-able) ● Capability (e.g. 2.1 × std) | ● Internal processor ● Control programs | ● Wired communication bus with 4" × " rate of thruput ● Sensing array type to com- municate with cartridge & device | ● Wake-up & communication protocol to talk w/cartridge ● Encryption key to decode signal ● What can be sensed? |

FIG. 60

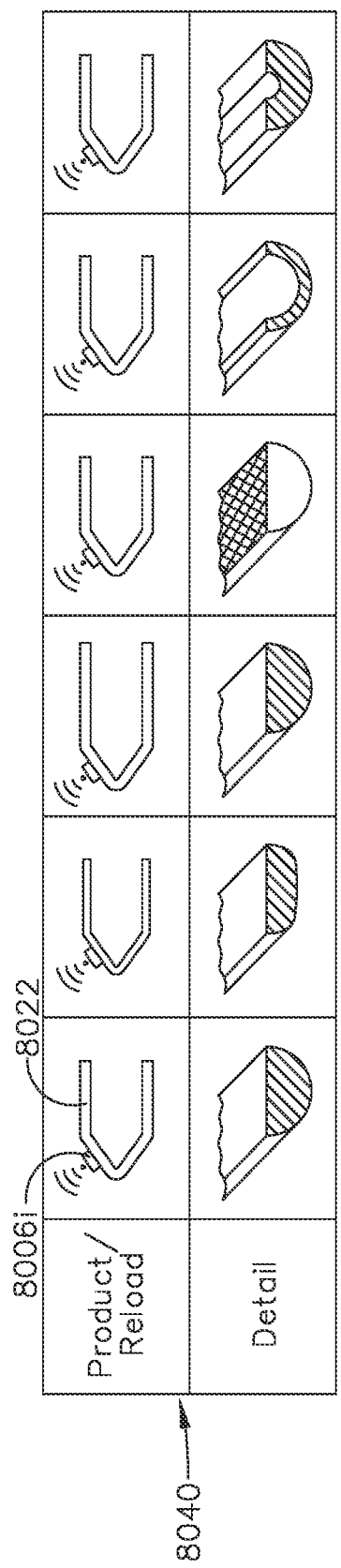
FIG. 63
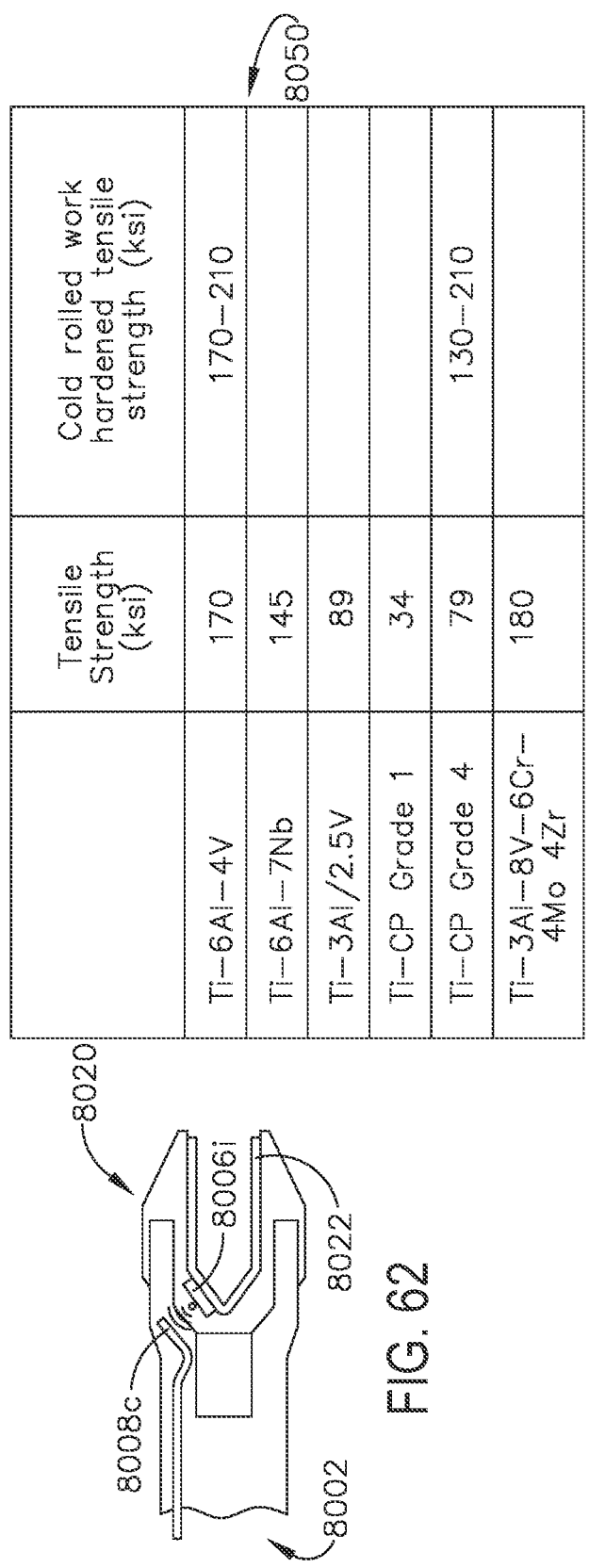
FIG. 64
FIG. 62

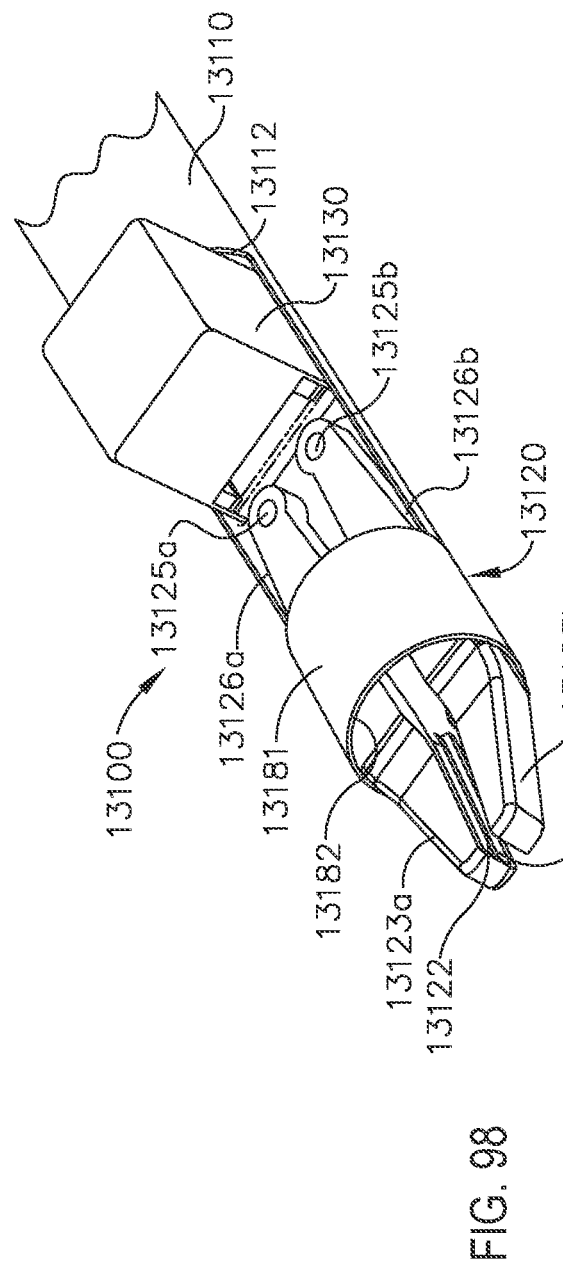
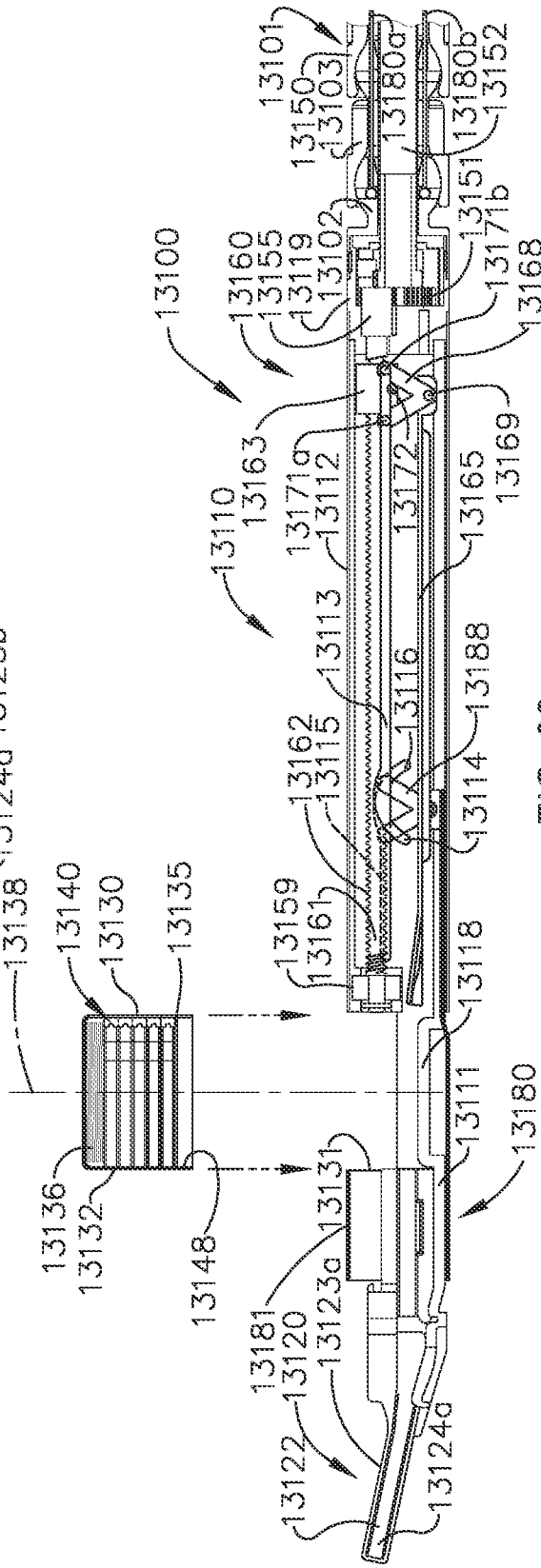
FIG. 98
FIG. 99

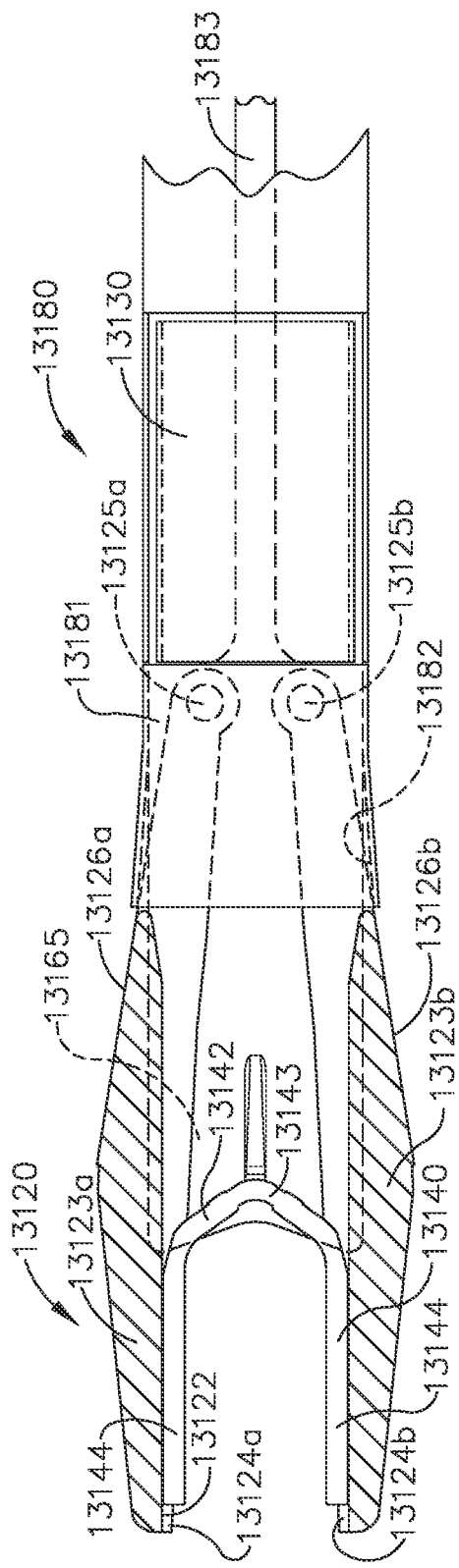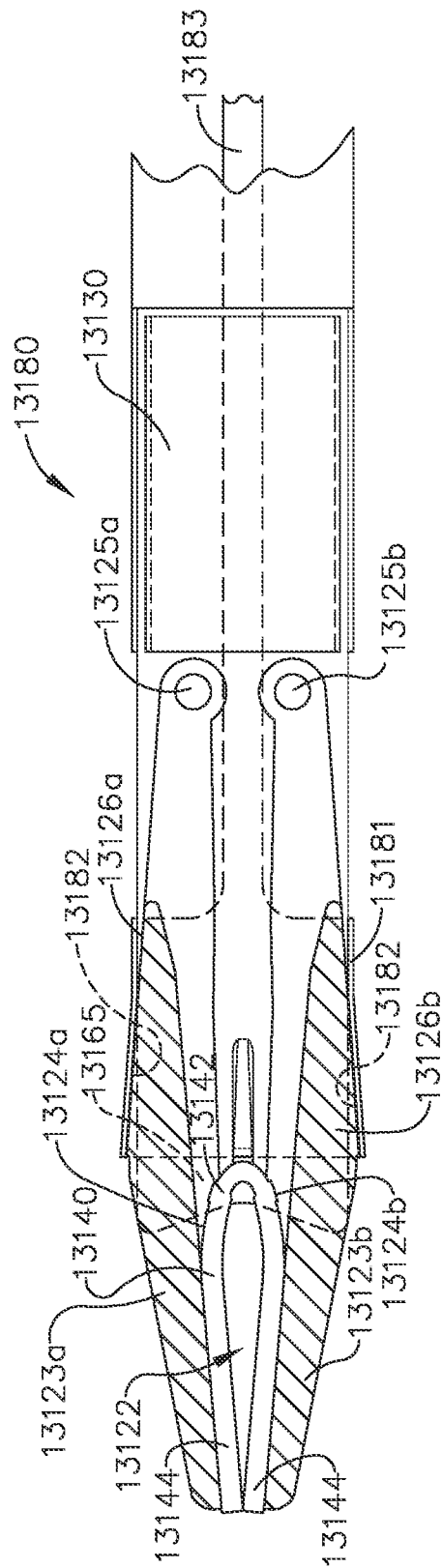

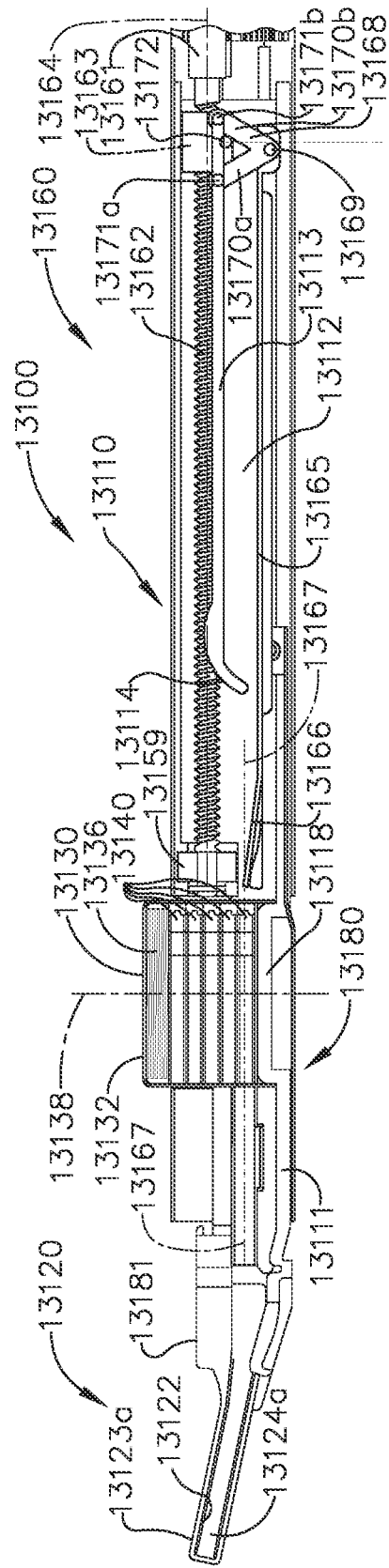
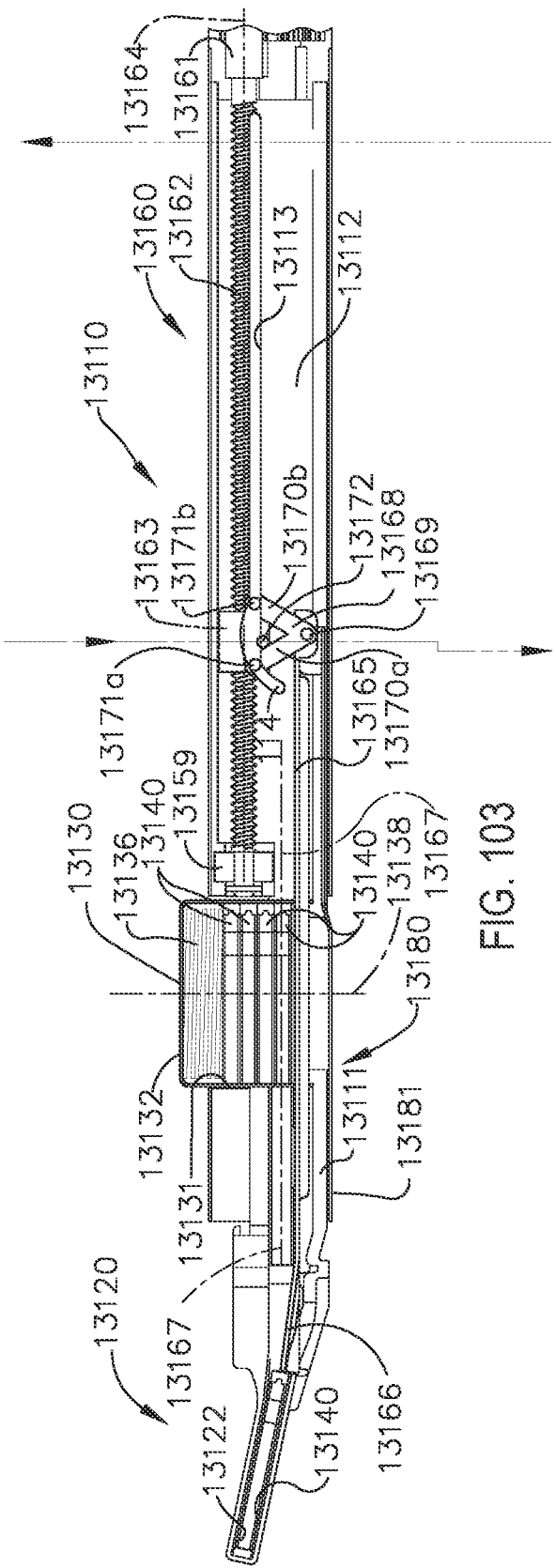
FIG. 102
FIG. 103

METHOD OF USING MULTIPLE RFID CHIPS WITH A SURGICAL ASSEMBLY

CROSS-REFERENCE TO RELATED APPLICATIONS

This application is a continuation application claiming priority under 35 U.S.C. § 120 to U.S. patent application Ser. No. 18/127,164, entitled METHOD OF USING MULTIPLE RFID CHIPS WITH A SURGICAL ASSEMBLY, filed Mar. 28, 2023, now U.S. Patent Application Publication No. 2023/0414219, which is a continuation application claiming priority under 35 U.S.C. § 120 to U.S. patent application Ser. No. 17/361,574, entitled METHOD OF USING MULTIPLE RFID CHIPS WITH A SURGICAL ASSEMBLY, filed Jun. 29, 2021, which issued on Jun. 27, 2023 as U.S. Pat. No. 11,684,369, which is a continuation application claiming priority under 35 U.S.C. § 120 to U.S. patent application Ser. No. 16/458,107, entitled METHOD OF USING MULTIPLE RFID CHIPS WITH A SURGICAL ASSEMBLY, filed on Jun. 30, 2019, which issued on Feb. 8, 2022 as U.S. Pat. No. 11,241,235, the entire disclosures of which are hereby incorporated by reference herein.

U.S. patent application Ser. No. 16/458,107 is a nonprovisional application claiming priority under 35 U.S.C. § 119(e) to U.S. Provisional Patent Application Ser. No. 62/868,457, entitled SURGICAL SYSTEMS WITH MULTIPLE RFID TAGS, filed on Jun. 28, 2019, the entire disclosures of which are hereby incorporated by reference herein.

BACKGROUND

The present invention relates to surgical instruments and, in various embodiments, to surgical cutting and stapling instruments and staple cartridges therefor that are designed to cut and staple tissue. In various embodiments, RFID technology can be used to identify the components of a surgical instrument, such as staple cartridges, for example. Examples of surgical systems which use RFID technology can be found in the disclosures of U.S. Pat. No. 7,959,050, entitled ELECTRICALLY SELF-POWERED SURGICAL INSTRUMENT WITH MANUAL RELEASE, which issued on Jun. 14, 2011, and U.S. Patent Application No. 2015/0053743, entitled ERROR DETECTION ARRANGEMENTS FOR SURGICAL INSTRUMENT ASSEMBLIES, which published on Feb. 26, 2015, and both of which are incorporated by reference herein in their entireties.

BRIEF DESCRIPTION OF THE DRAWINGS

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 60 illustrates a table of surgical instrument component data, in accordance with at least one aspect of the present disclosure.

FIG. 62 illustrates a sectional view of a surgical instrument including an RFID scanner configured to detect an RFID tag associated with a consumable device, in accordance with at least one aspect of the present disclosure.

FIG. 63 illustrates a table of surfaces for various surgical clip types, in accordance with at least one aspect of the present disclosure.

FIG. 64 illustrates a table of mechanical properties for various surgical clip types, in accordance with at least one aspect of the present disclosure.

FIG. 98 is a partial perspective view of a clip applier.

FIG. 99 is a cross-sectional view of an end effector of the clip applier of FIG. 98 comprising a removable clip cartridge, a reciprocating firing drive for sequentially advancing the clips, a receiver for receiving the clips, and a crimping drive for deforming the clips.

FIG. 100 is a partial cross-sectional view of the clip applier of FIG. 98 in an open configuration.

FIG. 101 is a partial cross-sectional view of the clip applier of FIG. 98 in a closed configuration.

FIG. 102 is a cross-sectional view of the end effector of FIG. 99 in an unfired condition.

FIG. 103 is a cross-sectional view of the end effector of FIG. 99 illustrating the firing drive in a partially fired condition in which a firing member of the firing drive has advanced a clip into the receiver.

DESCRIPTION

Figure 1:
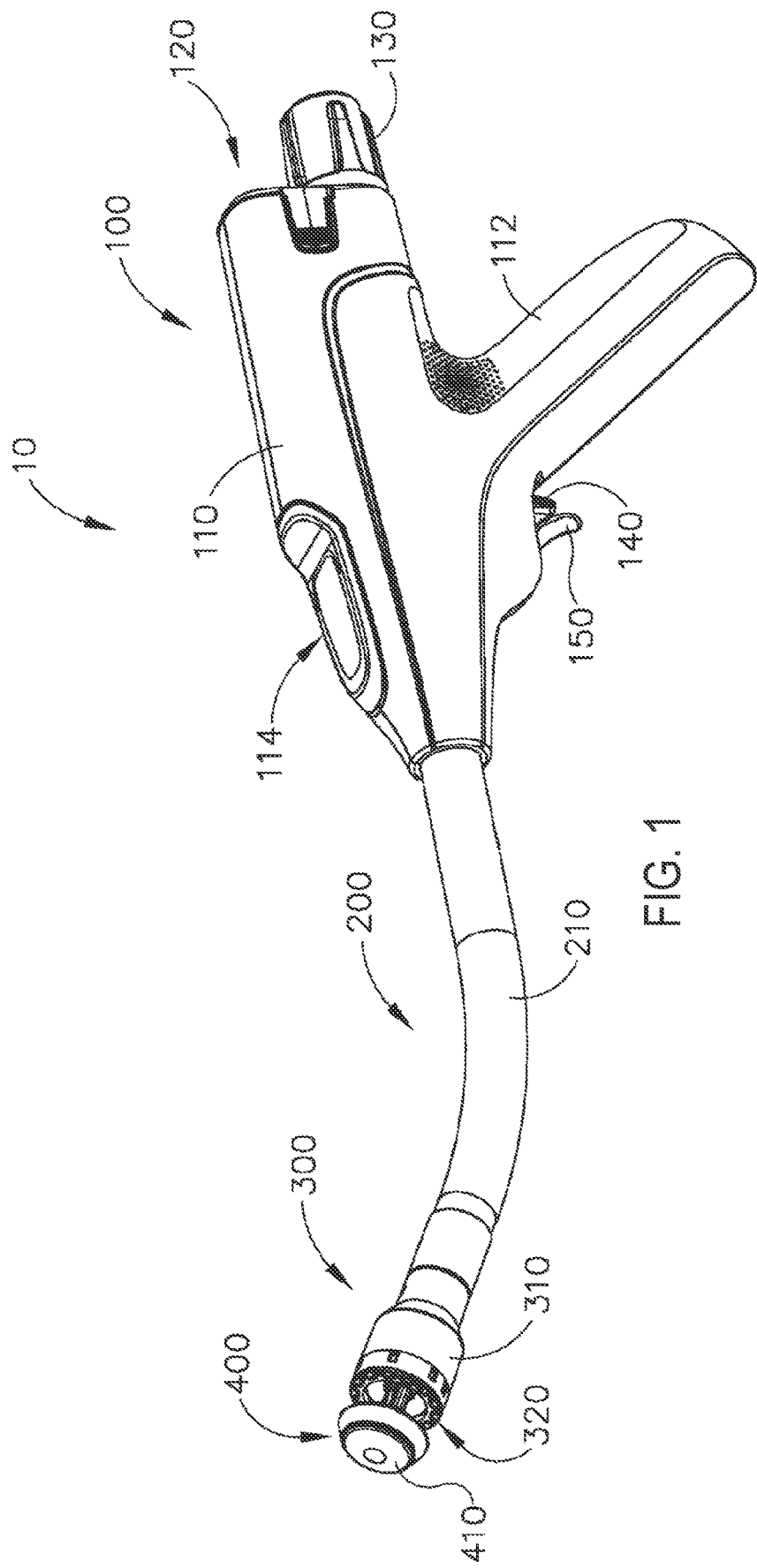
FIG. 1 depicts a perspective view of an exemplary circular stapler, in accordance with at least one aspect of the present disclosure.

Applicant of the present application owns the following U.S. patent applications that were filed on Jun. 30, 2019 and which are each herein incorporated by reference in their respective entireties:

U.S. patent application Ser. No. 16/458,104, entitled METHOD FOR AUTHENTICATING THE COMPATIBILITY OF A STAPLE CARTRIDGE WITH A SURGICAL INSTRUMENT, now U.S. Pat. No. 11,229,437;

U.S. patent application Ser. No. 16/458,108, entitled SURGICAL INSTRUMENT SYSTEM COMPRISING AN RFID SYSTEM, now U.S. Pat. No. 11,376,098;

U.S. patent application Ser. No. 16/458,111, entitled SURGICAL INSTRUMENT COMPRISING AN RFID SYSTEM FOR TRACKING A MOVABLE COMPONENT, now U.S. Pat. No. 11,464,601;

U.S. patent application Ser. No. 16/458,114, entitled SURGICAL INSTRUMENT COMPRISING AN ALIGNED RFID SENSOR, now U.S. Pat. No. 11,350,968;

U.S. patent application Ser. No. 16/458,105, entitled SURGICAL STAPLING SYSTEM HAVING AN INFORMATION DECRYPTION PROTOCOL, now U.S. Pat. No. 12,004,740;

U.S. patent application Ser. No. 16/458,110, entitled SURGICAL STAPLING SYSTEM HAVING AN INFORMATION ENCRYPTION PROTOCOL, now U.S. Pat. No. 11,259,803;

U.S. patent application Ser. No. 16/458,120, entitled SURGICAL STAPLING SYSTEM HAVING A LOCKOUT MECHANISM FOR AN INCOMPATIBLE CARTRIDGE, now U.S. Pat. No. 11,298,127;

U.S. patent application Ser. No. 16/458,125, entitled SURGICAL STAPLING SYSTEM HAVING A FRANGIBLE RFID TAG, now U.S. Pat. No. 11,246,678; and U.S. patent application Ser. No. 16/458,103, entitled PACKAGING FOR A REPLACEABLE COMPONENT OF A SURGICAL STAPLING SYSTEM, now U.S. Pat. No. 11,771,419.

Applicant of the present application owns the following U.S. patent applications that were filed Jun. 30, 2019 and which are each herein incorporated by reference in their respective entireties:

U.S. patent application Ser. No. 16/458,109, entitled MECHANISMS FOR PROPER ANVIL ATTACHMENT SURGICAL STAPLING HEAD ASSEMBLY, now U.S. Pat. No. 11,426,167;

U.S. patent application Ser. No. 16/458,119, entitled MECHANISMS FOR MOTOR CONTROL ADJUSTMENTS OF A MOTORIZED SURGICAL INSTRUMENT, now U.S. Pat. No. 11,399,837;

U.S. patent application Ser. No. 16/458,115, entitled SURGICAL INSTRUMENT WITH BATTERY COMPATIBILITY VERIFICATION FUNCTIONALITY, now U.S. Pat. No. 11,291,451;

U.S. patent application Ser. No. 16/458,117, entitled SURGICAL SYSTEM WITH RFID TAGS FOR UPDATING MOTOR ASSEMBLY PARAMETERS, now U.S. Pat. No. 11,660,163;

U.S. patent application Ser. No. 16/458,121, entitled SURGICAL SYSTEMS WITH MULTIPLE RFID TAGS, now U.S. Pat. No. 11,224,497;

U.S. patent application Ser. No. 16/458,122, entitled RFID IDENTIFICATION SYSTEMS FOR SURGICAL INSTRUMENTS, now U.S. Pat. No. 11,853,835;

U.S. patent application Ser. No. 16/458,106, entitled RFID IDENTIFICATION SYSTEMS FOR SURGICAL INSTRUMENTS, now U.S. Pat. No. 11,638,587;

U.S. patent application Ser. No. 16/458,112, entitled SURGICAL RFID ASSEMBLIES FOR DISPLAY AND COMMUNICATION, now U.S. Pat. No. 11,553,971;

U.S. patent application Ser. No. 16/458,116, entitled SURGICAL RFID ASSEMBLIES FOR COMPATIBILITY DETECTION, now U.S. Pat. No. 11,361,176; and U.S. patent application Ser. No. 16/458,118, entitled SURGICAL RFID ASSEMBLIES FOR INSTRUMENT OPERATIONAL SETTING CONTROL, now U.S. Pat. No. 11,684,434.

Applicant of the present application owns the following U.S. patent applications that were filed on May 1, 2018 and which are each herein incorporated by reference in their respective entireties:

U.S. Provisional patent application Ser. No. 62/665,129, entitled SURGICAL SUTURING SYSTEMS;

U.S. Provisional patent application Ser. No. 62/665,139, entitled SURGICAL INSTRUMENTS COMPRISING CONTROL SYSTEMS;

U.S. Provisional patent application Ser. No. 62/665,177, entitled SURGICAL INSTRUMENTS COMPRISING HANDLE ARRANGEMENTS;

U.S. Provisional patent application Ser. No. 62/665,128, entitled MODULAR SURGICAL INSTRUMENTS;

U.S. Provisional patent application Ser. No. 62/665,192, entitled SURGICAL DISSECTORS; AND U.S. Provisional Patent Application Ser. No. 62/665,134, entitled SURGICAL CLIP APPLIER.

Applicant of the present application owns the following U.S. patent applications that were filed on Aug. 24, 2018 which are each herein incorporated by reference in their respective entireties:

U.S. patent application Ser. No. 16/112,129, entitled SURGICAL SUTURING INSTRUMENT CONFIGURED TO MANIPULATE TISSUE USING MECHANICAL AND ELECTRICAL POWER, now U.S. Pat. No. 11,602,366;

U.S. patent application Ser. No. 16/112,155, entitled SURGICAL SUTURING INSTRUMENT COMPRISING A CAPTURE WIDTH WHICH IS LARGER THAN TROCAR DIAMETER, now U.S. Pat. No. 11,564,703;

U.S. patent application Ser. No. 16/112,168, entitled SURGICAL SUTURING INSTRUMENT COMPRISING A NON-CIRCULAR NEEDLE, now U.S. Pat. No. 11,925,373;

U.S. patent application Ser. No. 16/112,180, entitled ELECTRICAL POWER OUTPUT CONTROL BASED ON MECHANICAL FORCES, now U.S. Pat. No. 12,121,255;

U.S. patent application Ser. No. 16/112,193, entitled REACTIVE ALGORITHM FOR SURGICAL SYSTEM, now U.S. Pat. No. 10,932,806;

U.S. patent application Ser. No. 16/112,099, entitled SURGICAL INSTRUMENT COMPRISING AN ADAPTIVE ELECTRICAL SYSTEM, now U.S. Pat. No. 11,793,537;

U.S. patent application Ser. No. 16/112,112, entitled CONTROL SYSTEM ARRANGEMENTS FOR A MODULAR SURGICAL INSTRUMENT, now U.S. Patent Application Publication No. 2019/0125320;

U.S. patent application Ser. No. 16/112,119, entitled ADAPTIVE CONTROL PROGRAMS FOR A SURGICAL SYSTEM COMPRISING MORE THAN ONE TYPE OF CARTRIDGE, now U.S. Pat. No. 11,819,231;

U.S. patent application Ser. No. 16/112,097, entitled SURGICAL INSTRUMENT SYSTEMS COMPRISING BATTERY ARRANGEMENTS, now U.S. Pat. No. 11,648,022;

U.S. patent application Ser. No. 16/112,109, entitled SURGICAL INSTRUMENT SYSTEMS COMPRISING HANDLE ARRANGEMENTS, now U.S. Pat. No. 11,759,224;

U.S. patent application Ser. No. 16/112,114, entitled SURGICAL INSTRUMENT SYSTEMS COMPRISING FEEDBACK MECHANISMS, now U.S. Pat. No. 10,980,560;

U.S. patent application Ser. No. 16/112,117, entitled SURGICAL INSTRUMENT SYSTEMS COMPRISING LOCKOUT MECHANISMS, now U.S. Patent Application Publication No. 2019/0125476;

U.S. patent application Ser. No. 16/112,095, entitled SURGICAL INSTRUMENTS COMPRISING A LOCKABLE END EFFECTOR SOCKET, now U.S. Pat. No. 11,291,465;

U.S. patent application Ser. No. 16/112,121, entitled SURGICAL INSTRUMENTS COMPRISING A SHIFTING MECHANISM, now U.S. Pat. No. 11,026,712;

U.S. patent application Ser. No. 16/112,151, entitled SURGICAL INSTRUMENTS COMPRISING A SYSTEM FOR ARTICULATION AND ROTATION COMPENSATION, now U.S. Pat. No. 10,772,651;

U.S. patent application Ser. No. 16/112,154, entitled SURGICAL INSTRUMENTS COMPRISING A BIASED SHIFTING MECHANISM, now U.S. Patent Application Publication No. 2019/0125321;

U.S. patent application Ser. No. 16/112,226, entitled SURGICAL INSTRUMENTS COMPRISING AN ARTICULATION DRIVE THAT PROVIDES FOR HIGH ARTICULATION ANGLES, now U.S. Patent Application Publication No. 2019/0125379;

U.S. patent application Ser. No. 16/112,062, entitled SURGICAL DISSECTORS AND MANUFACTURING TECHNIQUES, now U.S. Pat. No. 10,959,744;

U.S. patent application Ser. No. 16/112,098, entitled SURGICAL DISSECTORS CONFIGURED TO APPLY MECHANICAL AND ELECTRICAL ENERGY, now U.S. Patent Application Publication No. 2019/0125430;

U.S. patent application Ser. No. 16/112,237, entitled SURGICAL CLIP APPLIER CONFIGURED TO STORE CLIPS IN A STORED STATE, now U.S. Pat. No. 11,026,713;

U.S. patent application Ser. No. 16/112,245, entitled SURGICAL CLIP APPLIER COMPRISING AN EMPTY CLIP CARTRIDGE LOCKOUT, now U.S. Pat. No. 11,051,836;

U.S. patent application Ser. No. 16/112,249, entitled SURGICAL CLIP APPLIER COMPRISING AN AUTOMATIC CLIP FEEDING SYSTEM, now U.S. Pat. No. 11,109,878;

U.S. patent application Ser. No. 16/112,253, entitled SURGICAL CLIP APPLIER COMPRISING ADAPTIVE FIRING CONTROL, now U.S. Pat. No. 11,103,268; and U.S. patent application Ser. No. 16/112,257, entitled SURGICAL CLIP APPLIER COMPRISING ADAP- TIVE CONTROL IN RESPONSE TO A STRAIN GAUGE CIRCUIT, now U.S. Pat. No. 11,071,560.

Applicant of the present application owns the following U.S. patent applications that were filed on Oct. 26, 2018 which are each herein incorporated by reference in their respective entireties:

U.S. patent application Ser. No. 16/172,130, entitled CLIP APPLIER COMPRISING INTERCHANGEABLE CLIP RELOADS, now U.S. Pat. No. 11,406,390;

U.S. patent application Ser. No. 16/172,066, entitled CLIP APPLIER COMPRISING A MOVABLE CLIP MAGAZINE, now U.S. Pat. No. 11,045,197;

U.S. patent application Ser. No. 16/172,078, entitled CLIP APPLIER COMPRISING A ROTATABLE CLIP MAGAZINE, now U.S. Pat. No. 11,123,070;

U.S. patent application Ser. No. 16/172,087, entitled CLIP APPLIER COMPRISING CLIP ADVANCING SYSTEMS, now U.S. Pat. No. 11,026,687;

U.S. patent application Ser. No. 16/172,094, entitled CLIP APPLIER COMPRISING A CLIP CRIMPING SYSTEM, now U.S. Pat. No. 11,317,919;

U.S. patent application Ser. No. 16/172,128, entitled CLIP APPLIER COMPRISING A RECIPROCATING CLIP ADVANCING MEMBER, now U.S. Pat. No. 11,413,042;

U.S. patent application Ser. No. 16/172,168, entitled CLIP APPLIER COMPRISING A MOTOR CONTROLLER, now U.S. Pat. No. 11,141,160;

U.S. patent application Ser. No. 16/172,164, entitled SURGICAL SYSTEM COMPRISING A SURGICAL TOOL AND A SURGICAL HUB, now U.S. Pat. No. 11,229,436; and U.S. patent application Ser. No. 16/172,303, entitled METHOD FOR OPERATING A POWERED ARTICULATING MULTI-CLIP APPLIER, now U.S. Pat. No. 11,911,045.

Applicant of the present application owns the following U.S. patent applications, filed on Dec. 4, 2018, the disclosure of each of which is herein incorporated by reference in its entirety:

U.S. patent application Ser. No. 16/209,385, titled METHOD OF HUB COMMUNICATION, PROCESSING, STORAGE AND DISPLAY, now U.S. Pat. No. 11,937,769;

U.S. patent application Ser. No. 16/209,395, titled METHOD OF HUB COMMUNICATION, now U.S. Pat. No. 11,659,023;

U.S. patent application Ser. No. 16/209,403, titled METHOD OF CLOUD BASED DATA ANALYTICS FOR USE WITH THE HUB, now U.S. Patent Publication No. 2019/0206569;

U.S. patent application Ser. No. 16/209,407, titled METHOD OF ROBOTIC HUB COMMUNICATION, DETECTION, AND CONTROL, now U.S. Pat. No. 11.559.307;

U.S. patent application Ser. No. 16/209,416, titled METHOD OF HUB COMMUNICATION, PROCESSING, DISPLAY, AND CLOUD ANALYTICS, now U.S. Pat. No. 11,576,677;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Pat. No. 11,969,142;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Pat. No. 11,389,164;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Pat. No. 12,096,916;

U.S. patent application Ser. No. 16/209,447, titled METHOD FOR SMOKE EVACUATION FOR SURGICAL HUB, now U.S. Pat. No. 12,127,729;

U.S. patent application Ser. No. 16/209,453, titled METHOD FOR CONTROLLING SMART ENERGY DEVICES, now U.S. Pat. No. 11,589,888;

U.S. patent application Ser. No. 16/209,458, titled METHOD FOR SMART ENERGY DEVICE INFRASTRUCTURE, now U.S. Pat. No. 11,559,308;

U.S. patent application Ser. No. 16/209,465, titled METHOD FOR ADAPTIVE CONTROL SCHEMES FOR SURGICAL NETWORK CONTROL AND INTERACTION, now U.S. Pat. No. 11,304,699;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Pat. No. 11,871,901;

U.S. patent application Ser. No. 16/209,490, titled METHOD FOR FACILITY DATA COLLECTION AND INTERPRETATION, now U.S. Patent Application Publication No. 2019/0206564; and U.S. patent application Ser. No. 16/209,491, titled METHOD FOR CIRCULAR STAPLER CONTROL ALGORITHM ADJUSTMENT BASED ON SITUATIONAL AWARENESS, now U.S. Pat. No. 11,109,866.

Before explaining various aspects of surgical devices and systems in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various surgical systems and instruments (e.g. surgical stapling instrument, surgical clip applier, surgical suturing instrument) are described in connection with the present disclosure. The surgical systems and/or instruments comprise a radio-frequency identification (RFID) system that includes one or more RFID scanners and one or more RFID tags, as will be discussed in greater detail below. Examples of surgical systems which use RFID technology are disclosed in U.S. Pat. No. 7,959,050 and U.S. Patent Application No. 2015/0053743, both of which are incorporated by reference herein in their entireties.

Radio-frequency identification (RFID) is used in a variety of industries to track and identify objects. RFID relies on radio waves to transfer digitally-stored information from a RFID tag to a RFID reader or receiver configured to receive the information. RFID technology uses RFID tags, sometimes referred to as chips, which contain electronically-stored information, and RFID readers, which serve to identify and communicate with the RFID tags. There are two different types of RFID systems—active RFID systems and passive RFID systems. Active RFID systems include RFID tags that comprise an on-board power source to broadcast their signals. Active RFID tags can include a battery within the RFID tag which allows the active RFID tag to function independently from the RFID reader. As such, RFID tags in an active RFID system do not need to wait to receive a signal from a RFID reader before sending out information. Instead, the active RFID tags are free to continuously send out a signal, or beacon. Many commercially available active RFID systems often operate at one of two main frequency ranges—433 MHZ and 915 MHz, but any suitable frequency range can be used. Typically, a RFID tag must be within a specific distance or frequency range in order to be identified by its corresponding RFID reader.

Passive RFID systems include RFID tags which do not comprise an on-board power source but instead receive the energy needed to operate from an RFID reader. Contrary to active RFID tags, RFID tags in a passive RFID system do not actively send out a signal before receiving a prompt. Instead, passive RFID tags wait to receive information from a RFID reader before sending out a signal. Many commercially-available passive RFID systems often operate within three frequency ranges—Low Frequency ("LF"), High Frequency ("HF") & Near-Field Communication ("NFC"), and Ultra High Frequency ("UHF"). The LF bandwidth is 125-134 KHz and includes a longer wavelength with a short read range of approximately one to ten centimeters. The HF and NFC bandwidth is 13.56 MHz and includes a medium wavelength with a typical read range of one centimeter to one meter. The UHF bandwidth is 865-960 MHz and includes a short, high-energy wavelength of one meter which translates into a long read range. The above being said, any suitable frequency can be used.

A variety of RFID systems comprising differently-sized RFID tags exist. However, some are better suited for use in technology areas that require the tracking of very small objects. For example, Hitachi Chemical Co. Ltd. is a leading manufacturer in the RFID technology field. The Ultra Small size UHF RFID tag manufactured by Hitachi Chemical Co. Ltd. is typically no larger than 1.0 to 13 mm and enables communication between a RFID tag and a RFID reader at distances of several centimeters or more. Due to its compact nature, the Hitachi RFID tag is suitable for very small products which need to be identified. Each Hitachi RFID tag comprises an antenna, an IC chip connected to the antenna, and a sealing material that seals the IC chip and the antenna. Because the Hitachi RFID tag incorporates an antenna and an IC chip in a single unit, the Hitachi RFID tag is convenient enough to easily affix to any small object using an adhesive or tape, for example.

The Hitachi RFID tag comprises a square stainless steel plate and a metal antenna. The antenna comprises a LC resonant circuit or any other suitable circuit and is electrically connected to the plate. After the plate and the antenna are connected to one another, the antenna and plate are sealed together in a single unit with a sealing material. The sealing material is primarily composed of epoxy, carbon, and silica to enhance the heat resistance capabilities of the Hitachi RFID tag. That is, the heat resistance of the RFID tag substantially depends on the heat resistance capabilities of the sealing material. The sealing material has a high heat resistance withstanding temperatures of up to 250 to 300° C. for shorter time periods, such as a few seconds, and is resistant to heat for longer periods of time up to 150° C. Accordingly, the Hitachi RFID tag has a higher heat resistance than conventional RFID tags and can still operate normally even at high temperatures. Additional information regarding the Hitachi RFID tag can be found in U.S. Pat. No. 9,171,244, which is incorporated by reference herein in its entirety.

Figure 2:
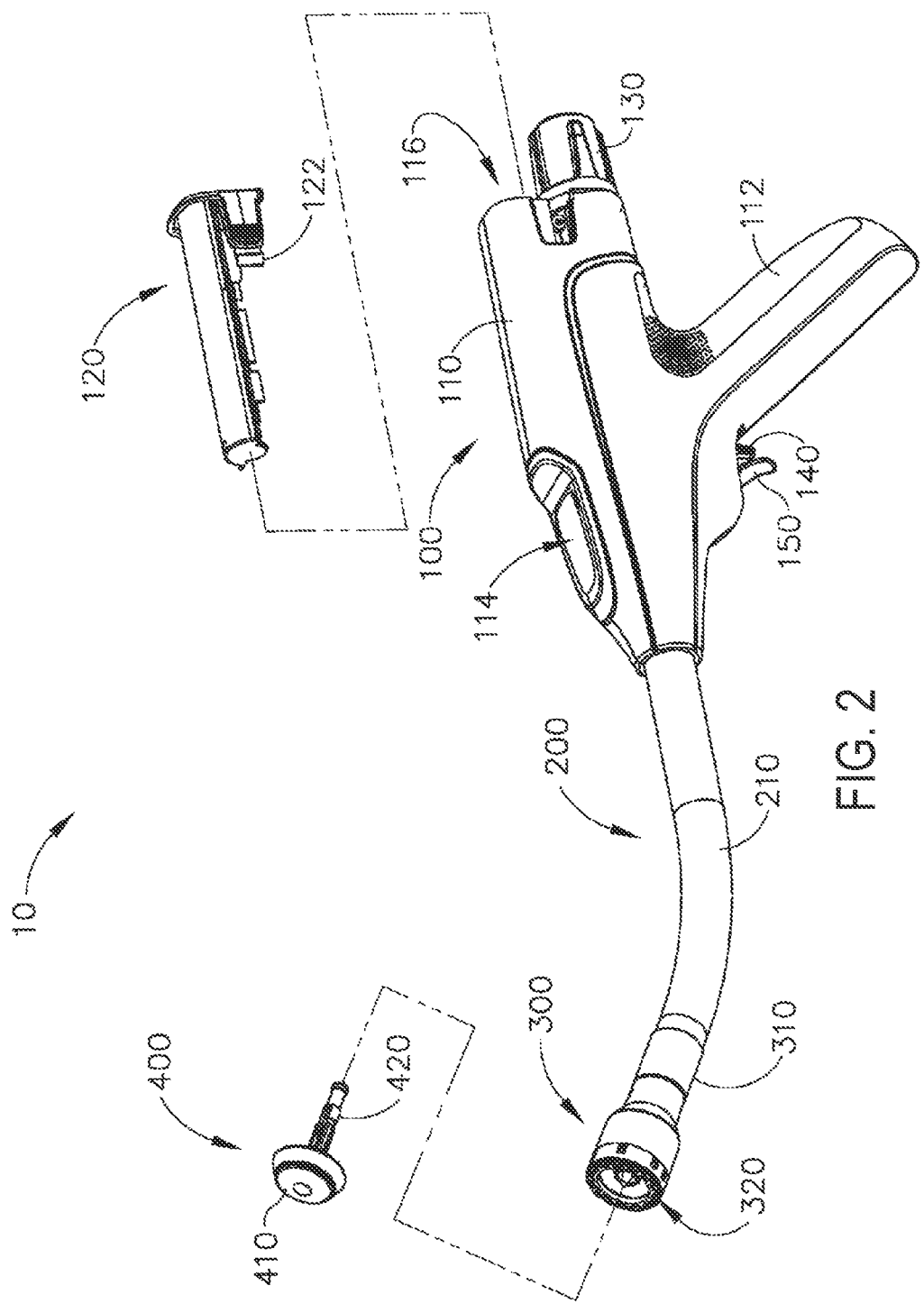
FIG. 2 depicts a perspective view of the circular stapler of FIG. 1, with a battery pack removed from a housing assembly and an anvil removed from a stapling head assembly, in accordance with at least one aspect of the present disclosure.

FIGS. 1-2 depict an example surgical circular stapling instrument 10 that can be adapted to include an RFID system and a control system thereof, in accordance with at least one aspect of the present disclosure. The stapling instrument 10 may be used to provide an end-to-end anastomosis between two sections of an anatomical lumen such as a portion of a patient's digestive tract. Instrument 10 of this example comprises a housing assembly 100, a shaft assembly 200, a stapling head assembly 300, and an anvil 400. Housing assembly 100 comprises a casing 110 defining an obliquely oriented pistol grip 112. Although the housing assembly 100 is depicted in the form of a handle, this is not limiting. In various instances, the housing assembly 100 can be a component of a robotic system, for example.

Housing assembly 100 further includes a window 114 that permits viewing of a movable indicator needle. In some versions, a series of hash marks, colored regions, and/or other fixed indicators are positioned adjacent to window 114 in order to provide a visual context for indicator needle, thereby facilitating operator evaluation of the position of needle within window 114. The movement of the indicator needle corresponds to a closing motion of the anvil 400 relative to the stapling head assembly 300. The hash marks, colored regions, and/or other fixed indicators can define an optimal anvil closure zone for firing the instrument 10. Accordingly, when the indicator needle is in the optimal anvil closure zone, the user may fire the instrument 10. Various suitable alternative features and configurations for housing assembly 100 will be apparent to those of ordinary skill in the art in view of the teachings herein.

Instrument 10 of the present example further includes a power source which can be in the form of a battery pack 120. Battery pack 120 is operable to provide electrical power to a motor 160 (FIG. 15) in pistol grip 112. In various aspects, battery pack 120 is removable from housing assembly 100. In particular, as shown in FIGS. 1-2, battery pack 120 may be inserted into a socket 116 defined by casing 110. Once battery pack 120 is fully inserted in socket 116, latches 122 of battery pack 120 may resiliently engage interior features of casing 110 to provide a snap fit. To remove battery pack 120, the operator may press latches 122 inwardly to disengage latches 122 from the interior features of casing 110 then pull battery pack 120 proximally from socket 116. It should be understood that battery pack 120 and housing assembly 100 may have complementary electrical contacts, pins and sockets, and/or other features that provide paths for electrical communication from battery pack 120 to electrically powered components in housing assembly 100 when battery pack 120 is inserted in socket 116. It should also be understood that, in some versions, battery pack 120 is unitarily incorporated within housing assembly 100 such that battery back 120 cannot be removed from housing assembly 100.

Shaft assembly 200 extends distally from housing assembly 100 and includes a preformed bend. In some versions, the preformed bend is configured to facilitate positioning of stapling head assembly 300 within a patient's colon. Various suitable bend angles or radii that may be used will be apparent to those of ordinary skill in the art in view of the teachings herein. In some other versions, shaft assembly 200 is straight, such that shaft assembly 200 lacks a preformed bend. Various exemplary components that may be incorporated into shaft assembly 200 will be described in greater detail below.

Stapling head assembly 300 is located at the distal end of shaft assembly 200. As shown in FIGS. 1-2, anvil 400 is configured to removably couple with shaft assembly 200, adjacent to stapling head assembly 300. Anvil 400 and stapling head assembly 300 are configured to cooperate to manipulate tissue in three ways, including clamping the tissue, cutting the tissue, and stapling the tissue. A knob 130 at the proximal end of housing assembly 100 is rotatable relative to casing 110 to provide precise clamping of the tissue between anvil 400 and stapling head assembly 300. When a safety trigger 140 of housing assembly 100 is pivoted away from a firing trigger 150 of housing assembly 100, firing trigger 150 may be actuated to thereby provide cutting and stapling of the tissue.

In the following discussion of anvil 400, the terms "distal" and "proximal" and variations thereof will be used with reference to the orientation of anvil 400 when anvil 400 is coupled with shaft assembly 200 of instrument 10. Thus, proximal features of anvil 400 will be closer to the operator of instrument 10; while distal features of anvil 400 will be further from the operator of instrument 10.

Figure 4:
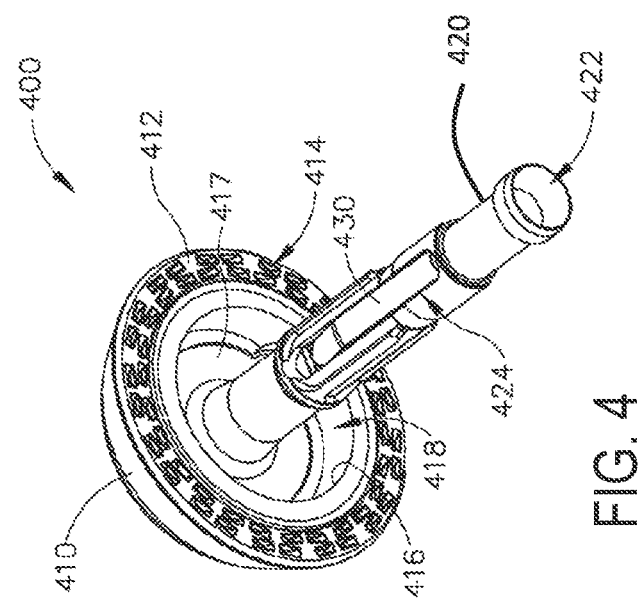
FIG. 4 depicts another perspective view of the anvil of FIG. 3, in accordance with at least one aspect of the present disclosure.

Referring to FIG. 4, anvil 400 of the present example comprises a head 410 and a shank 420. Head 410 includes a proximal surface 412 that defines a plurality of staple forming pockets 414. Staple forming pockets 414 are arranged in two concentric annular arrays. In some other versions, staple forming pockets 414 are arranged in three or more concentric annular arrays. Staple forming pockets 414 are configured to deform staples as the staples are driven into staple forming pockets 414. For instance, each staple forming pocket 414 may deform a generally "U" shaped staple into a "B" shape as is known in the art. As best seen in FIG. 4, proximal surface 412 terminates at an inner edge 416, which defines an outer boundary of an annular recess 418 surrounding shank 420.

Shank 420 defines a bore 422 and includes a pair of pivoting latch members 430 positioned in bore 422. Latch members 430 are positioned within bore 422 such that their distal ends are positioned at the proximal ends of lateral openings 424, which are formed through the sidewall of shank 420.

Lateral openings 424 thus provide clearance for the distal ends 434 of the latch members 430 to deflect radially outwardly from the longitudinal axis defined by shank 420. However, latch members 430 are configured to resiliently bias their distal ends radially inwardly toward the longitudinal axis defined by shank 420. Latch members 430 thus act as retaining clips. This allows anvil 400 to be removably secured to a trocar 330 of stapling head assembly 300. It should be understood, however, that latch members 430 are merely optional. Anvil 400 may be removably secured to a trocar 330 using any other suitable components, features, or techniques.

In addition to or in lieu of the foregoing, anvil 400 may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

Figure 3:
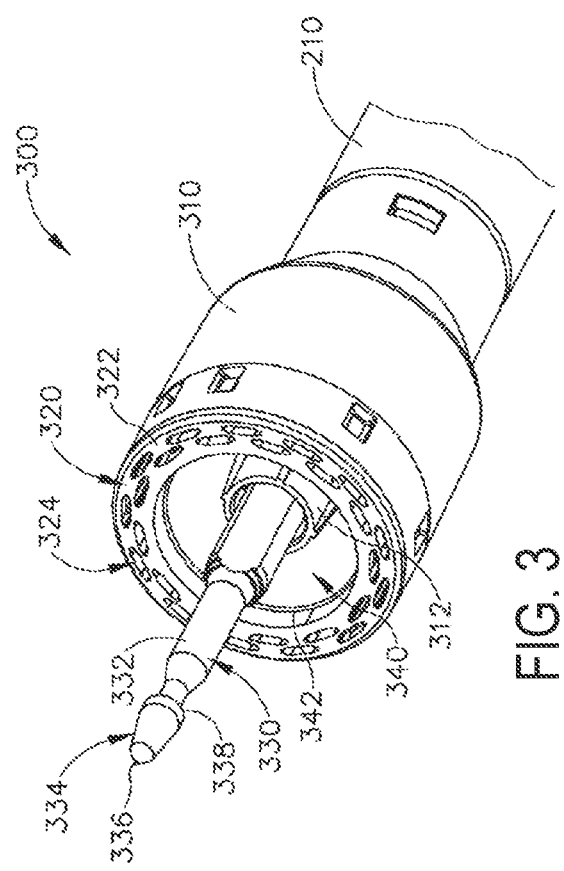
FIG. 3 depicts a perspective view of the stapling head assembly of the circular stapler of FIG. 1, in accordance with at least one aspect of the present disclosure.

Referring to FIG. 3, stapling head assembly 300 of the present example is coupled to a distal end of shaft assembly 200 and comprises a tubular casing 310 housing a slidable staple driver member. A cylindrical inner core member 312 extends distally within tubular casing 310. Tubular casing 310 is fixedly secured to an outer sheath 210 of shaft assembly 200, such that tubular casing 310 serves as a mechanical ground for stapling head assembly 300.

Trocar 330 is positioned coaxially within inner core member 312 of tubular casing 310. Trocar 330 is operable to translate distally and proximally relative to tubular casing 310 in response to rotation of knob 130 relative to casing 110 of housing assembly 100. Trocar 330 comprises a shaft 332 and a head 334. Head 334 includes a pointed tip 336 and an inwardly extending proximal surface 338. Shaft 332 thus provides a reduced outer diameter just proximal to head 334, with surface 338 providing a transition between that reduced outer diameter of shaft 332 and the outer diameter of head 334. While tip 336 is pointed in the present example, tip 336 is not sharp. Tip 336 will thus not easily cause trauma to tissue due to inadvertent contact with tissue. Head 334 and the distal portion of shaft 332 are configured for insertion in bore 422 of anvil 420. Anvil 400 is thus secured to trocar 330 through a snap fit due to latch members 430.

Figure 5:
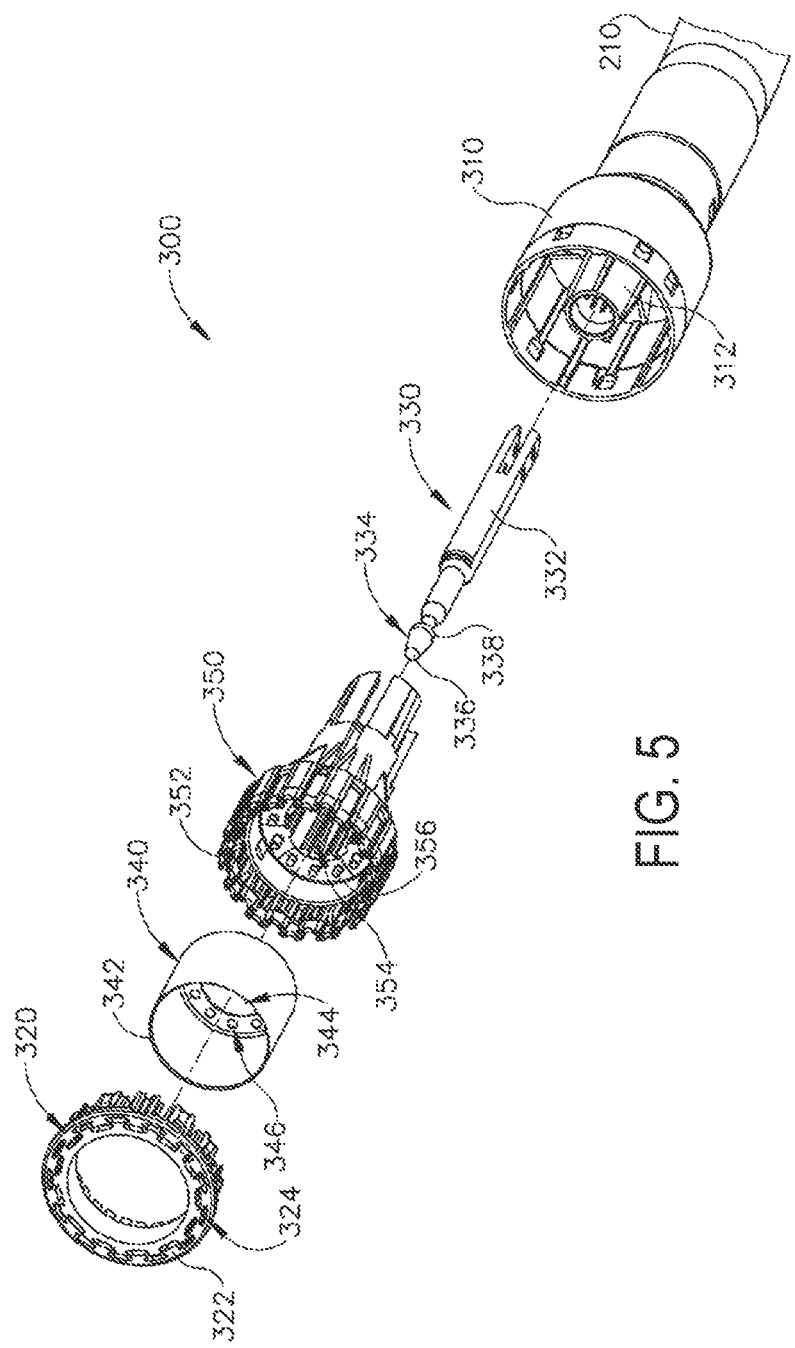
FIG. 5 depicts an exploded perspective view of the stapling head assembly of FIG. 3, in accordance with at least one aspect of the present disclosure.

As illustrated in FIG. 5, Staple driver member 350 is operable to actuate longitudinally within tubular casing 310 in response to activation of a motor 160. Staple driver member 350 includes two distally presented concentric annular arrays of staple drivers 352. Staple drivers 352 are arranged to correspond with the arrangement of staple forming pockets 414 described above. Thus, each staple driver 352 is configured to drive a corresponding staple into a corresponding staple forming pocket 414 when stapling head assembly 300 is actuated. It should be understood that the arrangement of staple drivers 352 may be modified just like the arrangement of staple forming pockets 414 as described above. Staple driver member 350 also defines a bore 354 that is configured to coaxially receive core member 312 of tubular casing 310. An annular array of studs 356 project distally from a distally presented surface surrounding bore 354.

A cylindrical knife member 340 is coaxially positioned within staple driver member 350. Knife member 340 includes a distally presented, sharp circular cutting edge 342. Knife member 340 is sized such that knife member 340 defines an outer diameter that is smaller than the diameter defined by the inner annular array of staple drivers 352. Knife member 340 also defines an opening that is configured to coaxially receive core member 312 of tubular casing 310. An annular array of openings 346 formed in knife member 340 is configured to complement the annular array of studs 356 of staple driver member 350, such that knife member 340 is fixedly secured to staple driver member 350 via studs 356 and openings 346. Other suitable structural relationships between knife member 340 and stapler driver member 350 will be apparent to those of ordinary skill in the art in view of the teachings herein.

A deck member 320 is fixedly secured to tubular casing 310. Deck member 320 includes a distally presented deck surface 322 defining two concentric annular arrays of staple openings 324. Staple openings 324 are arranged to correspond with the arrangement of staple drivers 352 and staple forming pockets 414 described above. Thus, each staple opening 324 is configured to provide a path for a corresponding staple driver 352 to drive a corresponding staple through deck member 320 and into a corresponding staple forming pocket 414 when stapling head assembly 300 is actuated. It should be understood that the arrangement of staple openings 322 may be modified just like the arrangement of staple forming pockets 414 as described above. It should also be understood that various structures and techniques may be used to contain staples within stapling head assembly 300 before stapling head assembly 300 is actuated. Such structures and techniques that are used to contain staples within stapling head assembly 300 may prevent the staples from inadvertently falling out through staple openings 324 before stapling head assembly 300 is actuated. Various suitable forms that such structures and techniques may take will be apparent to those of ordinary skill in the art in view of the teachings herein.

Figure 6:
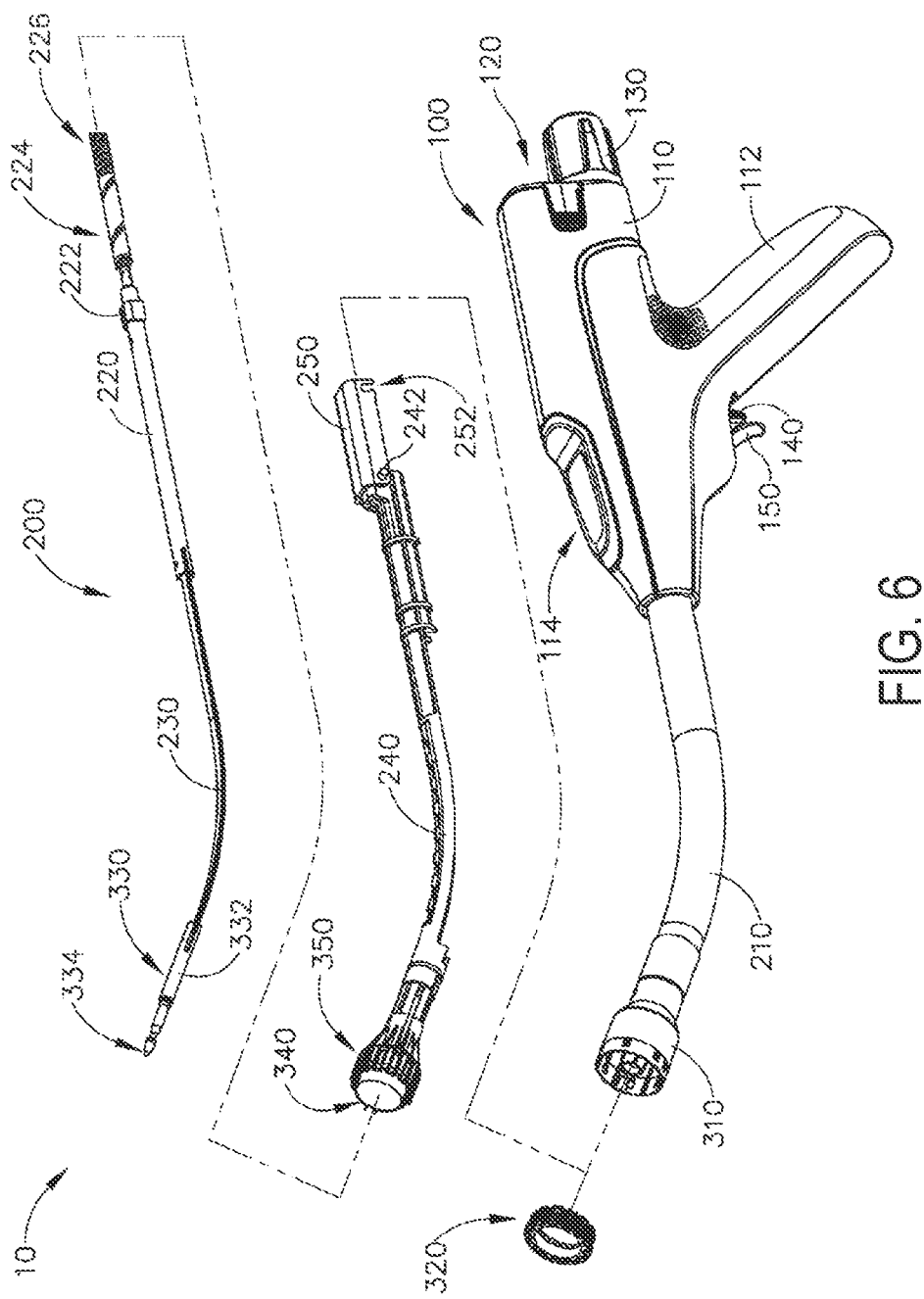
FIG. 6 depicts an exploded perspective view of the circular stapler of FIG. 1, with portions of the shaft assembly shown separately from each other, in accordance with at least one aspect of the present disclosure.
Figure 7:
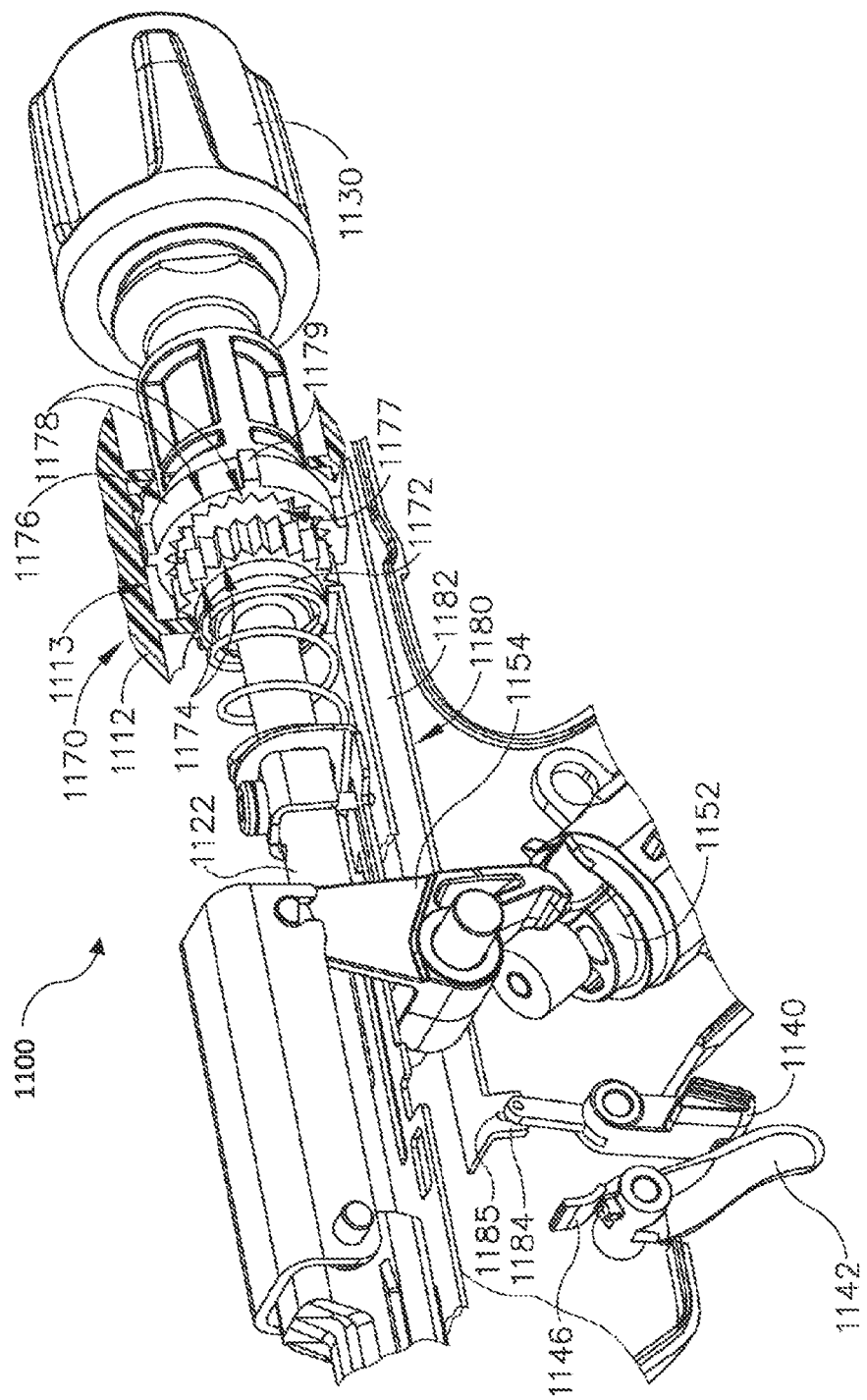
FIG. 7 depicts a detailed perspective view of an anvil actuation assembly of the housing assembly of FIG. 6, in accordance with at least one aspect of the present disclosure.

As best seen in FIG. 6, deck member 320 defines an inner diameter that is just slightly larger than the outer diameter defined by knife member 340. Deck member 320 is thus configured to allow knife member 340 to translate distally to a point where cutting edge 342 is distal to deck surface 322.

In addition to or in lieu of the foregoing, stapling head assembly 300 may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the entire disclosures of which are incorporated by reference herein. Still other suitable configurations will be apparent to one of ordinary skill in the art in view of the teachings herein.

FIG. 6 shows various components of shaft assembly 200, which couples components of stapling head assembly 300 with components of housing assembly 100. In particular, and as noted above, shaft assembly 200 includes an outer sheath 210 that extends between housing assembly 100 and tubular casing 310. In the present example, outer sheath 210 is rigid and includes a preformed curved section as noted above.

Shaft assembly 200 further includes a trocar actuation rod 220 and a trocar actuation band assembly 230. The distal end of trocar actuation band assembly 230 is fixedly secured to the proximal end of trocar shaft 332. The proximal end of trocar actuation band assembly 230 is fixedly secured to the distal end of trocar actuation rod 220. It should therefore be understood that trocar 330 will translate longitudinally relative to outer sheath 210 in response to translation of trocar actuation band assembly 230 and trocar actuation rod 220 relative to outer sheath 210. Trocar actuation band assembly 230 is configured to flex such that trocar actuation band assembly 230 may follow along the preformed curve in shaft assembly 200 as trocar actuation band assembly 230 is translated longitudinally relative to outer sheath 210. However, trocar actuation band assembly 230 has sufficient column strength and tensile strength to transfer distal and proximal forces from trocar actuation rod 220 to trocar shaft 332. Trocar actuation rod 220 is rigid. A clip 222 is fixedly secured to trocar actuation rod 220 and is configured to cooperate with complementary features within housing assembly 100 to prevent trocar actuation rod 220 from rotating within housing assembly 100 while still permitting trocar actuation rod 220 to translate longitudinally within housing assembly 100. Trocar actuation rod 220 further includes a coarse helical threading 224 and a fine helical threading 226.

Shaft assembly 200 further includes a stapling head assembly driver 240 that is slidably received within outer sheath 210. The distal end of stapling head assembly driver 240 is fixedly secured to the proximal end of staple driver member 350. The proximal end of stapling head assembly driver 240 is secured to a drive bracket 250 via a pin 242. It should therefore be understood that staple driver member 350 will translate longitudinally relative to outer sheath 210 in response to translation of stapling head assembly driver 240 and drive bracket 250 relative to outer sheath 210. Stapling head assembly driver 240 is configured to flex such that stapling head assembly driver 240 may follow along the preformed curve in shaft assembly 200 as stapling head assembly driver 240 is translated longitudinally relative to outer sheath 210. However, stapling head assembly driver 240 has sufficient column strength to transfer distal forces from drive bracket 250 to staple driver member 350.

It should be understood that shaft assembly 200 may further include one or more spacer elements within outer sheath 210. Such spacer elements may be configured to support trocar actuation band assembly 230 and/or stapling head assembly driver 240 as trocar actuation band assembly 230 and/or stapling head assembly driver 240 translate through outer sheath 210. For instance, such spacer elements may prevent trocar actuation band assembly 230 and/or stapling head assembly driver 240 from buckling as trocar actuation band assembly 230 and/or stapling head assembly driver 240 translate through outer sheath 210. Various suitable forms that such spacer elements may take will be apparent to those of ordinary skill in the art in view of the teachings herein.

In addition to or in lieu of the foregoing, shaft assembly 200 may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein in their entireties. Still other suitable configurations will be apparent to one of ordinary skill in the art in view of the teachings herein.

Additional operational details of the surgical instrument 10, and other instruments suitable for use with the present disclosure, are also described in U.S. Pat. No. 10,905,415, titled SURGICAL STAPLER WITH ELECTROMECHANICAL LOCKOUT, filed Jun. 26, 2015, which issued on Feb. 2, 2021, which is hereby incorporated by reference herein in its entirety.

Figure 8:
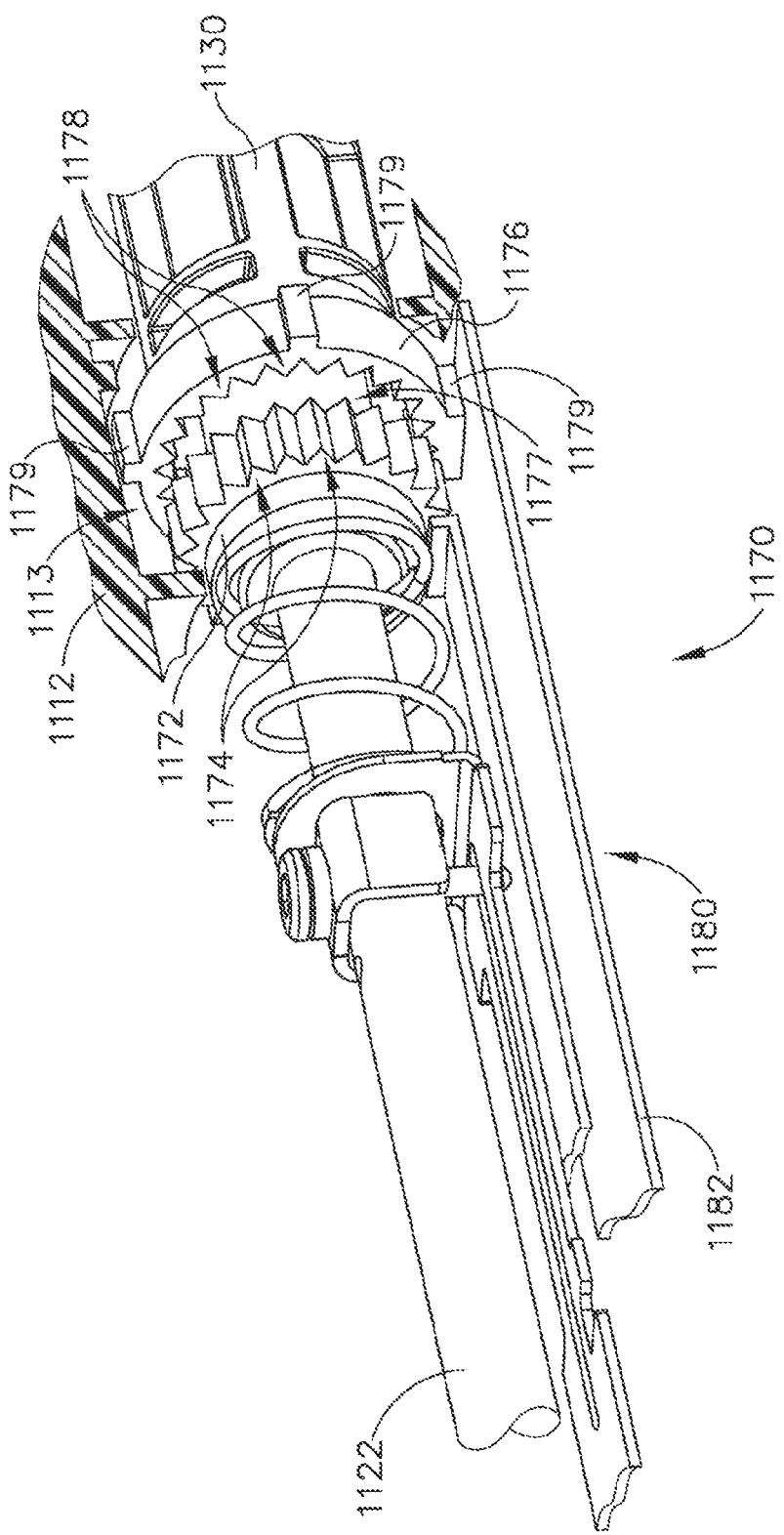
FIG. 8 depicts a detailed perspective view of an anvil lockout assembly of the anvil actuation assembly of FIG. 7, with the anvil lockout assembly in an unlocked position, in accordance with at least one aspect of the present disclosure.
Figure 12:
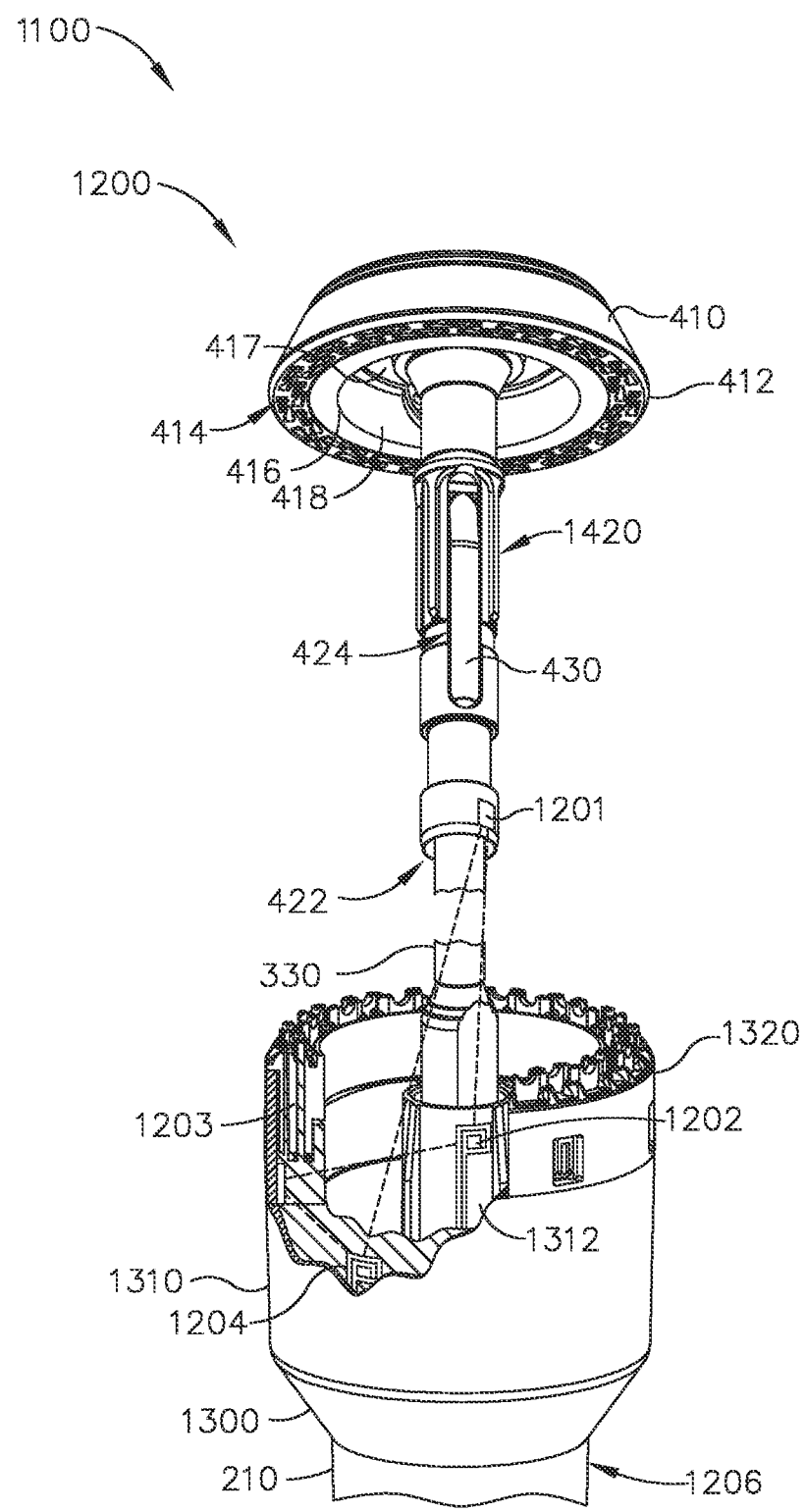
FIG. 12 depicts stapling head assembly and an anvil being coupled to a trocar of the stapling head assembly, in accordance with at least one aspect of the present disclosure.

Instrument 1100 is similar in many respects to instrument 10. For example, like instrument 10, instrument 1100 is a surgical instrument configured to grasp, staple, and/or cut tissue. Also, like instrument 10, instrument 1100 includes a shaft assembly 1206 (FIG. 12), a stapling head assembly 1300 (FIG. 12), and an anvil 1200 (FIG. 12). In addition, Instrument 1100 includes a lockout assembly such as, for example, an anvil lockout assembly 1170. Anvil lockout assembly 1170 is generally configured to prevent further adjustment of the longitudinal position of the anvil once safety trigger 1140 is actuated. Such a feature may be desirable because lockout of the anvil may prevent an operator from improperly changing the gap distance d once a suitable gap distance d is reached. Anvil lockout assembly 1170 comprises an inner lockout member 1172, an outer lockout member 1176, and an actuation member 1180. As is best seen in FIG. 8, inner lockout member 1172 is disposed about a portion of a portion of knob 1130 and is fixedly secured thereto. Inner lockout member 1172 of the present example includes a plurality of triangular teeth 1174 extending radially outwardly from inner lockout member 1172. Teeth 1174 are configured to engage with corresponding teeth 1184 of outer lockout member 1176 to prevent rotation of knob 1130, thereby preventing translation of trocar actuation rod 1122.

Various lockout out assemblies that are suitable for use with the present disclosure are described in U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, which are incorporated by reference herein in their entireties.

Outer lockout member 1176 has a generally cylindrical shape and defines an opening 1177 that is sized to receive inner lockout member 1172. The inner diameter of outer lockout member 1176 defines a plurality of teeth 1178, which correspond to teeth 1147 of inner lockout member 1172. Teeth 1178 are configured to engage teeth 1174 of inner lockout member 1172 to prevent further adjustment of the longitudinal position of anvil 1200, by preventing further rotation of knob 1130. Outer lockout member 1176 further includes a plurality of protrusions 1179 protruding radially outwardly from the outer diameter of outer lockout member 1176. Protrusions 1179 are disposed in corresponding channels 1113 within casing 1112 to rotationally fix outer lockout member 1176 in position while still permitting at least some translation.

Although inner and outer lockout members 1172, 1176 of the present example are shown as including teeth 1174, 1178, it should be understood that in other examples any other suitable surfacing treatment or geometry may be used. For instance, in some examples lockout members 1172, 1176 include corresponding knurled surfaces, bumps, splines, ridges, detent features, or any other suitable surface treatment or geometry that may be configured to correspondingly engage to prevent relative rotational movement between lockout members 1172, 1176.

Actuation member 1180 comprises an elongate body 1182 extending from outer lockout member 1176 to safety trigger 1140. In particular, body 1182 includes a trigger bracket 1184 that is configured to couple with safety trigger 1140. Trigger bracket 1184 includes a channel 1185 that permits bracket 1184 to be pivotably coupled to safety trigger 1140. Similarly, the proximal end of body 1182 is configured to couple with at least one protrusion 1179 of outer lockout member 1176. Accordingly, movement of safety trigger 1140 is transferred to outer lockout member 1176 via actuation member 1180. In other words, outer lockout member 1176 translates longitudinally in response to pivoting of safety trigger 1140. Outer lockout member 1176 is generally responsive to safety trigger 1140 to selectively lock actuation of the anvil 1200.

Figure 9:
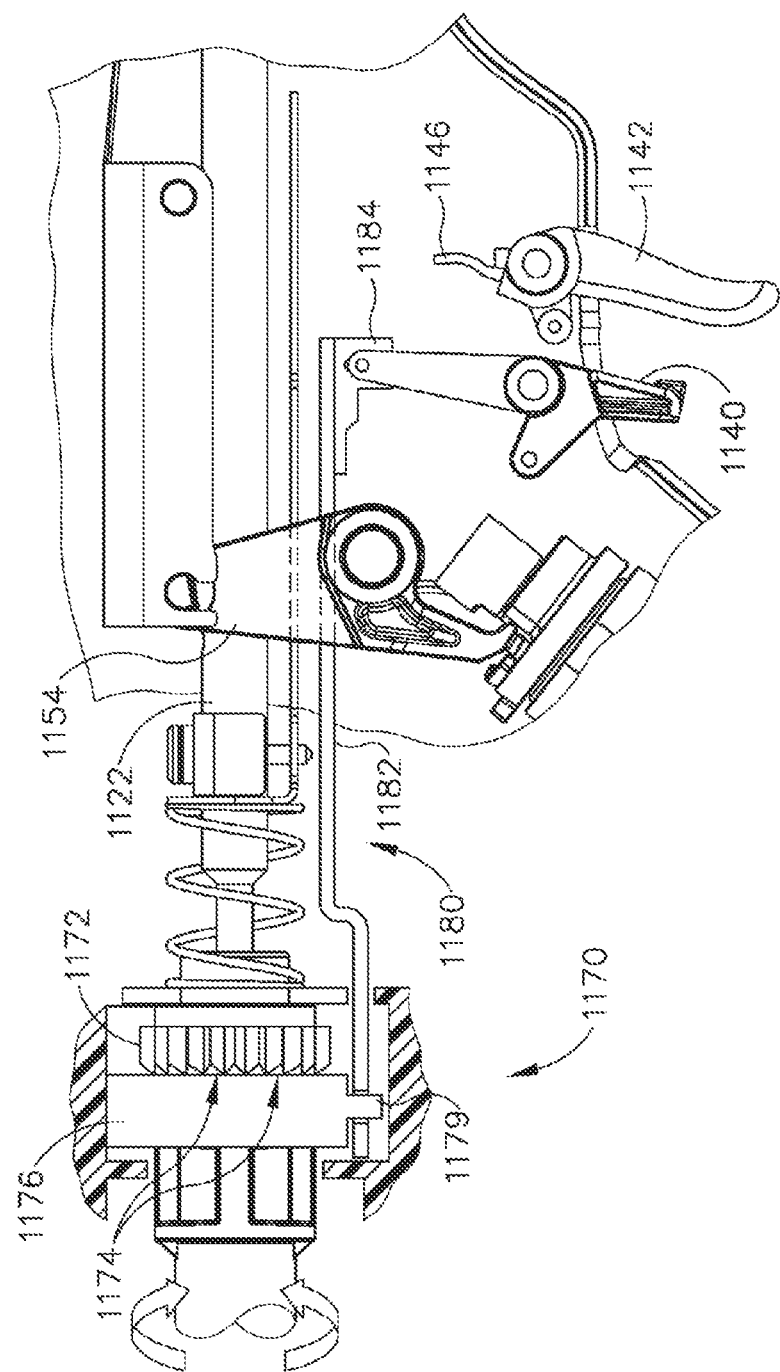
FIG. 9 depicts a detailed side elevational view of the anvil actuation assembly of FIG. 7, with the anvil lockout assembly of FIG. 8 in the unlocked position, in accordance with at least one aspect of the present disclosure.
Figure 10:
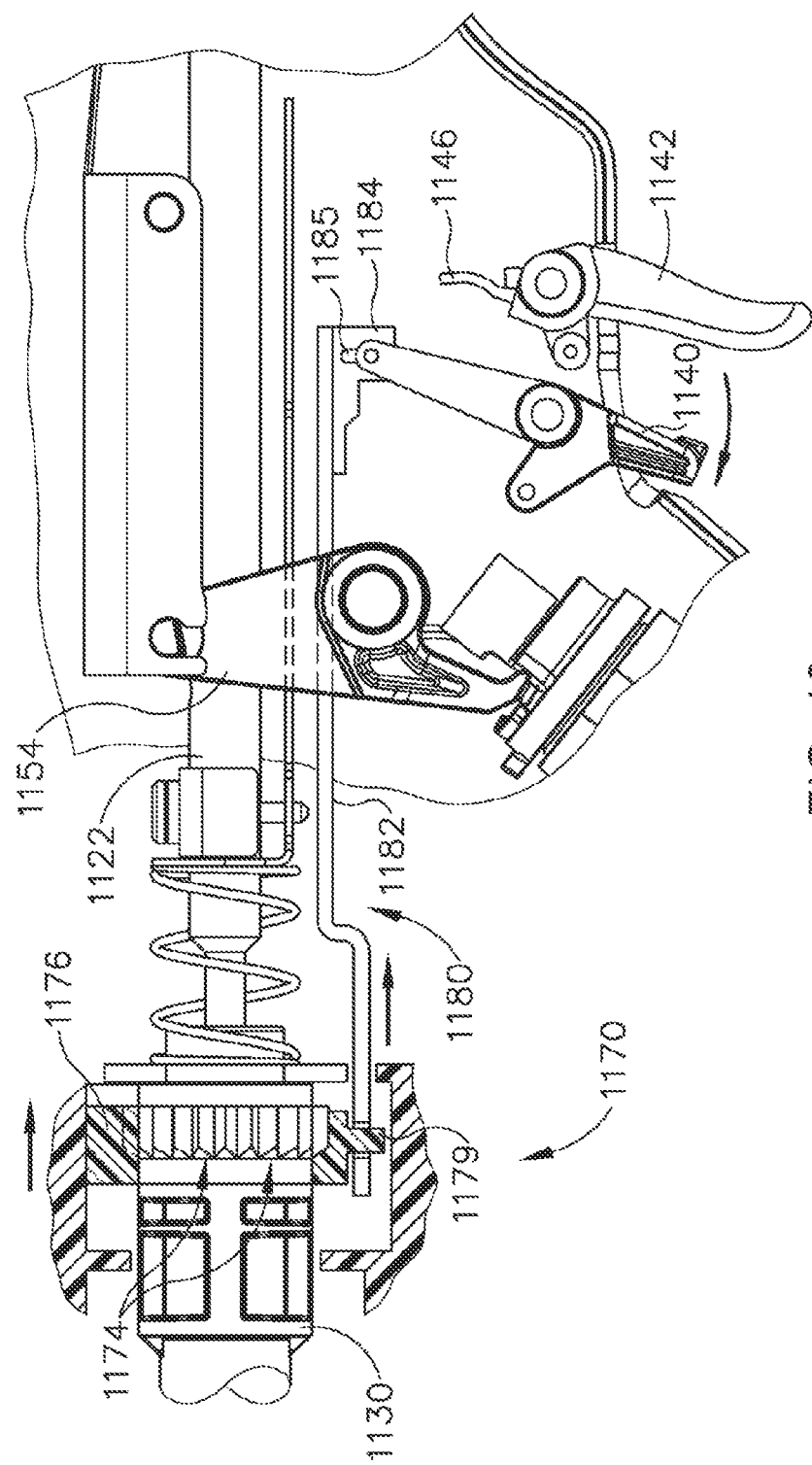
FIG. 10 depicts another detailed side elevational view of the anvil actuation assembly of FIG. 7, with the anvil lockout assembly of FIG. 8 in a locked position, in accordance with at least one aspect of the present disclosure.
Figure 11:
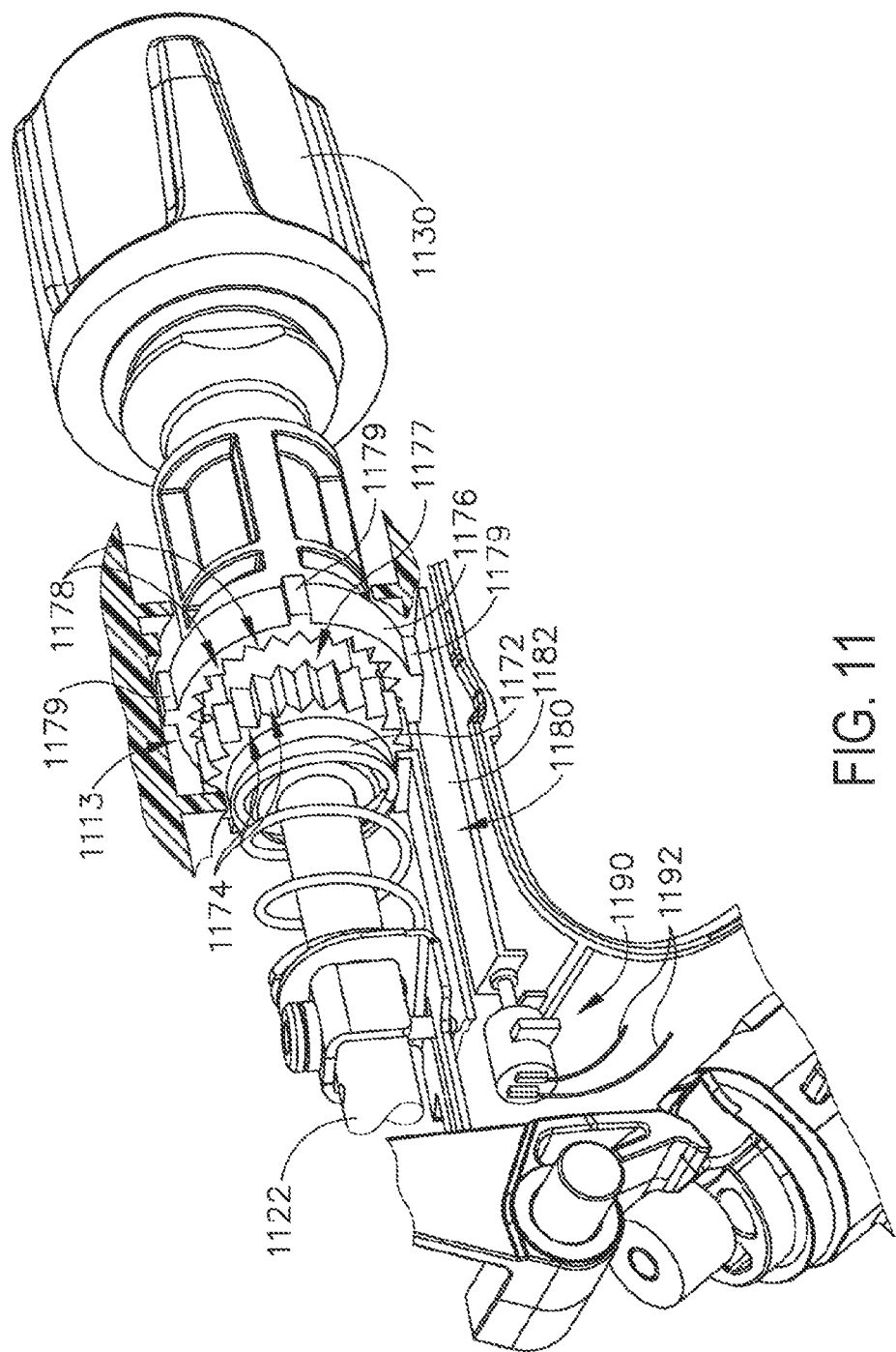
FIG. 11 depicts a detailed perspective view of an alternative configuration of the anvil lockout assembly of FIG. 8, in accordance with at least one aspect of the present disclosure.

FIGS. 9-11 show an exemplary sequence of operation of anvil lockout assembly 1170. As can be seen in FIG. 9, anvil lockout assembly 1170 initially begins in an unlocked state. In such a state, outer lockout member 1176 is positioned proximally away from inner lockout member 1172 such that inner lockout member 1172 is freely rotatable relative to outer lockout member 1176. It should be understood that when inner lockout member 1172 is freely rotatable, knob 1130 is similarly freely rotatable such that the longitudinal position of the anvil may be adjusted via trocar actuation rod 1122.

Once the operator has rotated knob 1130 to adjust the longitudinal position of the anvil to achieve an appropriate gap distance d, it may be desirable to prevent further adjustment of the longitudinal position of the anvil. FIG. 10 shows anvil lockout assembly 1170 in a locked state. To advance anvil lockout assembly 1170 to the locked state, the operator may pivot safety trigger 1140 proximally. Proximal movement of safety trigger 1140 causes safety trigger 1140 to drive actuation member 1180 distally.

Distal movement of actuation member 1180 results in corresponding movement of outer lockout member 1176. As outer lockout member 1176 is moved distally, teeth 1178 of outer lockout member 1176 will begin to engage teeth 1174 of inner lockout member 1176. Once teeth 1178 of outer lockout member 1176 fully engage with teeth 1174 of inner lockout member 1176, outer lockout member 1176 will prevent relative rotational movement of inner lockout member 1172 via protrusions 1179 and casing 1112. Because inner lockout member 1172 is fixedly secured to knob 1130, rotational movement of knob 1130 will also be prevented. With knob 1130 locked in position, further adjustment of the longitudinal position of the anvil will be prevented. With further adjustment of the longitudinal position of the anvil prevented, the operator may then actuate firing trigger 1142 to initiate the stapling sequence.

Figure 15:
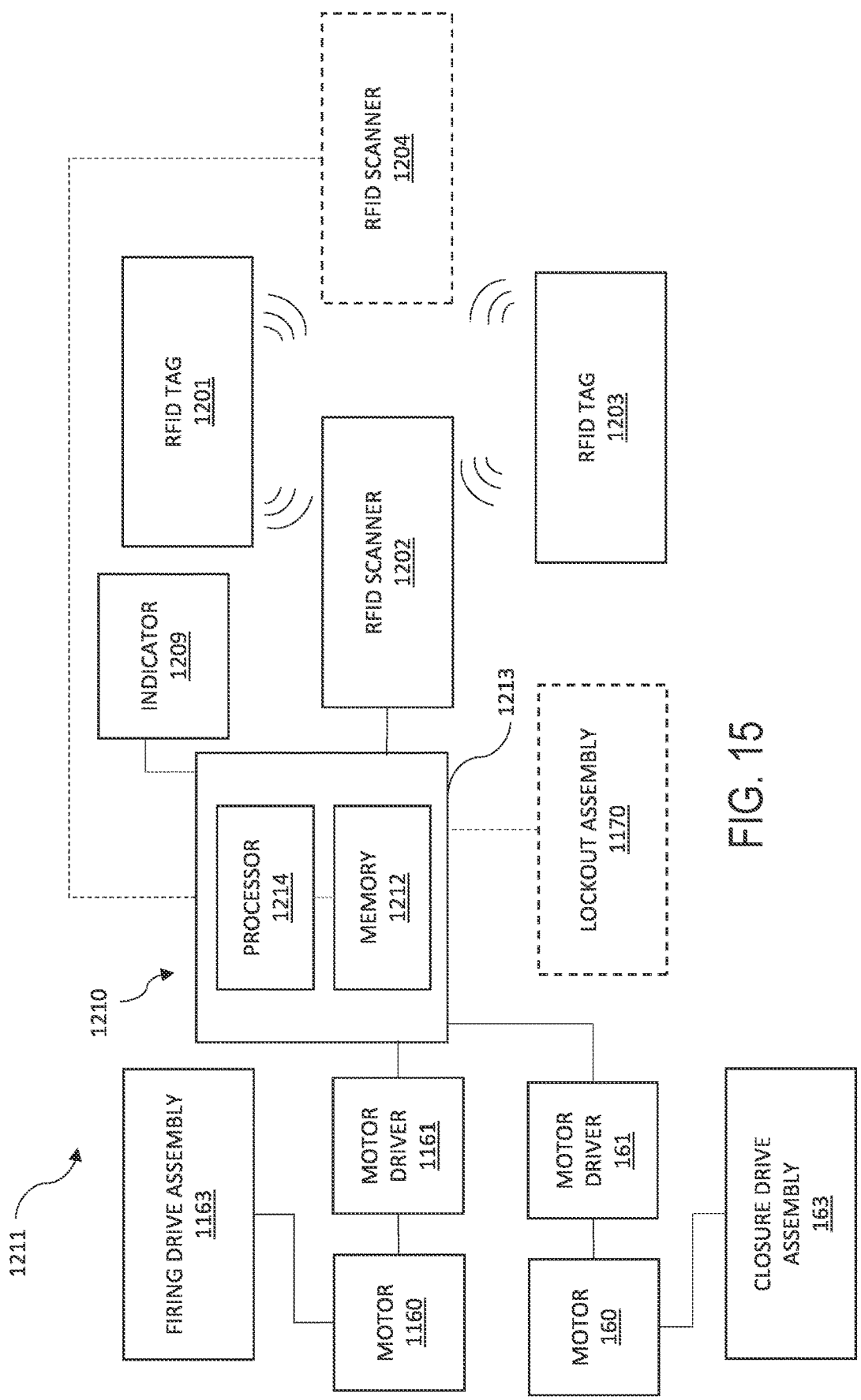
FIG. 15 depicts a control system of a surgical stapling instrument, in accordance with at least one aspect of the present disclosure.

In some examples, it may be desirable to drive outer lockout member 1176 using an actuation mechanism 1190 such as a solenoid. As illustrated in FIG. 11, actuation mechanism 1190 is aligned with the longitudinal axis of actuation member 1180 and is fixedly secured to actuation member 1180. To accommodate actuation mechanism 1190, actuation member 1180 may be shortened or otherwise modified to intersect with actuation mechanism 1190. Actuation mechanism 1190 includes a plurality of wires 1192 that may connect to a circuit board, switch, and/or sensor. In various examples, the wires 1192 are connected to the control circuit 1210 (FIG. 15). In various examples, the actuation mechanism 1190 may be actuated using safety trigger 1140 using a similar configuration as safety trigger 1040 of instrument 100. For instance, actuation of safety trigger 1140 may complete a circuit that activates actuation mechanism 1190, thereby driving lockout member 1176 longitudinally into engagement with lockout member 1172.

In operation, actuation mechanism 1190 generally provides the same function as safety trigger 1140, except actuation mechanism 1190 removes the necessity for actuation member 1180 to extend the entire distance to safety trigger 1140. Although actuation mechanism 1190 is shown and described herein as comprising a solenoid, it should be understood that any other suitable actuator may be used as will be apparent to those of ordinary skill in the art in view of the teachings herein.

Figure 13:
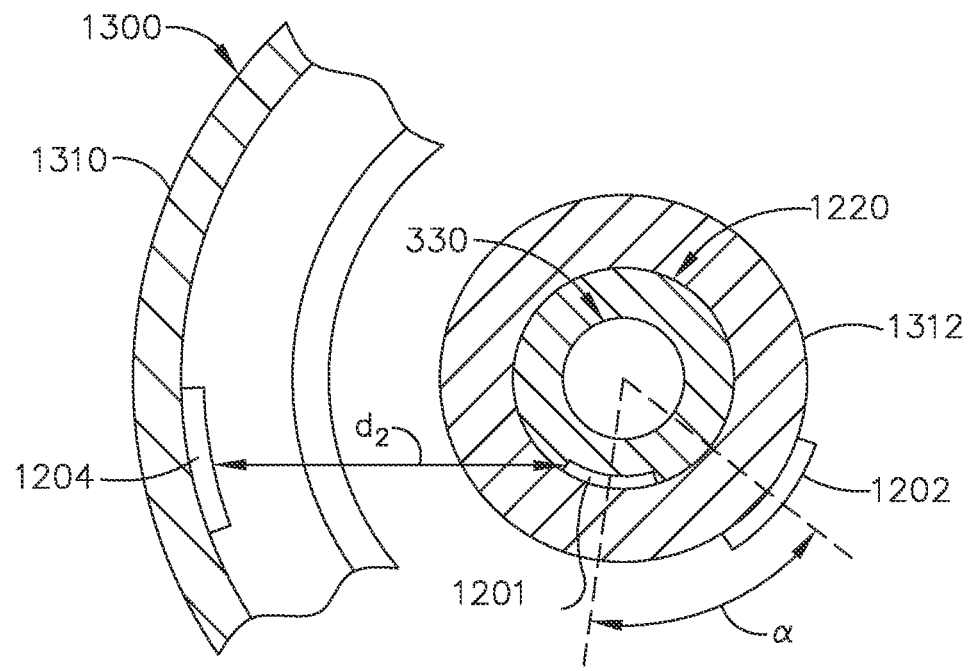
FIG. 13 depicts a partial transverse cross-sectional view of an anvil in an improper seating orientation with a stapling head assembly, in accordance with at least one aspect of the present disclosure.
Figure 14:
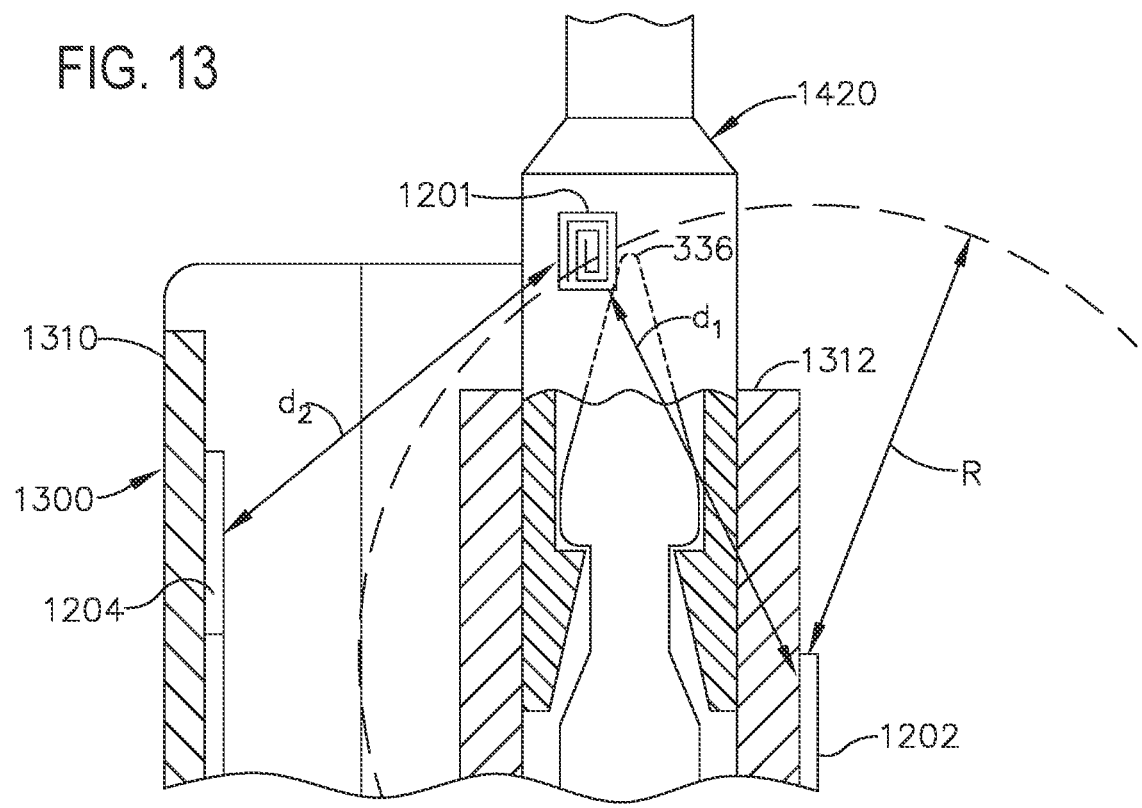
FIG. 14 depicts a partial longitudinal cross-sectional view of an anvil in an improper seating orientation with a stapling head assembly, in accordance with at least one aspect of the present disclosure.

Referring primarily to FIGS. 12-14, a distinct issue with circular staplers is that their anvils are detachable from their stapling head assemblies, and must be separately introduced to a surgical site in different manners and from different access points. Accordingly, unlike other stapling instruments, circular staplers are at risk of anvil-staple head assembly mismatching and/or anvil-staple cartridge mismatching. Further, to be properly assembled or coupled an anvil and a stapling head assembly must be properly oriented with respect to each other at a specific orientation at the surgical site. Improper orientation of an anvil and a corresponding stapling head assembly, as illustrated in FIG. 13, can lead to a misalignment between the staple forming pockets 414 (FIG. 12) of the anvil and staple openings 324 (FIG. 3) of a staple cartridge 1320, which may lead to improper staple formation. In addition, the improper orientation of an anvil and a corresponding stapling head assembly can lead to improper seating of the anvil with respect to the stapling head assembly. An improperly seated, or partially seated, anvil may become unseated, or separated from the stapling head assembly, due to externally applied loads from the tissue captured between the anvil and the stapling head assembly during closure.

To address the issues above, the surgical instrument 1100 includes an anvil 1200 equipped with a radio-frequency identification (RFID) tag 1201 recognizable or detectable by an RFID scanner 1202 on a stapling head assembly 1300 of the surgical instrument 1100. Likewise, the staple cartridge 1320 includes an RFID tag 1203 also recognizable or detectable by the RFID scanner 1202. The RFID tag 1201 stores information about the anvil 1200, and the RFID tag 1203 stores information about the staple cartridge 1320. As described below, the information can be checked and compared for authentication and/or compatibility.

The identification mechanisms described herein can either be active systems or passive systems. In various embodiments, a combination of active and passive identification systems are used. Passive systems can include, for example, a barcode, a quick response (QR) code, and/or a radio frequency identification (RFID) tag. Passive systems do not comprise an internal power source, and the passive systems described herein require a reader and/or scanner to send a first signal, such as an interrogation signal, for example.

Passive radio frequency identification (RFID) systems communicate information by using radio frequencies. Such passive RFID systems comprise an RFID scanner and an RFID tag with no internal power source. The RFID tag is powered by electromagnetic energy transmitted from the RFID scanner. Each RFID tag comprises a chip, such as a microchip, for example, that stores information about the replaceable component and/or a surgical instrument with which the replaceable component is compatible. While the chip may only contain an identification number, in various instances, the chip can store additional information such as, for example, the manufacturing data, shipping data, and/or maintenance history. Each RFID tag comprises a radio antenna that allows the RFID tag to communicate with the RFID scanner. The radio antenna extends the range in which the RFID tag can receive signals from the RFID scanner and transmit response signals back to the RFID scanner. In a passive RFID system, the RFID scanner, which also comprises its own antenna, transmits radio signals that activate RFID tags that are positioned within a pre-determined range. The RFID scanner is configured to receive the response signals that are "bounced back" from RFID tags, allowing the RFID scanner is to capture the identification information representative of the replaceable component. In various instances, the one or more response signals comprise the same signal as the interrogation signal. In various instances, the one or more response signals comprise a modified signal from the interrogation signal. In various instances, the RFID scanner is also able to write, or encode, information directly onto the RFID tag. In any event, the RFID scanner is able to pass information about the replaceable component to a controller, such as the control system of a surgical instrument and/or a remote surgical system or hub. The RFID scanner is configured to read multiple RFID tags at once, as the RFID tags are activated by radio signals. Additionally, in certain instances, the RFID scanner is able to update, or rewrite, information stored on an RFID tag in signal range with the RFID scanner. The updates can, for example, be transmitted to the RFID scanner from a surgical hub, or any suitable server. Various surgical hubs are described in described in U.S. patent application Ser. No. 16/209,395, titled METHOD OF HUB COMMUNICATION, and filed Dec. 4, 2018, which is hereby incorporated by reference in its entirety.

Active radio frequency identification (RFID) systems also comprise an RFID tag and an RFID scanner. However, the RFID tag in an active RFID system comprises an internal power source. Active RFID systems utilize battery-powered RFID tags that are configured to continuously broadcast their own signal. One type of active RFID tag is commonly referred to as a "beacon." Such beacon RFID tags do not wait to receive a first signal from an RFID scanner. Instead, the beacon RFID tag continuously transmits its stored information. For example, the beacon can send out its information at an interval of every 3-5 seconds. Another type of active RFID tag comprises a transponder. In such systems, the RFID scanner transmits a signal first. The RFID transponder tag then sends a signal back to the RFID scanner with the relevant information. Such RFID transponder tag systems are efficient, as they conserve battery life when, for example, the RFID tag is out of range of the RFID scanner. In various instances, the active RFID tag comprises an on-board sensor to track an environmental parameter. For example, the on-board sensor can track moisture levels, temperature, and/or other data that might be relevant.

In operation the anvil 1200 is coupled or attached to the stapling head assembly 1300, as illustrated in FIG. 12. When the RFID tag 1201 is at or below an attachment threshold distance, defined by the radius (R) of a perimeter extending around the RFID scanner 1202, the RFID scanner 1202 is able to detect or recognize the RFID tag 1201. The attachment distance is the distance between the RFID tag 1201 and the RFID scanner 1203 while the anvil 1200 is coupled or attached to stapling head assembly 1300.

Further to the above, the RFID tag 1303 is positioned under the deck member 320 of the stapling head assembly 1300, and can be detected as well by the RFID scanner 1202. As described in greater detail below, signal strength between the RFID scanner 1202 and one or both of the RFID tags 1201, 1203 can be used to determine whether the anvil 1200 is properly oriented and/or fully seated with respect to the stapling head assembly 1300.

Referring to FIG. 12, the anvil 1200 is similar in many respects to the anvil 400. For example, like the anvil 400, the anvil 1200 includes the head 410, the staple forming pockets 414, and a shank 1420. In the example of FIG. 12, the RFID tag 1201 is supported by the shank 1420, on an outer surface thereof, near the bore 422. In at least one example, a recess or pocket is defined in the shank 1420, and the RFID tag 1201 is positioned in the recess or pocket. The RFID tag 1201 can be held in place in the recess, or pocket, using any suitable technique such as, for example, friction fitting or biocompatible adhesive.

As described above in greater detail, the anvil 1200 is coupled or assembled with the stapling head assembly 1300 by advancing the anvil 1200 toward the trocar 330 such that the trocar 330 is received through the bore 422, as illustrated in FIG. 12. Proximal surface 338 of the head 334 of the trocar 330 and latch shelves 436 of the shank 1420 have complementary positions and configurations such that latch shelves 436 engage proximal surface 338 when shank 1420 of anvil 1200 is fully seated on trocar 330 of the stapling head assembly 1300, as illustrated in FIG. 14. Anvil 1200 is thus secured to trocar 330 through a snap fit due to latch members 430. In the example illustrated in FIG. 14, the RFID tag 1201 is at a first longitudinal position that is distal, or slightly distal, to a second longitudinal position of the pointed tip 226 of the head 334 of the trocar 330.

In at least one example, the RFID tag 1201 is positioned on the shank 1420 at a first longitudinal position that corresponds, or substantially corresponds, to a second longitudinal position of the tip 336 of the head 334 of the trocar 330 when the anvil 1200 is properly oriented and fully seated with respect to the stapling head assembly 1300. In other words, the tip 336 of the head 334 of the trocar 330, when it is received in the shank 1420 at its final seating position, is transversely aligned, or at least substantially aligned, with the RFID tag 1201. In at least one example, the RFID tag 1201 is positioned on the shank 1420 at a position distal to the bore 422 and proximal to the lateral openings 424 and/or proximal to the latch members 430 (FIGS. 3-4).

Referring to FIG. 12, the RFID scanner 1202 is located on an outer surface of a cylindrical inner core member 1312 that extends distally within a tubular casing 1310 of the stapling head assembly 1300. Tubular casing 1310 is fixedly secured to an outer sheath 210 of shaft assembly 1206, such that tubular casing 1310 serves as a mechanical ground for stapling head assembly 1300. The RFID scanner 1202 is supported by the inner core member 1312, on an outer surface thereof, near its distal end. In at least one example, a recess or pocket is defined in the inner core member 1312, and the RFID scanner 1202 is positioned in the recess or pocket. The RFID scanner 1202 can be held in place in the recess, or pocket, using any suitable technique such as, for example, friction fitting or biocompatible adhesive. Alternatively, the RFID scanner 1202 can be positioned on an inner surface of the cylindrical inner core member 1312. In the example of FIG. 12, the RFID scanner 1202 is located at a distal portion of the inner core member 1312 below the deck member 320 of the staple cartridge 1320. In various example, the RFID tag 1201 and the RFID tag 1203 are insulated from the shank 1420 and the inner core member 1312, respectively, using any suitable insulative material.

In various examples, RFID tag 1201 and the RFID tag 1203 are recognizable or detectable by the RFID scanner 1202 in a closed configuration of the instrument 1100 where tissue is captured between the anvil 1200 and stapling head assembly 1300.

FIG. 15 illustrates a logic diagram of a control system 1211 of a surgical instrument or tool in accordance with one or more aspects of the present disclosure. The control system 1211 includes a control circuit 1210 that can be integrated with the RFID scanner 1202 or can be coupled to, but positioned separately from, the RFID scanner 1202 in the housing assembly 100, for example. The control circuit 1210 can be configured to receive input from the RFID scanner 1202 indicative of the information about the staple cartridge 1320 stored in the RFID tag 1203 and/or information about the anvil 1200 stored in the RFID tag 1201.

In various examples, the RFID tag 1203 stores identification information of the staple cartridge 1320 and the RFID tag 1201 stores identification information of the anvil 1200. In such examples, the control circuit 1210 receives input from the RFID scanner 1202 indicative of the identification information of the staple cartridge 1320 and verifies the identity of the staple cartridge 1320 based on the input. Further, the control circuit 1210 receives input from RFID scanner 1202 indicative of the identification information of the anvil 1200 and verifies the identity of the anvil 1200 based on the input.

In at least one example, the control circuit 1210 includes a microcontroller 1213 that has a processor 1214 and a storage medium such as, for example, a memory 1212. The memory 1212 stores program instructions for performing various processes such as, for example, identity verification. The program instructions, when executed by the processor 1214, cause the processor 1214 to verify the identity of the staple cartridge 1320 and the identity of the anvil 1200 by comparing the identification information received from the RFID tags 1201, 1203 to identification information stored in the memory 1212 in the form of an identity database or table, for example.

In at least one example, the control circuit 1210 can be configured to check compatibility of the anvil 1200 with staple cartridge 1320 of the stapling head assembly 1300 based on input from the RFID scanner 1202. The processor 1214 can, for example, check the identity information of the anvil 1200 and the staple cartridge 1320 against a compatibility database or table stored in memory 1212.

In various examples, the memory 1212 comprises a local memory of the instrument 1100. In other examples, identity databases or tables and/or compatibility databases or tables can be downloaded from a remote server. In various aspects, the instrument 1100 may transmit the information received from RFID tags 1201, 1203 to a remote server that stores the databases or tables for performing the identity and/or compatibility checks remotely.

Figure 16:
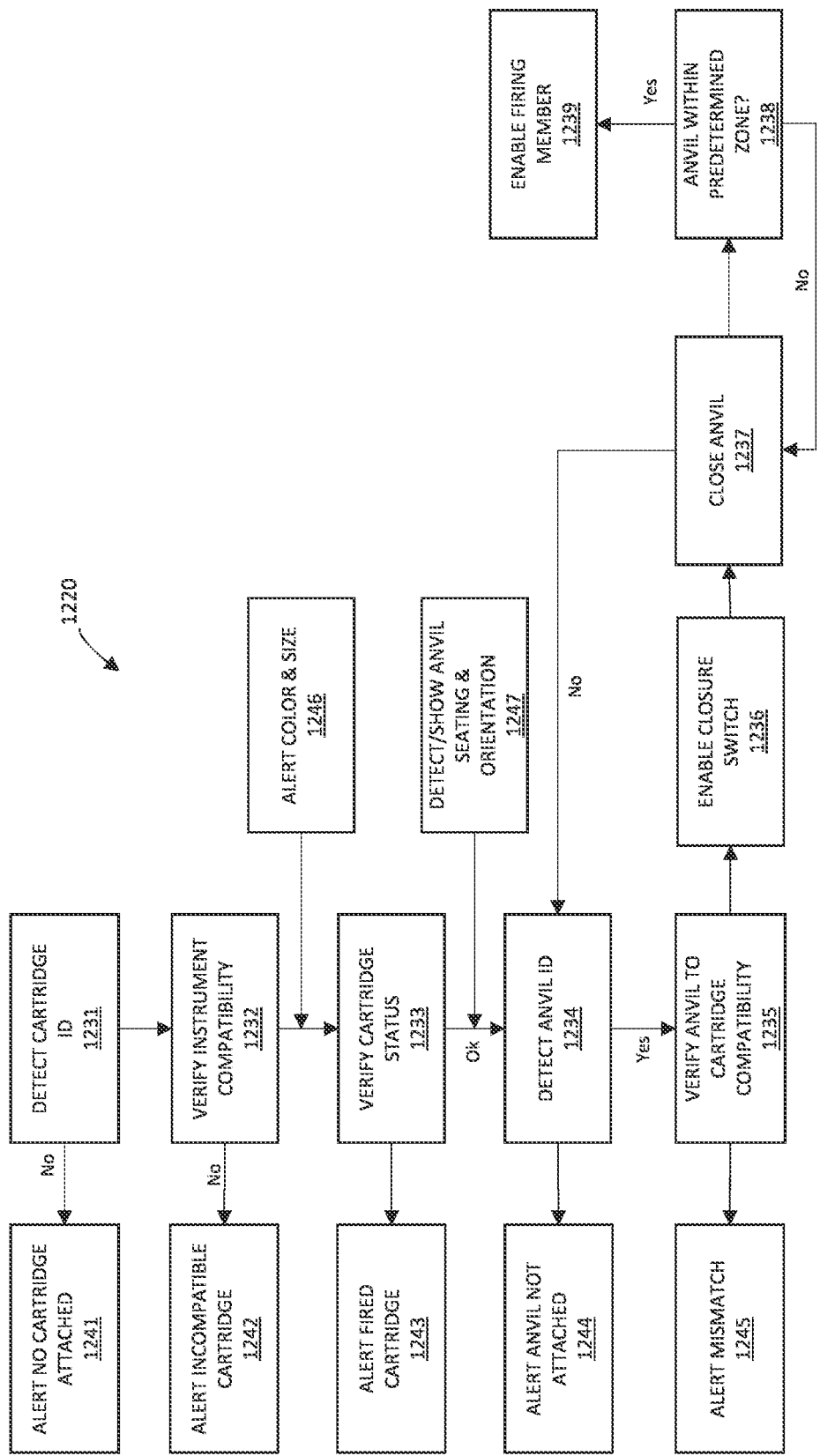
FIG. 16 depicts a logic flow diagram of a process depicting a control program or a logic configuration for operating a surgical stapling instrument, in accordance with at least one aspect of the present disclosure.

FIG. 16 is a logic flow diagram of a process 1220 depicting a control program or a logic configuration for operating a surgical stapling instrument such as, for example, the instrument 1100. In at least one example, the process 1220 is executed by a control circuit 1210 (FIG. 15) that includes a processor 1214 and a memory 1212 storing a set of computer-executable instructions that, when executed by the processor 1214, cause the processor 1214 to perform of the process 1220. In certain examples, a set of computer-executable instructions, stored in the memory 1212 may cause the processor 1214 to perform discrete portions of the process 1220. Although the process 1220 is described as being executed by a control circuit 1210, this is merely for brevity, and it should be understood that the process 1220 and other processes described herein, or portions thereof, can be executed by circuitry that can include a variety of hardware and/or software components and may be located in or associated with various suitable systems such as, for example, combinational logic circuits or sequential logic circuits.

As illustrated in FIG. 16, the process 1220 includes detecting 1231 identification information of the staple cartridge 1320. In at least one example, the control circuit 1210 receives input from the RFID scanner 1202 indicative of the identification information of the staple cartridge 1320 stored in the RFID tag 1203. If authentication of the staple cartridge ID is not successful, or staple cartridge ID is not detected, the control circuit 1210 causes an indicator 1209 to alert 1241 that the staple cartridge 1320 is not attached and/or that the staple cartridge authentication failed.

In various instances, the indicator 1209 may comprise one or more visual feedback systems such as display screens, backlights, and/or LEDs, for example. In certain instances, the indicator 1209 may comprise one or more audio feedback systems such as speakers and/or buzzers, for example. In certain instances, the indicator 1209 may comprise one or more haptic feedback systems, for example. In certain instances, the indicator 1209 may comprise combinations of visual, audio, and/or haptic feedback systems, for example.

The process 1220 further includes verifying 1232 compatibility of the staple cartridge 1320 and the instrument 1100. In at least one example, the control circuit 1210 checks the identification information of the staple cartridge 1320 against staple cartridge-instrument compatibility database or table, which can be stored in the memory 1212, for example. If compatibility is verified 1232, the control circuit 1210 causes the indicator 1209 to alert 1242 that the staple cartridge 1320 is compatible with the instrument 1100. At this stage, the control circuit 1210 may also cause the indicator 1209 to alert 1246 the user regarding color and/or size of the attached staple cartridge 1320.

The process 1220 further includes verifying 1233 a cartridge firing status. Staple cartridges are generally disposed of after filing. To ensure that a previously fired staple cartridge is not accidently re-used without staples, the RFID tag 1201 of a staple cartridge 1320 that has been previously fired stores a previously-fired status. In at least one example, the control circuit 1210 causes the RFID scanner 1202 to change the firing status of a staple cartridge 1320 from an unfired status to a previously fired status after completion of a firing sequence. Further, if the control circuit 1210 received input from the RFID scanner 1202 indicating that an attached staple cartridge 1320 has been previously fired, the control circuit 1210 may cause the indicator 1209 to alert 1243 the user of the same.

The process 1220 further includes detecting 1234 identification information of the anvil 1200. In at least one example, the control circuit 1210 receives input from the RFID scanner 1202 indicative of the identification information of the anvil 1200 stored in the RFID tag 1201. If authentication of the anvil ID is not successful, or if no anvil ID is received, the control circuit 1210 may cause an indicator 1209 to alert 1244 that the anvil is not attached and/or that the anvil authentication failed.

Referring still to FIG. 16, if a proper anvil identification is detected 1234, the process 1220 further checks 1235 compatibility of the anvil 1200 and the staple cartridge 13020. If the anvil 1200 and the staple cartridge 13020 are incompatible, the process 1220 alerts 1245 a user regarding the mismatch. If, however, the anvil 1200 and the staple cartridge 13020 are compatible, the control circuit 1210 permits 1236 closure drive assembly 136 (FIG. 15) to proceed 1237 with anvil closure. During anvil closure, the control circuit 1210 continues to monitor the RFID scanner 1202 to ensure that the anvil 1200 remains attached or coupled to the stapling head assembly 1300 throughout the closure process. If during closure the RFID scanner 1202 loses the signal from the RFID tag 1201, the control circuit 1210 causes the closure drive assembly 136 to pause the closure, and alert 1244 the user that the anvil 1200 is not attached, or at least not detected. Otherwise, the anvil closure continues until a closed configuration between the anvil 1200 and the stapling head assembly 1300 is achieved 1238 by reaching 1238 a predetermined zone or threshold. At, or beyond, the predetermined zone or threshold, the control circuit 1210 permits 1239 the firing drive assembly 1136 to begin a firing sequence to staple and cut tissue captured between the anvil 1200 and the staple cartridge 1320 in the closed configuration.

The process 1220 further includes assessing or detecting 1247 anvil orientation and/or seating with respect to the stapling head assembly 1300. As illustrated in FIG. 12, the shank 1420 of anvil 1200 is fully seated on trocar 330 of the stapling head assembly 1300 when latch shelves 436 engage proximal surface 338. At this point, the RFID tag 1201 reaches or crosses the attachment threshold distance and, as such, is detected by the RFID scanner 1202. The detection of the RFID tag 1201 by the RFID scanner 1202 indicates full seating of the anvil 1200 with respect to the stapling head assembly 1300. In at least one example, receiving an input from the RFID scanner 1202 indicative of detection of the RFID tag 1201 causes the control circuit 1210 to determine that the anvil 1200 is fully seated with respect to the stapling head assembly 1300.

Referring to FIGS. 12 and 15, in various examples, an RFID scanner 1204 is employed in addition to the RFID scanner 1202 to detect the RFID tag 1201 and/or the RFID tag 1203. The RFID scanner 1204 can be positioned within the stapling head assembly 1300. In the example illustrated in FIG. 12, the RFID scanner 1204 is supported by the tubular casing 1310. The control circuit 1210 can be configured to receive input from the RFID scanner 1204 in addition to the input from the RFID scanner 1202. In at least one example, the RFID scanner 1204 is configured to detect the RFID tag 1203 while the RFID scanner 1202 can be configured to detect the RFID tag 1201.

With regard to anvil orientation, the control circuit 1210 is configured to determine whether an attached anvil 1200 is properly oriented with respect to the stapling head assembly 1300 by using the RFID scanner 1202 and/or the RFID scanner 1204 to detect and measure strength of the signal transmitted by the RFID tag 1201. In a proper orientation of the anvil 1200, the RFID scanner 1202 detects the signal from the RFID tag 1201 and measures a unique first signal strength that corresponds to the distance d1 between the RFID tag 1201 and the RFID scanner 1202. Likewise, the RFID scanner 1204 detects the signal from the RFID tag 1201 and measures a unique second signal strength that corresponds to the distance d2 between the RFID tag 1201 and the RFID scanner 1204. The control circuit 1210 can be configured to assess proper orientation of the anvil 1200 based on the first signal strength and/or the second signal strength.

FIG. 13 depicts an improper orientation of the anvil 1200 where the shank 1420 is at an angle α away from proper orientation with the stapling head assembly 1300. The misalignment between the anvil 1200 and the stapling head assembly 1300 causes the distances d1, d2 to be different from their values at proper orientation, which causes the first signal strength and second signal strength to be different from their values at a proper orientation. In the example of FIG. 13, the misalignment between the anvil 1200 and the stapling head assembly 1300 increases the value of the distance d1 and decreases the value of the distance d2. As such, the misalignment at FIG. 13 decreases the first signal strength and increases the second signal strength from their values at a proper orientation.

Accordingly, by monitoring the strength of the signal transmitted by the RFID tag 1201, the control circuit 1210 is able to assess whether the anvil 1200 is properly oriented with respect to the 1300. In various instances, the memory 1212 stores a database or table of signal strength values, or ranges, that represent a proper orientation of the anvil 1200. In such instances, the control circuit 1210 may check the signal strength values collected by the RFID scanner 1202 and/or RFID scanner 1204 against the values, or ranges, in the database, or table, to assess whether the anvil 1200 is properly oriented.

In various examples, proper orientation of an anvil 1200 with respect to the stapling head assembly 1300 is examined by the control circuit 1210 after determining that the anvil 1200 is fully seated, as described above. In other examples, proper orientation of an anvil 1200 with respect to the stapling head assembly 1300 is examined by the control circuit 1210 at a closed, or at least partially closed, configuration of the instrument 1100. In certain examples, proper orientation of an anvil 1200 with respect to the stapling head assembly 1300 is continuously examined by the control circuit 1210 following the detection of the RFID tag 1201 by the RFID scanner 1202 and/or RFID scanner 1204.

Figure 17:
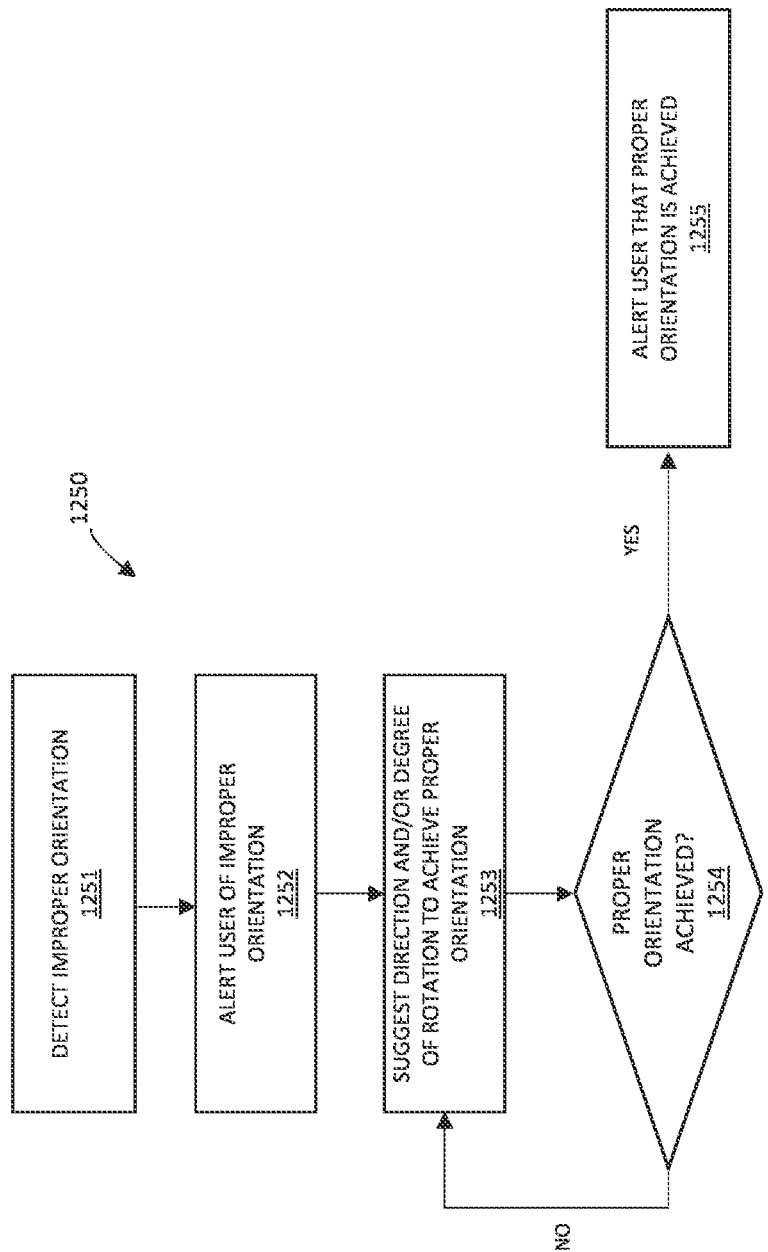
FIG. 17 depicts a logic flow diagram of a process depicting a control program or a logic configuration for properly orienting an anvil with respect to stapling head assembly of a surgical stapling instrument, in accordance with at least one aspect of the present disclosure.

FIG. 17 depicts a logic flow diagram of a process 1250 depicting a control program or a logic configuration for properly orienting an anvil with respect to stapling head assembly of a surgical stapling instrument. In at least one example, the process 1250 is executed by a control circuit 1210 (FIG. 15) that includes a processor 1214 and a memory 1212 storing a set of computer-executable instructions that, when executed by the processor 1214, cause the processor 1214 to perform of the process 1250. In certain examples, a set of computer-executable instructions, stored in the memory 1212 may cause the processor 1214 to perform discrete portions of the process 1250. Although the process 1250 is described as being executed by a control circuit 1210, this is merely for brevity, and it should be understood that the process 1250 and other processes described herein, or portions thereof, can be executed by circuitry that can include a variety of hardware and/or software components and may be located in or associated with various suitable systems such as, for example, combinational logic circuits or sequential logic circuits.

Referring to FIGS. 15 and 17, the control circuit 1210 is configured to detect 1251 an improper orientation of the anvil 1200 with respect to the stapling head assembly 1300, as described above. Further, the control circuit 1210 may employ the indicator 1209 to alert 1252 a user regarding the improper orientation. In addition, the control circuit 1210 may suggest 1253 through the indicator 1209 a direction and/or degree of rotation of the anvil 1200 to achieve a proper orientation. The control circuit 1210 may continue to check 1254 whether proper orientation is achieved based on input from the RFID scanner 1201 and/or RFID scanner 1204. When proper orientation is detected by the control circuit 1210, the control circuit 1210 may further cause the indicator 1209 to alert 1255 the user that the anvil 1200 now properly aligned with the stapling head assembly 1300.

As described above in greater detail, the instrument 1100 includes an anvil lockout assembly 1170. The anvil lockout assembly 1170 is generally configured to prevent further adjustment of the longitudinal position of the anvil once safety trigger 1140 is actuated. In various examples, the anvil lockout assembly 1170 includes an outer lockout member 1176 that is generally responsive to a safety trigger 1140 to selectively lock actuation of the anvil 1200. In other examples, the control circuit 1210 is configured to drive outer lockout member 1176 using an actuation mechanism 1190 such as a solenoid. In either event, the anvil lockout assembly 1170 is configured to transition between an unlocked state and a locked state, wherein: (i) in the unlocked state, the lockout assembly 1170 is configured to permit translation of the anvil 1200, and (ii) in the locked state, the lockout assembly 1170 is configured to prevent translation of the anvil 1200. In various examples, the control circuit 1210 employs the indicator 1209 to alert a user that it is safe to transition the lockout assembly 1170 to the unlocked state based on input from the RFID scanner 1202 and/or the RFID scanner 1204 indicative of detecting the RFID tag 1201. In other examples, the control circuit 1210 employs the actuation mechanism 1190 to transition the lockout assembly 1170 to the unlocked state based on input from the RFID scanner 1202 and/or the RFID scanner 1204 indicative of detecting the RFID tag 1201.

Further to the above, in certain examples, the control circuit 1210 detects detachment of the anvil 1200 from the stapling head assembly 1300 based on a loss of the input from the RFID scanner 1202 and/or the RFID scanner 1204, or an input from the RFID scanner 1202 and/or the RFID scanner 1204 indicative of a loss of the signal transmitted by RFID tag 1201. In response, the control circuit 1210 may cause the indicator 1209 to alert a user of the detachment of the anvil 1200 and, optionally, provide instructions regarding reattachment of the anvil 1200 to the stapling head assembly 1300. Additionally, or alternatively, the control circuit 1210 may cause the actuation mechanism 1190 to transition the lockout assembly 1170 to the locked state until reattachment of the anvil 1200 is detected by the control circuit 1210 based on input from RFID scanner 1202 and/or the RFID scanner 1204 indicative of redetection of the signal from the RFID tag 1201, for example.

Referring to FIG. 15, motors 160, 1160 are coupled to motor drivers 161 and 1161, respectively, which are configured to control the operation of the motors 160 and 1160 including the flow of electrical energy from a power source (e.g. battery pack 120) to the motors 160 and 1160. In various examples, the processor 1214 is coupled to the motors 160, 1160 through the motor drivers 1160, 1161. In various forms, the motor 160 and/or the motor 1160 may be a brushed direct current (DC) motor with a gearbox and mechanical links to effect a tissue treatment by a surgical end effector. In one aspect, motor drivers 1160, 1161 may be in the form of an A3941 available from Allegro Microsystems, Inc. Other motor drivers may be readily substituted for use with the control system 11211.

In various forms, the motors 160, 1160 may be a brushed DC driving motor having a maximum rotational speed of approximately 25,000 RPM. In other arrangements, the motors 160, 1160 may include a brushless motor, a cordless motor, a synchronous motor, a stepper motor, or any other suitable electric motor. The motor driver 161, 1161 may comprise an H-bridge driver comprising field-effect transistors (FETs), for example. The motors 160, 1160 can be powered by a power source. The power source may comprise a battery which may include a number of battery cells connected in series that can be used as the power source to power the surgical instrument or tool. In certain circumstances, the battery cells of the power source may be replaceable and/or rechargeable. In at least one example, the battery cells can be lithium-ion batteries which can be couplable to and separable from the power source.

In various aspects, a motor driver in accordance with the present disclosure may be a full-bridge controller for use with external N-channel power metal-oxide semiconductor field-effect transistors (MOSFETs) specifically designed for inductive loads, such as brush DC motors. The motor driver may comprise a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the low-side FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

In various aspects, one or more of the motors of the present disclosure can include a rotatable shaft that operably interfaces with a gear assembly that is mounted in meshing engagement with a set, or rack, of drive teeth on a displacement member of a firing drive assembly 1163 or a closure drive assembly 163, for example. A sensor element may be operably coupled to a gear assembly such that a single revolution of the position sensor element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable a closure member, firing member, firing bar, I-beam, or combinations thereof.

In certain examples, as illustrated in FIG. 15, transition of the anvil 1200 to a closed configuration with the stapling head assembly 1300 is driven by the motor 1160. In such examples, the control circuit 1210 permits the motor 1160 to drive closure of the anvil 1200 if proper orientation, full seating, and/or proper identity of the anvil 1200 is detected by the control circuit 1210 based on input from the RFID scanner 1202 and/or RFID scanner 1204, as described above. Accordingly, a detected failure at establishing one or more of proper orientation, full seating, and/or proper identity of the anvil 1200 causes the control circuit 1210 to prevent the motor 1160 from starting and/or completing closure of the anvil 1200.

In certain examples, the control circuit 1210 permits the motor 160 to drive staple firing and advancement of the cylindrical knife member 340 if staple cartridge-anvil compatibility is confirmed based on the information stored in the RFID tags 1201, 1203 as reported by RFID scanners 1202, 1204. Conversely, the control circuit 1210 is configured to prevent the motor 160 from driving staple firing and advancement of the cylindrical knife member 340 if the staple cartridge-anvil compatibility cannot be established based on the information stored in the RFID tags 1201, 1203 as reported by RFID scanners 1202, 1204.

In various examples, antennas of one or more of the RFID tags 1201, 1203 and the RFID scanners 1202, 1204 may be supplemented with booster antennas that are engaged upon connection. In various examples, the antennas of active RFID tags on the surgical instrument 1100 such as, for example, the RFID tag 1201 and RFID tag 1203 can be cut during normal operation of the surgical instrument 1100 in planned manner. The lost signals from such RFID tags can signify completion of a surgical task.

In various aspects, an RFID tag can be positioned along the pathway of the cylindrical knife member 340. The RFID tag may transmit a signal through its antenna to the RFID scanner 1202, for example. When the antenna is severed by the knife member 340, the signal is lost. The signal loss can confirm advancement of the knife member 340.

In one example, the RFID tag is positioned on a breakable washer of the anvil 1200. In such example, the breakable washer is broken by the knife member 340 toward the end of a full distal range of motion of the knife member 340. The knife member 340 cuts the antenna of the RFID tag while breaking the breakable washer. When the antenna is severed, the signal transmitted from the RFID tag to the RFID scanner 1202, for example, is lost. The RFID scanner 1202 can be coupled to the control circuit 1210, and can report the signal loss to the control circuit 1210. The signal loss is interpreted by the control circuit 1210 to indicate completion of a firing sequence of the surgical instrument 1100.

In various aspects, as described above greater detail, a surgical instrument such as, for example, the instrument 1100 includes an anvil 1200 movable toward a stapling head assembly 1300 to capture tissue therebetween in a closed configuration. The tissue is then stapled and cut in a firing sequence of the surgical instrument 1100. The instrument 1100 further includes an RFID tag such as, for example, the RFID tag 1201 and an RFID scanner such as, for example, the RFID scanner 1202 that is configured to read and/or write to the RFID tag 1201. The RFID tag 1201 and the RFID scanner 1202 define an RFID system that can be employed by a control circuit 1210 to determine a characteristic of the tissue based on the RF signal backscatter from the tissue.

The positions of the RFID tag 1201 and the RFID scanner 1202 with respect to the tissue grasped between the anvil 1200 and the stapling head assembly 1300 can be selected for optimal measurements of the RF signal backscatter. In at least one example, the RFID tag 1201 and the RFID scanner 1202 can be positioned on opposite sides of the tissue.

The RF signal from the backscatter data can be gathered and correlated with known tissue characteristics to permit tissue analysis. In various aspects, the spectral characteristics of the backscatter data can be analyzed to determine various characteristic of the tissue. In at least one example, the backscatter data is employed to identify boundary features within the tissue. In at least one example, the backscatter data can be used to assess thickness of the tissue grasped between the anvil 1200 and the stapling head assembly 1300.

Figure 18:
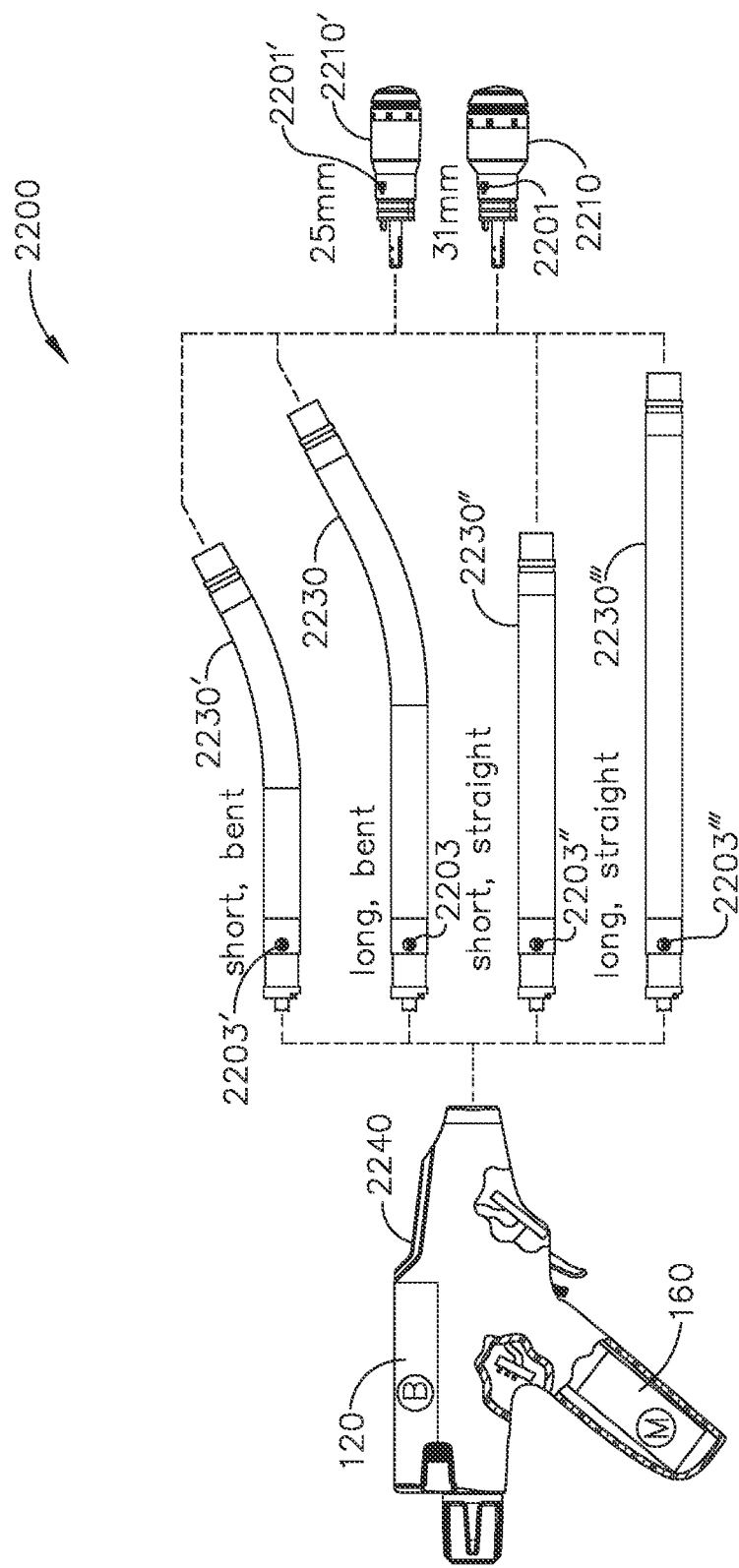
FIG. 18 depicts a surgical instrument that can be selectively assembled from any one of a number of different end effectors, any one of a number of different shafts, and a housing assembly, in accordance with at least one aspect of the present disclosure.

FIG. 18 depicts a surgical instrument 2200 that can be selectively assembled from any one of a number of different end effectors such as, for example, end effectors 2210, 2210', any one of a number of different shafts such as, for example, shafts 2230, 2230', 2230", 2230''', and a housing assembly 2240. Components of the surgical instrument 2200 are selected based on various factors including surgical procedure type, tissue type, and/or patient anatomy.

In various instances, the end effectors of the surgical instrument 2200 are circular stapler end effectors of different sizes. In the example of FIG. 18, 25 mm and 31 mm circular stapler end effectors are depicted. However this is not limiting, other suitable end effectors can be readily utilized with the surgical instrument 2200. In the example illustrated in FIG. 18, the shafts 2230, 2230', 2230", 2230''' comprise profiles that are different in length and/or curvature. However this is not limiting, shafts with other suitable shaft profiles can be readily used with the surgical instrument 2200.

Further to the above, the shafts 2230, 2230', 2230", 2230''' comprise RFID tags 2203, 2203', 2203", 2203''', respectively, which store shaft information, as described in greater detail below. In addition, the end effectors 2210, 2210' comprise RFID tags 2201, 2201', respectively, which store end-effector information, as described in greater detail below.

Figure 19:
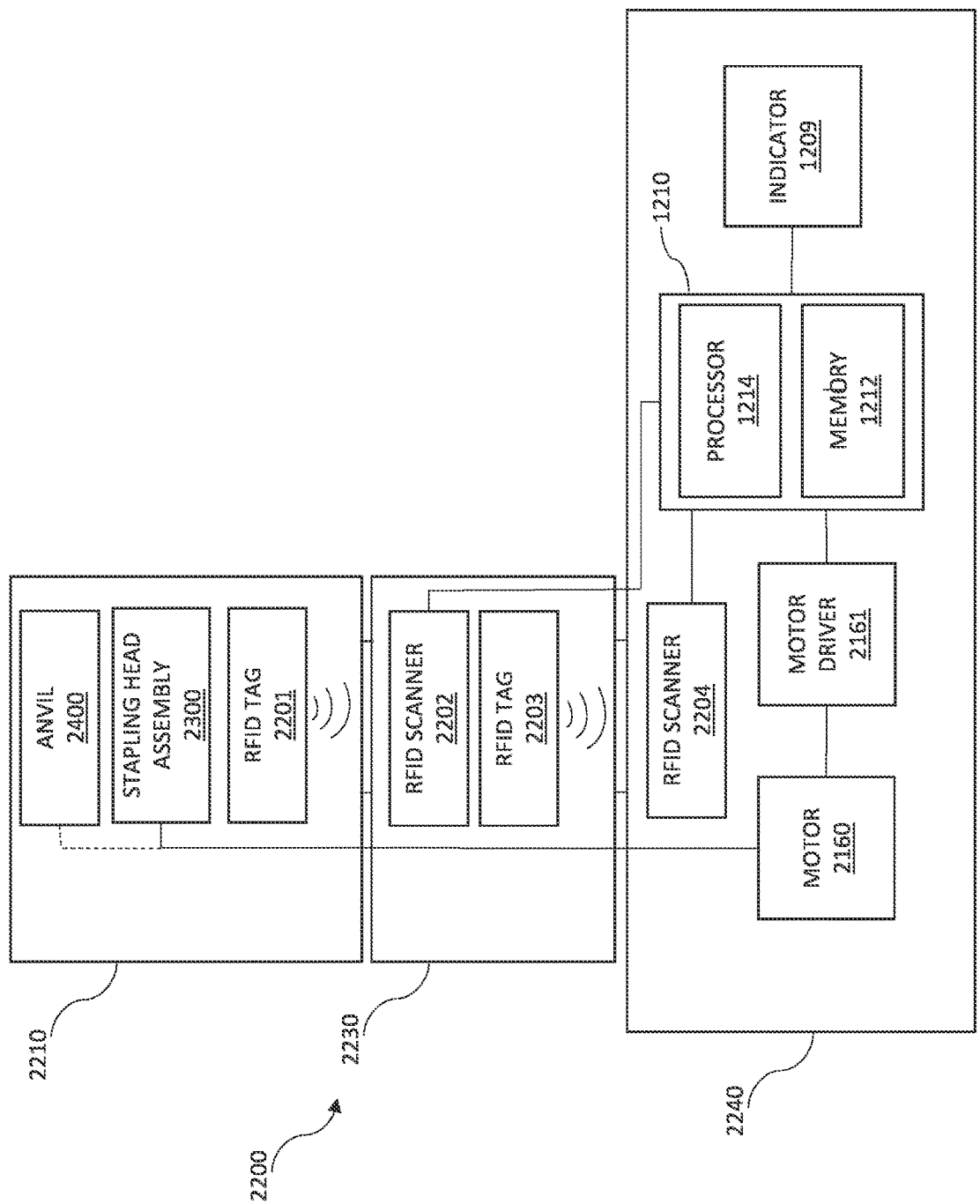
FIG. 19 depicts a schematic diagram of an assembled surgical instrument, in accordance with at least one aspect of the present disclosure.

FIG. 19 depicts a schematic diagram an example surgical instrument 2200 assembled from the end effector 2210, the shaft 2230, and a housing assembly 2240. Various components and/or connections between components of the end effector 2210, the shaft 2230, and a housing assembly 2240 are removed for clarity. The surgical instrument 2200 is similar in many respects to the surgical instruments 100, 1100. For example, the end effector 2210 has a stapling head assembly 2300 that is similar in many respect to the stapling head assemblies 300, 1300, and an anvil 2400 that is similar in many respects to the anvils 400, 1200.

In operation, as described above in greater detail with respect to the surgical instruments 100, 1100, the anvil 2400 is coupled to the stapling head assembly 2300. The anvil 2400 is then retracted from a starting position toward the stapling head assembly 2300 a closure stroke or distance "d" to transition the stapling head assembly 2300 from an open configuration to a closed configuration. Tissue is grasped between the anvil 2400 and the stapling head assembly 2300 in the closed configuration. Further, the stapling head assembly 2300 includes a staple cartridge that houses staples that are deployed from the staple cartridge toward the anvil 2400 in the closed configuration. The staples are deployed through the grasped tissue and are formed by Staple forming pockets 414 of the anvil 2400. In addition, a knife member 340 is translated distally to a point where cutting edge 342 is distal to a deck surface 322 of the stapling head assembly 2300 to cut the tissue.

In addition to or in lieu of the foregoing, stapling head assembly 2300 and anvil 2400 may be further constructed and operated in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the entire disclosures of which are incorporated by reference herein. Still other suitable configurations will be apparent to one of ordinary skill in the art in view of the teachings herein.

Referring still to FIG. 19, the housing assembly 2240 includes one or more motors 2160 and one or more motor drivers 2161, which are similar in many respects to motors 160,1160 and motor drivers 161, 1161. In various examples, the control circuit 1210 is configured to control a motor driver 2161 to cause a motor 2160 to move the anvil 2400 a closure stroke or distance "d" toward the stapling head assembly 2300 to transition the end effector 2210 from the open configuration to the closed configuration. The control circuit 1210 is further configured to control a motor driver 2161 to cause a motor 2160 to apply a load onto the end effector 2210 in a firing motion to deploy the staples into tissue grasped by the end effector 1210 in the closed configuration, and cut the grasped tissue by advancing the knife member 340 distally through the tissue. In at least one example, the knife member 340 is advanced toward a breakable washer of the anvil 2400. In such example, the breakable washer is broken by the knife member 340 toward the end of a full distal range of motion of the knife member 340.

Figure 20:
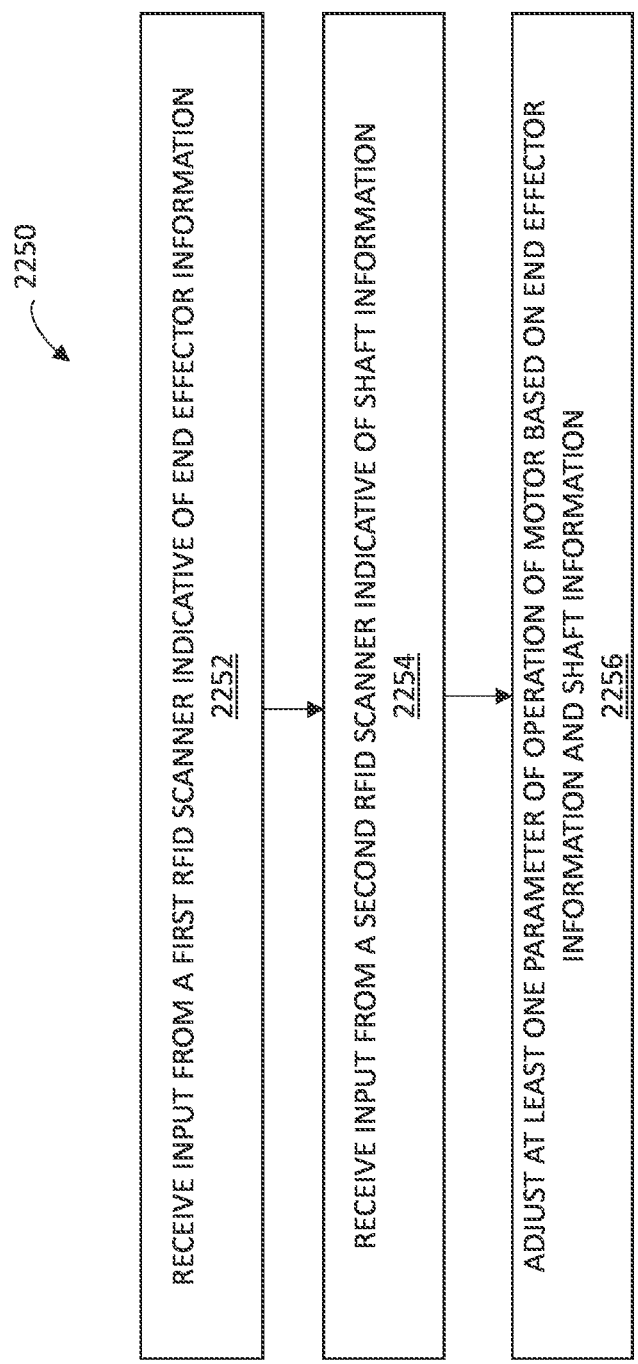
FIG. 20 depicts a logic flow diagram of a process depicting a control program or a logic configuration for adjusting at least one operational parameter of a motor of the surgical instrument of FIG. 19.

To properly staple and cut tissue by a surgical instrument 2200, operational parameters of the motor(s) 2160 need to be adjusted to yield closure distances and/or firing loads that are suitable for a selected end effector 2210 and/or shaft 2230 of the surgical instrument 2200. Longer and/or curved shafts, for example, require different closure distances than shorter ones. Likewise, larger staple cartridges generally require higher firing loads than smaller ones. To address this matter, the end effectors of a surgical instrument 2200 are equipped with RFID tags 2201 that store end-effector information, and are detectable by RFID scanners 2202. Additionally, in certain instances, the shafts of the surgical instrument 2200 are also equipped with RFID tags 2203 that store shaft information, and are detectable by RFID scanners 2204. As illustrated in FIG. 20, in accordance with a process 2250, the control circuit 1210 can be configured to receive 2252 input from an RFID scanner 2202 indicative of the end-effector information, receive 2254 input from an RFID scanner 2204 indicative of the shaft information, and adjust 2256 at least one parameter of operation of the motor(s) 2160 to yield closure distances and/or firing loads that are based on the end-effector information and the shaft information.

In at least one example, the process 2250 is executed by a control circuit 1210 (FIG. 15) that includes a processor 1214 and a memory 1212 storing a set of computer-executable instructions that, when executed by the processor 1214, cause the processor 1214 to perform of the process 2250. In certain examples, a set of computer-executable instructions, stored in the memory 1212 may cause the processor 1214 to perform discrete portions of the process 2250. Although the process 2250 is described as being executed by a control circuit 1210, this is merely for brevity, and it should be understood that the process 2250 and other processes described herein, or portions thereof, can be executed by circuitry that can include a variety of hardware and/or software components and may be located in or associated with various suitable systems such as, for example, combinational logic circuits or sequential logic circuits.

In the example illustrated in FIG. 19, the RFID tag 2201 and corresponding RFID scanner 2202 are arranged such that the RFID tag 2201 is within the detection range of the RFID scanner 2202 when the end effector 2210 is an assembled configuration with the shaft 2230. Also, the RFID tag 2203 and corresponding RFID scanner 2204 are arranged such that the RFID tag 2203 is within the detection range of the RFID scanner 2204 when the shaft 2230 is an assembled configuration with housing assembly 2240. Accordingly, the RFID scanner 2202 is positioned at the distal portion of the shaft 2230 while the RFID tag 2203 is positioned at the proximal portion of the shaft 2230. In at least one example, one or both of the RFID tag 2201 and the RFID scanner 2202 are positioned at an interface between the end effector 2210 and the shaft 2230. Additionally, or alternatively, one or both of the RFID tag 2203 and the RFID scanner 2204 are positioned at an interface between the shaft 2230 and housing assembly 2240.

Further to the above, end-effector information stored in the RFID tag 2201 can be read by the RFID scanner 2202 in the assembled configuration, and can be communicated to the control circuit 1210. Also, shaft information stored in the RFID tag 2203 can be read by the RFID the scanner 2204, and can be communicated to the control circuit 1210. In various aspects, the end effector-information can include identification information, manufacturer information, staple cartridge size, type, and/or color, anvil type, and/or one more suitable adjustment values for default closure distances and/or firing loads. Likewise, the shaft information can include identification information, manufacturer information, shaft profiles, and/or one more suitable adjustment values for default closure distances and/or firing loads.

Figure 21:
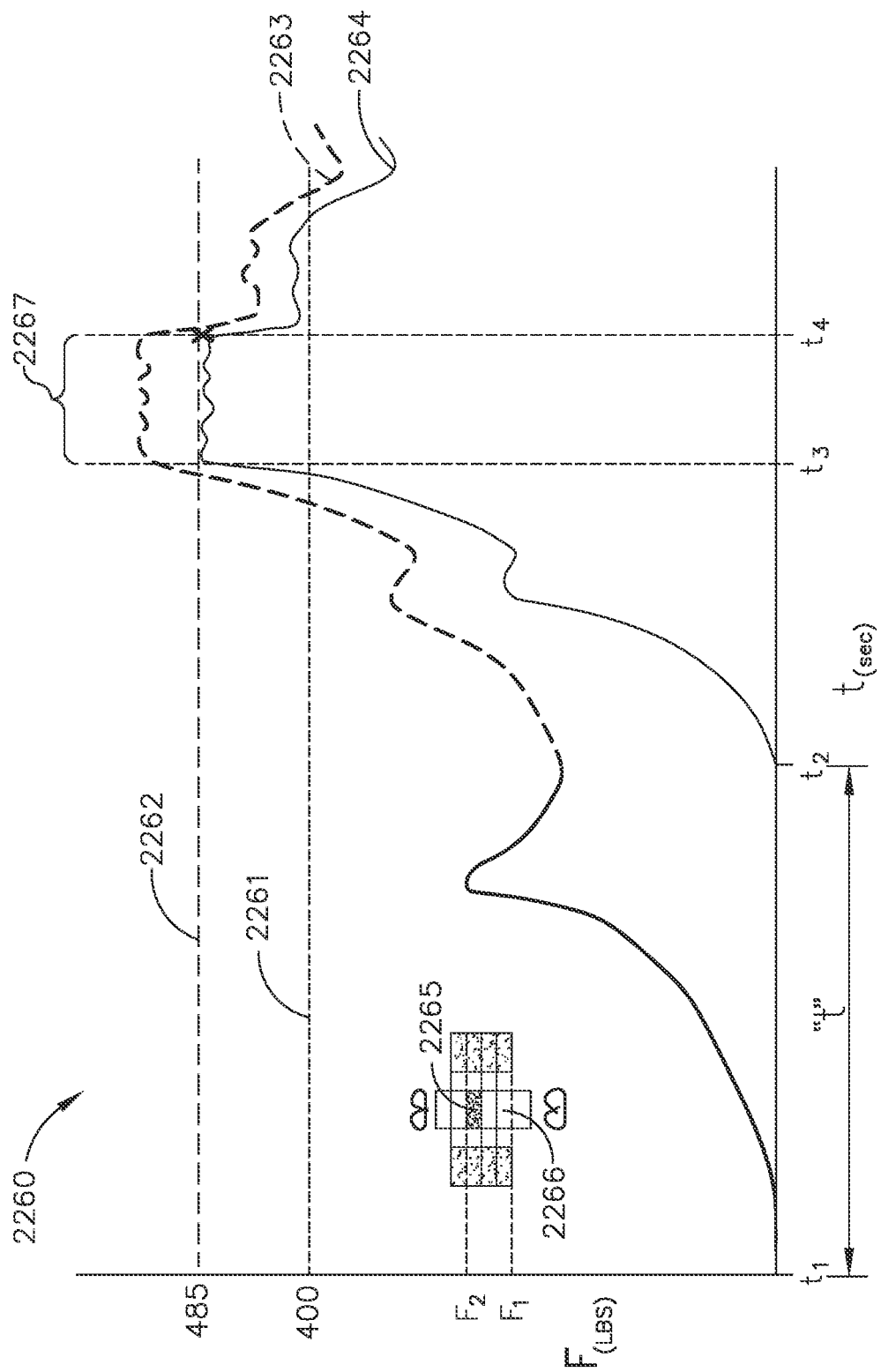
FIG. 21 depicts a graph illustrating firing loads of the surgical instrument of FIG. 19 in accordance with two different firing algorithms.

Referring to FIG. 21, a graph 2260 represents a relationship between firing Load (lbs) on the Y-axis and firing time (sec) on the X-axis. Graph 21 depicts a default, unadjusted, firing algorithm 2263 and an adjusted firing algorithm 2264. The graph 2260 further depicts a default maximum firing load threshold 2261 (e.g. 400 lbs) and a final maximum firing load threshold 2262 (e.g. 485 lbs) for a firing load applied by a motor 2160 to the end effector 2210 of the surgical instrument 2200. The default maximum firing load threshold 2261 is adjusted to the final maximum firing load threshold 2262 based on end-effector information of the end effector 2210 that is stored in the RFID tag 2201 and read by the RFID scanner 2202 of the surgical instrument 2200. In the example of FIG. 21, the end-effector information represents a staple cartridge that comprises a larger size (e.g. 31 mm) than a default staple cartridge (e.g. 25 mm). The default staple cartridge size (e.g. 25 mm) is associated with the default firing algorithm 2263 and default maximum firing load threshold 2261. Meanwhile, the larger staple cartridge size (e.g. 31 mm) is associated with the final firing algorithm 2264 and final maximum firing load threshold 2262.

The end-effector information stored in the RFID tag 2201 can include the staple cartridge size and/or a firing load adjustment value (e.g. 85 lbs) based on the cartridge size. In the event of the staple cartridge size, the control circuit 1210 can use a database or a lookup table of staple cartridge sizes and corresponding firing load adjustment values to look up a suitable firing load adjustment values.

Further, input from the RFID scanner 2201 indicative of the end-effector information causes the control circuit 1210 to adjust the default maximum firing load threshold 2261 (e.g. 400) to the final maximum firing load threshold 2262 (e.g. 485 lbs), and maintain a firing algorithm 2264 below the final maximum firing load threshold 2262, as illustrated in FIG. 20.

In the example of FIG. 21, the control circuit 1210 adjusts or introduces a minimum wait-time "t" before causing the motor 2160 to apply the firing algorithm 2263 to the end effector 2210. In various instances, the minimum wait-time "t" is a time period between completion of a closure sequence of an end effector of the surgical instrument 2200, where tissue is grasped by the end effector in a closed configuration, and commencement of a firing sequence of the end effector, where the grasped tissue is stapled and cut. The minimum wait time "t" permits tissue creep where the grasped tissue adjusts to a lower average pressure thereby reducing the maximum firing load necessary to complete the firing sequence of the end effector 2210 to a value at or below the final maximum firing load threshold 2262. In the default firing algorithm 2263, without the minimum wait-time "t", the firing algorithm 2263 must be interrupted 2267 for a time period t' from time t3 to time t4 to prevent the firing load from exceeding the final maximum firing load threshold 2262. By comparison, the firing algorithm 2264 is continued through the time period between t3 and t4, as illustrated in FIG. 21

Referring still to FIG. 21, another factor that can influence the minimum wait time "t" is the user-selected form height of the staples deployed from the stapling head assembly 2300. The control circuit 1210 can prompt a user through the indicator 1209 to select a desired form height of the staples. In at least one example, the control circuit 1210 can present the user with a number of form height options to choose from. Additionally, or alternatively, the control circuit 1210 can recommend an optimal form height based on the tissue being treated by the surgical instrument 2200. In any event, the user-selected form height can cause the control circuit 1210 to further adjust the minimum wait time "t". In at least one example, the memory 1212 stores, in a database or a lookup table, form heights and corresponding wait-time adjustments. The control circuit 1210 can adjust the minimum wait time "t" by identifying a wait-time adjustment associated with a user-selected form height, and then adjusting the minimum wait time "t" in accordance with the identified wait-time adjustment.

Generally, a more formed staple is associated with a greater firing load, and requires a greater minimum wait time "t" than a lesser formed staple. In the example of FIG. 21, the user-selected form height 2265 is associated with a firing load "F2", and is greater than a minimum form height 2266 associated with a minimum firing load "F1". The minimum firing loads "F1" and "F2" represent firing loads at which staple legs begin to buckle. Accordingly, the wait time "t" of the example of FIG. 21 is a result of the greater (31 mm) than the default (25 mm) staple cartridge size, and the selected form height 2265.

Figure 22:
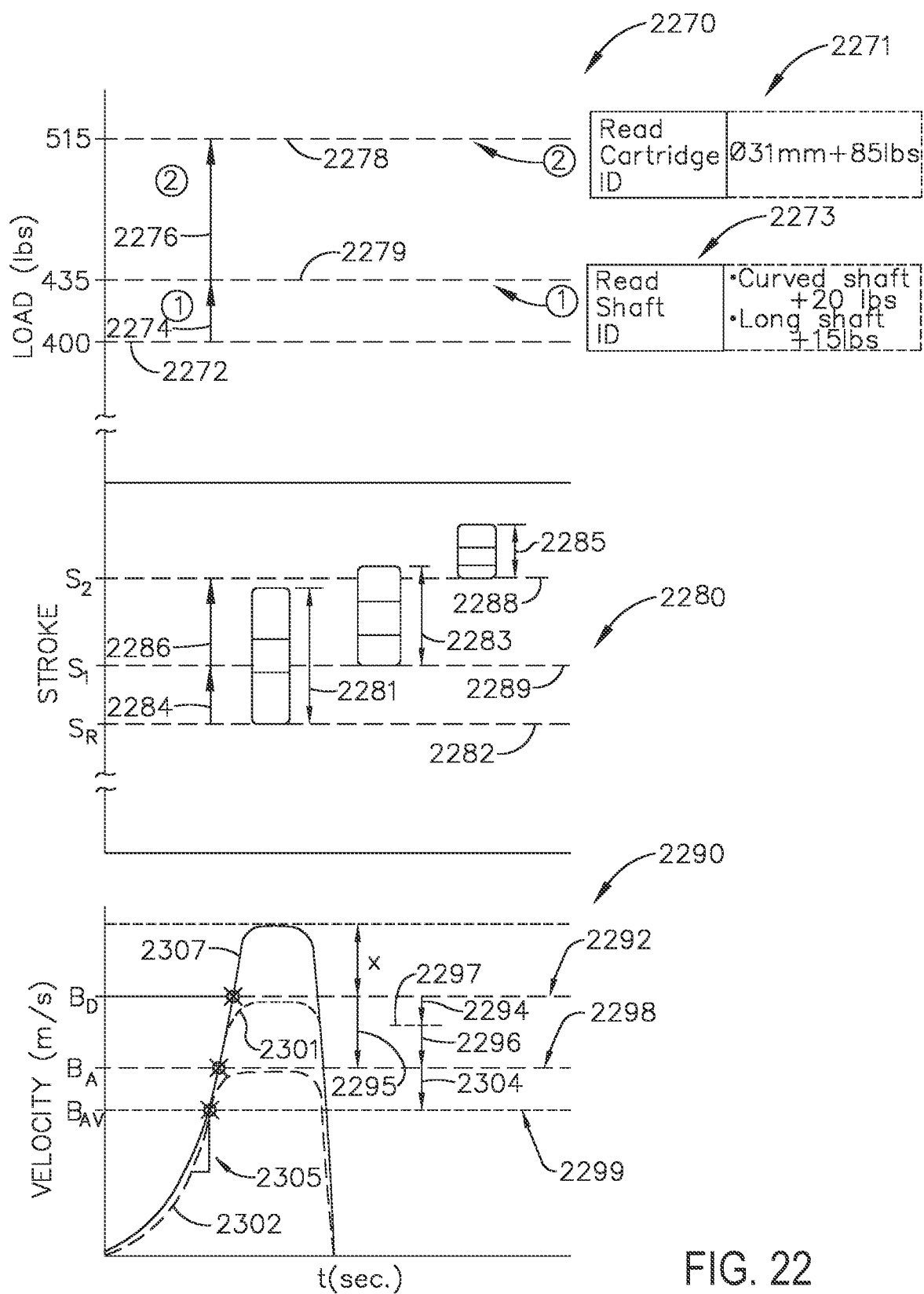
FIG. 22 depicts graphs illustrating adjustments of various closure and firing thresholds of the surgical instrument of FIG. 19.

Referring to FIG. 22, Graph 2270 illustrates adjustments made to a default maximum firing load threshold 2272 (e.g. 400 lbs) of the surgical instrument 2200. The adjustments are based on end-effector information 2271 and shaft information 2273 received by a control circuit 1210 from RFID scanners 2202, 2204, as described above in greater detail. The shaft information 2273 identifies a long curved shaft 2230, and provides a corresponding first adjustment value 2274 (e.g. 35 lbs) to the default maximum firing load threshold 2272. Similarly, the end-effector information 2271 identifies an end effector 2210 with staple cartridge comprising a size of 31 mm, and provides a corresponding second adjustment value 2276 (e.g. 85 lbs) to the default maximum firing load threshold 2272. Adding the adjustment values 2274, 2276 to the default maximum firing load threshold 2272 yields a final maximum firing load threshold 2278. As described above, the adjustment values 2274, 2276 can be part of the end-effector information 2271 and the shaft information 2273, respectively, or can be determined by the control circuit 1210 from a database or lookup table stored in the memory 1212, for example, based on the identification information of the end effector 2210 and the shaft 2230.

In at least one example, a surgical instrument 2200 can be assembled from a curved long shaft 2230 and an end effector 2210' comprising a default staple cartridge size (e.g. 25 mm). In such examples, the end effector information yields a zero adjustment value, and the shaft information yields the first adjustment value 2274 that modifies the default maximum firing load threshold 2272 to a final maximum firing load threshold 2279, as illustrated in Graph 2270. In other examples, the surgical instrument 2200 can be assembled from various combinations of end effectors and shafts that yield different adjustment values for modifying the default maximum firing load threshold 2272.

Referring to FIG. 22, Graph 2280 illustrates adjustments made to a default minimum closure stroke or distance 2282 of the surgical instrument 2200. A minimum closure stroke or distance a surgical instrument 2200 is a minimum permissible or recommended closure stroke or distance that bring an end effector of the surgical instrument 2200 such as, for example, the end effector 2210 to a closed configuration suitable for deploying staples into tissue grasped between an anvil and a staple cartridge of the end effector. The adjustments to the default minimum closure stroke or distance 2282 are based on end-effector information 2271 and shaft information 2273 received by a control circuit 1210 from RFID scanners 2202, 2204, as described above in greater detail.

The shaft information 2273 identifies a long curved shaft 2230, and provides a corresponding first adjustment value 2284 to the default minimum closure stroke or distance 2282. The added length and curvature of the shaft 2230, in comparison to a default shaft, yields a longer minimum closure stroke or distance 2289 than the default minimum closure stroke or distance 2282. Similarly, the end-effector information 2271 identifies an end effector 2210 with a staple cartridge comprising a size of 31 mm, and provides a corresponding second adjustment value 2286 to the default minimum closure stroke or distance 2282. Adding the adjustment values 2284, 2286 to the default minimum closure stroke or distance 2282 yields a final default minimum closure stroke or distance 2288. As described above, the adjustment values 2284, 2286 can be part of the end-effector information 2271 and the shaft information 2273, respectively, or can be determined by the control circuit 1210 from a database or lookup table stored in the memory 1212, for example, based on identification information of the end effector 2210 and the shaft 2230.

In at least one example, a surgical instrument 2200 can be assembled from a curved long shaft 2230 and an end effector 2210' comprising a default staple cartridge size (e.g. 25 mm). In such examples, the end effector information yields a zero adjustment value and the shaft information yields the first adjustment value 2284, which modify the default minimum closure stroke or distance 2282 to a final minimum closure stroke or distance 2289, as illustrated in Graph 2280. In other examples, the surgical instrument 2200 can be assembled from various combinations of end effectors and shafts that yield different adjustment values for modifying the default minimum closure stroke or distance 2282.

Further to the above, the end-effector information 2271 and the shaft information 2273 can cause the control circuit 1210 to adjust a default closure range 2281 of user-selectable closure strokes or distances of the surgical instrument 2200. A closure range of a surgical instrument 2200 is a range of permissible or recommended closure strokes or distances that bring an end effector of the surgical instrument 2200 such as, for example, the end effector 2210 to a closed configuration suitable for deploying staples into tissue grasped between an anvil and a staple cartridge of the end effector. In at least one example, the closure range of a surgical instrument 2200 can be in the form of a visual guide presented to a user by the indicator 1209.

In various examples, the closure range of a surgical instrument 2200 is defined by the control circuit 1210 based on the end-effector information and/or the shaft information received from the RFID scanners 2203, 2204. Graph 2280 depicts, for example, a default closure range 2281, an adjusted closure range 2283, and an adjusted closure range 2285. The adjusted closure range 2283 is defined by the control circuit 1210 in response to the shaft information transmitted from the RFID scanner 2204. The adjusted closure range 2285 is defined by the control circuit 1210 in response to end-effector information transmitted from the RFID scanner 2202 and shaft information transmitted from the RFID scanner 2204. In other words, the adjusted closure range 2285 is defined by the cumulative impact of the end-effector information and the shaft information.

In various aspects, the transmitted shaft information can include the adjusted closure range 2283. Alternatively, the transmitted shaft information can includes upper and lower adjustment values of the default closure range 2281. Alternatively, the transmitted shaft information can include shaft identification information. In at least one example, the control circuit 1210 can determine an adjusted closure range 2283 from a database or lookup table stored in the memory 1212, for example, based on the shaft identification information.

In various aspects, the transmitted end-effector information can include an adjusted closure range. Alternatively, the transmitted end-effector information can includes upper and lower adjustment values of the default closure range 2281. Alternatively, the transmitted end-effector information can include end-effector identification information. In at least one example, the control circuit 1210 can determine an adjusted closure range from a database or lookup table stored in the memory 1212, for example, based the end-effector identification information.

In at least one example, the control circuit 1210 can determine an adjusted closure range 2285 from a database or lookup table stored in the memory 1212, for example, based on shaft identification information and end-effector identification information. In at least one example, the control circuit 1210 can determine an adjusted closure range 2285 from the cumulative impact of upper and lower adjustment values of the default closure range 2281, which are provided by the end-effector information and shaft information.

Referring still to FIG. 22, Graph 2290 illustrates firing velocity (m/s) on the Y-axis verses time (seconds) on the X-axis. In example of Graph 2290, the firing velocity represents the velocity of a longitudinally movable firing member coupled to a motor 2160 (FIG. 19) of the surgical instrument 2200, and configured to effect deployment of staples from the stapling head assembly 2307 toward the anvil 2400, and advancement of the knife member 340, as described above in greater detail. In other examples, the firing velocity can be a rotation velocity of the motor 2160.

Graph 2280 illustrates adjustments made to a default maximum threshold 2292 of the firing velocity of the surgical instrument 2200, which are based on end-effector information and shaft information received by a control circuit 1210 from RFID scanners 2202, 2204, as described above in greater detail. The shaft information identifies a long curved shaft 2230, and provides a corresponding first adjustment value 2294 to the default maximum threshold 2292. Similarly, the end-effector information identifies an end effector 2210 with a staple cartridge comprising a size of 31 mm, and provides a corresponding second adjustment value 2296 to the default maximum threshold 2292.

In the example of Graph 2290, the adjustment values 2294, 2296 are combined 2295 to reduce the default maximum threshold 2292 to a final maximum threshold 2298 of the firing velocity of the surgical instrument 2200. The adjustment values 2294, 2296 can be part of the end-effector information and the shaft information, respectively, or can be determined by the control circuit 1210 from a database or lookup table stored in the memory 1212, for example, based on identification information of the end effector 2210 and the shaft 2230.

In at least one example, a surgical instrument 2200 can be assembled from a curved long shaft 2230 and an end effector 2210' comprising a default staple cartridge size (e.g. 25 mm). In such examples, the end effector information yields a zero adjustment value and the shaft information yields the adjustment value 2294, which modify the default maximum threshold 2282 to a final maximum threshold 2297, as illustrated in Graph 2290. In other examples, the surgical instrument 2200 can be assembled from various combinations of end effectors and shafts that yield different adjustment values for modifying the default maximum threshold 2292 of the firing velocity.

Further to the above, Graph 2290 depicts three firing velocity curves 2307, 2301, 2302 that represent three different firing algorithms. The firing velocity curve 2307 represents a first firing algorithm that failed to comply with the default maximum threshold 2292 of the firing velocity due to failure to account for inertia of the firing member. The firing velocity curve 2301 represents a second firing algorithm that failed to comply with a statically adjusted maximum threshold 2298 due to failure to account for inertia of the firing member. The firing velocity curve 2302 represents a third firing algorithm that dynamically modified a statically adjusted final maximum threshold 2298 by an adjustment value 2304 to achieve a dynamically and statically adjusted final maximum threshold 2299. The adjustment value 2304 is based on a slope 2305 of the velocity curve 2302.

Figure 23:
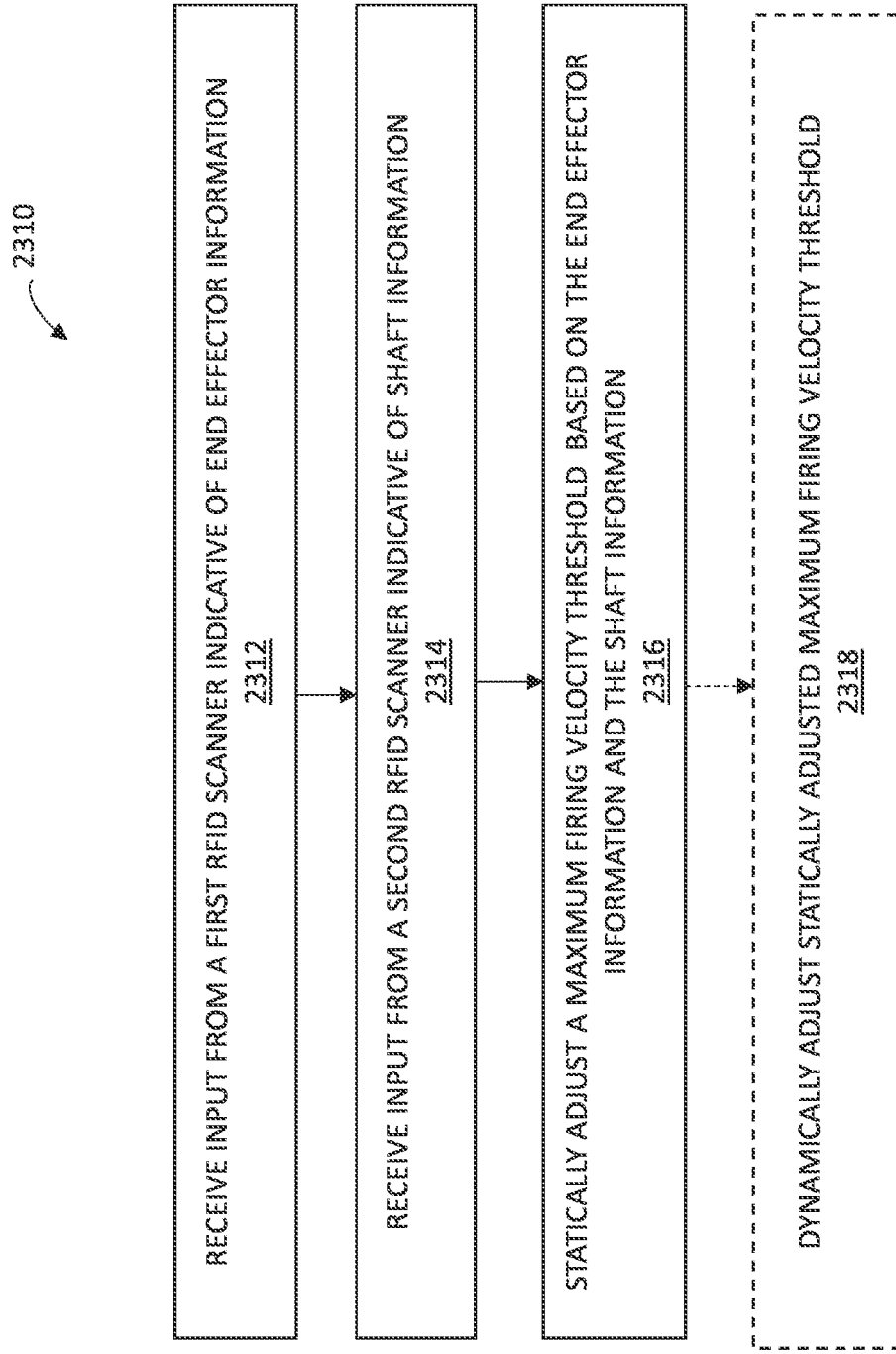
FIG. 23 depicts a logic flow diagram of a process depicting a control program or a logic configuration for operating a surgical stapling instrument, in accordance with at least one aspect of the present disclosure.

In at least one example, as illustrated in FIG. 23, a process 2310 depicting a control program or a logic configuration for operating the surgical instrument 2200, in accordance with at least one aspect of the present disclosure. In at least one example, the process 2310 is executed by a control circuit 1210 (FIG. 15) that includes a processor 1214 and a memory 1212 storing a set of computer-executable instructions that, when executed by the processor 1214, cause the processor 1214 to perform of the process 2310. In certain examples, a set of computer-executable instructions, stored in the memory 1212 may cause the processor 1214 to perform discrete portions of the process 2310. Although the process 2310 is described as being executed by a control circuit 1210, this is merely for brevity, and it should be understood that the process 2310 and other processes described herein, or portions thereof, can be executed by circuitry that can include a variety of hardware and/or software components and may be located in or associated with various suitable systems such as, for example, combinational logic circuits or sequential logic circuits.

Further to the above, the process 2310 comprises receiving 2312 input from the RFID scanner 2202 indicative of the end-effector information, receiving 2314 input from the RFID scanner 2204 indicative of the shaft information, and statically adjusting 2316 a default maximum threshold 2292 of the firing velocity of the surgical instrument 2200 to a final maximum threshold 2298 based on the end-effector information and the shaft information. Additionally, in certain instances, the process 2310 further comprises dynamically adjusting 2318 the final maximum threshold 2298 of the firing velocity to a new final maximum threshold 2299 based on the slope 2305 of the firing velocity curve 2302 to account for the firing member inertia, as illustrated in the example of Graph 2290.

Figure 24:
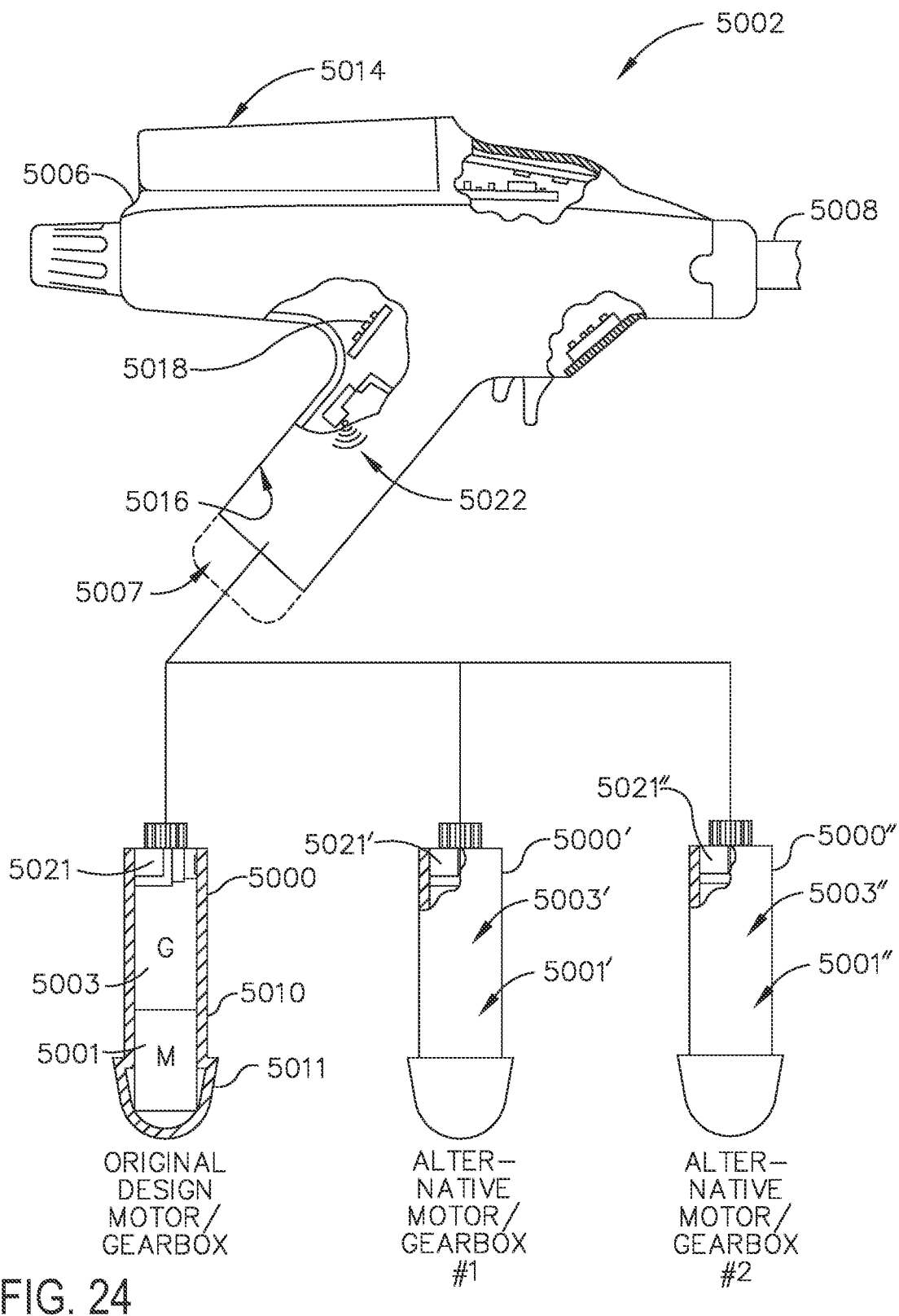
FIG. 24 depicts a partial elevational view of a surgical instrument and three motor assemblies for use with the surgical instrument, in accordance with at least one aspect of the present disclosure.

Referring primarily to FIG. 24, three motor assemblies 5000, 5000', 5000" are interchangeably usable with a surgical instrument 5002. The motor assemblies 5000, 5000', 5000" include motors 5001, 5001', 5001" and gearboxes 5003, 5003', 5003", respectively. The motors 5001, 5001', 5001", even with similar design parameters, have differing outputs based on winding techniques, wire quality, internal component quality, and/or magnetic densities. Further, the gearboxes 5003, 5003', 5003" associated with the motors 5001, 5001', 5001" also have variable losses and efficiencies based on their materials, lubrications, tolerance stack-up, and manufacturing methodologies. The implication of these variations is that motor assemblies such as, for example, the motor assemblies 5000, 5000', 5000" are likely to have dramatically different efficiencies and outputs for the same applied voltage and current, even if they are produced by a single supplier. In various aspects, the surgical instrument 5002 addresses these variations by employing an RFID system 5004 that is configured for detection and communication with a motor assembly 5000, for example, in order to retrieve information associated with the motor assembly 5000 that can aid the surgical instrument 5002 in addressing motor-assembly variations. In various aspects, the detection a motor assembly such as, for example, the motor assembly 5000 is achieved only when the surgical instrument 5002 is in an assembled configuration with the motor assembly 5000, as described in greater detail below.

Figure 26:
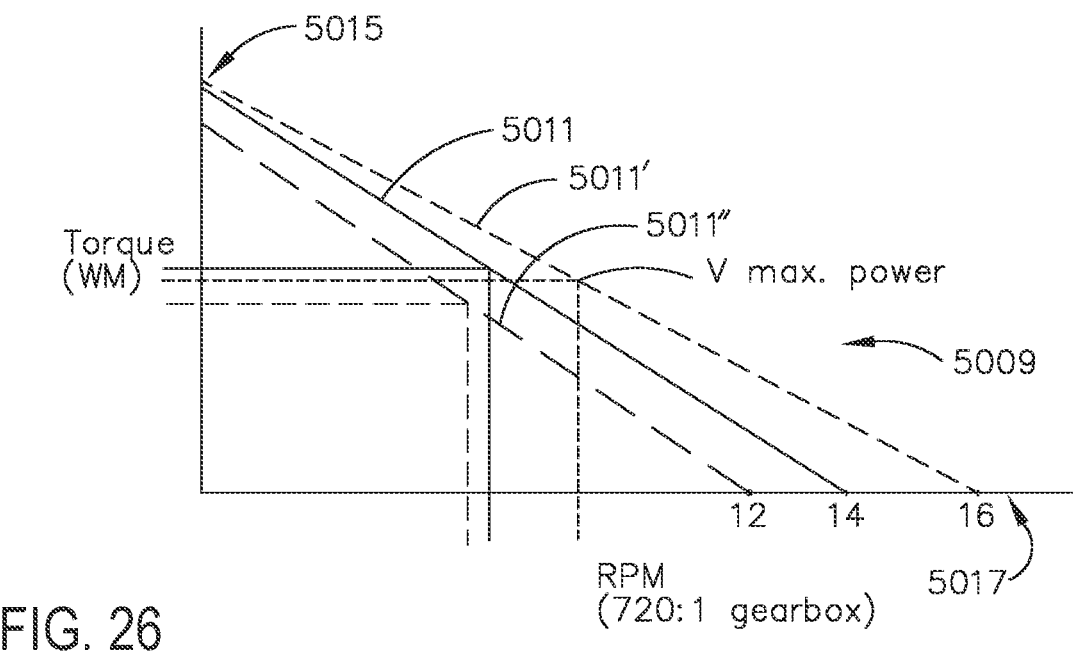
FIG. 26 is graph depicting a relationship between motor torque on the Y-axis and motor speed on the X-axis for three different motors, in accordance with at least one aspect of the present disclosure.

FIG. 26 is a graph 5009 with three lines 5011, 5011', 5011" that represent the relationship between motor torque (NM) on the Y-axis and motor speed (RPM) on the X-axis for the motors 5001, 5001', 5001", respectively. The lines 5011, 5011', 5011" demonstrate variations that exist among interchangeable motors. The lines 5011, 5011', 5011" intersect the Y-axis at different points that represent the motor-stall torques 5015, and intersect the X-axis at different points that represent the no-load speeds 5017. The graph 5009 also shows the motors' speeds at maximum suitable power. In various aspects, as described below in greater detail, information extracted from the relationships represented by the lines 5011, 5011', 5011" can used by a control circuit 1210 to adjust one or more operational parameters of a motor, select an a control algorithm, and/or adjust a default control algorithm to ensure delivery of predictable outputs from the motor assemblies 5000, 5000', 5000".

Referring still to FIG. 24, the surgical instrument 5002 includes a housing assembly 5006 that has a motor-assembly compartment 5007 configured to interchangeably receive, and be releasably coupled with, motor assemblies such as, for example the motor assemblies 5000, 5000', 5000". For brevity, the following description of the interaction between the surgical instrument 5002 and a motor assembly will focus on the motor assembly 5000. Nonetheless the following description is equally applicable to other suitable motor assemblies such as, for example, the motor assemblies 5000'. Although the housing assembly 5006 is depicted in the form of a handle, this is not limiting. In various instances, the housing assembly 100 can be a component of a robotic system, for example.

The surgical instrument 5002 is similar in many respects to other surgical instruments described elsewhere herein such as, for example, the surgical instruments 100, 1100. For example, the surgical instrument 5002 includes a shaft 5008 extending distally from the housing assembly 5006, and an end effector 5019 extending distally from the shaft 5008. Various end effectors suitable for use with the surgical instrument 5002 such as, for example, a circular stapler end effector that includes an anvil 400 and a stapling head assembly 300, are described elsewhere in the present disclosure and/or other disclosures incorporated by reference in the present disclosure.

The motor assembly 5000 is movable relative to the housing assembly 5006 between an assembled configuration and an unassembled configuration with the housing assembly 500. Various suitable electrical connectors can be employed to connect a power source 5014 in the housing assembly 5006 to the motor assembly 5000 to power to the motor 5001 in the assembled configuration. Also, various suitable mechanical connectors can be employed to operably transmit a motion, generated by the motor 5001, from the gearbox 5003 to the end effector to treat tissue grasped by the end effector.

U.S. Pat. No. 9,504,520, titled SURGICAL INSTRUMENT WITH MODULAR MOTOR, and issued Nov. 29, 2016, which is hereby incorporated by reference herein in its entirety, describes several mechanical and electrical connectors that are suitable for use with the surgical instrument 5002 and the motor assembly 5000. In at least one example, a motor assembly 5000 comprises a body 5010, a base 5011, and a pair of pogo pins, for example, that are configured to deliver electrical power to the motor 5001 housed within body 5010. Pogo pins can engage a plurality of wires in the housing assembly 5006, which are coupled to an electrical power source 5014. In various aspects, the motor assembly 5000 is secured or retained within, or at least partially within, the motor-assembly compartment 5007 of the housing assembly 5006 by latching members, clamps, clips, screw-down members, etc. When motor assembly 5000 is inserted into the motor-assembly compartment 5007, the mechanical and electrical connectors of the motor assembly 5000 are coupled to corresponding structures within the housing assembly 5006 through an electro-mechanical interface 5023 (FIG. 27) to form the assembled configuration.

Figure 27:
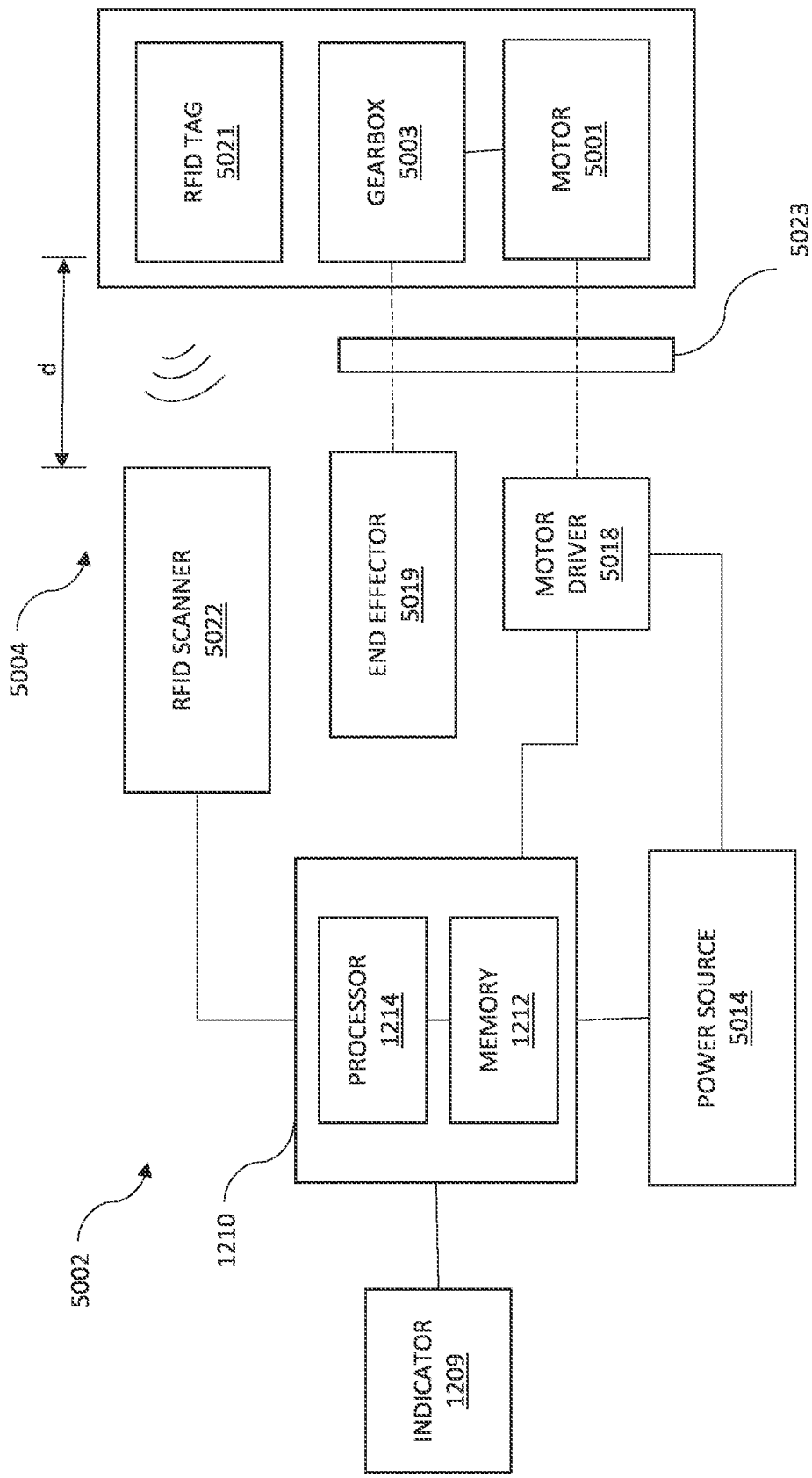
FIG. 27 depicts a control system of the surgical instrument of FIG. 24, in accordance with at least one aspect of the present disclosure.

Referring to FIG. 27, the RFID system 5004 includes an RFID scanner 5022 and RFID tag 5021 detectable by the RFID scanner in the assembled configuration. In various aspects, the RFID scanner 5022 is configured to read and/or write to the RFID tag 5021 in the assembled configuration. In the example illustrated in FIG. 27, the RFID scanner 5022 comprises a detection range defined by a distance "d". The RFID tag 5021 is at or within the detection range defined by the distance "d" when the motor assembly 5000 is in an assembled configuration with the housing assembly 5006.

Referring still to FIG. 27, the RFID scanner 5022 is coupled to a control circuit 1210 that includes a microcontroller comprising a processor 1214 and a storage medium such as, for example, the memory 1212, as described elsewhere herein in greater detail. The RFID tag 5021 stores information indicative of the motor assembly 5000, which is read by the RFID scanner 5022 while the motor assembly 5000 is retained by the motor-assembly compartment 5007 in the assembled configuration.

In at least one example, the control circuit 1210 receives an input from the RFID scanner 5022 indicative of the motor-assembly information, and adjusts one or more parameters of operation of the motor 5001 based on the motor-assembly information. The control circuit 1210 can employ a motor driver 5018 to perform the parameter adjustments. In the example illustrated in FIG. 27, the motor driver 5018 is positioned within the housing assembly 5006, and interfaces with the motor 5001 in the assembled configuration through the electro-mechanical interface 5023. In other examples, the motor driver 5018 is a part of the motor assembly 5000, and is configured to interface with the control circuit 1210 through the electro-mechanical interface 5023.

Figure 28:
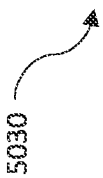
FIG. 28 depicts a table or database of various control algorithms of the surgical instrument of FIG. 25, in accordance with at least one aspect of the present disclosure.

Referring to FIG. 28, the processor 1214 of the control circuit 1210 can be configured to select a control algorithm of the surgical instrument 5002 based on the motor-assembly information retrieved from the RFID tag 5021 by the RFID scanner 5022. The control algorithms can be stored in the memory 1214, for example, in the form of a database or a look-up table 5030. Alternatively, or additionally, the motor-assembly information of a motor assembly can include a control algorithm recommended for use with the motor assembly.

In various examples, the motor-assembly information of a motor assembly 5000, for example, comprises one or more of identification information, manufacturer information, and specific tolerances of the motor 5001 and/or the gearbox 5003, for example. The motor-assembly information can include model numbers, lot numbers, manufacturing dates, and/or any other relevant information.

In the example illustrated in FIG. 28, each row represents a control algorithm associated with a motor assembly, which can be selected by the processor 1214 based on the retrieved motor-assembly information. The values in the outer left column are based on input from the RFID scanner 5022 indicative of the motor-assembly information of motor assemblies $MA_1$-$MA_n$. In at least one example, the values in the outer left column can be motor-assembly identification or model numbers. The middle columns include values of motor velocity, inertia/dynamic breaking, stroke length, current limits/force limits that are associated with each of the motor assemblies $MA_1$-$MA_n$. The values in the outer right column represent suitable voltage and discharge values of a power source 5014 configured to power motor assemblies $MA_1$-$MA_n$ when coupled to the surgical instrument 5002.

Referring still to FIG. 5, in various aspects, the control circuit 1210 is configured to employ the RFID system 5004 to retrieve motor-assembly information that identify a motor assembly coupled to the surgical instrument 5002. The control circuit 1210 then determines, from the look-up table 5030 suitable voltage and discharge values for the power source 5014 based on the retrieved motor-assembly information.

In various aspects, the control circuit 1210 employs a formula or calibration factor to adjust the operational parameters of a motor assembly 5000, for example. The formula or calibration factor can be stored by the RFID tag 5021, and received by the control circuit 1210 through input from the RFID scanner 5022. Alternatively, the formula or calibration factor can be retrieved from a storage medium such as, for example, the memory 1212 based on identification information of the memory assembly associated with such formula or calibration factor.

Figure 25:
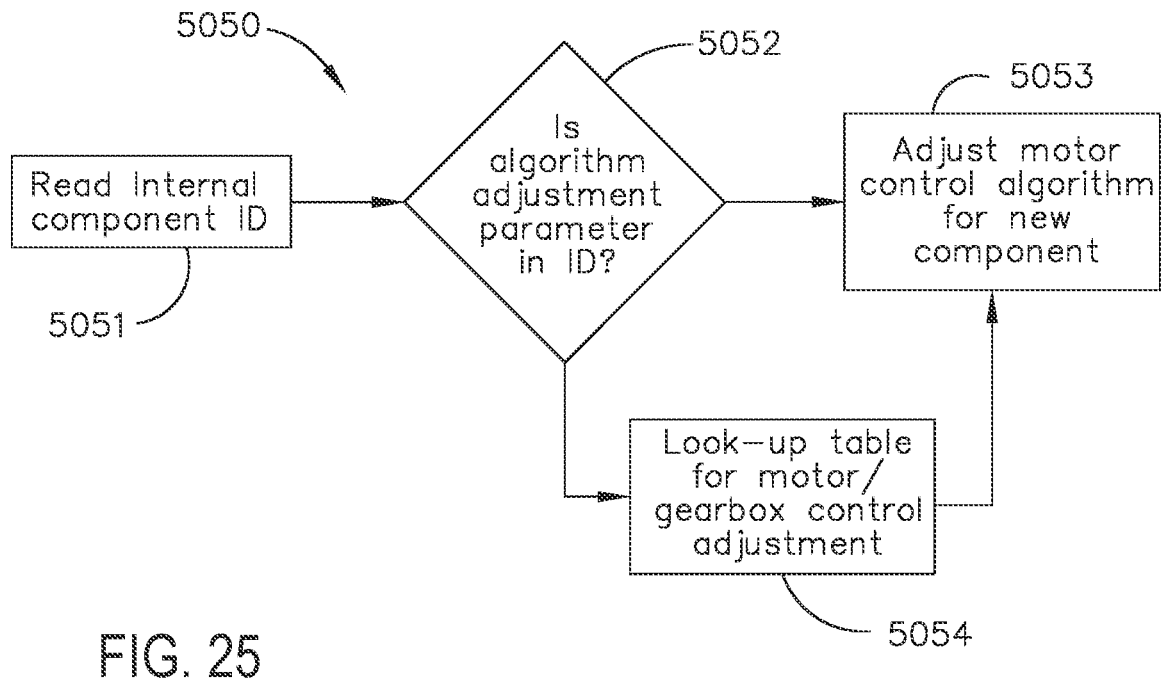
FIG. 25 depicts a logic flow diagram of a process depicting a control program or a logic configuration for adjusting operational parameters of a motor of the surgical instrument of FIG. 24, in accordance with at least one aspect of the present disclosure.

Referring to FIG. 25, a logic flow diagram of a process 5050 depicts a control program or a logic configuration for adjusting operational parameters of a motor 5001, for example, of the surgical instrument 5002. In at least one example, the process 5050 is executed by a control circuit 1210 (FIG. 27) that includes a processor 1214 and a memory 1212 storing a set of computer-executable instructions that, when executed by the processor 1214, cause the processor 1214 to perform of the process 5050. In certain examples, a set of computer-executable instructions, stored in the memory 1212 may cause the processor 1214 to perform discrete portions of the process 5050. Although the process 5050 is described as being executed by a control circuit 1210, this is merely for brevity, and it should be understood that the process 5050 and other processes described herein, or portions thereof, can be executed by circuitry that can include a variety of hardware and/or software components and may be located in or associated with various suitable systems such as, for example, combinational logic circuits or sequential logic circuits.

In various aspects, the process 5050 includes reading 5051 an internal component identification information from an RFID tag 5021 by an RFID scanner 5022, for example. In at least one example, the internal component is a motor assembly 5000, a motor 5001, a gearbox 5003, or a power source 5014. The process 5050 further determines 5052 whether an algorithm adjustment parameter is included with the internal component identification information. If so, the process 5050 adjusts 5053 a control algorithm associated with the internal component in accordance with the received algorithm adjustment parameter. If an algorithm adjustment parameter is included, the process 5050 uses 5054 the internal component identification information to retrieve an algorithm adjustment parameter, or select a suitable control algorithm, for the internal component based on a database or look-up table of internal component identification information and corresponding algorithm adjustment parameters, or control algorithms.

Many surgical instruments utilize a battery to provide the electrical power required to operate a surgical instrument.

Such batteries can include, for example, a primary cell/non-rechargeable battery such as an alkaline battery or a lithium battery, or a secondary cell/rechargeable battery such as a nickel metal hydride battery or a lithium ion battery. The different types of batteries can have different materials, chemistries, sizes, electrical characteristics (e.g., nominal voltages, discharge rates, etc.), discharge efficiencies, and costs. The type of battery utilized in a given surgical instrument is typically selected based on a variety of factors such as, among other things, disposable vs. rechargeable, size, output characteristics and cost.

As battery technology continues to advance, different battery chemistries having different capacities, output characteristics, etc. continue to evolve. It is now conceivable that throughout the useful life of a given surgical instrument, different battery packs which have differing capabilities and are made by different manufacturers may be utilized at different times with the given surgical instrument. For such instances, in order to optimize the performance of the surgical instrument, it is desirable for the given surgical instrument to be able to differentiate between the different batteries.

It is also now conceivable that throughout the useful life of a given battery, the given battery may be utilized to power different surgical instruments at different times, where the power requirements of the different surgical instruments can vary. Therefore, in order to match the capability of the battery with the power requirement of a given surgical instrument, it is desirable for the battery to be able to differentiate between the different surgical instruments and to be able to adjust the electrical characteristics of the battery as needed.

Figure 29:
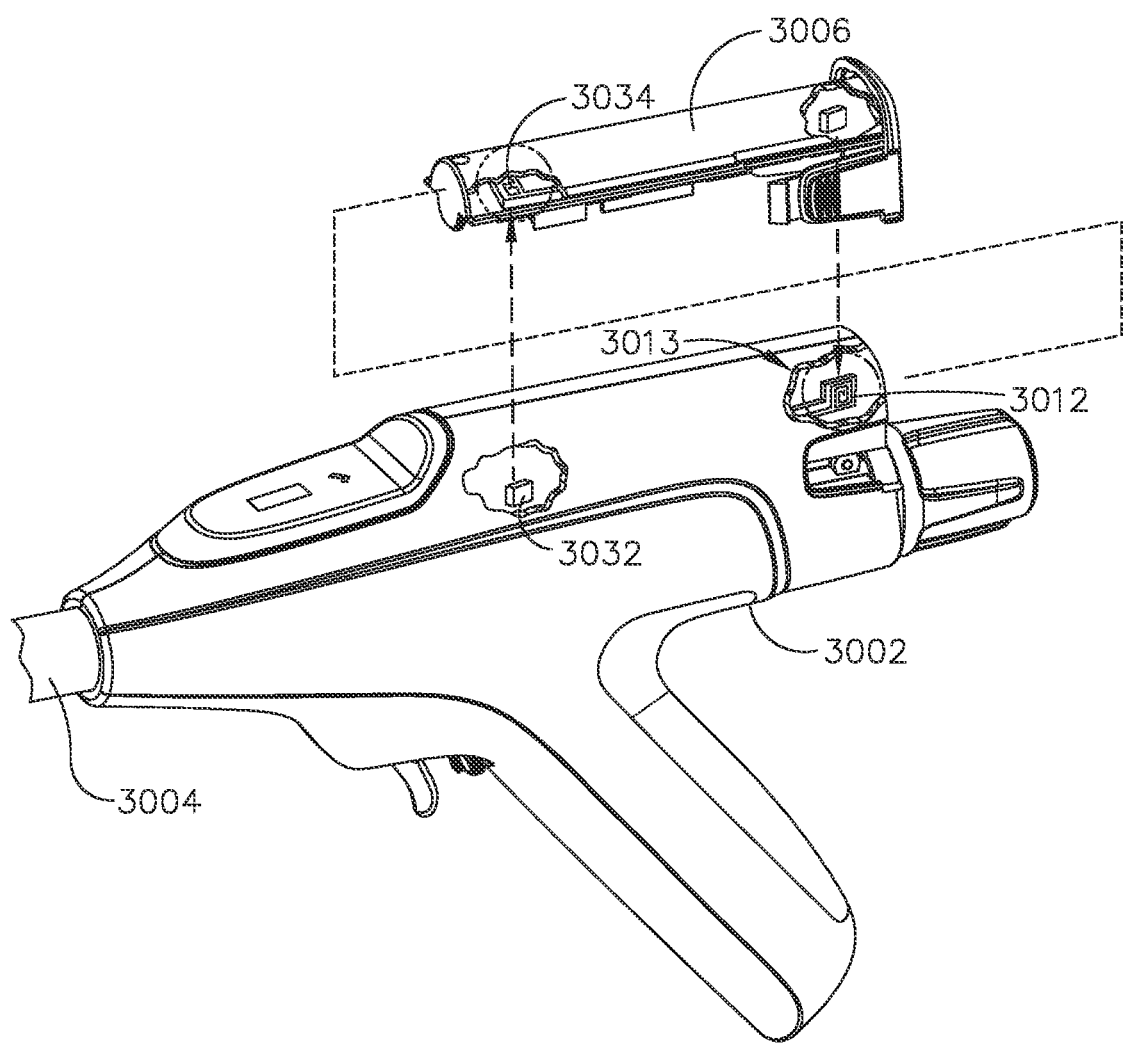
FIG. 29 illustrates a partial perspective view of a surgical instrument, in accordance with at least one aspect of the present disclosure.

FIG. 29 illustrates a partial perspective view of a surgical instrument 3000, in accordance with at least one aspect of the present disclosure. The surgical instrument 3000 is similar to the surgical circular stapling instrument 10 described hereinabove and includes a housing assembly 3002, a shaft assembly 3004, a stapling head assembly (not shown) and an anvil (not shown), where the housing assembly 3002 is similar or identical to the housing assembly 100, the shaft assembly 3004 is similar or identical to the shaft assembly 200, the stapling head assembly (not shown) is similar or identical to the stapling head assembly 300 and the anvil (not shown) is similar or identical to the anvil 400. As shown in FIG. 29, the surgical instrument 3000 is also configured to receive a battery 3006. In some aspects, the surgical instrument 3000 further includes the battery 3006. Although not shown for purposes of clarity in FIG. 29, the surgical instrument also includes an electric motor 3008 (See FIG. 30) which is similar or identical to the motor 160. The electric motor 3008 is couplable with the battery 3006, and is configured to move the anvil toward the staple head assembly to grasp tissue between the anvil and the staple head assembly, and to fire staples of the stapling head assembly into the grasped tissue. Although the surgical instrument 3000 is shown as a circular stapler, it will be appreciated that according to other aspects, the surgical instrument 3000 may be a linear stapler or other powered surgical instrument. In various aspects the adaptive surgical instrument 3194 is similar in many respects to the surgical instrument 2200, and can be assembled from one or more of the interchangeable components of the surgical instrument 2200 illustrated in FIG. 18.

The battery 3006 may be any suitable type of battery, and may include any suitable number of cells. For example, according to various aspects, the battery 3006 may include a lithium battery such as a lithium manganese oxide (Li—MnO$_2$) or CR123 battery, a lithium ion battery such as a 15270 battery, an alkaline battery such as a manganese oxide (MnO$_2$) battery, a nickel metal hydride battery, etc. In at least one aspect, the battery 3006 is in the form of a battery pack which includes a plurality of cells. For purposes of brevity, the battery 3006 will be referred to hereinafter as the battery pack 3006. The battery pack 3006 is similar to the battery pack 120 but is different in that the battery pack 3006 includes a radio-frequency identification (RFID) tag 3010 positioned within the battery pack 3006. The RFID tag 3010 stores information related to the battery pack 3006 and such information may include, for example, a battery identification number, the manufacturer/brand of batteries in the battery pack 3006, the chemistry/type of batteries (lithium, lithium-ion, etc.) in the battery pack 3006, whether the type of batteries in the battery pack 3006 are chargeable or non-rechargeable, the capacity of the battery pack 3006, the nominal voltage of the batteries in the battery pack 3006, the current draw characteristics of the batteries in the battery pack 3006, other output characteristics of the battery pack 3006, etc. The RFID tag 3010 is very compact in size (e.g., 13 mm square or less), thereby allowing for the RFID tag 3010 to be incorporated into the battery pack 3006 without unduly increasing the overall size of the battery pack 3006. According to various aspects, the RFID tag 3010 may be similar to the miniaturized RFID tag described in U.S. Pat. No. 9,171,244.

The surgical instrument 3000 is different from the surgical circular stapling instrument 10 in that the surgical instrument 3000 further includes an RFID scanner 3012. The RFID scanner 3012 is positioned within the housing assembly 3002 and is configured to read the information stored at the RFID tag 3010, where the stored information is related to the battery pack 3006. The RFID scanner 3012 is also configured to communicate data indicative of the read information to a control circuit 3014 (See FIG. 30) of the surgical instrument 3000 for processing. The RFID tag 3010 and the RFID scanner 3012 cooperate to collectively allow for the surgical instrument 3000 to be able to identify the battery pack 3006, and determine whether the battery pack 3006 is suitable for use with the surgical instrument 3000.

As illustrated in FIG. 29, the RFID scanner 3012 is positioned at a battery interface 3013 of the housing assembly 3002. The RFID tag 3010 is configured to be detected by the RFID scanner 3012 in an assembled, or at least partially assembled, configuration of the battery 3006 with the housing assembly 3002. This approach eliminates the need for a separate scanning step by tethering the detection of the RFID tag 3010 by the RFID scanner 3012 to the assembly of the battery 3006 to the housing assembly 3002. It also ensures that the detected battery 3006 is the one ultimately assembled with the housing assembly 3002. In various aspects, the detection range of an RFID scanner 3012 is limited such that it is only able to detect a corresponding RFID tag 3010 in an assembled, or at least partially assembled, configuration of the battery 3006 with the housing assembly 3002.

Similarly, the RFID tag 3032 is positioned at the battery interface 3013 of the housing assembly 3002. The RFID tag 3032 is configured to be detected by the RFID scanner 3034 in an assembled, or at least partially assembled, configuration of the battery 3006 with the housing assembly 3002. In various aspects, the detection range of an RFID scanner 3034 is limited such that it is only able to detect a corresponding RFID tag 3032 in an assembled, or at least partially assembled, configuration of the battery 3006 with the housing assembly 3002.

In various aspects, as illustrated in FIG. 29, the RFID scanner 3034 and the RFID tag 3010 are configured to be aligned with the RFID tag 3032 and the RFID scanner 3012, respectively, in the assembled configuration. The alignment, once achieved, brings the RFID tag 3010 within the detection range of the RFID scanner 3012, and the RFID tag 3032 within the detection range of the RFID scanner 3034.

Figure 30:
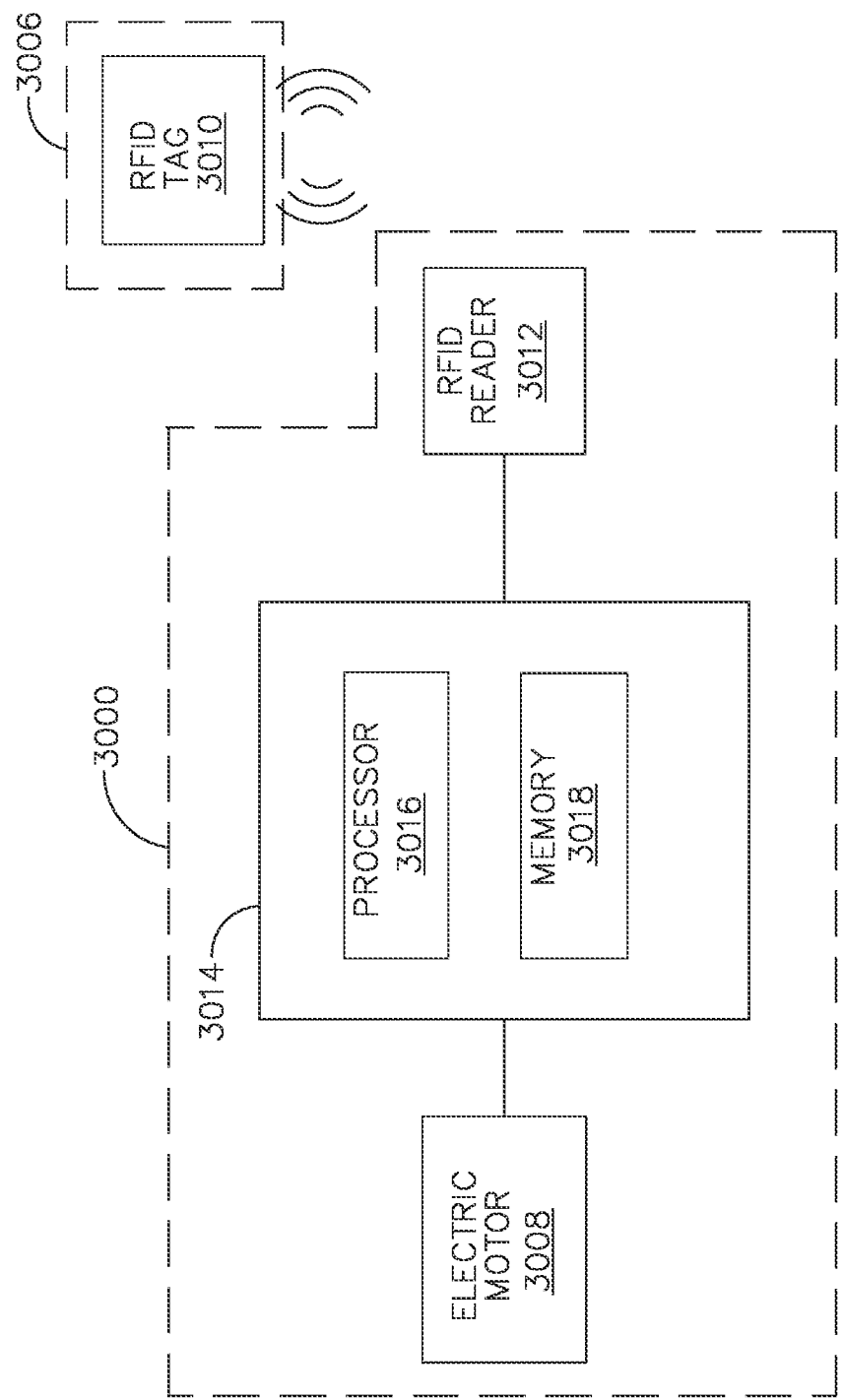
FIG. 30 illustrates a control circuit of the surgical instrument of FIG. 29, in accordance with at least one aspect of the present disclosure.

FIG. 30 illustrates a control circuit 3014 of the surgical instrument 3000, in accordance with at least one aspect of the present disclosure. The control circuit 3014 is communicably connected to the RFID scanner 3012 and is similar to the control circuit 1210 in that the control circuit 3014 includes a processor 3016 and a storage medium such as, for example, a memory 3018. The memory 3018 stores program instructions for performing various processes such as, for example, determining whether the battery pack 3006 is compatible for use with the surgical instrument 3000 (e.g., battery compatibility verification). The program instructions, when executed by the processor 3016, cause the processor 3016 to verify the compatibility of the battery pack 3006 with the surgical instrument 3000 by comparing the information received from the RFID tag 3010 to information stored in the memory 3018. The information stored at the memory 3018 may be in the form of, for example, a compatibility database or a lookup table which includes information regarding identification information for batteries which can be utilized with the surgical instrument 3000, output characteristics of batteries which can be utilized with the surgical instrument 3000, etc. According to various aspects, the control circuit 3014 is communicably connected to other processors and/or memories of the surgical instrument 3000 and/or a surgical hub system, and the described functionality of the control circuit 3014 can be realized with the other processors and/or memories of the surgical instrument 3000 and/or the surgical hub system. The surgical hub system is described in U.S. patent application Ser. No. 16/209,395, titled METHOD OF HUB COMMUNICATION, and filed Dec. 4, 2018, the entire content of which is hereby incorporated by reference herein.

Figure 31:
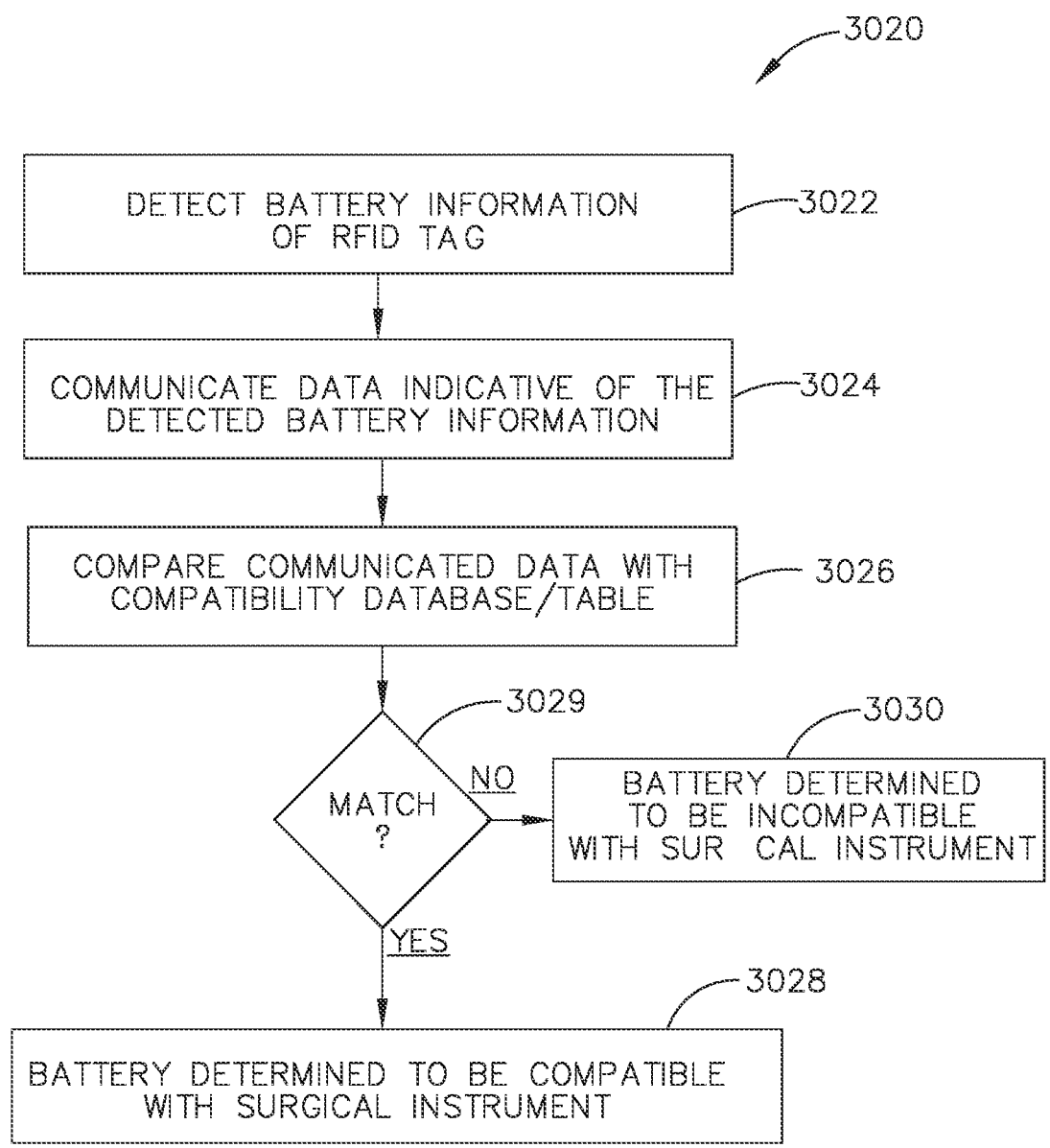
FIG. 31 illustrates a logic flow diagram of a process depicting a control program or a logic configuration for operating the surgical instrument of FIG. 29, in accordance with at least one aspect of the present disclosure.

FIG. 31 illustrates a logic flow diagram of a process 3020 depicting a control program or a logic configuration for operating the surgical instrument 3000, in accordance with at least one aspect of the present disclosure. In at least one example, the process 3020 is executed by the control circuit 3014. In certain examples, a set of computer-executable instructions, stored in the memory 3018 of the control circuit 3014, may cause the processor 3016 of the control circuit 3014 to perform discrete operations of the process 3020. Although the process 3020 is being described in the context of being executed by the control circuit 3014, it will be understood that the process 3020 and other processes described herein, or portions thereof, can be executed by circuitry that can include a variety of hardware and/or software components and may be located in or associated with various suitable systems such as, for example, combinational logic circuits or sequential logic circuits.

As illustrated in FIG. 31, the process 3020 includes detecting 3022 battery information of the RFID tag 3010 via the RFID scanner 3012. In various aspects, the RFID scanner 3012 can perform the detection whenever the battery pack 3006 is brought in close proximity to the surgical instrument 3000. In other instances, the RFID scanner 3012 performs the detection after the battery pack 3006 is inserted into the housing assembly 3002 of the surgical instrument 3000. The RFID scanner 3012 thereafter communicates 3024 data which is indicative of the detected battery information of the RFID tag 3010 to the control circuit 3014. The communication of the data may be realized by wired communication or by wireless communication. The processor 3016 of the control circuit 3014 thereafter checks/compares 3026 the communicated data against a battery/surgical instrument compatibility database or lookup table which may be stored in the memory 3018 of the control circuit 3014. If the check/comparison 3026 results in a match 3029, the processor 3016 determines 3028 the battery pack 3006 is compatible for use with the surgical instrument 3000, and a user of the surgical instrument 3000 may be alerted to the compatibility by a visual or audible indicator such as, for example, a light emitting diode or a speaker. However, if the check/comparison 3026 does not result in a match 3029, the processor 3016 determines 3030 the battery pack 3006 is incompatible for use with the surgical instrument 3000, and a user of the surgical instrument 3000 may be alerted to the incompatibility by a visual or audible indicator such as, for example, a light emitting diode or a speaker. Additionally, in at least one aspect, when the processor 3016 determines that the battery pack 3006 is incompatible with the surgical instrument 3000, the processor 3016 may communicate a signal or instruction which operates to cause one or more functionalities of the surgical instrument 3000 to be electrically locked out (e.g., by preventing power being applied to the electric motor 3008 of the surgical instrument 3000). Although the process 3020 was described in the context of a given battery pack 3006, it will be appreciated that the above-described process 3020 may be repeated any number of times for any number of different battery packs.

Returning to FIG. 29, in at least one aspect, the surgical instrument 3000 further includes an RFID tag 3032 positioned within the housing assembly 3002, and the battery pack 3006 further includes an RFID scanner 3034 positioned within the battery pack 3006. The RFID tag 3032 is similar to the RFID tag 3010, and stores information related to the surgical instrument 3000. Such information may include, for example, a surgical instrument identification number, the manufacturer/brand of the surgical instrument, the type of surgical instrument (circular stapler, linear stapler, grasper, etc.), type of motor in the surgical device (brushed, brushless), performance capabilities of the surgical instrument, control algorithms residing at the surgical instrument, etc. The RFID scanner 3034 is similar to the RFID scanner 3012, and is configured to read the information stored at the RFID tag 3032, where the stored information is related to the surgical instrument 3000, and communicate data which is indicative of the read information to a control circuit 3040 (See FIG. 32) of the battery pack 3006 for processing. The RFID tag 3032 and the RFID scanner 3034 collectively allow for the battery pack 3006 to be able to identify the surgical instrument 3000, and verify that the surgical instrument 3000 is suitable for use with the battery pack 3006.

Figure 32:
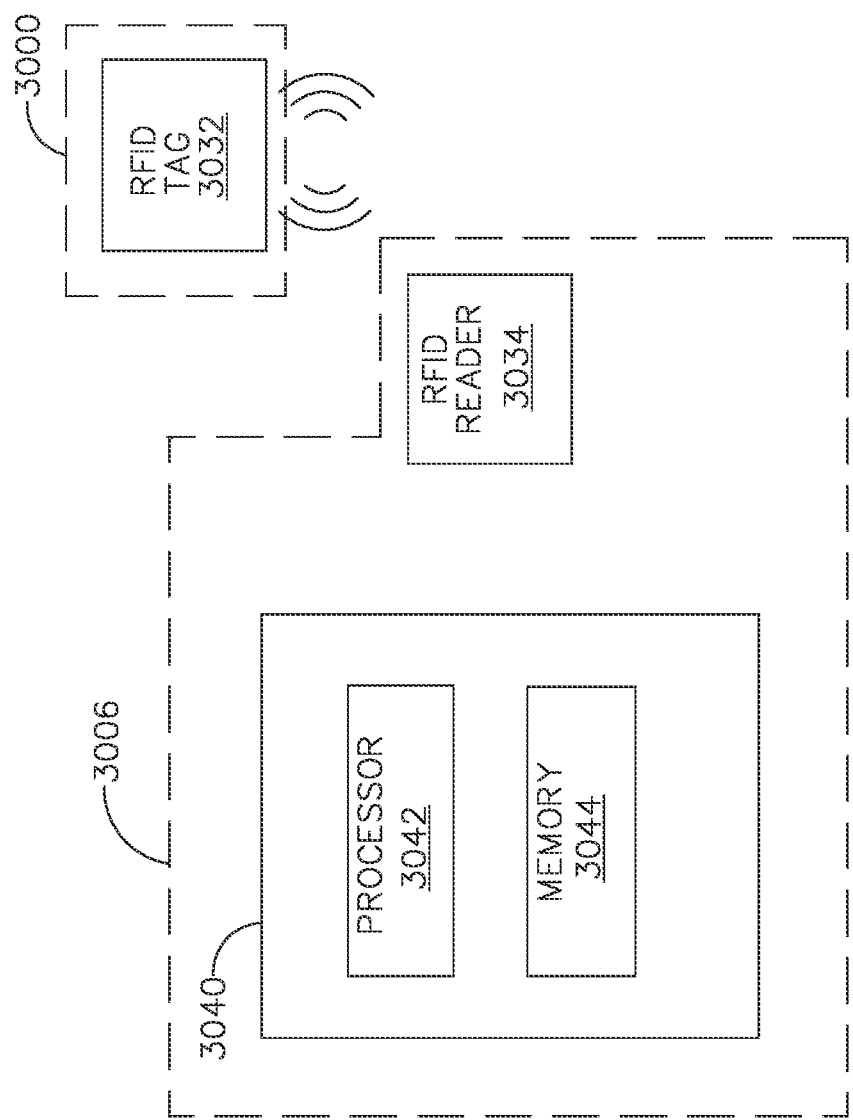
FIG. 32 illustrates a control circuit of the battery pack, in accordance with at least one aspect of the present disclosure.

FIG. 32 illustrates a control circuit 3040 of the battery pack 3006, in accordance with at least one aspect of the present disclosure. The control circuit 3040 is communicably connected to the RFID scanner 3034 and is similar to the control circuit 3014 in that the control circuit 3040 includes a processor 3042 and a storage medium such as, for example, a memory 3044. The memory 3044 stores program instructions for performing various processes such as, for example, determining whether the surgical instrument 3000 is compatible for use with the battery pack 3006 (e.g., surgical instrument compatibility verification). The program instructions, when executed by the processor 3042, cause the processor 3044 to verify the compatibility of the surgical instrument 3000 with the battery pack 3006 by comparing the information received from the RFID tag 3032 to information stored in the memory 3044. The information stored at the memory 3044 may be in the form of, for example, a compatibility database or a lookup table which includes information regarding identification information for various surgical instruments, power requirements of the various surgical instruments, performance parameters of the various surgical instruments, etc. The process executed by the control circuit 3040 to verify the compatibility of the surgical instrument 3000 with the battery pack 3006 is analogous to the process 3020 utilized by the control circuit 3014 to verify the compatibility of the battery pack 3006 with the surgical instrument 3000. For example, when the processor 3042 determines that the surgical instrument 3000 is incompatible with the battery pack 3006, the processor 3042 may communicate a signal or instruction which operates to electrically lockout the battery pack 3006 and prevent the battery pack 3006 from providing power to the surgical instrument 3000.

In view of the above-described aspects, it will be appreciated that a number of different batteries can be compatible with the surgical instrument 3000. Stated differently, the surgical instrument 3000 can be compatible with a number of different batteries. When the surgical instrument 3000 includes the RFID scanner 3012 and the RFID tag 3032, and various batteries include a RFID tag and a RFID scanner with functionality similar or identical to those of the RFID tag 3010 and the RFID scanner 3034, the surgical instrument 3000 can identify a plurality of different batteries and determine the compatibility of each of those batteries with the surgical instrument 3000. Similarly, when the battery pack 3006 includes the RFID tag 3010 and the RFID scanner 3034, and various surgical instruments include a RFID tag and a RFID scanner with functionality similar or identical to those of the RFID tag 3032 and the RFID scanner 3032, the battery pack 3006 can identify a plurality of different surgical instruments and determine the compatibility of each of those surgical instruments with the battery pack 3006.

Figure 33:
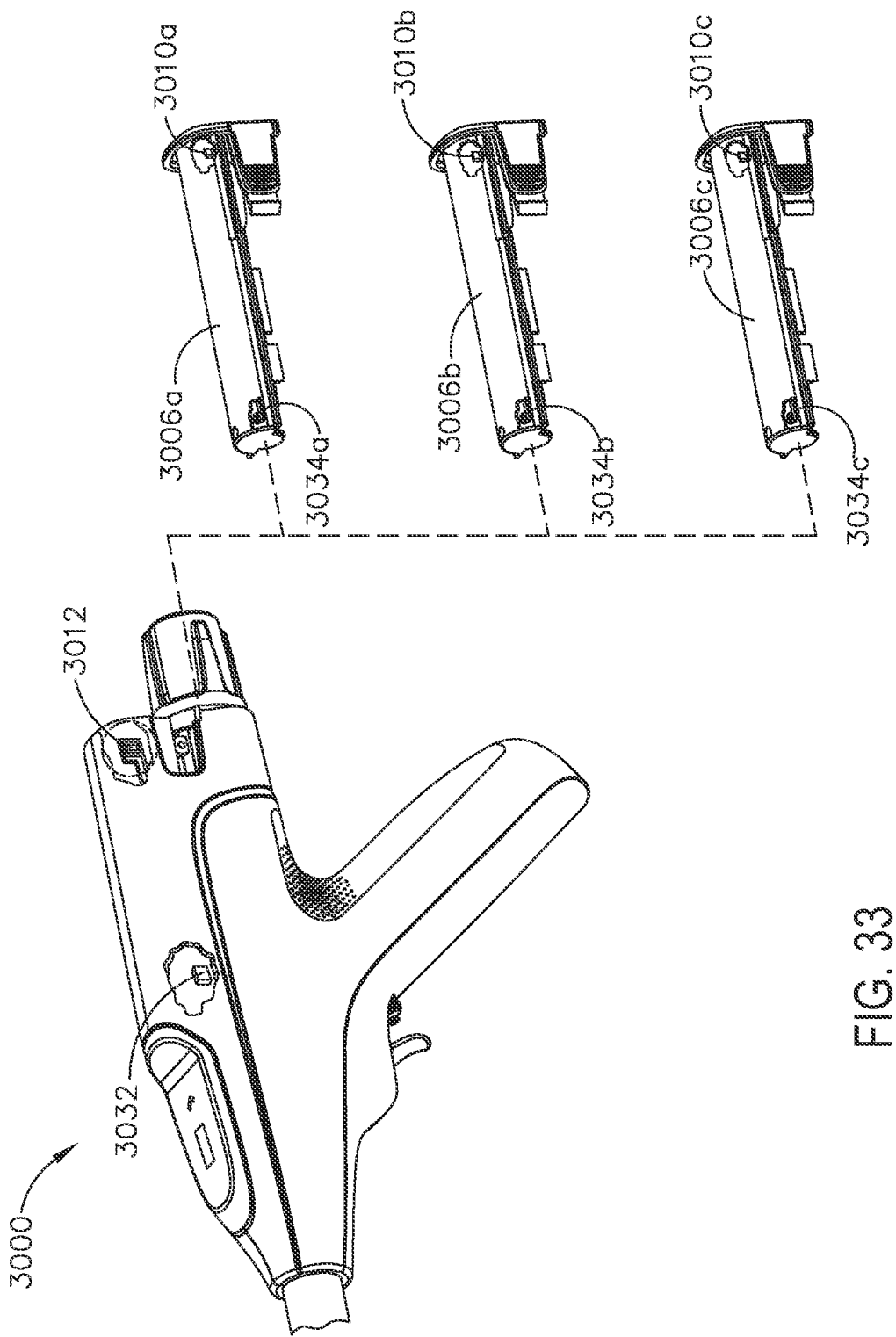
FIG. 33 illustrates the compatibility of the surgical instrument of FIG. 29 with a plurality of different battery packs, in accordance with at least one aspect of the present disclosure.

FIG. 33 illustrates the compatibility of the surgical instrument 3000 with a plurality of different battery packs 3006a, 3006b, 3006c, in accordance with at least one aspect of the present disclosure. The battery pack 3006a includes a RFID tag 3010a and a RFID scanner 3034a positioned therein, the battery pack 3006b includes a RFID tag 3010b and a RFID scanner 3034b positioned therein, and the battery pack 3006c includes a RFID tag 3010c and a RFID scanner 3034c positioned therein. According to various aspects, the battery pack 3006a includes a CR123/lithium battery, the battery pack 3006b includes a 15270/lithium ion battery, and the battery pack 3006c includes a battery other than a lithium battery or a lithium ion battery. When any one of the battery packs 3006a, 3006b, 3006c is in proximity to or is received by the surgical instrument 3000, as described above, the respective RFID tag/RFID scanner pairs allow for (1) the surgical instrument 3000 to be able to identify the applicable battery pack 3006a, 3006b, 3006c, and determine whether the applicable battery pack 3006a, 3006b, 3006c is compatible with/suitable for use with the surgical instrument 3000 and (2) any of the battery packs 3006a, 3006b, 3006c to be able to identify the surgical instrument 3000 and determine whether the surgical instrument 3000 is compatible with/suitable for use with the applicable battery pack 3006a, 3006b, 3006c.

Figure 34:
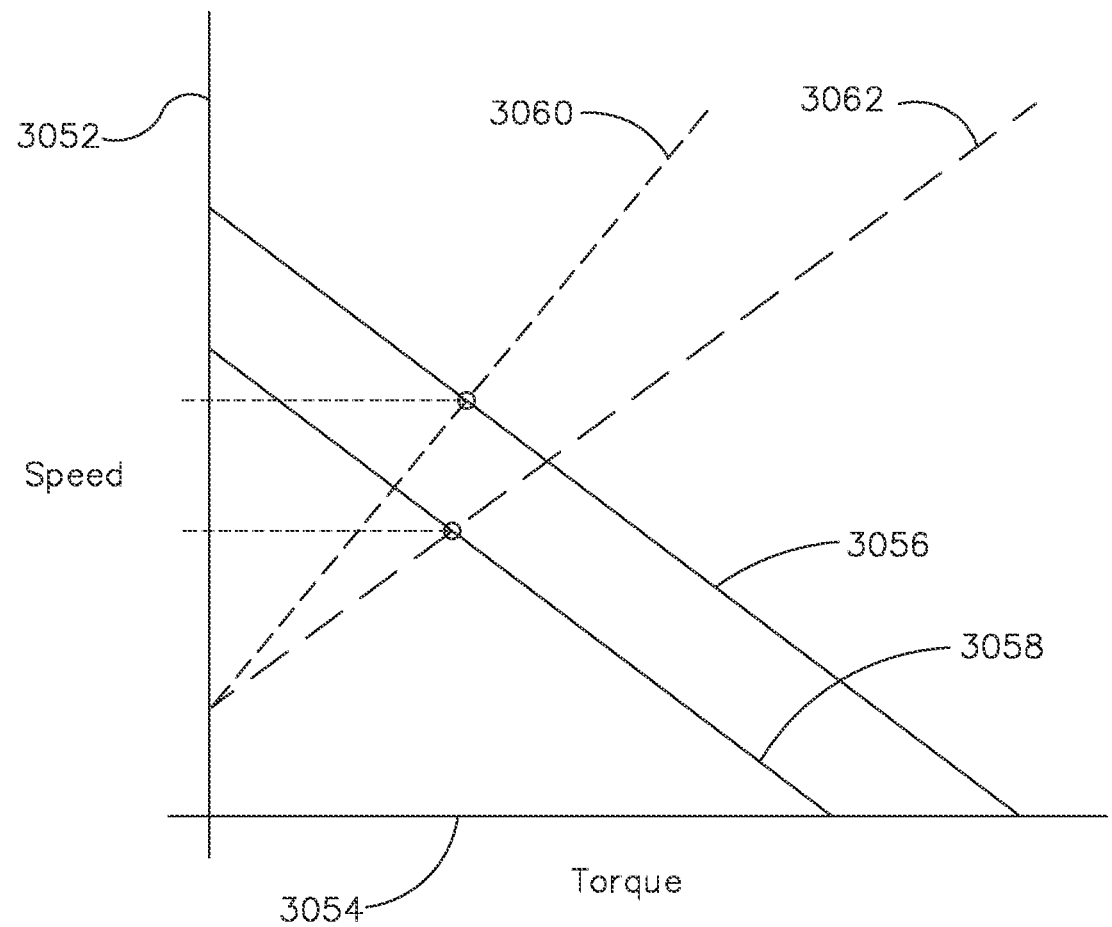
FIG. 34 illustrates a graph which shows various motor torque/speed/current relationships for the surgical instrument of FIG. 29 when powered by different battery packs, in accordance with at least one aspect of the present disclosure.

Different batteries can have different chemistries, different capacities, different output characteristics, different operational abilities, etc., and different surgical instruments can have different power requirements. FIG. 34 illustrates a graph 3050 which shows various motor torque/speed/current relationships for the surgical instrument 3000 when powered by different battery packs, in accordance with at least one aspect of the present disclosure. For the graph 3050, units of speed (or current) are shown along the vertical axis 3052 and units of torque are shown along the horizontal axis 3054. The solid line 3056 represents the torque-speed relationship for a lithium ion/15270 battery, where the left end of the solid line 3056 represents the no load speed and the right end of the solid line 3056 represents the stall torque. The solid line 3058 represents the torque-speed relationship for a lithium/CR-123 battery, where the left end of the solid line 3058 represents the no load speed and the right end of the solid line 3058 represents the stall torque. In general, the torque is inversely proportional to the speed of an output shaft of the electric motor 3008 of the surgical instrument 3000. In other words, the greater the speed—the lower the torque (or the greater the torque, the lower the speed).

The dashed line 3060 represents the current drawn from a lithium ion/15270 battery, where the left end of the dashed line 3060 represents the no load current and the right end of the dashed line 3060 represents the stall current. The dashed line 3062 represents the current drawn from a lithium/CR-123 battery, where the left end of the dashed line 3062 represents the no load current and the right end of the dashed line 3062 represents the stall current. For both batteries, the no-load current is greater than zero because it takes a certain amount of current to overcome the internal friction of the electric motor 3008. In general, when an external load is applied, the current drawn from the respective batteries increases to produce the torque required to match it (the torque is proportional to the applied current), and the speed of the electric motor 3008 is reduced. As the external load is further increased, the speed of the electric motor 3008 is further reduced, eventually reaching stall. In view of the above, it will be appreciated that the motor torque/speed/current relationships can vary appreciably based on the specific battery pack utilized to power the surgical instrument 3000.

Figure 35:
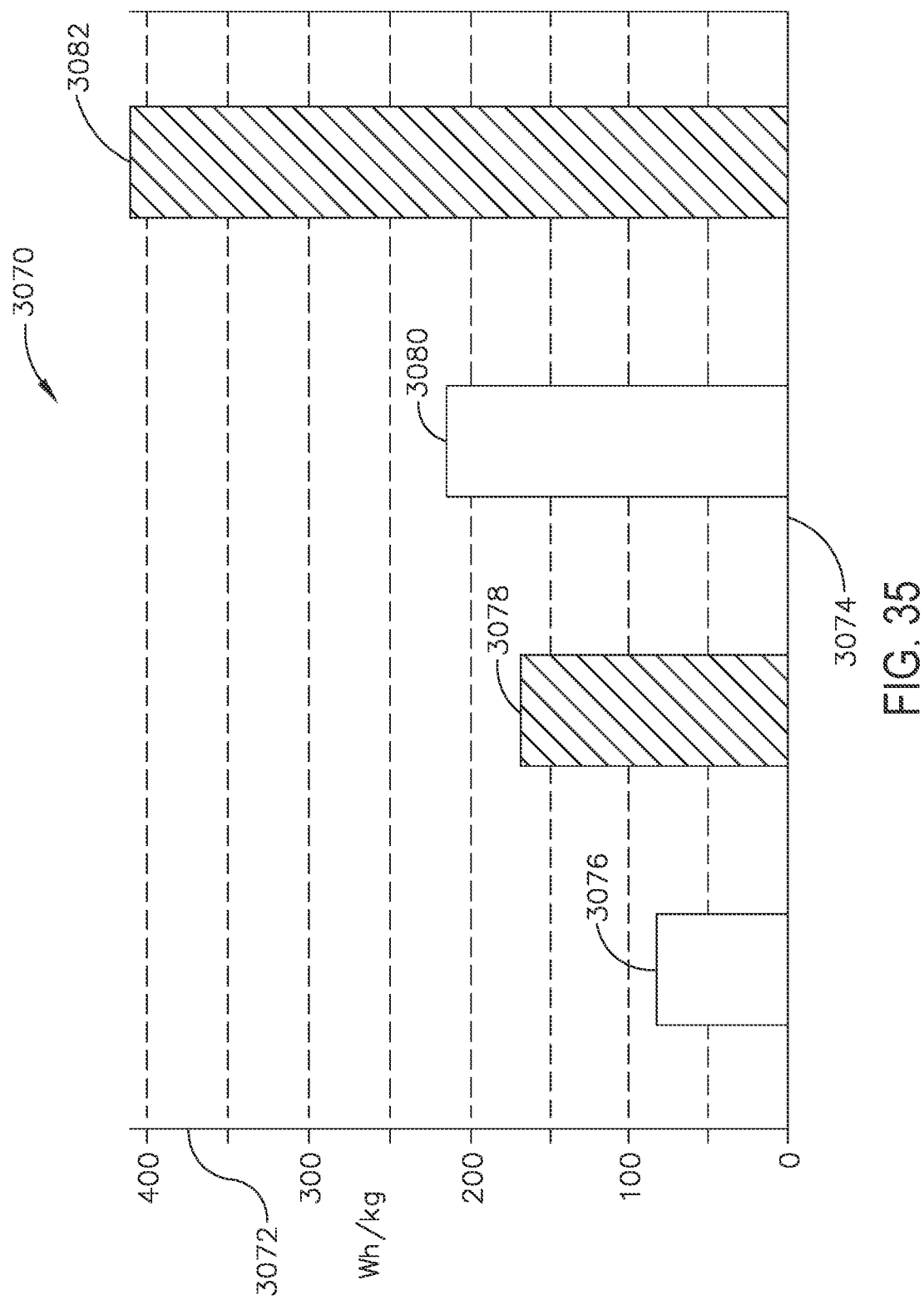
FIG. 35 illustrates a bar graph which shows various energy densities for different battery packs which can be utilized with the surgical instrument of FIG. 29, in accordance with at least one aspect of the present disclosure.

FIG. 35 illustrates a bar graph 3070 which shows various energy densities for different battery packs which can be utilized with the surgical instrument 3000, in accordance with at least one aspect of the present disclosure. The respective energy densities are representative of the amounts of energy stored in the different battery packs per unit mass. For the graph 3070, watt-hours per kilogram of mass (Wh/Kg) are shown along the vertical axis 3072 and the different battery packs are shown along the horizontal axis 3074. The bar 3076 representative of the energy density of a nickel metal hydride rechargeable battery is shown as being approximately 80 Wh/Kg, the bar 3078 representative of the energy density of a lithium ion rechargeable battery is shown as being approximately 160 Wh/Kg, the bar 3080 representative of the energy density of an alkaline manganese oxide ($MnO_2$) battery is shown as being approximately 205 Wh/Kg, and the bar 3082 representative of the energy density of a primary/disposable lithium battery is shown as being approximately 400 Wh/Kg. In view of the above, it will be appreciated that the energy densities of the various battery packs which can be utilized with the surgical instrument 3000 can vary appreciably.

Figure 36:
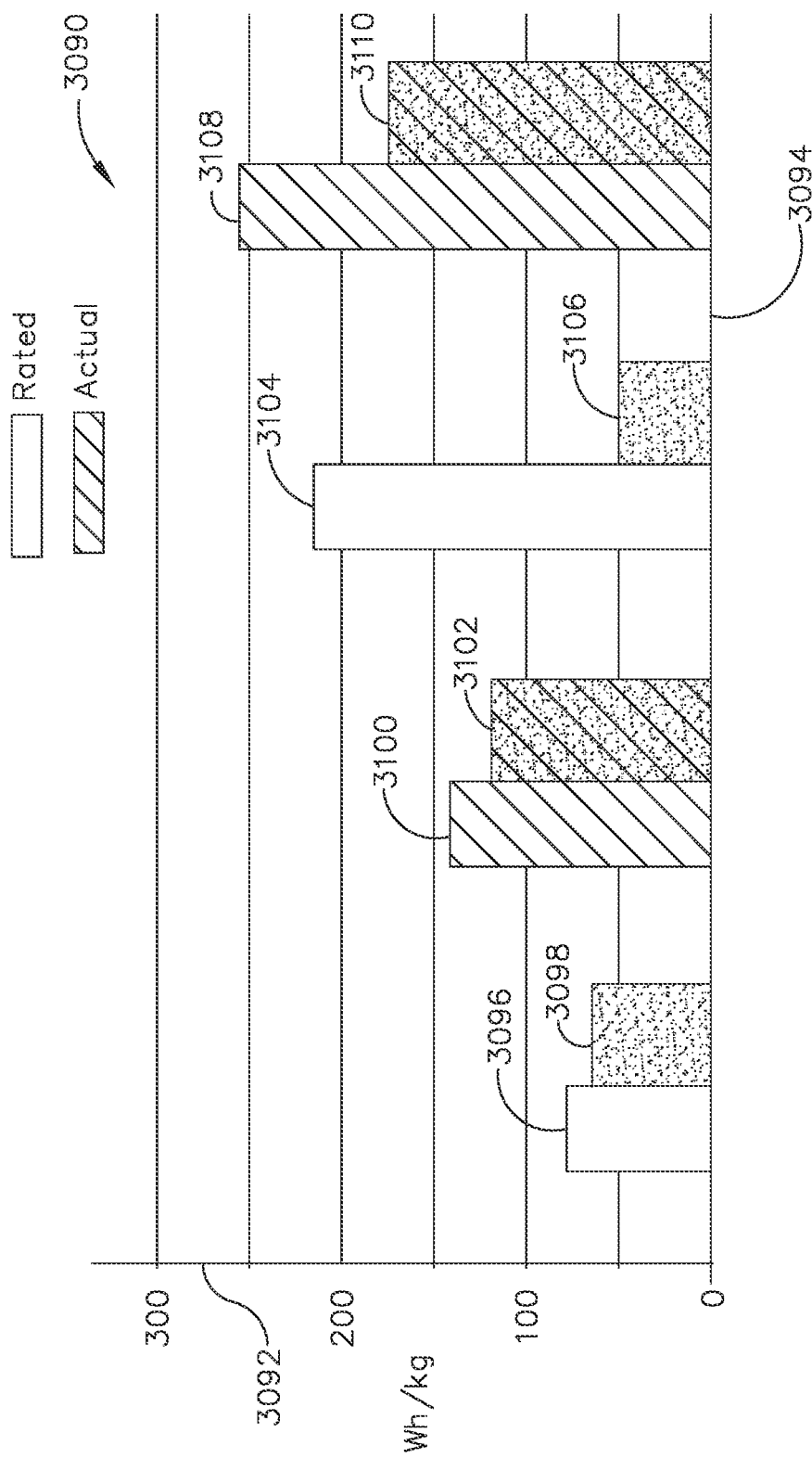
FIG. 36 illustrates a bar graph which shows comparisons of actual energy densities vs. rated energy densities for different battery packs which can be utilized with the surgical instrument of FIG. 29, in accordance with at least one aspect of the present disclosure.

FIG. 36 illustrates a bar graph 3090 which shows comparisons of actual energy densities vs. rated energy densities for different battery packs which can be utilized with the surgical instrument 3000, in accordance with at least one aspect of the present disclosure. For the graph 3090, watt-hours per kilogram of mass (Wh/Kg) are shown along the vertical axis 3092 and the different battery packs are shown along the horizontal axis 3094. For each different type of battery, the actual energy density is less than the rated energy density. In some instances such as for a nickel metal hydride rechargeable battery or a lithium ion rechargeable battery, the actual energy density is only approximately 15%-20% less than the rated energy density. For a primary/disposable lithium battery, the actual energy density is approximately 30% less than the rated energy density. For the alkaline manganese oxide (MnO$_2$) battery, the actual energy density is approximately 75% less than the rated energy density. More specifically, for a nickel metal hydride rechargeable battery, the bar 3096 representative of the rated energy density is shown as being approximately 75 Wh/Kg and the bar 3098 representative of the actual energy density is shown as being approximately 60 Wh/Kg. For a primary/disposable lithium ion battery, the bar 3100 representative of the rated energy density is shown as being approximately 140 Wh/Kg and the bar 3102 representative of the actual energy density is shown as being approximately 120 Wh/Kg. For the alkaline manganese oxide (MnO$_2$) battery, the bar 3104 representative of the rated energy density is shown as being approximately 210 Wh/Kg and the bar 3106 representative of the actual energy density is shown as being approximately 50 Wh/Kg. For the primary/disposable lithium battery, the bar 3108 representative of the rated energy density is shown as being approximately 250 Wh/Kg and the bar 3110 representative of the actual energy density is shown as being approximately 170 Wh/Kg. In view of the above, it will be appreciated that the calculated/rated energy density of a given battery which can be utilized with the surgical instrument 3000 can vary appreciably.

Figure 37:
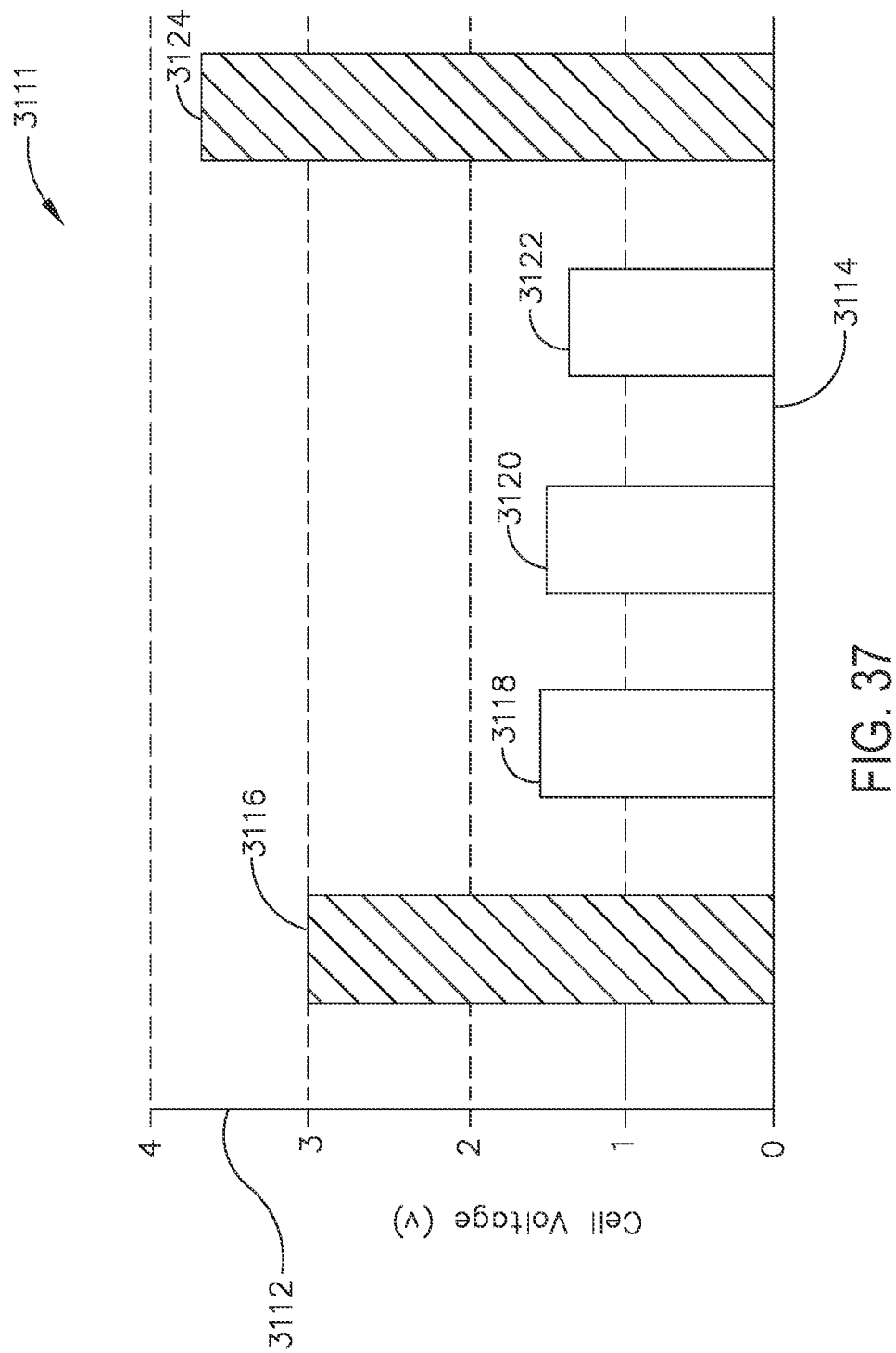
FIG. 37 illustrates a bar graph which shows nominal voltages of different battery packs which can be utilized with the surgical instrument of FIG. 29, in accordance with at least one aspect of the present disclosure.

FIG. 37 illustrates a bar graph 3111 which shows nominal voltages of different battery packs which can be utilized with the surgical instrument 3000, in accordance with at least one aspect of the present disclosure. For the graph 3111, units of cell voltage (V) are shown along the vertical axis 3112 and the different battery packs are shown along the horizontal axis 3114. For a primary/disposable lithium battery, the bar 3116 representative of the nominal cell voltage is shown as being approximately 3.0 volts. For a silver oxide battery, the bar 3118 representative of the nominal cell voltage is shown as being approximately 1.6 volts. For an alkaline manganese oxide (MnO$_2$) battery, the bar 3120 representative of the nominal cell voltage is shown as being approximately 1.5 volts. For a nickel metal hydride rechargeable battery, the bar 3122 representative of the nominal cell voltage is shown as being approximately 1.3 volts. For a lithium ion rechargeable battery, the bar 3124 representative of the nominal cell voltage is shown as being approximately 3.8 volts. In view of the above, it will be appreciated that the nominal voltages of different battery cells which can be utilized with the surgical instrument 3000 can vary appreciably.

Different brands of batteries, which can be made by different companies, can have different capacities (e.g., Ampere-Hours) for a given discharge rate (e.g., current/hour). For example, different brands of CR-123A/CR17335 batteries can have different capacities for given discharge rates. Different capacities for given discharge rates for different brands of CR-123A/CR17335 batteries are set forth in Table B1 below, where the respective discharge currents will discharge the respective batteries in one hour.

TABLE B1

Figure 38:
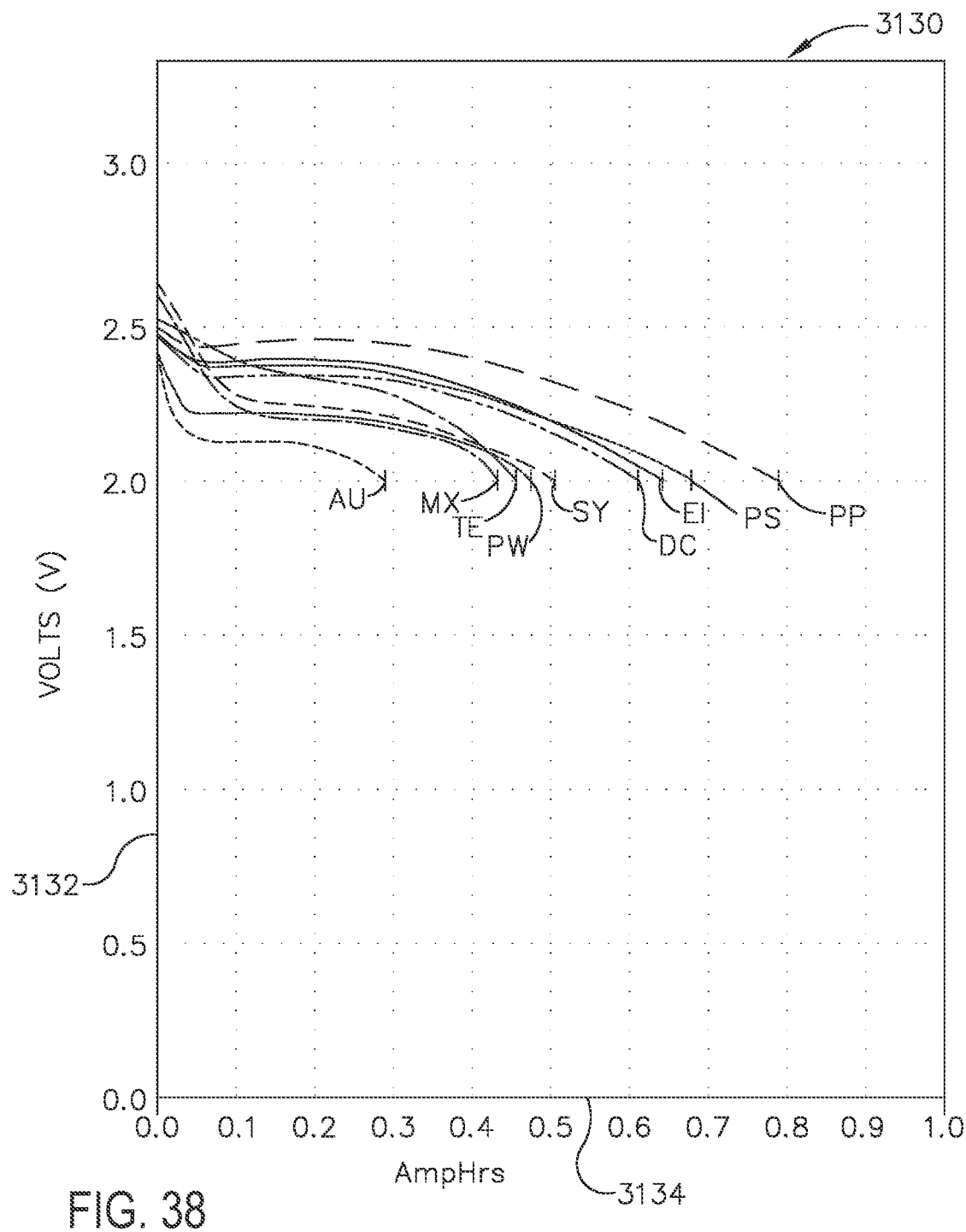
FIG. 38 illustrates a graph which shows discharge curves of different battery packs which can be utilized with the surgical instrument of FIG. 29, in accordance with at least one aspect of the present disclosure.

| Brand Name | Code Used in FIG. 38 | Amp-Hrs @ 100 mA Discharge Current | Amp-Hrs @ 700 mA Discharge Current | Amp-Hrs @ 1500 mA Discharge Current | Amp-Hrs @ 2200 mA Discharge Current |
|---|---|---|---|---|---|
| Autec | AU | 0.616 | 0.688 | 0.439 | 0.625 |
| Duracell | DC | | 1.234 | 0.632 | 0.730 |
| Energizer | EI | | 1.210 | 0.655 | 0.700 |
| Maxell | MX | | 1.100 | 0.466 | 0.543 |
| Panasonic | PS | | 1.260 | 0.692 | 0.692 |
| Powerizer | PW | | 0.880 | 0.499 | 0.502 |
| PowPower | PP | | 1.040 | 0.801 | 0.817 |
| Sanyo | SY | | 1.080 | 0.487 | 0.557 |
| Tenergy | TE | | 0.900 | 0.488 | 0.626 |

As shown in Table B1, the capacity of a battery can vary based on the discharge current. For example, for the Autec battery, the capacity is shown in Table B1 as being 0.616 Amp-Hrs at a 100 mA discharge current, 0.688 Amp-Hrs at a 700 mA discharge current, 0.439 Amp-Hrs at a 1500 mA discharge current and 0.625 AmpHrs at a 2200 mA discharge current. As also shown in Table B1, at a discharge current of 700 MA, the capacities of the different brands of CR-123A/CR17335 batteries can vary from a low of 0.688 Amp-Hrs for the Autec battery to a high of 1.260 Amp-Hrs for the Panasonic battery. At a discharge current of 1500 mA, the capacities of the different brands of CR-123A/CR17335 batteries can vary from a low of 0.439 Amp-Hrs for the Autec brand to a high of 0.801 Amp-Hrs for the PowPower brand. At a discharge current of 2200 mA, the capacities of the different brands of CR-123A/CR17335 batteries can vary from a low of 0.543 Amp-Hrs for the Maxell brand to a high of 0.817 Amp-Hrs for the PowPower brand. In view of the above, it will be appreciated that the capacities of different batteries which can be utilized with the surgical instrument 3000 can vary appreciably based on both the manufacturer/brand of the battery and the discharge current of the battery.

FIG. 38 illustrates a graph 3130 which shows discharge curves of different CR123A/CR17335 batteries which can be utilized with the surgical instrument 3000, in accordance with at least one aspect of the present disclosure. For the graph 3130, units of voltage (Volts) are shown along the vertical axis 3132, units of energy charge in Ampere-Hours (Amp-Hrs) are shown along the horizontal axis 3134, and the respective discharge curves are labeled with the two-letter codes listed in Table B1 (e.g., AU, DC, EI, MX, PS, PW, PP, SY, TE) for the different brands of batteries. The respective discharge curves correspond to the different brands of CR-123A/CR17335 batteries listed in Table B1 above, and are based on a discharge current of 1500 mA. As shown in FIG. 38, each brand of CR-123A/CR17335 battery can have its own characteristic nominal voltage and its own characteristic discharge curve. Stated differently, each brand of CR-123A/CR17335 battery can provide different voltages for different amounts of time. For example, the Autec battery (Au) is shown as having provided 0.3 Amp-Hrs of energy charge before its voltage drops to 2.0 volts whereas the PowPower battery (PP) is shown as having provided approximately 0.8 Amp-Hrs of energy charge before its voltage drops to 2.0 volts. In view of the above, it will be appreciated that the energy charge provided by different batteries which can be utilized with the surgical instrument 3000 can vary appreciably.

Figure 39:
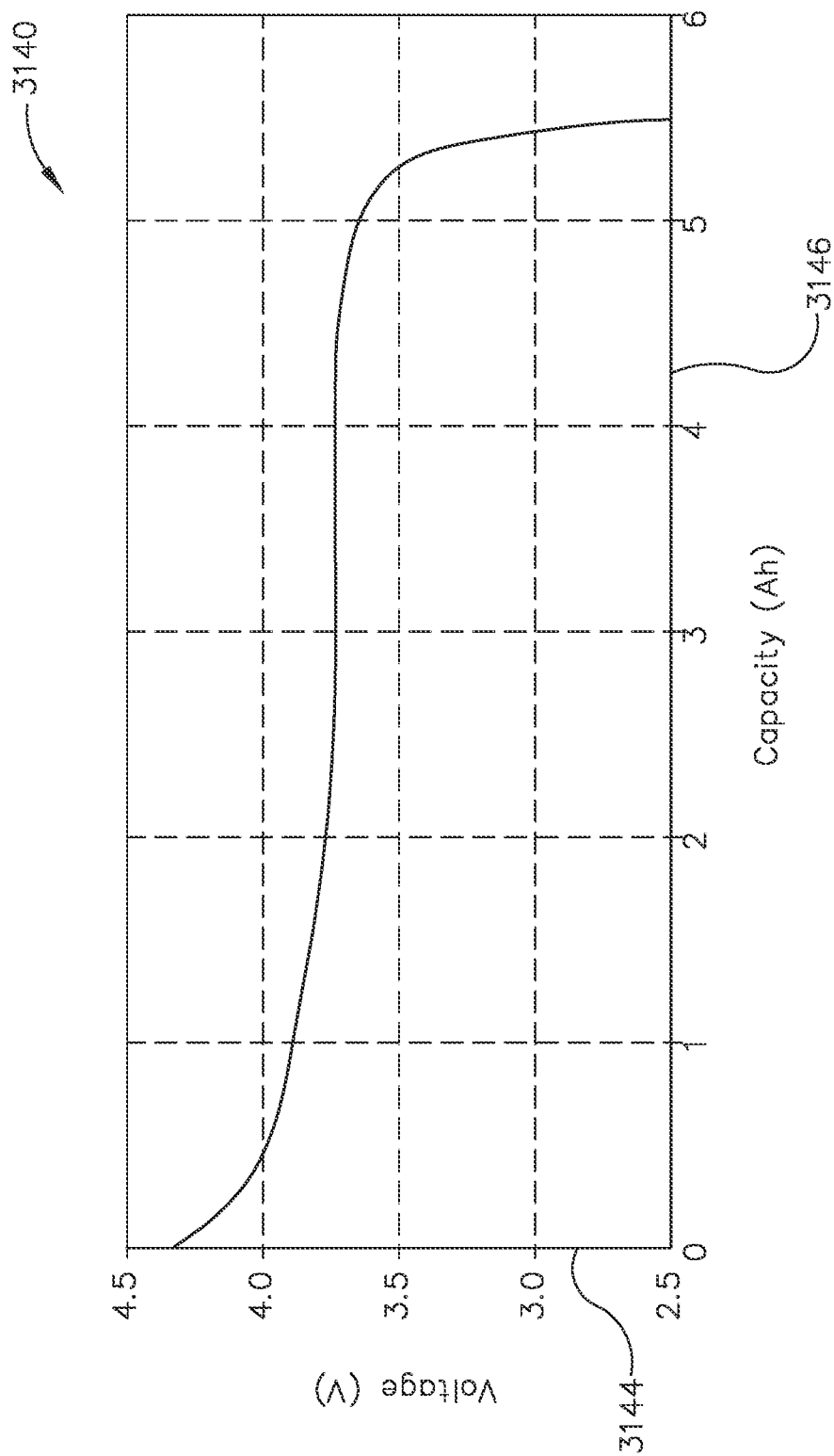
FIG. 39 illustrates a graph which shows a discharge curve for a lithium-Ion battery which can be utilized with the surgical instrument of FIG. 29, in accordance with at least one aspect of the present disclosure.

FIG. 39 illustrates a graph 3140 which shows a discharge curve 3142 for a lithium-ion battery which can be utilized with the surgical instrument 3000, in accordance with at least one aspect of the present disclosure. For the graph 3140, units of voltage (Volts) are shown along the vertical axis 3144 and units of capacity (Ah) are shown along the horizontal axis 3146. As shown in FIG. 39, the nominal voltage of the lithium-ion battery is approximately 4.3 volts, the lithium-ion battery provides a voltage of at least approximately 3.75 volts until the lithium-ion battery has discharged approximately 5.0 Ah of capacity, then the voltage provided by the lithium-ion battery drops significantly thereafter until the lithium-ion battery has fully discharged approximately 5.5 Ah of its capacity.

Figure 40:
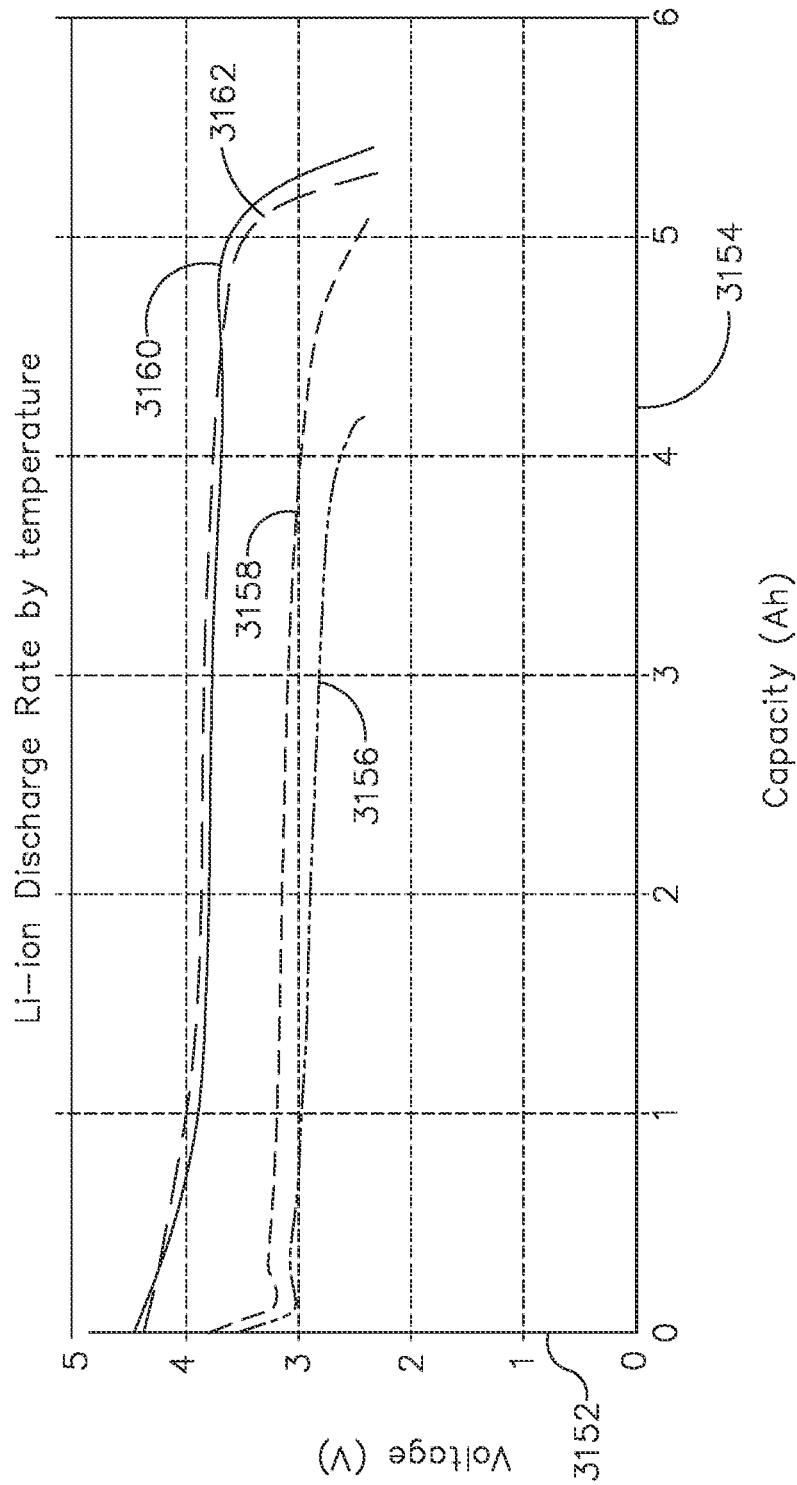
FIG. 40 illustrates a graph which shows different discharge curves for different temperatures of a lithium-ion battery which can be utilized with the surgical instrument of FIG. 29, in accordance with at least one aspect of the present disclosure.

The discharge rate of a given battery can vary by temperature, sometimes dramatically. FIG. 40 illustrates a graph 3150 which shows different discharge curves for different temperatures of a lithium-ion battery which can be utilized with the surgical instrument 3000, in accordance with at least one aspect of the present disclosure. For the graph 3150, units of voltage (Volts) are shown along the vertical axis 3152, units of capacity (Ah) are shown along the horizontal axis 3154, and the discharge current is 1100 mA which is equivalent to a C/5 rate for the lithium-ion battery. A C-rate is a measure of the rate at which a battery is discharged relative to its maximum capacity. As shown in FIG. 40, for the discharge curve 3156, which represents the discharge curve for the lithium-ion battery at −40° C., the lithium-ion battery provides a voltage of at least 3.0 volts until the lithium-ion battery has discharged approximately 2.0 Ah of capacity, then provides a voltage slightly below 3.0 volts until the lithium-ion battery has discharged approximately 3.5 Ah of capacity, then the voltage provided by the lithium-ion battery begins to drop significantly thereafter. For the discharge curve 3158, which represents the discharge curve for the lithium-ion battery at −30° C., the lithium-ion battery provides a voltage of at least 3.0 volts until the lithium-ion battery has discharged approximately 4.1 Ah of capacity, then the voltage provided by the lithium-ion battery begins to drop significantly thereafter. For the discharge curve 3160, which represents the discharge curve for the lithium-ion battery at 20° C., the lithium-ion battery provides a voltage of at least 3.8 volts until the lithium-ion battery has discharged approximately 4.8 Ah of capacity, then the voltage provided by the lithium-ion battery begins to drop significantly thereafter. For the discharge curve 3162, which represents the discharge curve for the lithium-ion battery at 60° C., the lithium-ion battery provides a voltage of at least 3.80 volts until the lithium-ion battery has discharged approximately 4.5 Ah of capacity, then the voltage provided by the lithium-ion battery begins to drop significantly thereafter. In view of the above, it will be appreciated that the discharge rate of a given lithium-ion battery does not vary linearly by temperature, and temperatures which are too cold or too hot can negatively affect the performance of the lithium-ion battery.

Figure 41:
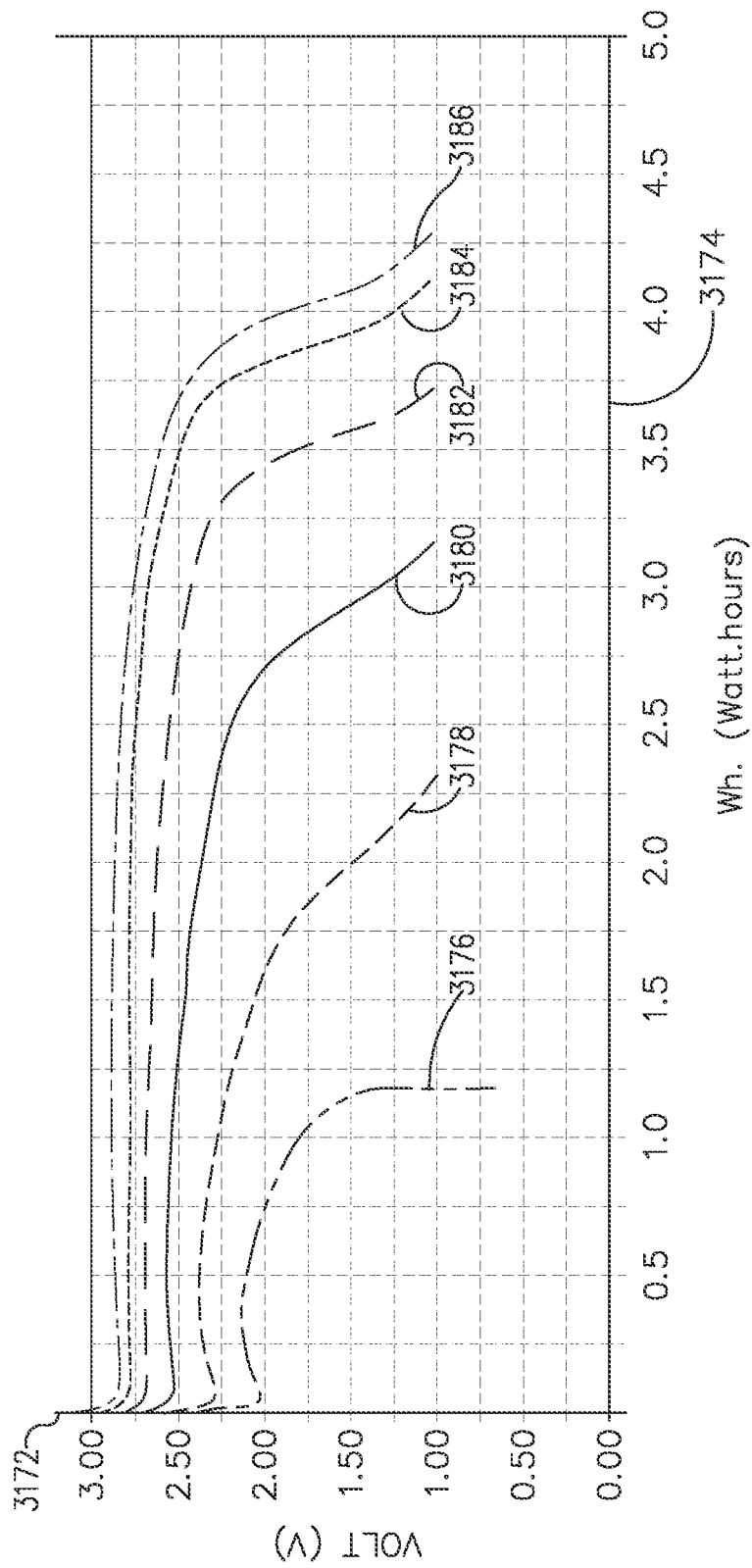
FIG. 41 illustrates a graph which shows different discharge curves for different discharge rates of a CR123 battery which can be utilized with the surgical instrument of FIG. 29, in accordance with at least one aspect of the present disclosure.

The energy capacity of a given battery can vary based on the rate the battery is discharged. FIG. 41 illustrates a graph 3170 which shows different discharge curves for different discharge rates of a CR123 battery which can be utilized with the surgical instrument 3000, in accordance with at least one aspect of the present disclosure. For the graph 3170, units of voltage (Volts) are shown along the vertical axis 3172, units of power in Watt-Hours (Wh) are shown along the horizontal axis 3174, and the CR123 battery is a Panasonic Lithium Power battery. As shown by the discharge curve 3176, for a discharge current of 3.0 amperes, the energy capacity of the battery is approximately 1.2 Wh. As shown by the discharge curve 3178, for a discharge current of 2.0 amperes, the energy capacity of the battery is approximately 2.3 Wh. As shown by the discharge curve 3180, for a discharge current of 1.0 amperes, the energy capacity of the battery is approximately 3.2 Wh. As shown by the discharge curve 3182, for a discharge current of 0.5 amperes, the energy capacity of the battery is approximately 3.7 Wh. As shown by the discharge curve 3184, for a discharge current of 0.2 amperes, the energy capacity of the battery is approximately 4.1 Wh. As shown by the discharge curve 3186, for a discharge current of 0.1 amperes, the energy capacity of the battery is approximately 4.25 Wh. In view of the above, it will be appreciated that, in general, the lower the discharge current, the greater the energy capacity of the CR123 battery. Stated differently, in general, the higher the discharge current, the lower the energy capacity of the CR123 battery.

Figure 42:
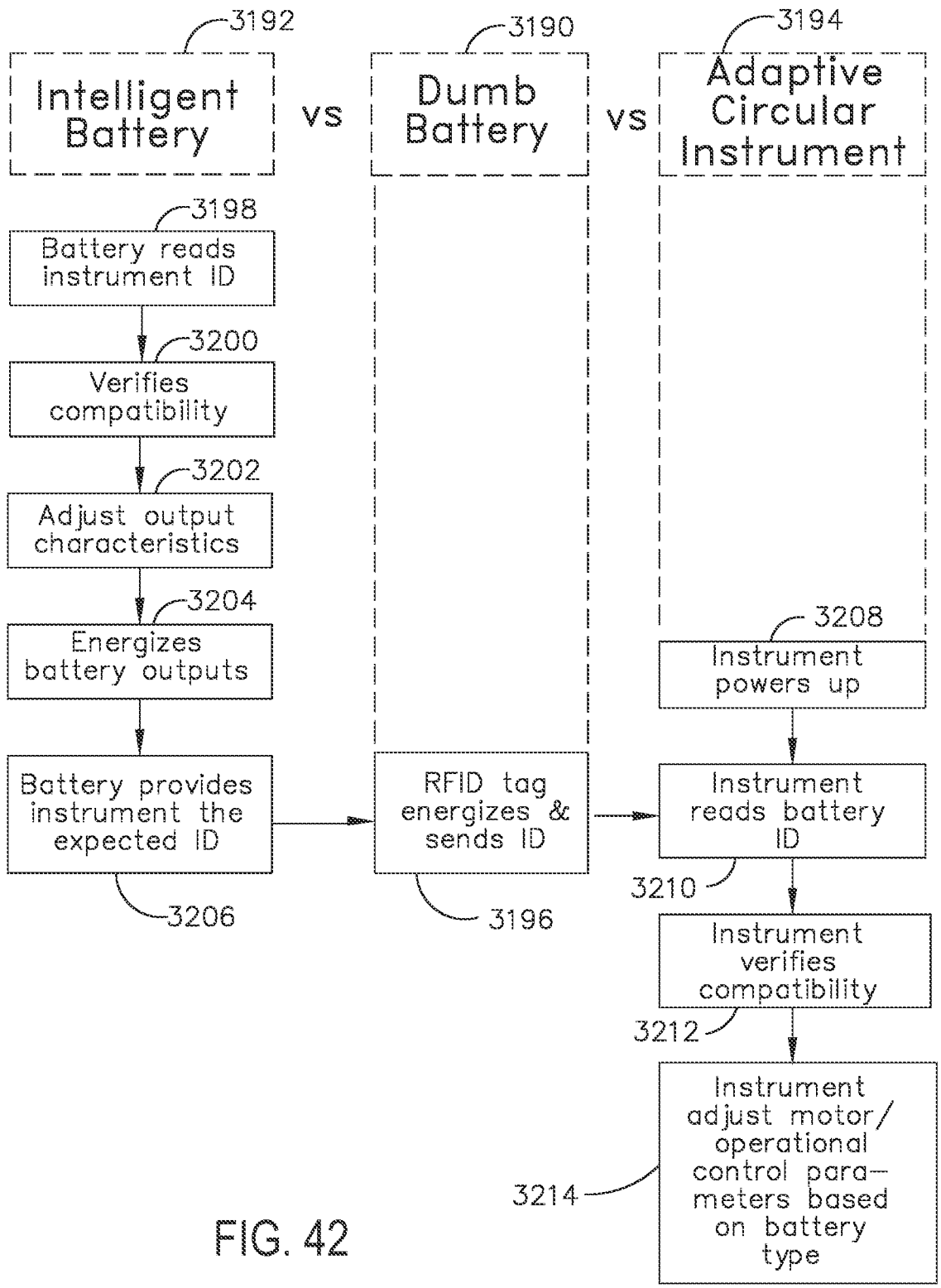
FIG. 42 illustrates various operational differences between a dumb battery, an intelligent battery and an adaptive surgical instrument, in accordance with at least one aspect of the present disclosure.

FIG. 42 illustrates various operational differences between a dumb battery 3190, an intelligent battery 3192 and an adaptive surgical instrument 3194, in accordance with at least one aspect of the present disclosure. In various aspects, the battery pack 3006 can be configured as the dumb battery 3190. For the dumb battery 3190, an RFID tag of the dumb battery 3190 is energized 3196 when the dumb battery 31900 is brought into proximity with or received by a surgical instrument (e.g., the surgical instrument 3000), and the dumb battery 3190 then communicates battery identification information to an RFID scanner of the surgical instrument. The surgical instrument may then utilize the battery identification information as described above to verify the compatibility of the dumb battery 3190 with the surgical instrument.

In various aspects, the battery pack 3006 can be configured as the intelligent battery 3192. The intelligent battery 3192 is configured to read 3198 identification information of a surgical instrument, determine/verify 3200 whether the identified surgical instrument is compatible for use with the intelligent battery 3192, adjust 3202 the output characteristics of the intelligent battery 3192 as needed for proper performance of the identified surgical instrument, energize 3204 the outputs of the intelligent battery 3192, then provide 3206 the identified surgical instrument with expected battery identification information so that the identified surgical instrument recognizes it is being powered by a known compatible battery. In this way, newer more intelligent batteries that are not necessarily identified in compatibility databases/lookup tables of the identified surgical instrument can nonetheless be permitted to provide power to the identified surgical instrument. As described in more detail hereinafter, the intelligent battery 3192 can mimic the performance of a known compatible battery.

In various aspects, the surgical instrument 3000 can be configured as the adaptive surgical instrument 3194. For the adaptive surgical instrument 3194, the adaptive surgical instrument 3194 powers up 3208, reads 3210 the battery identification information provided by a battery such as, for example, the intelligent battery 3192 or the dumb battery 3190 when the battery is brought in proximity to or is received by the adaptive surgical instrument 3194, determines/verifies 3212 whether the identified battery is compatible for use with the adaptive surgical instrument 3194, then adjusts 3214 the operation (e.g., motor operation, operational control parameters, etc.) of the adaptive surgical instrument 3194 based on the received battery identification information. For example, in various aspects, the operation of the adaptive surgical instrument 3194 can vary depending on whether the identified battery is rechargeable or non-rechargeable, the chemistry of the identified battery (e.g., nickel metal hydride, lithium ion, alkaline manganese oxide, lithium, etc.) and/or the output capabilities of the identified battery. In this way, the adaptive surgical instrument 3194 can utilize a much wider variety of different batteries than otherwise possible.

For a given battery pack, the relationship between the voltage potential of the battery pack and the current drawn from the battery pack is given by the equation V=IR, where V is the voltage of the battery pack, I is the current drawn from the battery pack and R is the resistance of the load connected to the battery pack. Because different battery packs can have different voltage potentials and different internal resistances, the current to be drawn from the battery pack can vary from battery pack to battery pack when powering a given surgical instrument. Voltage and current values for two different battery packs, one which includes four CR123A batteries and one which includes four 15270 batteries, are shown in Table B2 below for various resistances.

TABLE B2

| Battery | Resistance | Voltage | Current |
| --- | --- | --- | --- |
| CR123A | 1.5 ohms | 7.5 volts | 5.0 amperes |
| 15270 | 1.68 ohms | 15.0 volts | 8.9 amperes |

Figure 43:
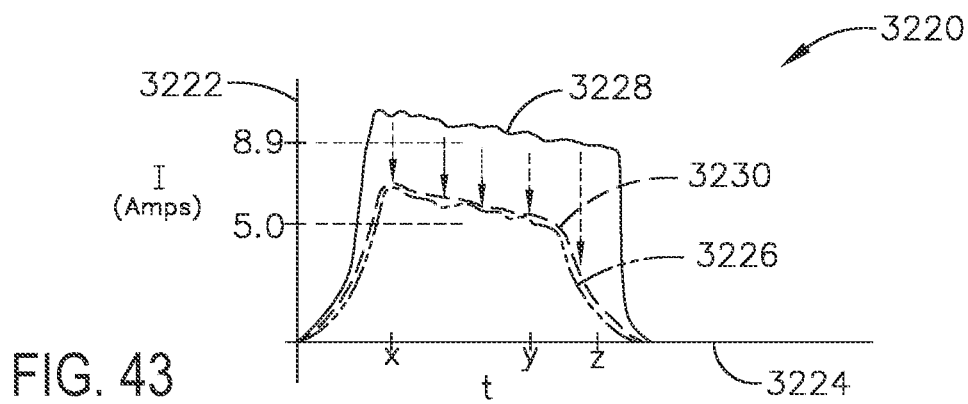
FIG. 43 illustrates a graph which shows the output current capabilities of different battery packs when utilized with the adaptive surgical instrument of FIG. 42, in accordance with at least one aspect of the present disclosure.

FIG. 43 illustrates a graph 3220 which shows the output current capabilities of different battery packs when utilized with the adaptive surgical instrument 3194, in accordance with at least one aspect of the present disclosure. For the graph 3220, units of current I (amperes) are shown along the vertical axis 3222 and units of time are shown along the horizontal axis 3224. As shown in FIG. 43, the current output 3226 from a standard CR-123 battery pack (e.g., 4 batteries) can average approximately 5.0 amperes between the times X and Y, and the current output 3228 from a standard 15270 battery can average approximately 8.9 amperes between the times X and Z. By utilizing the above-described RFID capability, the adaptive surgical instrument 3194 can cause the current drawn from the standard 15270 battery pack to mimic 3230 the current which would be drawn from the standard CR-123 battery pack. In various aspects, the adaptive surgical instrument 3194 can achieve this by adapting a speed control algorithm of the adaptive surgical instrument 3194 to lower the speed of the electric motor 3008, by increasing the resistance which is seen by the 15270 battery pack, by using a voltage divider, etc. to cause the 15270 battery pack to adjust its current output to effectively mimic the current output of the standard CR-123 battery pack. For example, according to various aspects, a processor of a control circuit of the adaptive surgical instrument 3194 can communicate an instruction which operates to adapt a speed control algorithm of the adaptive surgical instrument 3194 or by using a voltage divider, for example. As the surgical instrument 3000 may be configured as the adaptive surgical instrument 3194, the control circuit of the adaptive surgical instrument 3194 may be similar or identical to the control circuit 1210 and/or the control circuit 3014. For instances where the 15270 battery pack is an intelligent battery pack (e.g., the intelligent battery 3192), the adaptive surgical instrument 3194 can communicate instructions to the intelligent battery pack to operate as a CR-123 battery pack would.

Figure 44:
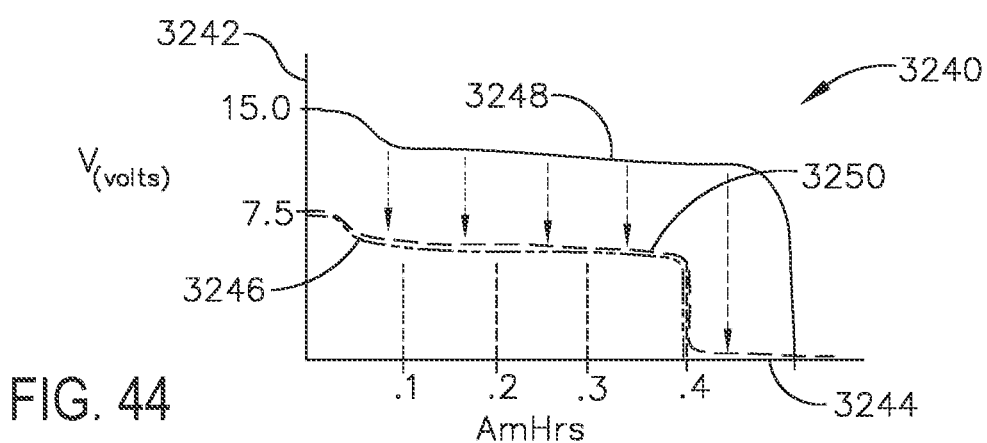
FIG. 44 illustrates a graph which shows the output voltage capabilities of different battery packs when utilized with the adaptive surgical instrument of FIG. 42, in accordance with at least one aspect of the present disclosure.

FIG. 44 illustrates a graph 3240 which shows the output voltage capabilities of different battery packs when utilized with the adaptive surgical instrument 3194, in accordance with at least one aspect of the present disclosure. For the graph 3240, units of voltage (Volts) are shown along the vertical axis 3242 and units of capacity in Ampere-Hours (AmHrs) are shown along the horizontal axis 3244. As shown in FIG. 44, the voltage output 3246 from a standard CR-123 battery pack discharging at a rate of 1.25 amperes per hour can average approximately 7.0 volts during the time the standard CR-123 battery pack has discharged from approximately 0.05 AmHrs to approximately 0.4 AmHrs, and the voltage output 3248 from a standard 15270 battery pack can average approximately 14.0 volts during the time the standard 15270 battery pack has discharged from approximately 0.08 AmHrs to approximately 0.5 AmHrs. By utilizing the above-described RFID capability, the adaptive surgical instrument 3194 can cause the voltage provided by the standard 15270 battery pack to mimic 3250 the voltage provided by the standard CR-123 battery pack. In various aspects, the adaptive surgical instrument 3194 can achieve this by adapting a speed control algorithm of the adaptive surgical instrument 3194 to lower the speed of the electric motor 3008, by increasing the resistance which is seen by the 15270 battery pack, etc. to cause the 15270 battery pack to adjust its voltage output to effectively mimic the voltage output of the standard CR-123 battery pack. For instances where the 15270 battery pack is an intelligent battery pack (e.g., the intelligent battery 3192), the adaptive surgical instrument 3194 can communicate instructions to the intelligent battery pack to operate as a CR-123 battery pack would. In at least one example, a voltage divider could be employed to adjust the voltage output of the battery pack.

Figure 45:
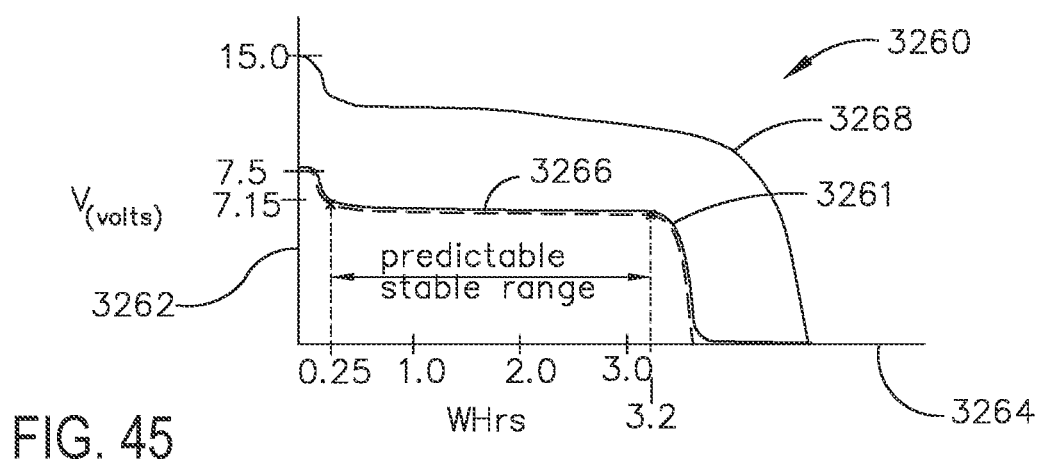
FIG. 45 illustrates a graph which shows the output voltage capabilities of different battery packs when utilized with the adaptive surgical instrument of FIG. 42, in accordance with at least one aspect of the present disclosure.

FIG. 45 illustrates a graph 3260 which shows the output voltage capabilities of different battery packs when utilized with the adaptive surgical instrument 3194, in accordance with at least one aspect of the present disclosure. For the graph 3260, units of voltage (Volts) are shown along the vertical axis 3262 and units of power in Watt-Hours (Whrs) are shown along the horizontal axis 3264. The graph 3260 is similar to the graph 3240, but is different in that units of power are shown along the horizontal axis 3264. As shown in FIG. 45, the voltage output 3266 from a standard CR-123 battery pack can average approximately 7.15 volts during the time the standard CR-123 battery pack has provided approximately 0.25 watt-hours of power to the time the standard CR-123 battery pack has provided approximately 3.2 watt-hours of power. During this time period, the voltage provided by the standard CR-123 battery pack is both predictable and stable. Therefore, when the above-described RFID capability is utilized by the adaptive surgical instrument 3194 to cause the voltage 3268 provided by the standard 15270 battery pack to mimic 3261 the voltage provided by the standard CR-123 battery pack. It follows that the "adjusted" voltage provided by the standard CR-123 battery pack is also both predictable and stable during the above-described time period.

The dimensional size of many surgical instruments continues to get smaller and smaller. Despite the reduced size, many of the surgical instruments have to accommodate increasing loads, higher performance requirements, and higher over stress conditions. For surgical instruments which include radio-frequency identification (RFID) technology such as radio-frequency identification tags and/or radio-frequency identification scanners, in order to meet the reduced size requirements, the profile of the RFID tags and/or RFID scanners and the associated electronics are continually getting smaller and lower. These smaller systems may not have the memory overhead, processing power, or capacities (range, power, etc.) necessary to accomplish all of the tasks a user would like from the identification systems of the surgical instruments. Therefore, in order to provide additional capabilities like encryption, authentication of multiple components, compatibility verification of multiple components, reprocessing tracking, etc., in various aspects, it can be desirable to utilize encryption/decryption keys which are external to the surgical instrument, and printed or secondary stored data locations to help expand the capabilities and capacities of these smaller less capable systems.

Returning to FIG. 42, it will be appreciated that the above-described functionality of the adaptive surgical instrument 3194 is dependent upon the RFID tag 3010 of the battery pack 3006 being able to communicate the battery identification information to the adaptive surgical instrument 3194 and the RFID scanner 3012 of the adaptive surgical instrument 3194 being able to read the battery identification information provided by the RFID tag 3010 of the battery pack 3006. In certain instances, the adaptive surgical instrument 3194 is unable to determine the compatibility of the battery pack 3006. For example, in instances where the RFID tag 3010 of the battery pack 3006 has experienced a failure (e.g., a failure in an integrated circuit chip of the RFID tag 3010, a failure in the electrical connection between the integrated circuit chip and the antenna of the RFID tag 3010, etc.) such that the RFID tag 3010 fails to communicate the battery identification information, the adaptive surgical instrument 3194 is unable to determine the compatibility of the battery pack 3006. Similarly, in instances where the RFID scanner 3012 of the adaptive surgical instrument 3194 has experienced a failure (e.g., a failure of a wire in the circuitry of the RFID scanner 3012, a failure in a communication board of the RFID scanner 3012, etc.) such that the adaptive surgical instrument 3194 is not able to capture, process and/or communicate the battery identification information provided by the battery pack 3006, the adaptive surgical instrument 3194 is unable to determine the compatibility of the battery pack 3006. For such instances, it is desirable to have secondary/alternative ways of determining the compatibility of a given battery pack with a given adaptive surgical instrument.

Figure 46:
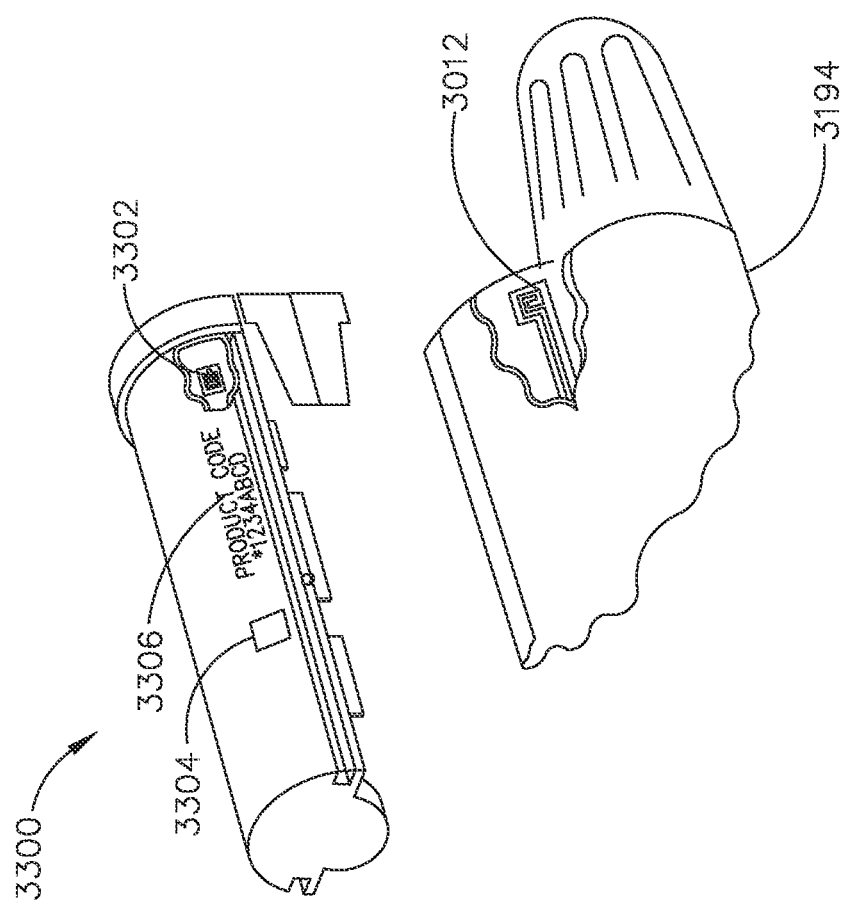
FIG. 46 illustrates a battery for use with the adaptive surgical instrument of FIG. 42, in accordance with at least aspect of the present disclosure.

FIG. 46 illustrates a battery 3300 for use with the adaptive surgical instrument 3194 of FIG. 42, in accordance with at least aspect of the present disclosure. The battery 3300 may be any suitable type of battery, and may include any suitable number of cells. For brevity, the battery 3300 will be referred to hereinafter as the battery pack 3300. The battery pack 3300 is similar to the battery pack 3006 in that the battery pack 3300 includes a radio-frequency identification (RFID) tag 3302, but is different in that the battery pack 3300 also includes a quick response (QR) code 3304 and/or a product code 3306 positioned on an external surface of the battery pack 3300. The RFID tag 3302 may be similar or identical to the RFID tag 3010.

The QR code 3304 is a machine-readable optical label which contains information about the battery pack 3300. Such information can include, for example, a battery identification number, the manufacturer/brand of batteries in the battery pack 3300, the chemistry/type of batteries (lithium, lithium-ion, etc.) in the battery pack 3300, whether the type of batteries in the battery pack 3300 are chargeable or non-rechargeable, the capacity of the battery pack 3300, the nominal voltage of the batteries in the battery pack 3300, the current draw characteristics of the batteries in the battery pack 3300, other output characteristics of the battery pack 3300, etc. In various aspects, a smartphone, tablet, etc. equipped with a camera and a QR code scanner application can be utilized to read the QR code 3304 from the battery pack 3300.

The product code 3306 may include any sequence of numbers, letters, symbols, etc. which uniquely identify the battery pack 3300. In some aspects, the product code 3306 may be utilized to assist the adaptive surgical instrument 3194 in determining whether the battery pack 3300 is compatible for use with the adaptive surgical instrument 3194.

Figure 47:
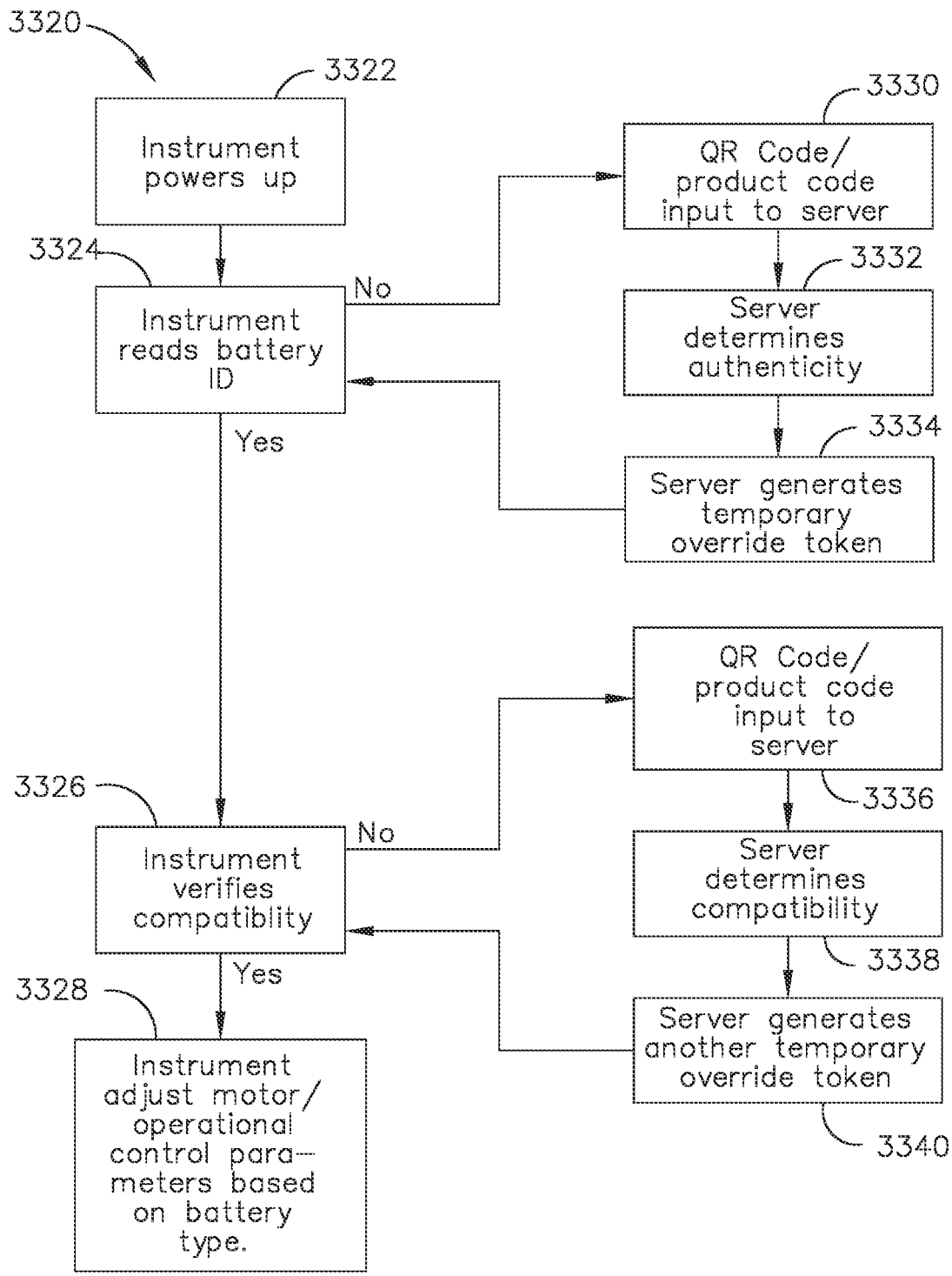
FIG. 47 illustrates a logic flow diagram of a process depicting a control program or a logic configuration for operating the adaptive surgical instrument of FIG. 42, in accordance with at least one aspect of the present disclosure.

FIG. 47 illustrates a logic flow diagram of a process 3320 depicting a control program or a logic configuration for operating the adaptive surgical instrument 3194, in accordance with at least one aspect of the present disclosure. In at least one example, the process 3320 is executed by a control circuit 1210 (FIG. 15) that includes a processor 1214 and a memory 1212 storing a set of computer-executable instructions that, when executed by the processor 1214, cause the processor 1214 to perform of the process 3320. In certain examples, a set of computer-executable instructions, stored in the memory 1212 may cause the processor 1214 to perform discrete portions of the process 3320. Although the process 3320 is described as being executed by a control circuit 1210, this is merely for brevity, and it should be understood that the process 3320 and other processes described herein, or portions thereof, can be executed by circuitry that can include a variety of hardware and/or software components and may be located in or associated with various suitable systems such as, for example, combinational logic circuits or sequential logic circuits.

The process 3320 includes ways/methods for determining whether a given battery pack such as, for example, the battery pack 3300, is compatible for use with the adaptive surgical instrument 3194. For brevity, the process 3320 will be described in the context of its applicability with the battery pack 3300. The alternative ways/methods may be utilized in instances where (1) the battery pack 3300 is unable to communicate the battery identification information to the adaptive surgical instrument 3194 and/or the RFID scanner 3012 of the adaptive surgical instrument 3194 is unable to read battery identification information provided by the RFID tag 3302 of the battery pack 3300 and (2) the adaptive surgical instrument 3194 is unable to determine/verify the compatibility of the battery pack 3300 with the adaptive surgical instrument 3194.

As shown in FIG. 47, the adaptive surgical instrument 3194 powers up 3322, then tries to read 3324 the battery identification information provided by the battery pack 3300, when the battery pack 3300 is brought in proximity to or is received by the adaptive surgical instrument 3194. In instances where the adaptive surgical instrument 3194 is able to read 3324 the battery identification information, a control circuit of the adaptive surgical instrument 3194 (e.g., the control circuit 3014 and/or another control circuit of the adaptive surgical instrument 3194) determines/verifies 3326 whether the identified battery is compatible for use with the adaptive surgical instrument 3194, then adjusts 3328 the operation (e.g., motor operation, operational control parameters, etc.) of the adaptive surgical instrument 3194 based on the received battery identification information, as described elsewhere herein in greater detail. For example, in various aspects, the operation of the adaptive surgical instrument 3194 can vary depending on whether the identified battery is rechargeable or non-rechargeable, the chemistry of the identified battery (e.g., nickel metal hydride, lithium ion, alkaline manganese oxide, lithium, etc.) and/or the output capabilities of the identified battery. In this way, the adaptive surgical instrument 3194 can utilize a much wider variety of different batteries than otherwise possible. In at least one aspect, in addition to storing information in the form of a compatibility database or a lookup table, the memory 3018 of the control circuit 3014 may also store information in the form of an authentication database.

However, in instances where the adaptive surgical instrument 3194 is unable to read 3324 the battery identification information (e.g., due to failures in either the RFID tag 3302 of the battery pack 3300 and/or failures of the RFID scanner 3012 of the adaptive surgical instrument 3194), an indication such as, for example, a visual indication or an audible indication, can be provided through the indicator 1209 (FIG. 19) which notifies a user of the failure of the adaptive surgical instrument 3194 to read 3324 the battery identification information. The user or another party may then cause the QR code 3304 and/or the product code 3306 of the battery pack 3300 to be input 3330 to a server. In at least one aspect, the smartphone, tablet, etc. utilized to capture the QR code 3304 may communicate the QR code 3304 to the server through a wired or wireless connection. The communication of the QR code 3304 to the server may be an encrypted communication, just as the communications between the battery pack 3300 and adaptive surgical instrument 3194 may be. The server may be any suitable server such as, for example, a server of a surgical hub system. An example of a surgical hub system is described in U.S. patent application Ser. No. 16/209,395, titled METHOD OF HUB COMMUNICATION, and filed Dec. 4, 2018, the entire content of which is hereby incorporated by reference herein.

The server is configured to compare the battery identification information provided by the QR code 3304 and/or the product code 3306 to a database/table to determine 3332 the authenticity of the battery pack 3300 identified by the QR code 3304 and/or product code 3306. For instances where the server determines that the battery pack 3300 identified by the QR code 3304 and/or product code 3306 is authenticated, the server can generate 3334 a temporary override token which is communicated through a wired or wireless connection to the adaptive surgical instrument 3194, where a control circuit of the adaptive surgical instrument 3194 (e.g., the control circuit 3014 and/or another control circuit of the adaptive surgical instrument 3194) utilizes the temporary override token as a substitute for the unread battery identification information. The communication of the temporary override token to the adaptive surgical instrument 3194 may be an encrypted communication. The temporary override token effectively acts to override the lockout of the operation of the adaptive surgical instrument 3194 which can occur when the battery pack 3300 is not authenticated by the adaptive surgical instrument 3194. In at least one aspect, the lockout operation is initiated and/or carried out by the control circuit 3014. For instances where the battery pack 3300 identified by the QR code 3304 and/or product code 3306 is not authenticated, an indication such as, for example, a visual indication or an audible indication, can be provided through the indicator 1209, which notifies a user of the failure to authenticate the battery pack 3300.

With the temporary override token in place, the adaptive surgical instrument 3194 may then determine/verify 3326 whether the identified battery pack 3300 is compatible for use with the adaptive surgical instrument 3194 as described above. However, if for any reason the adaptive surgical instrument 3194 is unable to verify that the identified battery pack 3300 is compatible with the adaptive surgical instrument 3194, an indication such as, for example, a visual indication or an audible indication, can be provided which notifies a user of the failure of the adaptive surgical instrument 3194 to verify the compatibility of the battery pack 3300 with the adaptive surgical instrument 3194. In such instances, the user or another party may then cause the QR code 3304 and/or the product code 3306 of the battery pack 3300 to be input 3336 to the server. The server is further configured to compare the battery identification information provided by the QR code 3304 and/or the product code 3306 to a database/table to determine 3338 whether the battery pack 3300 identified by the QR code 3304 and/or product code 3306 is compatible for use with the adaptive surgical instrument 3194. For instances where the server determines that the battery pack 3300 identified by the QR code 3304 and/or product code 3306 is compatible with the adaptive surgical instrument 3194, the server can generate 3340 another temporary override token which is communicated to the adaptive surgical instrument 3194, where a control circuit of the adaptive surgical instrument 3194 (e.g., the control circuit 3014 and/or another control circuit of the adaptive surgical instrument 3194) utilizes the temporary override token as a substitute for the unverified compatibility determination. The communication of another temporary override token to the adaptive surgical instrument 3194 may be an encrypted communication. The other temporary override token effectively acts to override the lockout of the operation of the adaptive surgical instrument 3194 which can occur when the compatibility of the battery pack 3300 is not verified by the adaptive surgical instrument 3194. The adaptive surgical instrument 3194 may thereafter adjust 3328 the operation (e.g., motor operation, operational control parameters, etc.) of the adaptive surgical instrument 3194 as described above.

Although the description of the process 3320 of FIG. 47 was limited to (1) determining authenticity of the battery pack 3300 and (2) determining/verifying compatibility of the battery pack 3300 and the adaptive surgical instrument 3194, the basic logic of the process 3320 may also be utilized to determine the compatibility of any number of components and/or sub-systems which can be utilized with the adaptive surgical instrument 3194. For example, by providing a given staple cartridge and a given anvil with the above-described RFID capability, the adaptive surgical instrument 3194 can receive staple cartridge identification information from the RFID tag of the given staple cartridge and anvil identification information from the RFID tag of the given anvil. In at least one aspect, the shaft assembly of the adaptive surgical instrument 3194 is configured to receive the anvil, and the adaptive surgical instrument 3194 is configured to receive the staple cartridge. In instances where the staple cartridge identification information and the anvil identification information are encrypted, a control circuit of the adaptive surgical instrument 3194 (e.g., the control circuit 3014 and/or another control circuit of the adaptive surgical instrument 3194) can utilize a universal private key to decrypt the received staple cartridge identification information and the received anvil identification information, then determine/verify the compatibility of the given staple cartridge with the given anvil, as well as the compatibility of the given staple cartridge and the given anvil with the adaptive surgical instrument 3194. In instances where it is determined that the staple cartridge is not compatible with the anvil, the server and/or another system may provide an indication of the source of the incompatibility issue and provide details regarding how to correct the incompatibility issue through the indicator 1209, for example.

Additionally, the basic logic of the process 3320, and QR codes, product codes and one or more servers as described above, can be utilized to determine authenticity/compatibility of any number of components and/or sub-systems when the adaptive surgical instrument 3194 is unable to receive/read the applicable identification information. For example, in addition to determining the authenticity of the battery pack 3300 and the compatibility of the battery pack 3300 with the adaptive surgical instrument 3194 when the adaptive surgical instrument 3194 is unable to receive/read the applicable identification information (e.g., due to a failure of the RFID tags and/or RFID scanners), the same basic process of utilizing the QR codes, product codes and one or more servers can be utilized to determine the authenticity of anvils and staple cartridges, as well as the compatibility of a given anvil with a given cartridge, as well as the compatibility of the given anvil and the given cartridge with the adaptive surgical instrument 3194. In instances where the server determines that the staple cartridge is not compatible with the anvil, the server and/or another system may provide an indication of the source of the incompatibility issue and provide details regarding how to correct the incompatibility issue.

Additionally, as many components and sub-systems which can be utilized with the adaptive surgical instrument 3194 come in a packaging, if applicable QR codes and/or product codes are included on the packaging, the basic logic of the process 3320, and QR codes, product codes and one or more servers as described above, can be utilized to determine authenticity/compatibility of any number of components and/or sub-systems which are presumed to be in the packaging.

Figure 48:
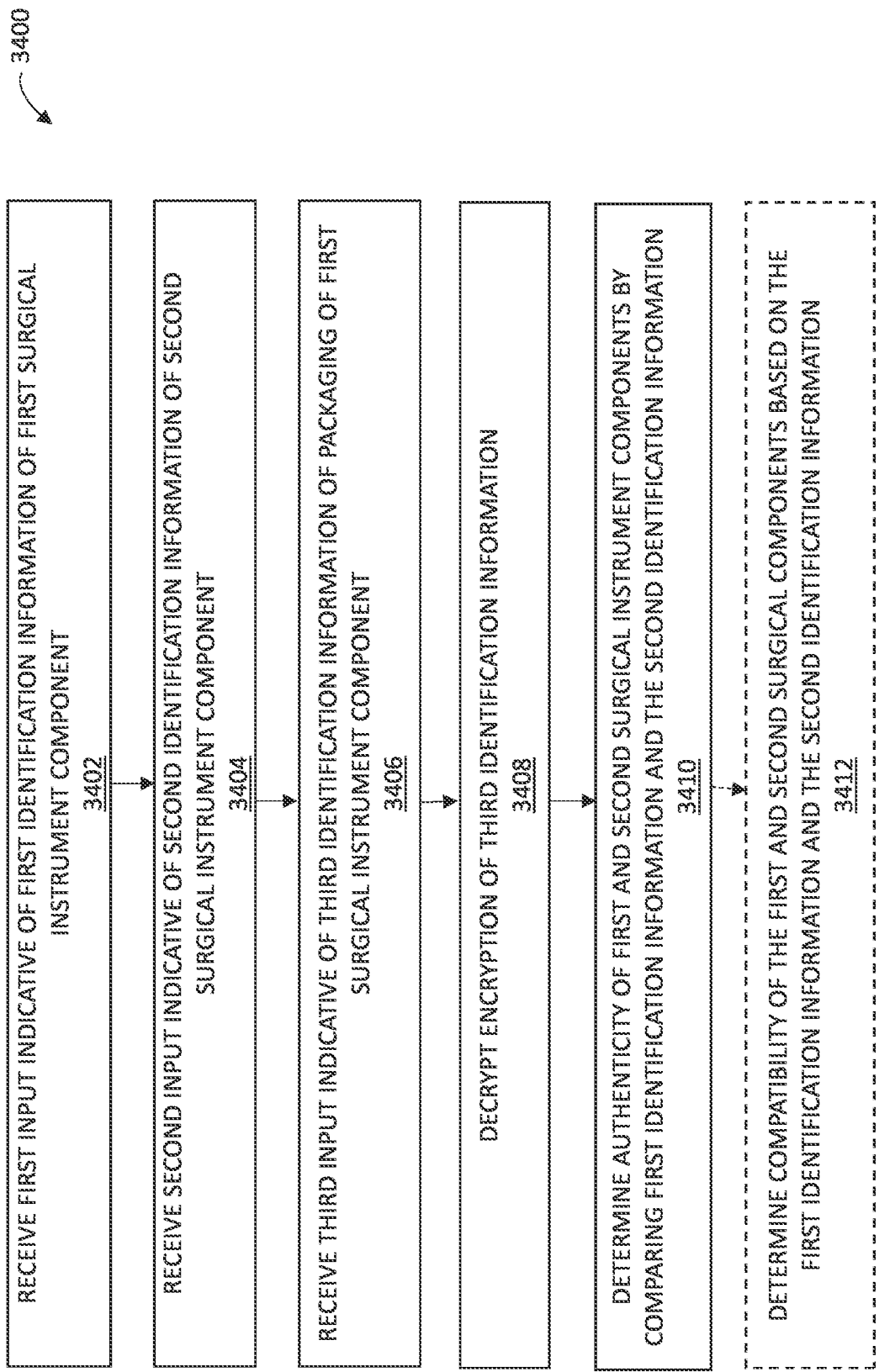
FIG. 48 illustrates a logic flow diagram of a process depicting a control program or a logic configuration for verifying authenticity and/or compatibility of surgical instruments components of a surgical instrument, in accordance with at least one aspect of the present disclosure.

FIG. 48 illustrates a logic flow diagram of a process 3400 depicting a control program or a logic configuration for verifying authenticity and/or compatibility of surgical instruments components of a surgical instrument such as, for example, the surgical instruments 2200, 3194. In at least one example, the process 3400 is executed by a control circuit 1210 (FIG. 15) that includes a processor 1214 and a memory 1212 storing a set of computer-executable instructions that, when executed by the processor 1214, cause the processor 1214 to perform of the process 3400. In certain examples, a set of computer-executable instructions, stored in the memory 1212 may cause the processor 1214 to perform discrete portions of the process 3400. Although the process 3320 is described as being executed by a control circuit 1210, this is merely for brevity, and it should be understood that the process 3400 and other processes described herein, or portions thereof, can be executed by circuitry that can include a variety of hardware and/or software components and may be located in or associated with various suitable systems such as, for example, combinational logic circuits or sequential logic circuits.

In various examples, the control circuit 1210, for example, can employ the process 3400 to verify authenticity and/or compatibility of a surgical instrument and a battery pack releasably couplable to the surgical instrument between an assembled configuration and an unassembled configuration. In other examples, the control circuit 1210, for example, can employ the process 3400 verifies authenticity and/or compatibility of an anvil and a staple cartridge of a surgical instrument.

As illustrated in FIG. 48, the process 3400 includes receiving 3402 a first input indicative of a first identification information of a first surgical instrument component of a surgical instrument such as, for example, the surgical instrument 2200 (FIG. 19). The first identification information can be stored in a first RFID tag of the first surgical instrument component. The process 3400 includes receiving 3404 a second input indicative of a second identification information of a second surgical instrument component of the surgical instrument. The second identification information can be stored in a second RFID tag of the second surgical instrument component. As illustrated in FIG. 19, for example, control circuit 1210 can be coupled to one or more RFID scanner configured to read the stored identification information.

The process 3400 further includes receiving 3406 a third input indicative of a third identification information of a packaging of the first surgical instrument component of the surgical instrument. In a first example, the packaging comprises an RFID tag that stores the third identification information. In a second example, the packaging comprises a CR code that comprises the third identification information. In a third example, the packaging comprises a product number that comprises the third identification information. The third identification information is an encrypted conglomeration of the first identification information and the second identification information, and can be retrieved by the control circuit 1210 via an RFID scanner in the first example, or any suitable smartphone, tablet, etc. equipped with a camera in the second and third examples.

In various instances, the process 3400 further includes decrypting 3408 the encryption of the third identification information, and determining 3410 authenticity of the first and second surgical instrument components by comparing the first identification information and the second identification information to the decrypted third identification information. In certain instances, the memory 1212 may store a decryption key that can be utilized by the processor 1214 to decrypt the encryption of the third identification information.

Furthermore, in certain examples, the process 3400 may include determining 3412 compatibility of the first and second surgical components based on the first identification information and the second identification information. In at least one example, the memory 1212 stores a compatibility database or lookup table that can be utilized by the processor 1214 to assess compatibility of the first and second surgical instrument components. In certain examples, the first identification information identify the surgical instrument itself, and can be stored in the memory 1212 of the control circuit 1210 where it can be retrieved by the processor 1214. In certain examples, the second surgical instrument component is a battery pack such as, for example, the battery pack 120. In at least one example, the first surgical instrument component is an anvil such as, for example, the anvil 2400, while the second surgical instrument component is a staple cartridge such as, for example, the staple cartridge of the stapling head assembly 2300. Other examples of first and second surgical instrument components suitable for use with the process 3400 are contemplated by the present disclosure.

Surgical Hubs

Figure 49:
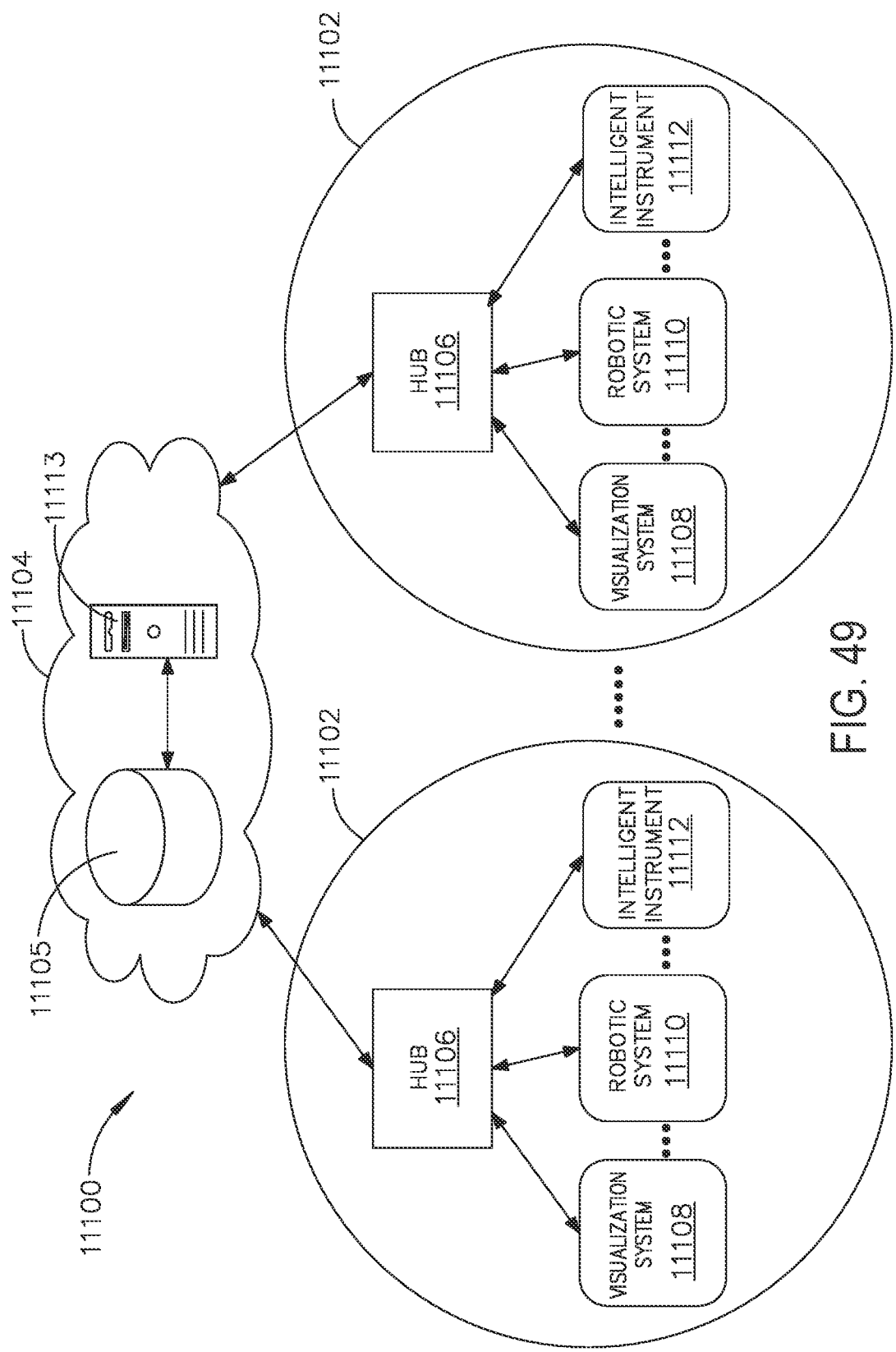
FIG. 49 is a block diagram of a computer-implemented interactive surgical system, in accordance with at least one aspect of the present disclosure.

Referring to FIG. 49, in various aspects, the RFID systems of the present disclosure can be utilized in conjunction with a computer-implemented interactive surgical system 11100 includes one or more surgical systems 11102 and a cloud-based system (e.g., the cloud 11104 that may include a remote server 11113 coupled to a storage device 105). Each surgical system 11102 includes at least one surgical hub 11106 in communication with the cloud 11104 that may include a remote server 11113. In one example, as illustrated in FIG. 49, the surgical system 11102 includes a visualization system 11108, a robotic system 11110, and a handheld intelligent surgical instrument 11112, which are configured to communicate with one another and/or the hub 11106. In some aspects, a surgical system 11102 may include an M number of hubs 11106, an N number of visualization systems 11108, an O number of robotic systems 11110, and a P number of handheld intelligent surgical instruments 11112, where M, N, O, and P are integers greater than or equal to one.

Figure 50:
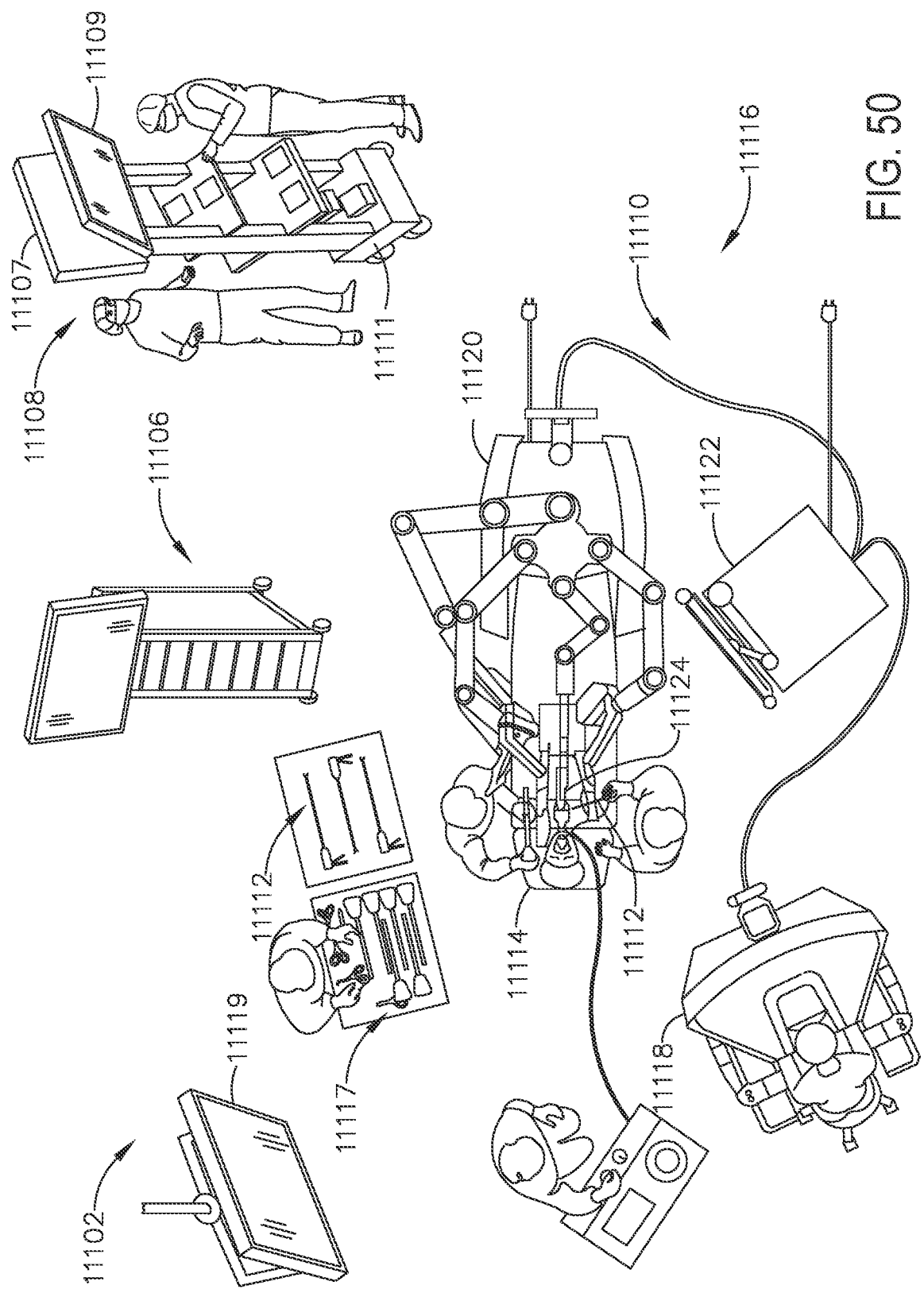
FIG. 50 is a surgical system being used to perform a surgical procedure in an operating room, in accordance with at least one aspect of the present disclosure.

FIG. 50 depicts an example of a surgical system 11102 being used to perform a surgical procedure on a patient who is lying down on an operating table 11114 in a surgical operating room 11116. A robotic system 11110 is used in the surgical procedure as a part of the surgical system 11102. The robotic system 11110 includes a surgeon's console 11118, a patient side cart 11120 (surgical robot), and a surgical robotic hub 11122. The patient side cart 11120 can manipulate at least one removably coupled surgical tool 11117 through a minimally invasive incision in the body of the patient while the surgeon views the surgical site through the surgeon's console 11118. An image of the surgical site can be obtained by a medical imaging device 11124, which can be manipulated by the patient side cart 11120 to orient the imaging device 11124. The robotic hub 11122 can be used to process the images of the surgical site for subsequent display to the surgeon through the surgeon's console 11118.

Other types of robotic systems can be readily adapted for use with the surgical system 11102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 11104 and are suitable for use with the present disclosure are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 11124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 11124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in the air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 11124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 11124 and its attachments and components. It will be appreciated that the sterile field may be considered a specified area, such as within a tray or on a sterile towel, that is considered free of microorganisms, or the sterile field may be considered an area, immediately around a patient, that has been prepared for a surgical procedure. The sterile field may include the scrubbed team members, who are properly attired, and all furniture and fixtures in the area.

In various aspects, the visualization system 11108 includes one or more imaging sensors, one or more image-processing units, one or more storage arrays, and one or more displays that are strategically arranged with respect to the sterile field, as illustrated in FIG. 50. In one aspect, the visualization system 11108 includes an interface for HL7, PACS, and EMR. Various components of the visualization system 11108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 50, a primary display 11119 is positioned in the sterile field to be visible to an operator at the operating table 11114. In addition, a visualization tower 11111 is positioned outside the sterile field. The visualization tower 11111 includes a first non-sterile display 11107 and a second non-sterile display 11109, which face away from each other. The visualization system 11108, guided by the hub 11106, is configured to utilize the displays 11107, 11109, and 11119 to coordinate information flow to operators inside and outside the sterile field. For example, the hub 11106 may cause the visualization system 11108 to display a snapshot of a surgical site, as recorded by an imaging device 11124, on a non-sterile display 11107 or 11109, while maintaining a live feed of the surgical site on the primary display 11119. The snapshot on the non-sterile display 11107 or 11109 can permit a non-sterile operator to perform a diagnostic step relevant to the surgical procedure, for example.

In one aspect, the hub 11106 is also configured to route a diagnostic input or feedback entered by a non-sterile operator at the visualization tower 11111 to the primary display 11119 within the sterile field, where it can be viewed by a sterile operator at the operating table. In one example, the input can be in the form of a modification to the snapshot displayed on the non-sterile display 11107 or 11109, which can be routed to the primary display 11119 by the hub 11106.

Referring to FIG. 50, a surgical instrument 11112 is being used in the surgical procedure as part of the surgical system 11102. The hub 11106 is also configured to coordinate information flow to a display of the surgical instrument 11112. For example, coordinate information flow is further described in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 11111 can be routed by the hub 11106 to the surgical instrument display 11237 (FIG. 53) within the sterile field, where it can be viewed by the operator of the surgical instrument 11112. Example surgical instruments that are suitable for use with the surgical system 11102 are described under the heading "Surgical Instrument Hardware" in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 51:
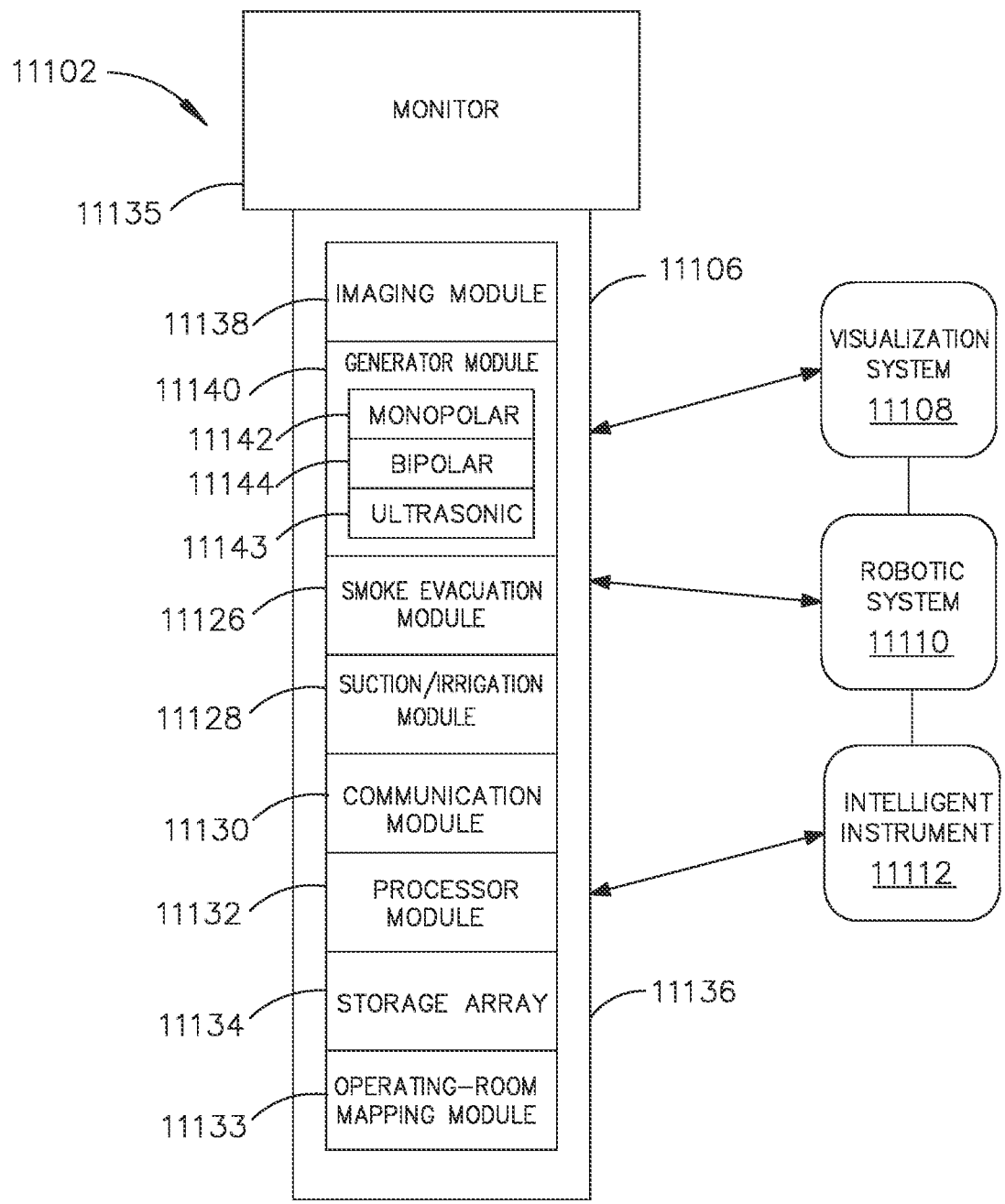
FIG. 51 is a surgical hub paired with a visualization system, a robotic system, and an intelligent instrument, in accordance with at least one aspect of the present disclosure.

Referring now to FIG. 51, a hub 11106 is depicted in communication with a visualization system 11108, a robotic system 11110, and a handheld intelligent surgical instrument 11112. The hub 11106 includes a hub display 11135, an imaging module 11138, a generator module 11140 (which can include a monopolar generator 11142, a bipolar generator 11144, and/or an ultrasonic generator 11143), a communication module 11130, a processor module 11132, and a storage array 11134. In certain aspects, as illustrated in FIG. 51, the hub 11106 further includes a smoke evacuation module 11126, a suction/irrigation module 11128, and/or an operating room mapping module 11133.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 11136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 11136 is configured to accommodate different generators and facilitate an interactive communication therebetween. One of the advantages of the hub modular enclosure 11136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 52:
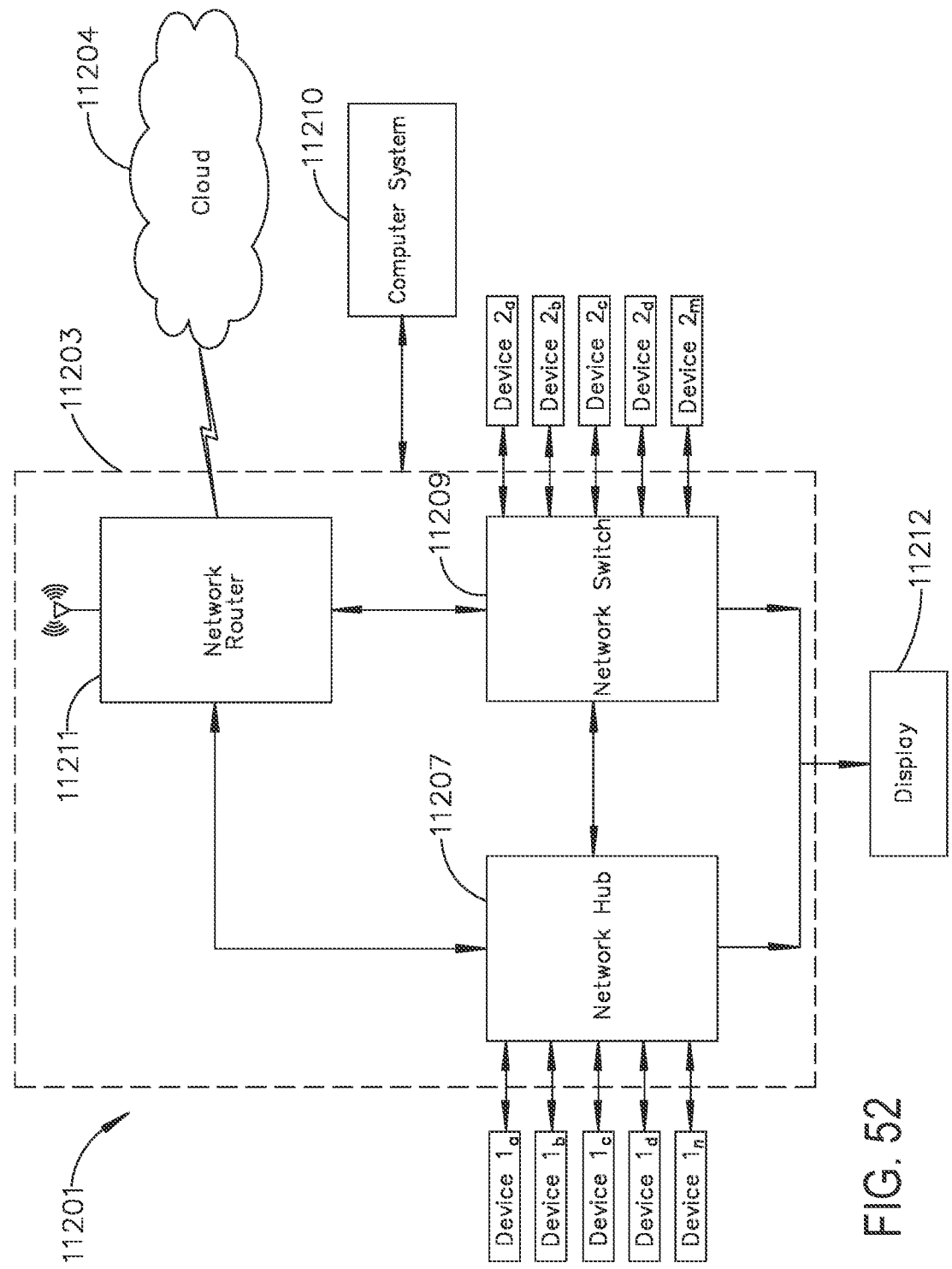
FIG. 52 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.
Figure 53:
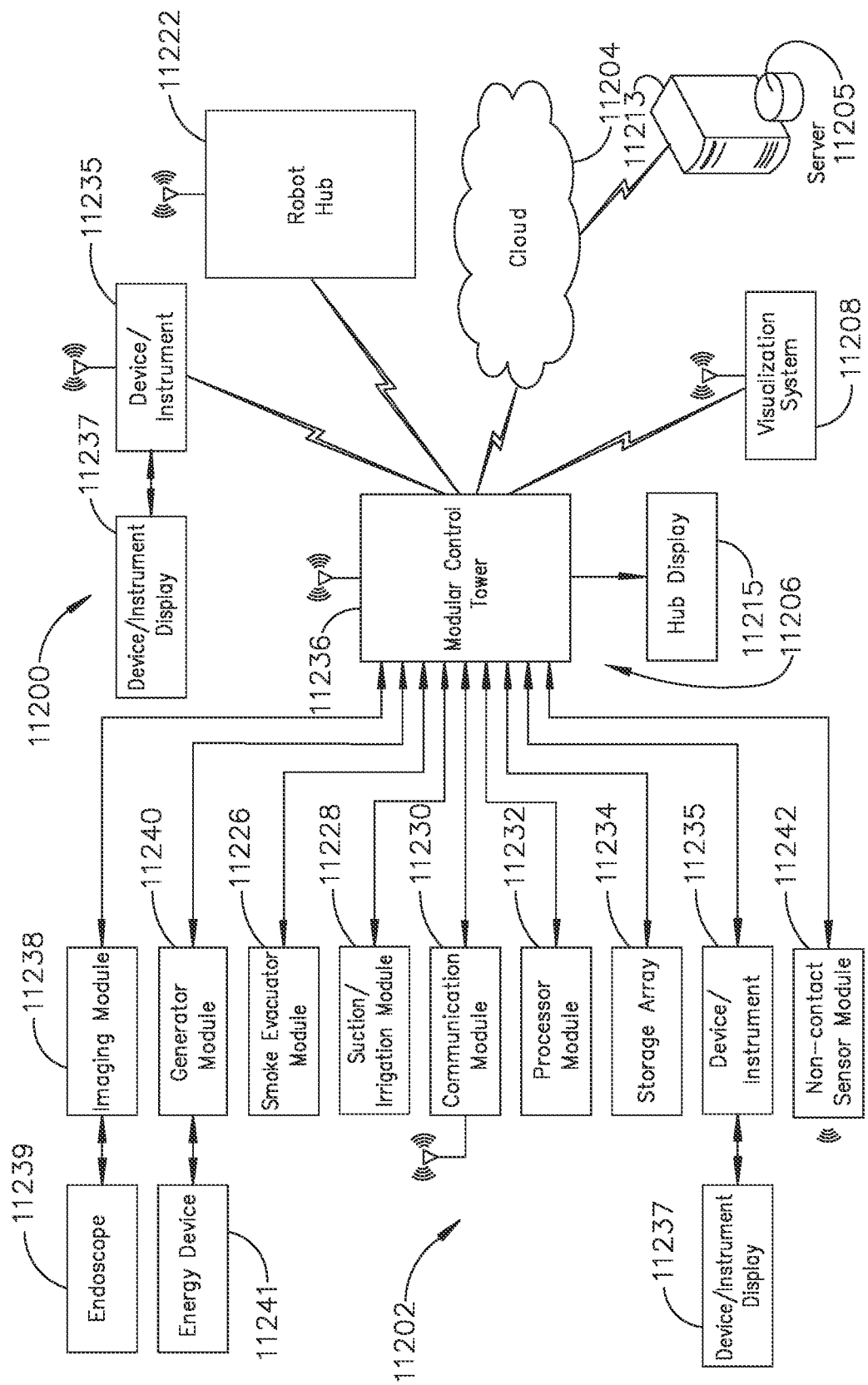
FIG. 53 illustrates a computer-implemented interactive surgical system, in accordance with at least one aspect of the present disclosure.

FIG. 52 illustrates a surgical data network 11201 comprising a modular communication hub 11203 configured to connect modular devices located in one or more operating theaters of a healthcare facility, or any room in a healthcare facility specially equipped for surgical operations, to a cloud-based system (e.g., the cloud 11204 that may include a remote server 11213 coupled to a storage device 11205, as shown in FIG. 53). In one aspect, the modular communication hub 11203 comprises a network hub 11207 and/or a network switch 11209 in communication with a network router. The modular communication hub 11203 also can be coupled to a local computer system 11210 to provide local computer processing and data manipulation. The surgical data network 11201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 11207 or network switch 11209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 11203. The network hub 11207 and/or the network switch 11209 may be coupled to a network router 11211 to connect the devices 1a-1n to the cloud 11204 or the local computer system 11210. Data associated with the devices 1a-1n may be transferred to cloud-based computers via the router for remote data processing and manipulation. Data associated with the devices 1a-1n may also be transferred to the local computer system 11210 for local data processing and manipulation. Modular devices 2a-2m located in the same operating theater also may be coupled to a network switch 11209. The network switch 11209 may be coupled to the network hub 11207 and/or the network router 11211 to connect to the devices 2a-2m to the cloud 11204. Data associated with the devices 2a-2n may be transferred to the cloud 11204 via the network router 11211 for data processing and manipulation. Data associated with the devices 2a-2m may also be transferred to the local computer system 11210 for local data processing and manipulation.

It will be appreciated that the surgical data network 11201 may be expanded by interconnecting multiple network hubs 11207 and/or multiple network switches 11209 with multiple network routers 11211. The modular communication hub 11203 may be contained in a modular control tower configured to receive multiple devices 1a-1n/2a-2m. The local computer system 11210 also may be contained in a modular control tower. The modular communication hub 11203 is connected to a display 11212 to display images obtained by some of the devices 1a-1n/2a-2m, for example, during surgical procedures. In various aspects, the devices 1a-1n/2a-2m may include, for example, various modules, such as an imaging module 11138 coupled to an endoscope, a generator module 11140 coupled to an energy-based surgical device, a smoke evacuation module 11126, a suction/irrigation module 11128, a communication module 11130, a processor module 11132, a storage array 11134, a surgical device coupled to a display, and/or a non-contact sensor module, among other modular devices that may be connected to the modular communication hub 11203 of the surgical data network 11201.

In one aspect, the surgical data network 11201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 11203 and/or computer system 11210 located in the surgical theater (e.g., a fixed, mobile, temporary, or field operating room or space) and to devices connected to the modular communication hub 11203 and/or computer system 11210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data, including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques, such as overlaying images captured by multiple imaging devices. The data gathered by the devices 1a-1n/2a-2m, including image data, may be transferred to the cloud 11204 or the local computer system 11210 or both for data processing and manipulation, including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 11203 over a wired channel or a wireless channel depending on the configuration of the devices 1a-1n to a network hub. The network hub 11207 may be implemented, in one aspect, as a local network broadcast device that works on the physical layer of the Open System Interconnection (OSI) model. The network hub provides connectivity to the devices 1a-1n located in the same operating theater network. The network hub 11207 collects data in the form of packets and sends them to the router in half-duplex mode. The network hub 11207 does not store any media access control/Internet Protocol (MAC/IP) to transfer the device data. Only one of the devices 1a-1n can send data at a time through the network hub 11207. The network hub 11207 has no routing tables or intelligence regarding where to send information and broadcasts all network data across each connection and to a remote server 11213 (FIG. 53) over the cloud 11204. The network hub 11207 can detect basic network errors, such as collisions, but having all information broadcast to multiple ports can be a security risk and cause bottlenecks.

In another implementation, the operating theater devices 2a-2m may be connected to a network switch 11209 over a wired channel or a wireless channel. The network switch 11209 works in the data link layer of the OSI model. The network switch 11209 is a multicast device for connecting the devices 2a-2m located in the same operating theater to the network. The network switch 11209 sends data in the form of frames to the network router 11211 and works in full duplex mode. Multiple devices 2a-2m can send data at the same time through the network switch 11209. The network switch 11209 stores and uses MAC addresses of the devices 2a-2m to transfer data.

The network hub 11207 and/or the network switch 11209 are coupled to the network router 11211 for connection to the cloud 11204. The network router 11211 works in the network layer of the OSI model. The network router 11211 creates a route for transmitting data packets received from the network hub 11207 and/or network switch 11209 to cloud-based computer resources for further processing and manipulation of the data collected by any one of or all the devices 1a-1n/2a-2m. The network router 11211 may be employed to connect two or more different networks located in different locations, such as, for example, different operating theaters of the same healthcare facility or different networks located in different operating theaters of different healthcare facilities. The network router 11211 sends data in the form of packets to the cloud 11204 and works in full duplex mode. Multiple devices can send data at the same time. The network router 11211 uses IP addresses to transfer data.

In one example, the network hub 11207 may be implemented as a USB hub, which allows multiple USB devices to be connected to a host computer. The USB hub may expand a single USB port into several tiers so that there are more ports available to connect devices to the host system computer. The network hub 11207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 11203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 11203 via a number of wireless or wired communication standards or protocols, including, but not limited to, Wi-Fi (IEEE 802.11 family), WiMAX (IEEE 802.16 family), IEEE 802.20, long-term evolution (LTE), Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 11203 may serve as a central connection for one or all of the operating theater devices 1a-1n/2a-2m and handles a data type known as frames. Frames carry the data generated by the devices 1a-1n/2a-2m. When a frame is received by the modular communication hub 11203, it is amplified and transmitted to the network router 11211, which transfers the data to the cloud computing resources by using a number of wireless or wired communication standards or protocols, as described herein.

The modular communication hub 11203 can be used as a standalone device or be connected to compatible network hubs and network switches to form a larger network. The modular communication hub 11203 is generally easy to install, configure, and maintain, making it a good option for networking the operating theater devices 1a-1n/2a-2m.

Figure 54:
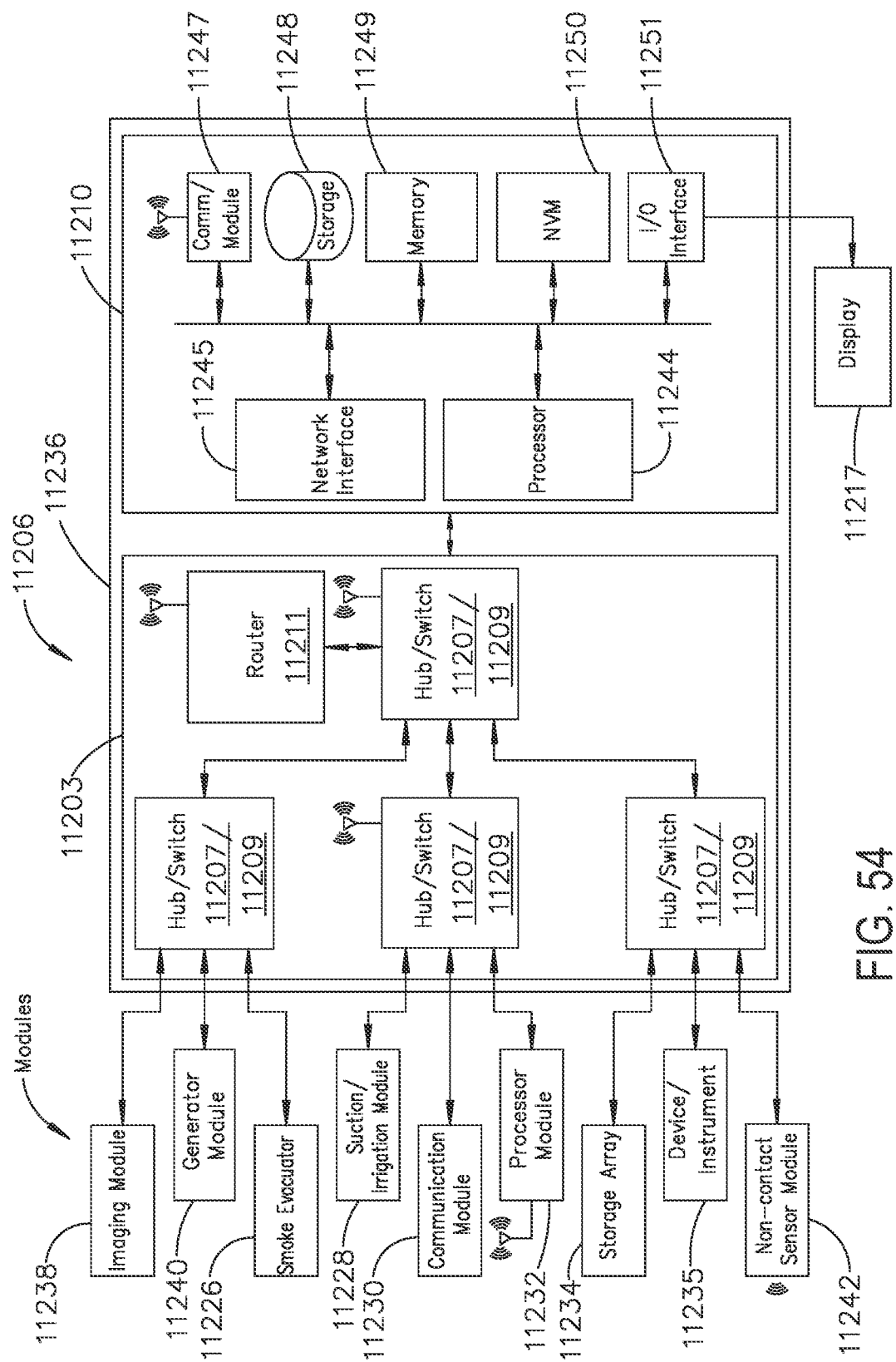
FIG. 54 illustrates a surgical hub comprising a plurality of modules coupled to the modular control tower, in accordance with at least one aspect of the present disclosure.

FIG. 53 illustrates a computer-implemented interactive surgical system 11200. The computer-implemented interactive surgical system 11200 is similar in many respects to the computer-implemented interactive surgical system 11100. For example, the computer-implemented interactive surgical system 11200 includes one or more surgical systems 11202, which are similar in many respects to the surgical systems 11102. Each surgical system 11202 includes at least one surgical hub 11206 in communication with a cloud 11204 that may include a remote server 11213. In one aspect, the computer-implemented interactive surgical system 11200 comprises a modular control tower 11236 connected to multiple operating theater devices such as, for example, intelligent surgical instruments, robots, and other computerized devices located in the operating theater. As shown in FIG. 54, the modular control tower 11236 comprises a modular communication hub 11203 coupled to a computer system 11210. As illustrated in the example of FIG. 53, the modular control tower 11236 is coupled to an imaging module 11238 that is coupled to an endoscope 11239, a generator module 11240 that is coupled to an energy device 11241, a smoke evacuator module 11226, a suction/irrigation module 11228, a communication module 11230, a processor module 11232, a storage array 11234, a smart device/instrument 11235 optionally coupled to a display 11237, and a non-contact sensor module 11242. The operating theater devices are coupled to cloud computing resources and data storage via the modular control tower 11236. A robot hub 11222 also may be connected to the modular control tower 11236 and to the cloud computing resources. The devices/instruments 11235 and visualization systems 11208, among others, may be coupled to the modular control tower 11236 via wired or wireless communication standards or protocols, as described herein. The modular control tower 11236 may be coupled to a hub display 11215 (e.g., monitor, screen) to display and overlay images received from the imaging module, device/instrument display, and/or other visualization systems 11208. The hub display also may display data received from devices connected to the modular control tower in conjunction with images and overlaid images.

FIG. 54 illustrates a surgical hub 11206 comprising a plurality of modules coupled to the modular control tower 11236. The modular control tower 11236 comprises a modular communication hub 11203, e.g., a network connectivity device, and a computer system 11210 to provide local processing, visualization, and imaging, for example. As shown in FIG. 54, the modular communication hub 11203 may be connected in a tiered configuration to expand the number of modules (e.g., devices) that may be connected to the modular communication hub 11203 and transfer data associated with the modules to the computer system 11210, cloud computing resources, or both. As shown in FIG. 54, each of the network hubs/switches in the modular communication hub 11203 includes three downstream ports and one upstream port. The upstream network hub/switch is connected to a processor to provide a communication connection to the cloud computing resources and a local display 11217. Communication to the cloud 11204 may be made either through a wired or a wireless communication channel.

The surgical hub 11206 employs a non-contact sensor module 11242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 11210 comprises a processor 11244 and a network interface 11245. The processor 11244 is coupled to a communication module 11247, storage 11248, memory 11249, non-volatile memory 11250, and input/output interface 11251 via a system bus. The system bus can be any of several types of bus structure(s), including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 11244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random-access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 11244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 11210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 11210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 11210 through input device(s) coupled to the I/O interface 11251. The input devices include, but are not limited to, a pointing device such as a mouse, trackball, stylus, touch pad, keyboard, microphone, joystick, game pad, satellite dish, scanner, TV tuner card, digital camera, digital video camera, Web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 11210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5, and the like. WAN technologies include, but are not limited to, point-to-point links, circuit-switching networks like Integrated Services Digital Networks (ISDN) and variations thereof, packet-switching networks, and Digital Subscriber Lines (DSL).

In various aspects, the computer system 11210 of FIG. 54, the imaging module 11238 and/or visualization system 11208, and/or the processor module 11232 of FIGS. 53-54, may comprise an image processor, image-processing engine, media processor, or any specialized digital signal processor (DSP) used for the processing of digital images. The image processor may employ parallel computing with single instruction; multiple data (SIMD); or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 11210. The hardware/software necessary for connection to the network interface includes, for illustrative purposes only, internal and external technologies such as modems, including regular telephone-grade modems, cable modems, DSL modems, ISDN adapters, and Ethernet cards.

RFID Detection Assemblies

In various aspects, the RFID systems of the present disclosure can be disposed on or otherwise associated with surgical instruments 11112 (FIGS. 49-51), components of surgical instruments 11112, consumables useable in conjunction with surgical instruments 11112, and/or other systems or devices associated with a surgical system 11100 (FIGS. 49-51), such as a visualization system 11108 (FIGS. 49-51), a robotic system 11110 (FIGS. 49-51), a hub 11106 (FIGS. 49-51), or components thereof. Further, the RFID tags described in greater detail below, can be utilized to store a datum or data identifying the device or component of the surgical system 11100 that the RFID tag is associated with. In addition, corresponding RFID scanners can be configured to read the RFID tags as the components of the surgical system 11100 are utilized in order to identify the components, devices, and/or systems that are in use in the operating theater and then control a surgical instrument 11112, hub 11106, visualization system 11108, or another component, device, and/or system accordingly.

In various examples, an RFID scanner can be positioned within or on a surgical instrument 11112 such that the RFID scanner can read RFID tags of components (e.g., batteries, shafts, or cartridges) as the surgical instrument 11112 is assembled. As another example, an RFID scanner could be associated with a surgical instrument 11112 such that the RFID scanner can read RFID tags associated with a hub 11106, visualization system 11108, and/or a robotic system 11110 as the surgical instrument 11112 is brought into proximity of or interacts with those systems. These and other RFID detection assemblies are described in greater detail below.

Further, various control systems for controlling the RFID systems, the surgical instruments associated therewith, and/or other devices or components of a surgical system 11100, are described herein. Example of such control systems include a control system 1211 (FIG. 55), a control system 8111 (FIG. 55A), and a processor module 11232 of a surgical hub 11206 (FIGS. 53 and 54). Such control systems can be directly integrated into the component or device that they are controlling. For example, the control system 1211 illustrated in FIG. 55 can control the surgical instrument 1100 (FIG. 56-58) into which it is integrated. In another example, the control system 8111 illustrated in FIG. 55A can control the surgical instrument 8002 (FIG. 59) into which it is integrated. Alternatively, such control systems can be communicably coupled to the component or device that they are controlling. For example, the processor module 11232 can be configured to control surgical instruments 11112 and/or other components or devices of a surgical system 11100 that are paired with or communicably coupled to the surgical hub 11206, as is described above. These control systems can include or be communicably coupled to RFID scanners for detecting RFID tags. The control systems can then control the subject devices according to the combination or arrangement of detected RFID tags.

Referring to FIGS. 55 and 56-58, the control system 1211 includes a control circuit 1210 that can be integrated with the RFID scanner 1202 or can be coupled to, but positioned separately from, the RFID scanner 1202, for example. The control circuit 1210 can be configured to receive input from the RFID scanner 1202 indicative of the information about a staple cartridge 1320 stored in the RFID tag 1203 and/or information about the anvil 1200 stored in the RFID tag 1201.

In various examples, the RFID tag 1203 stores identification information of the staple cartridge 1320 and the RFID tag 1201 stores identification information of the anvil 1200. In such examples, the control circuit 1210 receives input from the RFID scanner 1202 indicative of the identification information of the staple cartridge 1320 and verifies the identity of the staple cartridge 1320 based on the input. Further, the control circuit 1210 receives input from RFID scanner 1202 indicative of the identification information of the anvil 1200 and verifies the identity of the anvil 1200 based on the input.

In at least one example, the control circuit 1210 includes a microcontroller 1213 that has a processor 1214 and a storage medium such as, for example, a memory 1212. The memory 1212 stores program instructions for performing various processes such as, for example, identity verification. The program instructions, when executed by the processor 1214, cause the processor 1214 to verify the identity of the staple cartridge 1320 and the anvil 1200 by comparing the identification information received from the RFID tags 1201, 1203 to identification information stored in the memory 1212 in the form of an identity database or table, for example.

In at least one example, the control circuit 1210 can be configured to check compatibility of the anvil 1200 with staple cartridge 1320 of the stapling head assembly 1300 based on input from the RFID scanner 1202. The processor 1214 can, for example, check the identity information of the anvil 1200 and the staple cartridge 1320 against a compatibility database or table stored in memory 1212.

Figure 56:
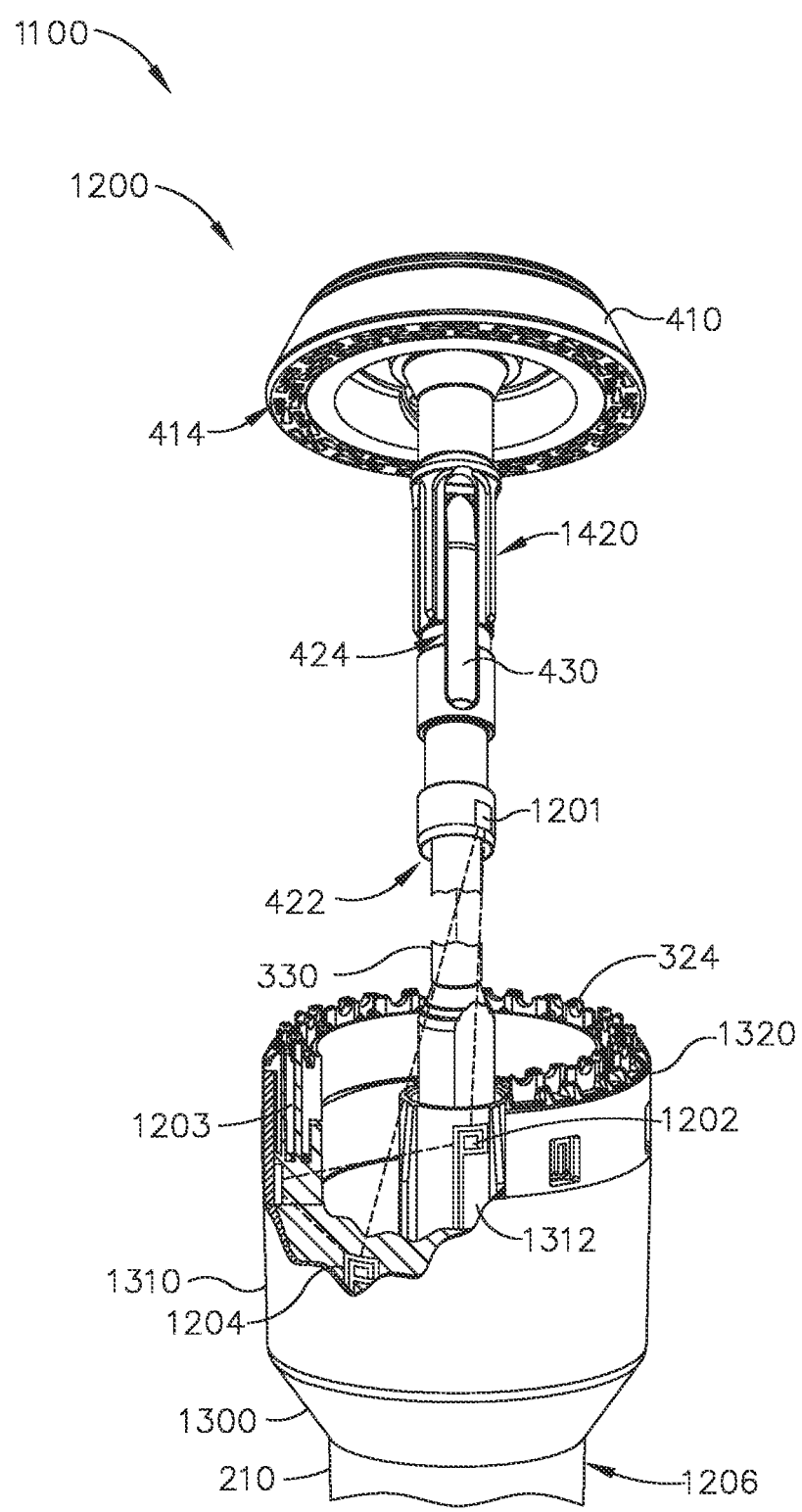
FIG. 56 depicts stapling head assembly and an anvil being coupled to a trocar of the stapling head assembly, in accordance with at least one aspect of the present disclosure.
Figure 57:
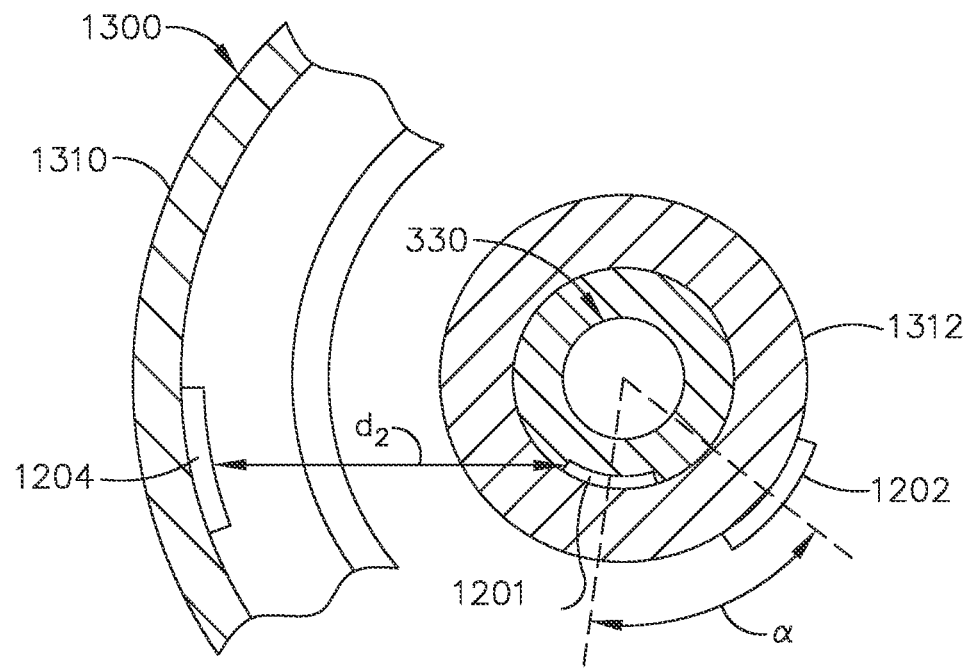
FIG. 57 depicts a partial transverse cross-sectional view of an anvil in an improper seating orientation with a stapling head assembly, in accordance with at least one aspect of the present disclosure.
Figure 58:
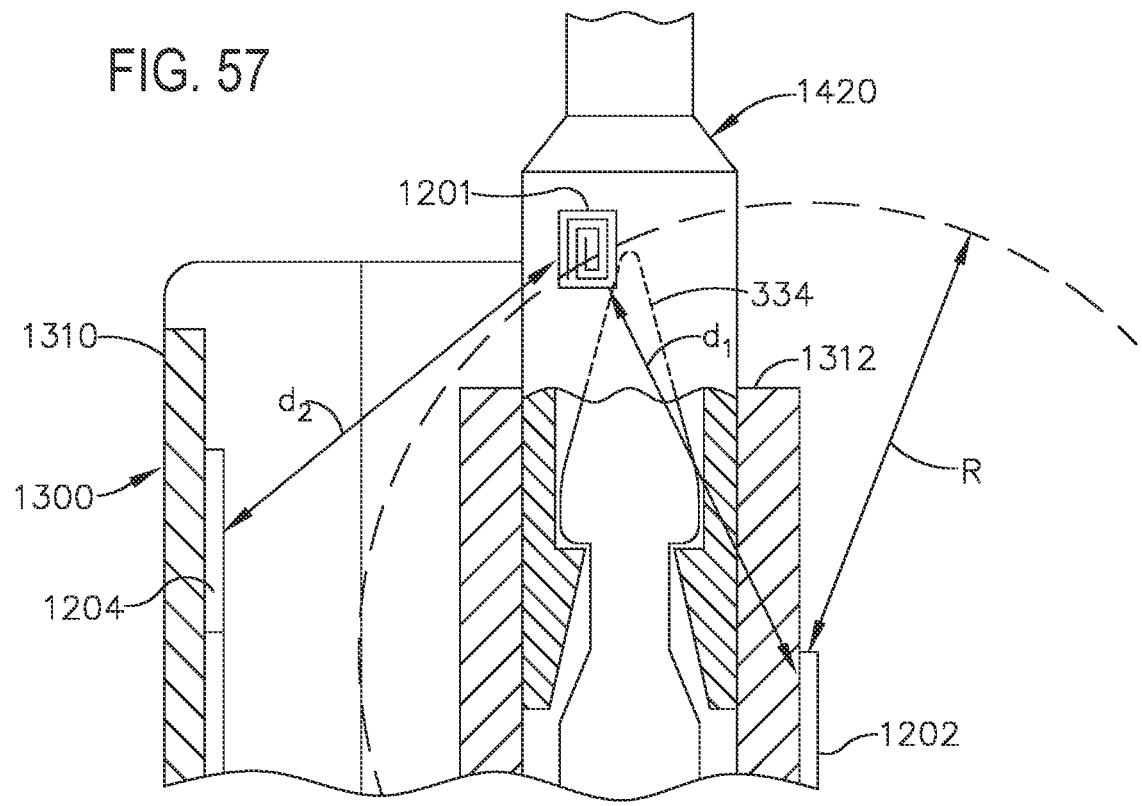
FIG. 58 depicts a partial longitudinal cross-sectional view of an anvil in an improper seating orientation with a stapling head assembly, in accordance with at least one aspect of the present disclosure.

In one aspect, an RFID scanner 1202 can be positioned within or otherwise associated with a surgical instrument to read a corresponding RFID tag 1201 that is configured to indicate the actions or operations performed by the surgical instrument. For example, FIGS. 56-58 illustrate one such configuration for a surgical instrument 1100 in the form of a circular stapler. A distinct issue with circular staplers is that their anvils are detachable from their stapling head assemblies, and must be separately introduced to a surgical site in different manners and from different access points. Accordingly, unlike other stapling instruments, circular staplers are at risk from anvil-staple head assembly mismatching and/or anvil-staple cartridge mismatching. Further, to be properly assembled or coupled an anvil and a stapling head assembly must be properly oriented with respect to each other at a specific orientation at the surgical site. Improper orientation of an anvil and a corresponding stapling head assembly, as illustrated in FIG. 57, can lead to a misalignment between the staple forming pockets 414 (FIG. 56) of the anvil and staple openings 324 (FIG. 56) of a staple cartridge 1320, which may lead to improper staple formation. In addition, the improper orientation of an anvil and a corresponding stapling head assembly can lead to improper seating of the anvil with respect to the stapling head assembly. An improperly seated, or partially seated, anvil may become unseated, or separated from the stapling head assembly, due to externally applied loads from the tissue captured between the anvil and the stapling head assembly during closure.

To address the issues above, the surgical instrument 1100 includes an anvil 1200 equipped with a radio-frequency identification (RFID) tag 1201 recognizable or detectable by an RFID scanner 1202 on a stapling head assembly 1300 of the surgical instrument. Likewise, the staple cartridge 1320 includes an RFID tag 1203 also recognizable or detectable by the RFID scanner 1202. The RFID tag 1201 stores information about the anvil 1200, and the RFID tag 1203 stores information about the staple cartridge 1320. As described below, the information can be checked and compared for authentication and/or compatibility.

Referring still to FIGS. 55 and 56-58, the anvil 1200 includes a head 410, staple forming pockets 414, and a shank 1420. In this example, the RFID tag 1201 is supported by the shank 1420, on an outer surface thereof, near a bore 422 defined by the shank 1420. The anvil 1200 is coupled or assembled with a stapling head assembly 1300 by advancing the anvil 1200 toward a trocar 330 of the stapling head assembly 1300 such that the trocar 330 is received through the bore 422, as illustrated in FIG. 56. In at least one example, the RFID tag 1201 is positioned on the shank 1420 at a first longitudinal position that corresponds, or substantially corresponds, to a second longitudinal position of a tip of the head 334 of the trocar 330 when the anvil 1200 is properly oriented and fully seated with respect to the stapling head assembly 1300. In other words, the tip of the head 334 of the trocar 330, when it is received in the shank 1420 at its final seating position, is transversely aligned, or at least substantially aligned, with the RFID tag 1201. In at least one example, the RFID tag 1201 is positioned on the shank 1420 at a position distal to the bore 422 and proximal to the lateral openings 424, which are formed through the sidewall of shank 1420, and/or proximal to latch members 430 of the shank 1420.

Referring to FIG. 56, the RFID scanner 1202 is located on an outer surface of a cylindrical inner core member 1312 that extends distally within a tubular casing 1310 of the stapling head assembly 1300. Tubular casing 1310 is fixedly secured to an outer sheath 210 of the shaft assembly 1206 of the surgical instrument, such that tubular casing 1310 serves as a mechanical ground for stapling head assembly 1300. The RFID scanner 1202 is supported by the inner core member 1312, on an outer surface thereof, near its distal end. In at least one example, a recess or pocket is defined in the inner core member 1312, and the RFID scanner 1202 is positioned in the recess or pocket. The RFID scanner 1202 can be held in place in the recess, or pocket, using any suitable technique such as, for example, friction fitting or biocompatible adhesive. Alternatively, the RFID scanner 1202 can be positioned on an inner surface of the cylindrical inner core member 1312. In the example of FIG. 56, the RFID scanner 1202 is located at a distal portion of the inner core member 1312 below the deck member of the staple cartridge 1320. In various example, the RFID tag 1201 and the RFID tag 1203 are insulated from the shank 1420 and the inner core member 1312 using any suitable insulative material.

In various examples, RFID tag 1201 and the RFID tag 1203 are recognizable or detectable by the RFID scanner 1202 in a closed configuration of the instrument where tissue is captured between the anvil 1200 and stapling head assembly 1300.

Additional details regarding the aspect illustrated in FIGS. 56-58 can be found in U.S. patent application Ser. No. 16/458,109, entitled MECHANISMS FOR PROPER ANVIL ATTACHMENT SURGICAL STAPLING HEAD ASSEMBLY, filed Jun. 30, 2019, now U.S. Patent Application Publication No. 2020/0405312, which is hereby incorporated by reference herein in its entirety.

Figure 55:
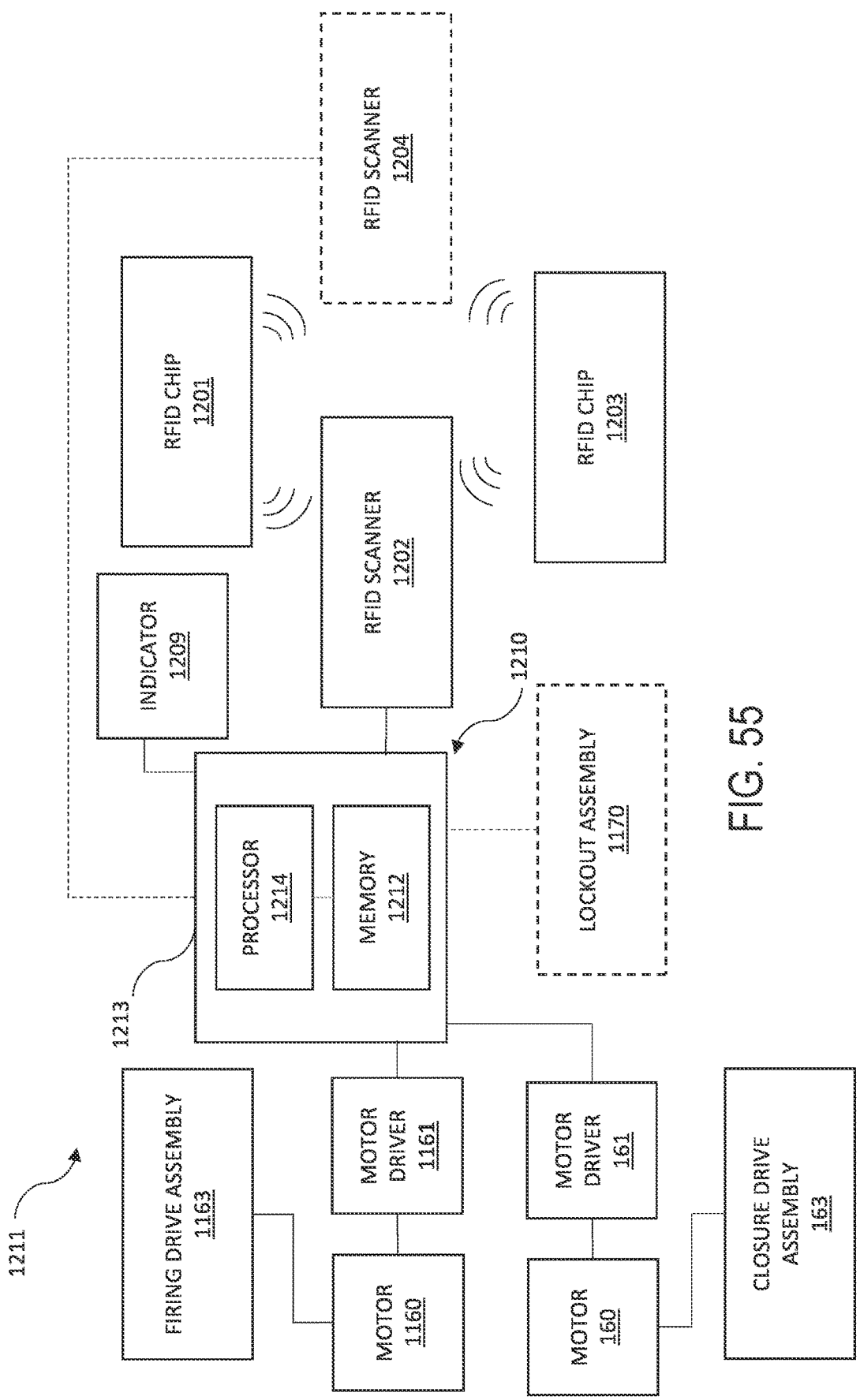
FIG. 55 depicts a control system of a surgical stapling instrument, in accordance with at least one aspect of the present disclosure.
Figure 55A:
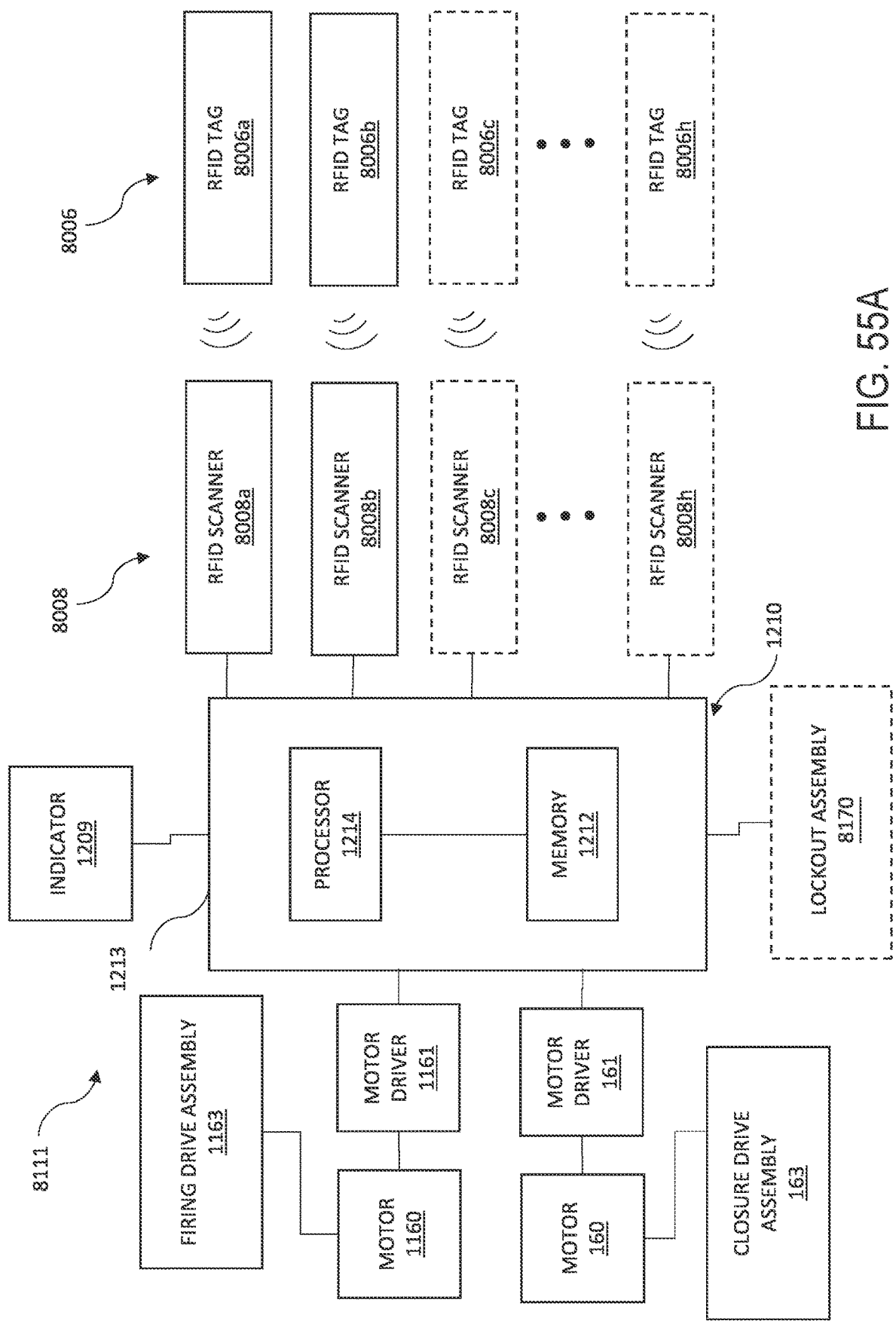
FIG. 55A depicts another control system of a surgical stapling instrument, in accordance with at least one aspect of the present disclosure.

FIG. 55A illustrates a block diagram of the control system 8111. Many of the components of the illustrated control system 8111 coincide with components of the control system 2111 described above with respect to FIG. 55; therefore, the descriptions of those components will not be repeated. In this aspect, the control system 8111 includes a set or assembly of multiple RFID scanners 8008 that are positioned or configured to read a corresponding set or assembly of RFID tags 8006. The RFID scanners 8008 are communicably coupled to a control circuit 1210 such that the control circuit 1210 can receive data from the RFID scanners 8008 and then take various actions based upon the read data, as are described below. In various aspects, the RFID scanners 8008 can be disposed on or otherwise associated with the surgical instrument or other surgical system component with which the control system 8111 is associated. In other aspects, the RFID scanners 8008 can be disposed on or otherwise associated with other surgical system components that are communicably couplable to the control system 8111. The RFID tags 8006 can be disposed on or associated with any type of surgical system component, including a surgical instrument 11112 (FIGS. 49-51), a visualization system 11108 (FIGS. 49-51), a robotic system 11110 (FIGS. 49-51), or other surgical system components (e.g., sterile drapes, rib spreaders, sponges, or adjuncts) or components thereof. In one aspect, each of the RFID scanners 8008a-h can be configured to read a corresponding RFID tag 8006a-h. Finally, it should be noted that although the control system 8111 in FIG. 55A is depicted as including eight RFID scanners 8008a-h that are configured to read a corresponding number of RFID tags 8006a-h, this particular number are arrangement of components is simply for illustrative purposes and should not be construed to be limiting in any way. In particular, the control system 8111 can include any number of RFID scanners 8008a-h that are configured to read any number of RFID tags 8006a-h.

Figure 59:
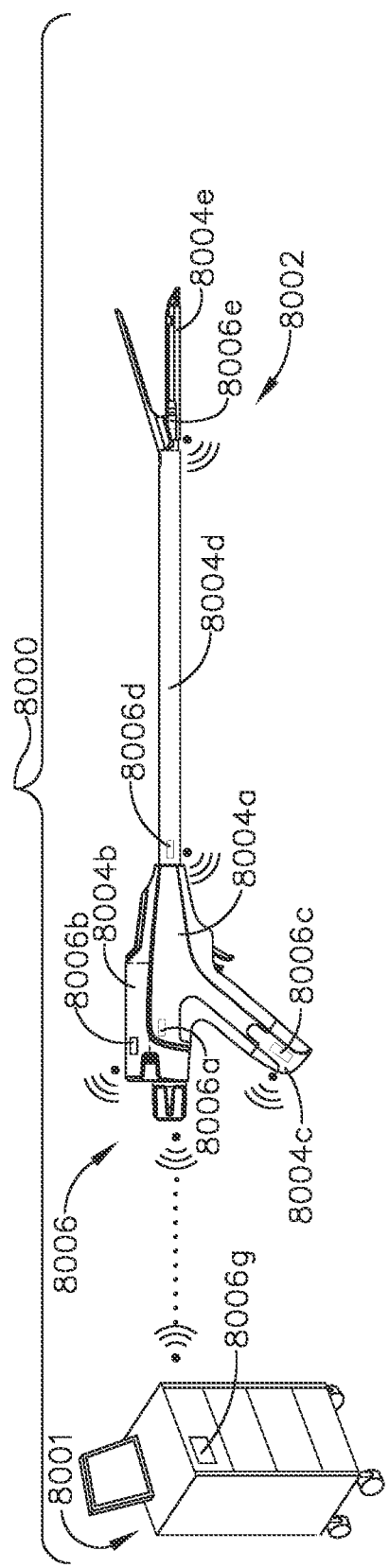
FIG. 59 illustrates a surgical instrument communicably coupled to a surgical hub, in accordance with at least one aspect of the present disclosure.

In one aspect, as described above under the heading SURGICAL HUBS and illustrated in FIG. 59, a surgical system 8000 can include a surgical instrument 8002 that is communicably couplable to a surgical hub 8001. Surgical instruments 8002 can include multiple different components that are couplable together to assemble the surgical instrument 8002 and/or consumable components that are insertable into the surgical instruments 8002 for firing or operating the surgical instruments 8002. For example, the illustrated surgical instrument 8002 can include a housing assembly 8004a, a battery 8004b removably couplable to the housing assembly 8004a, a motor assembly 8004c removably couplable to the housing assembly 8004a, a shaft 8004d removably couplable to the housing assembly 8004a, a cartridge 8004e removably insertable into the end effector of the shaft 8004d, and other such components.

The surgical system 8000 can further include the control system 8111. In the example of FIG. 59, the control system 8111 includes a set of RFIDs 8006 that are positioned on or otherwise associated with the various surgical instrument components 8004a-e. Each of the surgical instrument components 8004a-e can include an RFID tag 8006 that is configured to transmit information pertaining to the component with which the RFID tag 8006 is associated, such as the component type or component parameters, to a corresponding RFID scanner 8008 associated with the surgical instrument 8000 (e.g., the housing assembly 8004a), the surgical hub 8001, or another surgical system device. For example, in the depicted aspect, the housing assembly 8004a can include first RFID tag 8006a, the battery 8004b can include a second RFID tag 8006b, the motor assembly 8004c can include a third RFID tag 8006c, the shaft 8004d can include a fourth RFID tag 8006d, and the cartridge 8004e can include a fifth RFID tag 8006e. In one aspect, the RFID tags 8006a-e can be read by a single RFID scanner disposed on the surgical instrument 8002, the surgical hub 8001, or another component of a surgical system 8000. Accordingly, a control circuit 1210 of the control system 8111 can be communicably coupled to a single RFID scanner. In another aspect, the RFID tags 8006 can be read by multiple RFID scanners during the assembly or operation of the surgical instrument 8002. For example, the RFID scanners can be positioned on the surgical instrument 8002 such that the RFID tags 8006a-e are automatically read by a corresponding RFID scanner 8008a-e as a natural consequence of the assembly of the surgical instrument 8002 (an example of which is discussed in greater detail below with respect to FIG. 13) or the use of the surgical instrument 8002 (an example of which is discussed above with respect to FIGS. 56-58). Accordingly, the control circuit 1210 of the control system 8111 can be communicable coupled to multiple RFID scanners 8008 that are positioned to read one or more corresponding RFID tags 8006. Although the aspects depicted in FIGS. FIGS. 56-59, 61, and 62 illustrate particular positions for the RFID tags 8006 and the RFID scanners 8008, it should be noted that these positions are simply for illustrative purposes and the RFID tags 8006 and/or RFID scanners 8008 can be repositioned depending upon the geometry of the particular surgical system component, have their positions swapped with each other, or be otherwise reconfigured without departing from the overall structure and function of the described systems.

In addition to the surgical instrument 8002 or components thereof, including RFID tags 8006, other devices within the surgical system 8000 can likewise include RFID tags 8006 and/or RFID scanners 8008. For example, in the aspect illustrated in FIG. 59, the surgical hub 8001 can include an RFID tag 8006g that can be configured to be read by one or more RFID scanners 8008 (FIG. 61) associated with the surgical instrument 8002. In other aspects, RFID tags 8006 and/or scanners 8008 can additionally or alternatively be associated with visualization system 11108 (FIGS. 49-51), a robotic system 11110 (FIGS. 49-51), or components thereof. Accordingly, a surgical instrument 8002 including an RFID scanner 8008 can detect the various devices or systems being utilized in the surgical system configuration based on being within detection range of those devices or systems.

Figure 61:
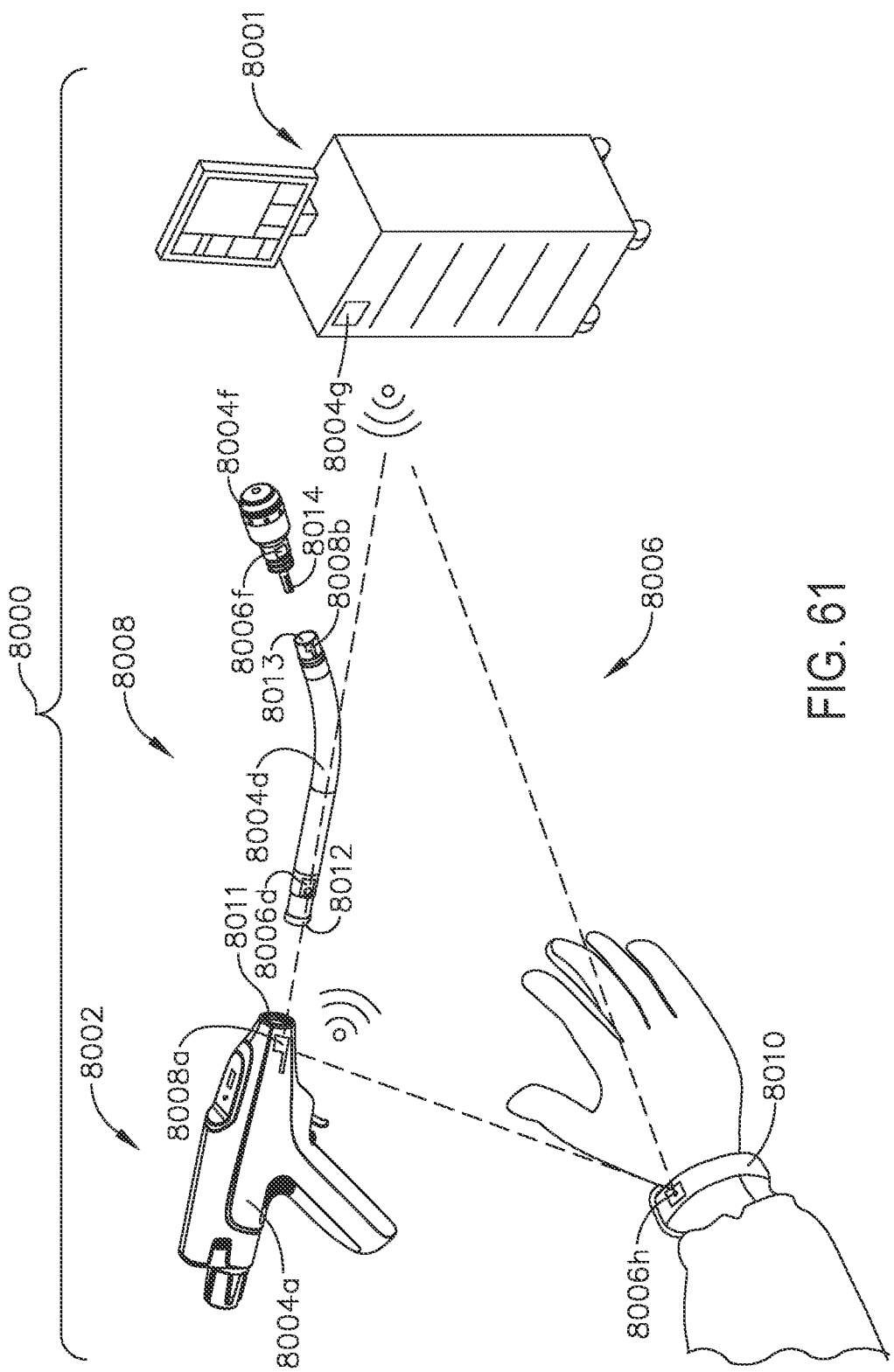
FIG. 61 illustrates a diagram of a surgical hub detecting RFID tags associated with a surgical instrument and a user, in accordance with at least one aspect of the present disclosure.

As illustrated in FIG. 61, a surgical system 8000 can also include a user identifier 8010 that can be worn or controlled by a user, such as a surgeon. The user identifier 8010 can include an RFID tag 8006h that is configured to store a unique identifier associated with the user, which can then be utilized by a control system to retrieve particular parameters or settings associated with that user. The user settings can be manually set by the user at a computer system (e.g., a surgical hub 8001 or a local computer system 11210 (FIG. 54)) or learned by a surgical hub 8001 through situational awareness, which is described in U.S. patent application Ser. No. 16/209,395, titled METHOD OF HUB COMMUNICATION, and filed Dec. 4, 2018, which is hereby incorporated by reference in its entirety. Further, the user settings can be stored in a database (e.g., storage 11248 (FIG. 54)) for retrieval by a control system.

In some aspects, RFID tags 8006 and RFID scanners 8008 can be positioned such that they are brought into detection range of each other during assembly of the surgical instrument 8002, or in an assembled configuration of the surgical instrument 8002. For example, FIG. 61 illustrates an aspect where the surgical instrument 8002 is a circular stapler including an assembly of RFID scanners 8008 that detect corresponding RFID tags 8006 during assembly of the surgical instrument 8002, or in the assembled configuration of the surgical instrument 8002. In particular, the housing assembly 8004a includes an RFID scanner 8008a positioned adjacent to its coupling portion 8011, which is configured to engage with a corresponding proximal coupling portion 8012 of the shaft assembly 8004d. The shaft assembly 8004d further includes an RFID tag 8006d that is brought into detection range of the RFID scanner 8008a when the aforementioned components are properly coupled together. In other words, the RFID scanner 8008a is positioned to read the RFID tag 8006d as a natural consequence of the assembly of the surgical instrument 8002. Likewise, the shaft assembly 8004d includes an RFID scanner 8008b positioned adjacent to a distal coupling portion 8013, which is configured to engage with a corresponding coupling portion 8014 of the end effector assembly 8004f. The end effector assembly 8004f further includes an RFID tag 8006f that is brought into detection range of the RFID scanner 8006f when the aforementioned components are properly coupled together.

Therefore, the control system for the surgical instrument 8002 associated with this aspect can read the instrument components as they are assembled or coupled together and thereby control the surgical instrument 8002 accordingly based upon the presence, type, and/or arrangement of components being utilized.

In some aspects, RFID tags 8006 and RFID scanners 8008 can be positioned such that they are brought into detection range of each other during use of the surgical instrument 8002. For example, FIGS. 56-58, which are described in greater detail above, illustrate an aspect where a surgical instrument includes a pair of RFID tags 1201, 1203 that are recognizable or detectable by an RFID scanner 1202 when the stapling head assembly 1300 is in a closed configuration, i.e., where tissue is captured between the anvil 1200 and stapling head assembly 1300. Therefore, the control system for the surgical instrument associated with this aspect can read the instrument components as the surgical instrument is utilized or operated (e.g., during a surgical procedure) and thereby control the surgical instrument accordingly based upon the state of or actions being performed by the surgical instrument.

The RFID tags 8006 can also be positioned on consumables utilized by the surgical instrument 8002 during the operation thereof. For example, FIG. 62 illustrates an aspect where the surgical instrument 8002 is a clip applier including an RFID scanner 8008*c* positioned adjacently to the jaws 8020 for crimping or applying a surgical clip 8022 at a surgical site. The clips 8022 can include RFID tags 8006*i* that can be read by the RFID scanner 8008*c* as a consequence of the clip 8022 being positioned within the jaws 8020. Therefore, the control system for the surgical instrument associated with this aspect can read the consumables as the surgical instrument 8002 is utilized or operated (e.g., during a surgical procedure) and thereby control the surgical instrument 8002 accordingly based upon the type or characteristics of the consumables being utilized with the surgical instrument 8002. In various aspects, clips 8022 are fed to the jaws 8020 of the clip applier, and the fed clips 8022 become detectable by the RFID scanner 8008*c* as they reach the jaws 8020.

RFID tags 8006 can be configured to transmit a variety of different information to an associated RFID scanner 8008. Further, the various RFID tags 8006 described herein can be configured to transmit data in either an active manner (i.e., actively transmitting data for receipt by an RFID scanner 8008) or a passive manner (i.e., in response to an interrogation signal transmitted by an RFID scanner 8008). For example, the table 8030 illustrated in FIG. 60 indicates data that can be transmitted by RFID tags 8006 associated with the various components of the surgical instrument 8002 shown in FIG. 59. In particular, the RFID tag 8006*a* associated with the housing assembly 8004*a* can store a datum identifying the device or surgical instrument type; the RFID tag 8006*b* associated with the battery 8004*b* can store a datum identifying the battery type; the RFID tag 8006*c* associated with the motor assembly or gearbox 8004*c* can store a datum identifying the motor type; the RFID tag 8006*d* associated with the shaft assembly 8004*d* can store data identifying the shaft type and/or characteristics associated with the shaft (e.g., length or articulation type); and the RFID tag 8006*e* associated with the cartridge 8004*e* can store data identifying the cartridge type and/or other cartridge characteristics (e.g., length, color, or gripping surface type). This data can be transmitted by the RFID tags 8006 when read by a corresponding RFID scanner 8008, which in turn can be coupled to a control system for controlling the surgical instrument 8002. The various control algorithms that can be affected based upon this data can include communication protocols implemented by the control system.

As another example, the tables 8040, 8050 illustrated in FIGS. 63 and 64 indicate data that can be transmitted by RFID tags 8006 associated with consumables, such as the surgical clips 8022 as shown in FIG. 62. In particular, the RFID tags 8006*i* can store a datum identifying the type of the consumable (e.g., a product name, product code, or serial number) or characteristics of the consumable (e.g., cross-sectional profile, length, surface type, tensile strength, or spring back properties for a surgical clip 8022) with which each RFID tag 8006*i* is associated. Further, this data can be transmitted by the RFID tags 8006*i* for receipt by a corresponding RFID scanner 8008*c*, which in turn can be coupled to a control circuit 1210 that can utilize the received data for controlling the operations or functions of the surgical instrument.

With the surgical system 8000 configurations illustrated in FIGS. 55-59, 61, and 62, control systems for surgical instruments 8002 and other surgical system components can utilize a variety of different algorithms or logics for controlling the actions or operations of their subject devices by detecting the arrangement and/or type of surgical system components present within the operating room and/or the identifying users present within the operating room through the described RFID detection assemblies. In various examples, the control systems and associated RFID detection assemblies can be utilized to control communication protocols utilized by surgical instruments 8002, information or alerts provided to users, and/or operational settings implemented by surgical instruments 8002 to customize their functions according to the particular equipment between utilized and/or user preferences. In the following descriptions of processes, reference should also be made to FIG. 55. Further, the following processes describe, in part, scanning or receiving data from devices for controlling a surgical instrument 8002. Such devices can include a variety of different surgical system components, such as surgical instrument components (e.g., as shown in FIGS. 59, 61, and 62), a visualization system 11108 (FIGS. 49-51), a surgical hub 11106 (FIGS. 49-51), a robotic system 11110 (FIGS. 49-51), and so on.

Figure 65:
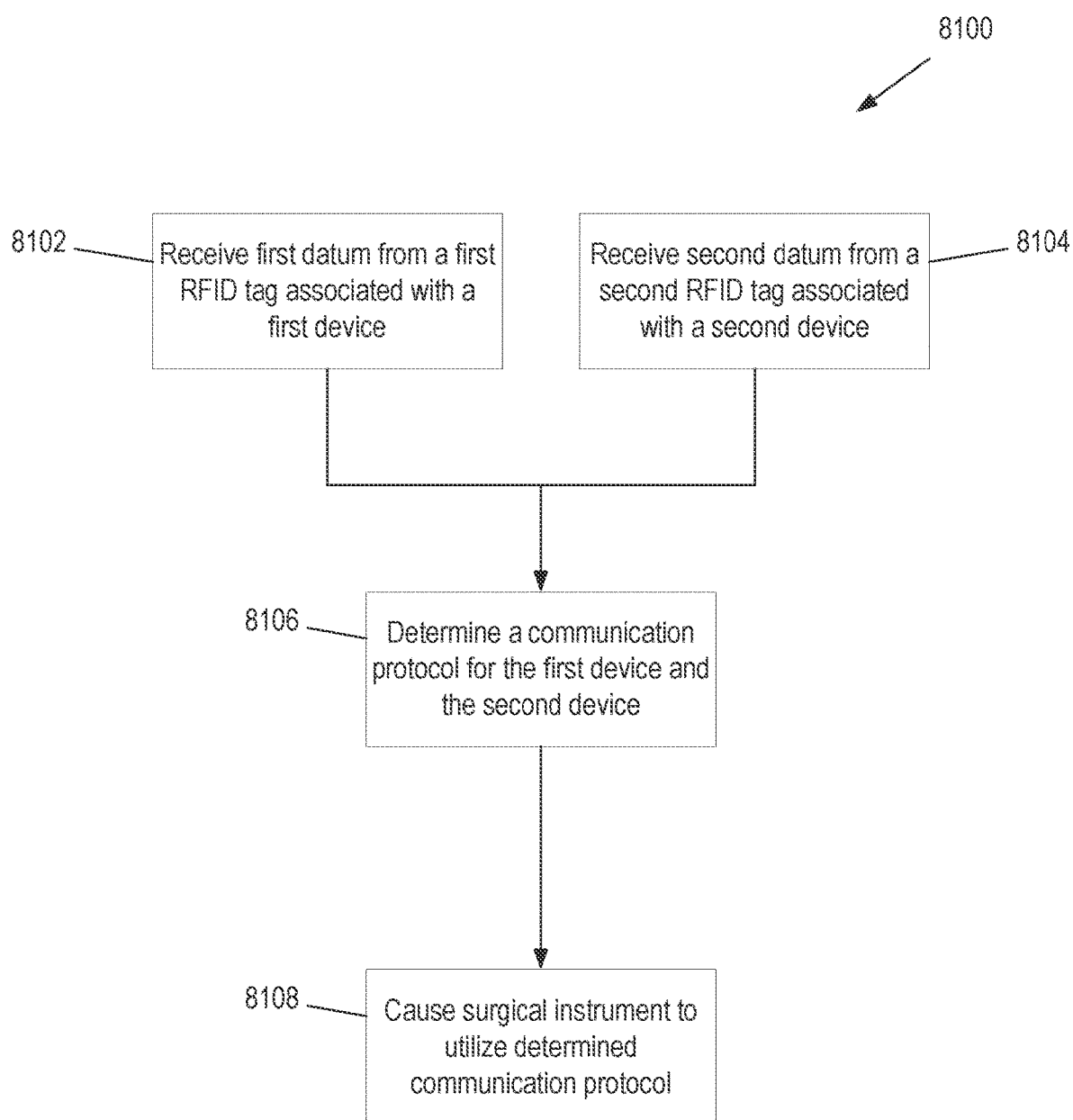
FIG. 65 illustrates a logic flow diagram of a process for determining a surgical instrument communication protocol via an RFID assembly, in accordance with at least one aspect of the present disclosure.

In one aspect, a control system 8111 for a surgical instrument 8002 can be configured to establish the communication protocol utilized by the surgical instrument 8002 for communicating with various other surgical system components according to RFIDs scanned thereby. For example, the control system 8111 can execute the process 8100 illustrated in FIG. 65. Accordingly, the control circuit 1210 receives 8102 a first datum from a first RFID tag associated with a first device and receives 8104 a second datum from a second RFID tag associated with a second device via one or more RFID scanners such as, for example, RFID scanners 8008 (FIG. 55A) to which the control circuit 1210 is coupled. The received data can indicate, for example, the serial number of a device, the device type, and/or characteristics or parameters associated with the device.

Accordingly, the control circuit 1210 determines 8106 a communication protocol for communicating with the first device and the second device. The control circuit 1210 can determine 8106 the appropriate communication protocol by, for example, querying a lookup table (e.g., stored in the memory 1212) with the received device data. The communication protocol can define, for example, encryption techniques, packet sizes, transmission speeds, or handshake techniques. Accordingly, the control circuit 1210 causes 8108 the surgical instrument 8002 to utilize the determined communication protocol for communicating with the surgical system components during the course of the surgical procedure.

In operation, a control system 8111 executing the illustrated process 8100 can read the RFID tags associated with the surgical system components present within the operating room, determine the appropriate communication protocol(s) for communicating with the particular arrangement of surgical system components, and then cause the surgical instrument 8002 to utilize the determined communication protocol. After establishment of communications between the surgical instrument 8002 and the corresponding surgical system components, the control circuit 1210 can be configured to receive an operational setting for the surgical instrument 8002 from at least one of the surgical system components. For example, if the surgical instrument 8002 is communicably coupled to a surgical hub 8001, 11106, the surgical instrument 8002 can download an updated control program setting forth updated operational settings or parameters from the surgical hub 8001, 11106. Alternatively, after establishment of communications between the surgical instrument 8002 and the corresponding surgical system components, the control circuit 1210 can be configured to transmit an operational setting for the surgical system component. For example, if the surgical instrument 8002 is communicably coupled to a robotic system 11110, the surgical instrument 8002 can transmit operational settings to the robotic system 11110 indicating how the surgical instrument 8002 should be controlled or actuated by the robotic system 11110 during a surgical procedure. Additionally, or alternatively, the surgical instrument 8002 can, for example, transmit sensor data to a surgical hub 8001, 11106.

Figure 66:
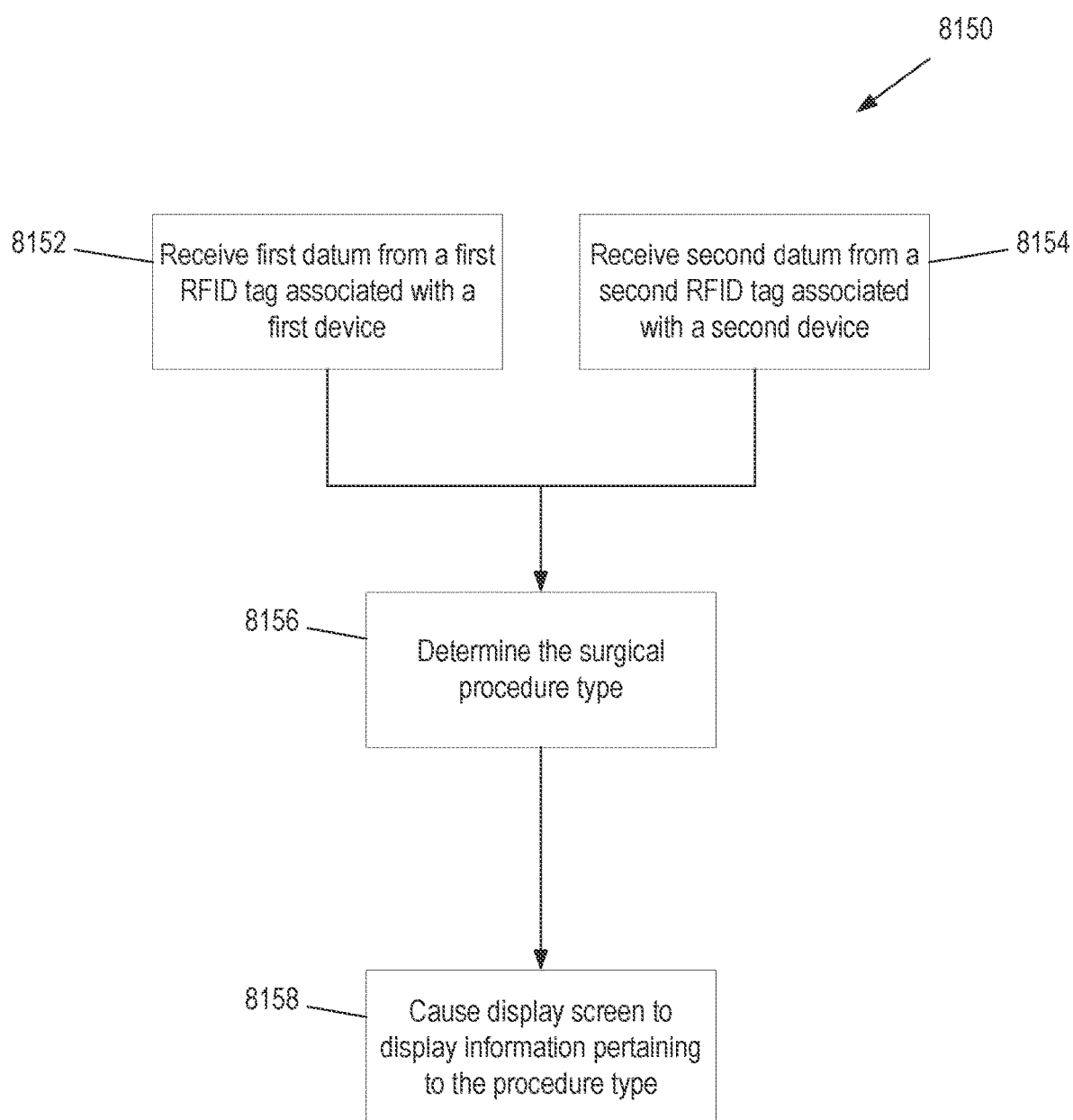
FIG. 66 illustrates a logic flow diagram of a process for determining surgical procedure information for display via an RFID assembly, in accordance with at least one aspect of the present disclosure.

In one aspect, a control system 8111 for a surgical instrument 8002 can be configured to automatically display information pertinent for the surgical procedure type. For example, the control system 8111 can execute the process 8150 illustrated in FIG. 66. Accordingly, the control circuit 1210 receives 8152 a first datum from a first RFID tag associated with a first device and receives 8154 a second datum from a second RFID tag associated with a second device via one or more RFID scanners such as, for example, RFID scanners 8008 (FIG. 55A) to which the control circuit 1210 is coupled. The received data can indicate, for example, the serial number of the device, the device type, and/or characteristics or parameters associated with the device.

Accordingly, the control circuit 1210 determines 8156 the type of surgical procedure that is being performed based upon the device data. The control circuit 1210 can make this determination because the particular combination or arrangement of device types within the operating room can indicate what type of surgical procedure is being performed. Further, the combination of data from multiple devices can indicate details of the surgical procedure that may not be possible to ascertain from scanning any individual device. For example, if a robotic system 11110 is present within the operating room along with a particular surgical instrument type (e.g., a circular stapler or a vascular stapler), then the surgical procedure corresponding to the surgical instrument type is likely going to be performed robotically. As another example, if an insufflator and a visualization system 11108 is presented within the operating room, then a laparoscopic procedure is likely going to be performed. In either of these examples, scanning an individual device would often not provide the full context for the procedure. The control circuit 1210 can determine 8156 the surgical procedure type by, for example, querying a lookup table (e.g., stored in the memory 1212) with the received device data. Subsequently, the control circuit 1210 causes 8158 a display screen (e.g., the indicator 1209 or the hub display 11215 (FIG. 53)) to display information relevant to the surgical procedure type. The displayed information can include, for example, steps for performing the surgical procedure, steps for assembling the surgical instrument 8002 or other surgical system components, relevant data or visualization screens for the surgical instrument types expected to be utilized in association with the procedure, and so on.

Figure 67:
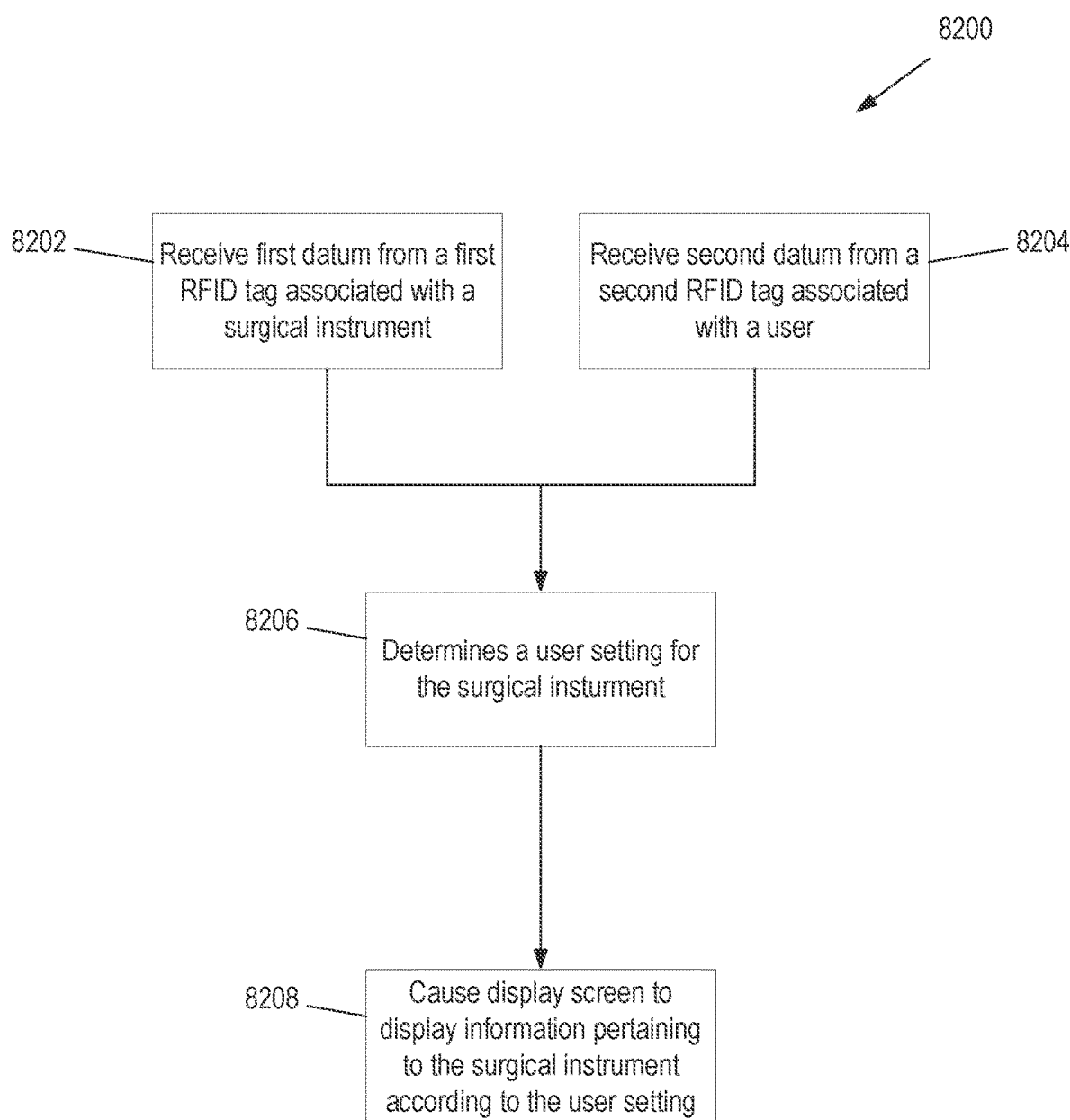
FIG. 67 illustrates a logic flow diagram of a process for determining information tailored to a user via an RFID assembly, in accordance with at least one aspect of the present disclosure.

In one aspect, a control system 8111 for a surgical instrument 8002 can be configured to automatically display information that is customized for the particular user. For example, the control system 8111 can execute the process 8200 illustrated in FIG. 67. Accordingly, the control circuit 1210 receives 8202 a first datum from a first RFID tag associated with a device or surgical instrument and receives 8204 a second datum from a second RFID tag associated with a user (e.g., from a user identifier 8010 as illustrated in FIG. 61) via one or more RFID scanners such as, for example, RFID scanners 8008 (FIG. 55A) to which the control circuit 1210 is coupled. The data received from the instrument or device can indicate, for example, the serial number of the device, the device type, and/or characteristics or parameters associated with the device. The data received from the user identifier 8010 can indicate, for example, the identity or title of the user.

Accordingly, the control circuit 1210 determines 8206 a user setting associated with the surgical instrument. The user settings can include a magnification for a particular scope type, instrument parameter information (e.g., temperature, force to fire, or power level), and so on. The control circuit 1210 can determine 8206 the user setting by retrieving the relevant user setting(s) (e.g., from the memory 1212). As noted above, the user settings can be manually set by the user at a computer system or automatically learned by the surgical system through situational awareness. Accordingly, the control circuit 1210 causes 8208 a display screen to display information pertaining to the surgical instrument according to the determined user setting(s).

Figure 68:
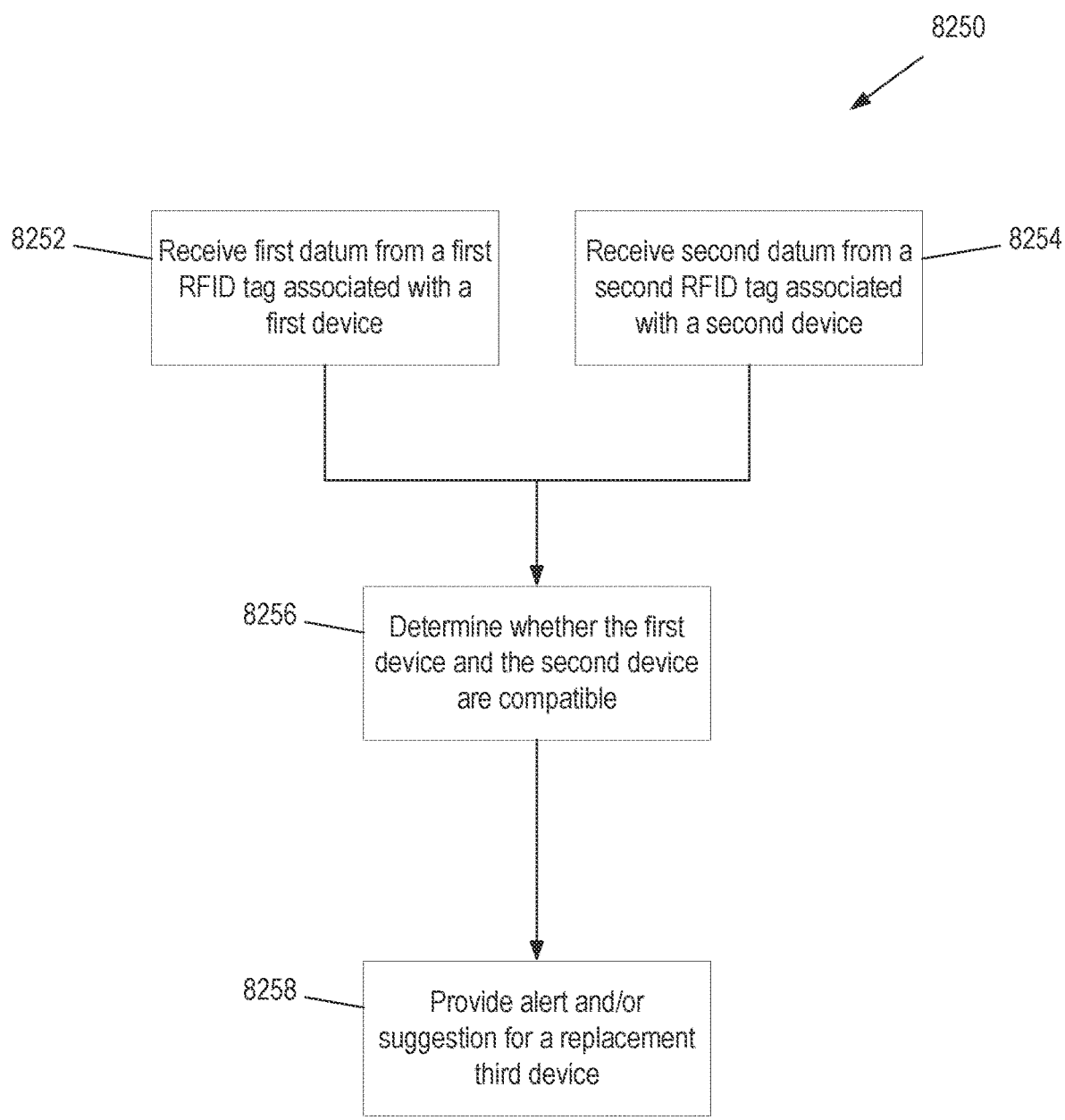
FIG. 68 illustrates a logic flow diagram of a process for determining whether surgical system components are compatible via an RFID assembly, in accordance with at least one aspect of the present disclosure.

In one aspect, a control system 8111 for a surgical instrument 8002 can be configured to determine whether surgical instrument components are compatible with each other and then take various correct actions. For example, the control system 8111 can execute the process 8250 illustrated in FIG. 68. Accordingly, the control circuit 1210 receives 8252 a first datum from a first RFID tag associated with a first device and receives 8254 a second datum from a second RFID tag associated with a second device via one or more RFID scanners such as, for example, RFID scanners 8008 (FIG. 55A) to which the control circuit 1210 is coupled. The received data can indicate, for example, the serial number of the device, the device type, and/or characteristics or parameters associated with the device.

Accordingly, the control circuit 1210 determines 8256 whether the first device and the second device are compatible. The control circuit 1210 can determine 8256 whether the devices are compatible by, for example, querying a lookup table (e.g., stored in the memory 1212) setting forth compatible surgical instrument device types with the received device data. The control system 8111 can be manufactured to store lists of compatible component types or receive compatible component types from a remote computing system (e.g., the cloud 11204 (FIG. 53)) to which the control system 8111 is communicably coupled, for example. If the components are determined 8256 to be incompatible with each other, the control circuit 1210 can provide 8258 an alert to the user that the components are incompatible and/or a suggestion of a replacement compatible component for one of the incompatible components. For example, if the user inserts a battery 8004*b* into the housing assembly 8004*a* of the surgical instrument 8002 that is incompatible with the motor assembly 8004*c*, the control system 8111 can cause the display (e.g., indicator 1209) to provide 8258 an alert or a suggestion for an alternative type of battery 8004*b* that is compatible with the motor assembly 8004*c*. In one aspect, the control circuit 1210 can further be configured to prevent the operation or activation of the surgical instrument 8002 in the event that the first and second devices are determined to be incompatible with each other.

In various aspects, preventing the operation or activation of a surgical instrument 8002 can be achieved using one or more suitable lockout assemblies such as, for example, a lockout assembly 8170. Various lockout out assemblies that are suitable for use with the present disclosure are described in U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, which are incorporated by reference herein in their entireties.

Figure 69A:
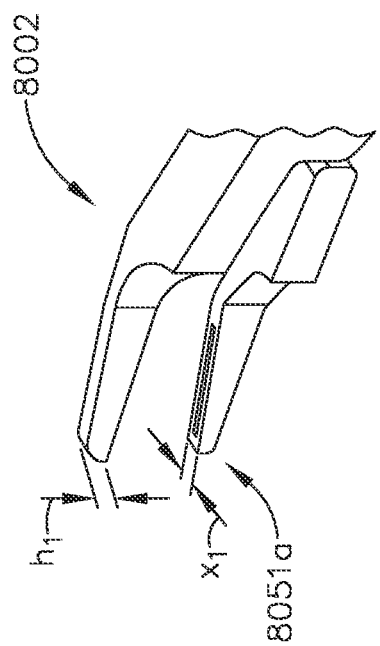
FIG. 69A illustrates a perspective view of a first jaw assembly for a surgical clip applier, in accordance with at least one aspect of the present disclosure.
Figure 69B:
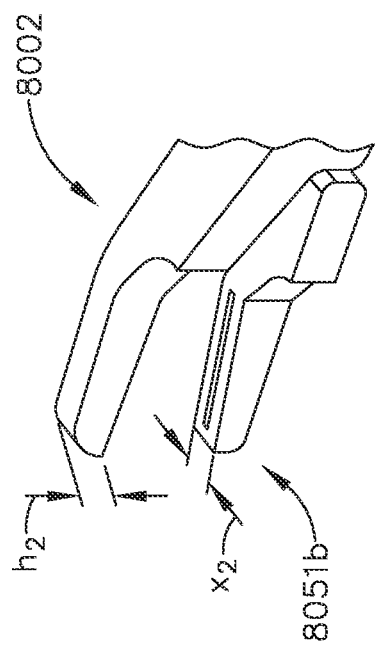
FIG. 69B illustrates a perspective view of a second jaw assembly for a surgical clip applier, in accordance with at least one aspect of the present disclosure.
Figure 70:
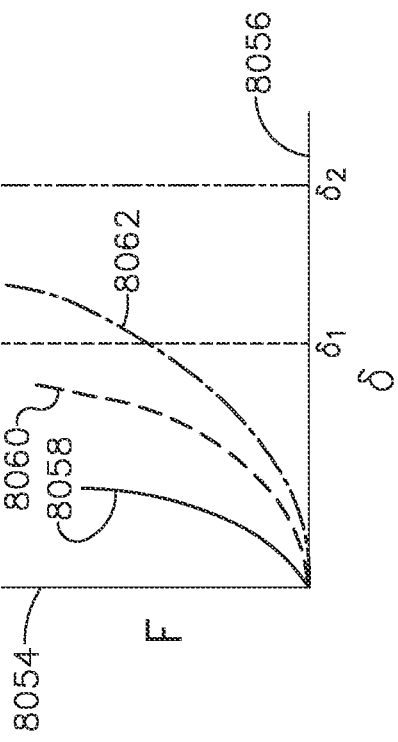
FIG. 70 illustrates a graph depicting force relative to displacement stroke for various surgical clip applier firings as controlled by a control system, in accordance with at least one aspect of the present disclosure.

As another example, a surgical instrument 8002 in the form of a surgical clip applier can have different types of jaw assemblies that are appropriate for different types of surgical clips 8022, such as a first, or thin, jaw assembly 8051*a* shown in FIG. 69A and a second, or thick, jaw assembly 8051*b* shown in FIG. 69B. FIG. 70 illustrates a graph 8052 depicting the relationship between force applied to form or crimp the surgical clip, represented by the vertical axis 8054, and a displacement stroke causing the force application, represented by the horizontal axis 8056, for multiple prophetic firings of a clip applier including a control system 8111 executing the process 8250 illustrated in FIG. 68. A first distance threshold $\delta_1$ represents the maximum stroke distance that a clip applier having a thin jaw assembly 8051*a* is capable of performing. Further, a second distance threshold $\delta_2$ represents the maximum stroke distance that a clip applier having a thick jaw assembly 8051*b* is capable of performing. As further illustrated in the table 8050 in FIG. 64, different types of surgical clips 8022 can have different mechanical properties; therefore, some types of surgical clips may not be suitable for use with all types of clip appliers. In this particular prophetic example, the first line 8058 represents a first clip type (e.g., a Ti-CP clip), the second line 8060 represents a second clip type (e.g., Ti-3Al/2.5V clip), and the third line 8062 represents a third clip type (e.g., a Ti-6Al-4V clip). In this implementation of the process 8250, the clip applier can be the first device and the surgical clip can be the second device. Accordingly, if a control circuit 1210 executing the process 8250 determines that the surgical clip read by the RFID scanner 8008 (e.g., when the clip is inserted into the clip applier) is the first type or the second type, then no alert or suggestion is provided to the user for either of the clip applier types shown in FIGS. 69A and 69B because both of these clip types are compatible with either clip applier type (as indicated by neither of the lines 8058, 8060 violating the respective thresholds $\delta_1$, $\delta_2$). However, if the control circuit 1210 determines that the surgical clip read by the RFID scanner 8008 is the third type and the clip applier is the thin jaw assembly type 8051*a*, then the control circuit 1210 can provide an alert and/or a suggestion for a replacement surgical clip because the maximum displacement stroke $\delta_1$ for the thin jaw assembly type 8051*a* is not long enough to properly form the third clip type (as indicated by the third line 8062 crossing the threshold $\delta_1$).

In one aspect, a control system 8111 for a surgical instrument 8002 can be configured to automatically establish the operational settings of the surgical instrument 8002 according to the scanned components. For example, the control system 8111 can execute a process 8300 illustrated in FIG. 71. Accordingly, the control circuit 1210 receives 8302 a first datum from a first RFID tag associated with a first device and receives 8304 a second datum from a second RFID tag associated with a second device via one or more RFID scanners such as, for example, RFID scanners 8008 (FIG. 55A) to which the control circuit 1210 is coupled. The received data can indicate, for example, the serial number of the device, the device type, and/or characteristics or parameters associated with the device. As one example, the devices can include two or more of the components of the surgical instrument 8002 illustrated in FIGS. 59 and 12. As another example, the devices can include two or more of the components of the surgical instrument 8002 illustrated in FIG. 61.

Accordingly, the control circuit 1210 can determine 8306 the surgical instrument type based upon the scanned components. The surgical instrument type can include, for example, the general instrument type (e.g., a surgical stapler, an electrosurgical instrument, an ultrasonic surgical instrument, or combinations thereof) in combination with particular instrument component parameters (e.g., shaft length, cartridge type, or battery power). In one aspect, the RFID scanner(s) 8008 can be positioned such that the RFID tags associated with each of the components are naturally read by the RFID scanner(s) 8008 as a natural consequence of the assembly or utilization of the surgical instrument 8002, as described above in connection with FIGS. 61 and 62. Accordingly, the control circuit 1210 can determine 8308 an operational setting according to the determined instrument type. The operational settings can dictate how the surgical instrument 8002 itself (or a component thereof) is controlled or how a third device (e.g., a surgical generator that the surgical instrument 8002 is coupled to) is controlled. The table 8030 illustrated in FIG. 60 indicates various settings that could be controlled by a control circuit 1210 according to the determined instrument type. For example, a control circuit 1210 executing the process 8300 could control the maximum power of the surgical instrument 8002 according to the detected battery type and the detected motor assembly type. As another example, a control circuit 1210 executing the process 8300 could control the force to fire a knife in a surgical stapler according to the detected motor assembly type and the detected cartridge type.

In one aspect, a control system 8111 for a surgical instrument 8002 can be configured to automatically establish the operational settings of the surgical instrument 8002 according to consumables that are scanned as they are assembled with and/or inserted into the surgical instrument 8002. For example, the control system 8111 can execute the process 8350 illustrated in FIG. 72. Accordingly, the control circuit 1210 receives 8352 a first datum from a first RFID tag associated with a device or surgical instrument 8002 and receives 8354 a second datum from a second RFID tag associated with a consumable via one or more RFID scanners such as, for example, RFID scanners 8008 (FIG. 55A) to which the control circuit 1210 is coupled. The received data can indicate, for example, the serial number of the surgical instrument 8002 or consumable, the surgical instrument 8002 or consumable type, and/or characteristics or parameters associated with the surgical instrument 8002 or consumable. For example, the surgical instrument 8002 can include a clip applier and the consumable can include a surgical clip 8022, as shown in FIG. 62. As another example, the surgical instrument 8002 can include a surgical stapler and the consumable can include staples disposed within a cartridge 8004e, as shown in FIG. 60.

Accordingly, the control circuit 1210 determines 8356 an operational setting according to the consumable type and the surgical instrument type. The control circuit 1210 can determine 8356 the operational setting by, for example, querying a lookup table (e.g., stored in the memory 1212) setting forth the appropriate operational settings for the surgical instrument according to the scanned consumable. The control system 8111 can be manufactured to store operational settings for various compatible device types or receive operational settings from a remote computing system (e.g., the cloud 11204 (FIG. 53)) to which the control system 8111 is communicably coupled, for example. Accordingly, the control circuit 1210 can then control 8358 the surgical instrument according to the determined operational setting(s).

Various prophetic implementations of the process 8350 are illustrated in connection with FIGS. 73 and 74. For example, FIG. 73 illustrates a graph 8064 depicting the relationship between force applied to the surgical clip, represented by the vertical axis 8066, and displacement stroke, represented by the horizontal axis 8068, for a clip applier including a control system 8111 executing the process 8350 illustrated in FIG. 72. In this example, the control circuit 1210 can determine that the surgical instrument is a clip applier and can determine the identity of the consumables as they are loaded into the clip applier, as discussed above in relation to FIG. 62. In a first firing of the clip applier, represented by the first line 8070, the control circuit 1210 further determines that the consumable is a first type of surgical clip (e.g., a Ti-CP clip). For this type of clip, the controlled operational parameters include a first force threshold $F_1$ and a first closure rate $V_1$. Accordingly, the control circuit 1210 controls the clip applier according to the determined operational parameters, i.e., closes the jaws of the clip applier at the first closure rate $V_1$ and halts closure at or below the first force threshold $F_1$. In a second firing of the clip appliers, represented by the second line 8072, the control circuit 1210 determines that the consumable is a second type of surgical clip (e.g., a Ti-6Al-4V clip). For this type of clip, the appropriate operational parameters include a second force threshold $F_2$ and a second closure rate $V_2$. Accordingly, the control circuit 1210 controls the clip applier according to the determined operational parameters, i.e., closes the jaws of the clip applier at the second closure rate $V_2$ and halts closure at or below the second force threshold $F_2$.

Figure 72:
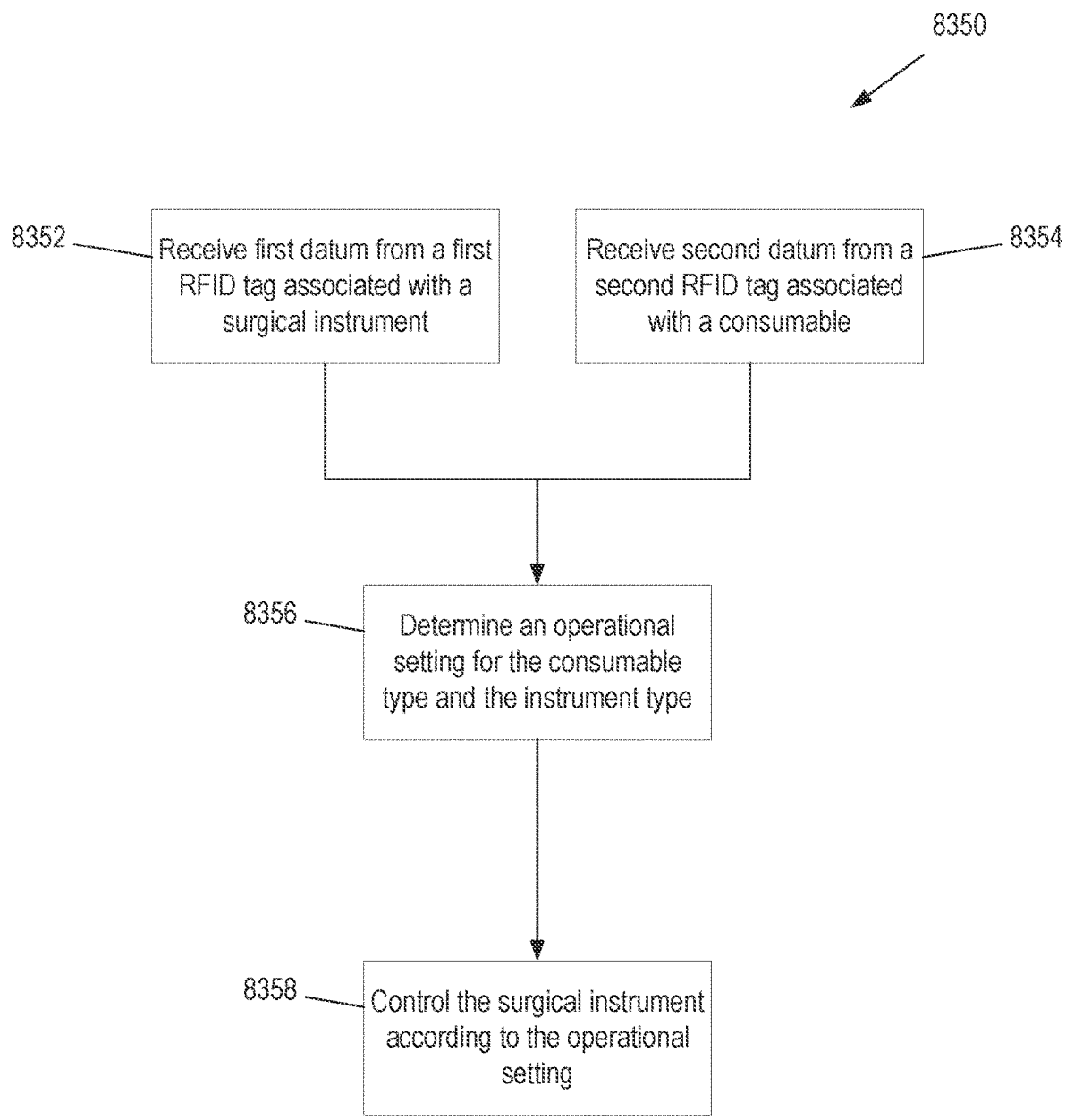
FIG. 72 illustrates a logic flow diagram of a process for determining surgical instrument operational settings according to consumable type via an RFID assembly, in accordance with at least one aspect of the present disclosure.
Figure 74:
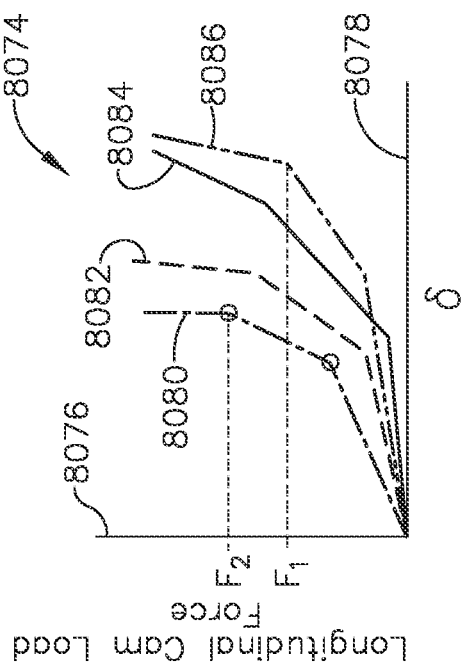
FIG. 74 illustrates a graph depicting longitudinal cam load force relative to displacement stroke for various surgical clip applier firings as controlled by a control system, in accordance with at least one aspect of the present disclosure.
Figure 73:
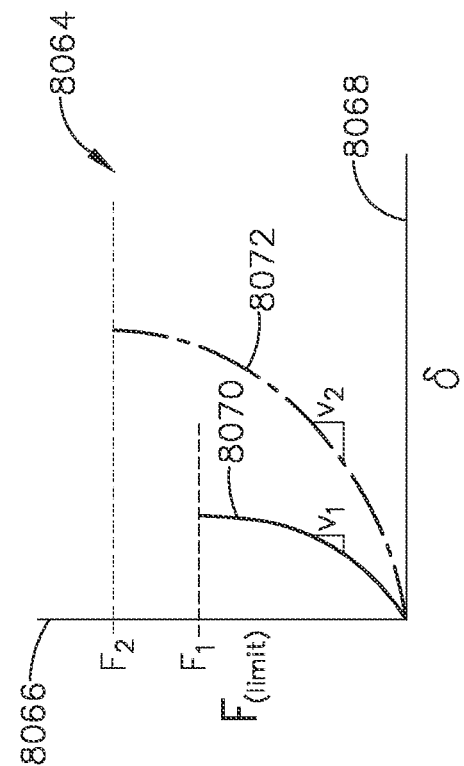
FIG. 73 illustrates a graph depicting force relative to displacement stroke for various surgical clip applier firings as controlled by a control system, in accordance with at least one aspect of the present disclosure.

As another example, FIG. 74 illustrates a graph 8074 depicting the relationship between longitudinal cam load force, represented by the vertical axis 8076, and displacement stroke, represented by the horizontal line 8078, for multiple prophetic firings of a clip applier including a control system 8111 executing the process 8350 illustrated in FIG. 72. In a clip applier, a camming assembly can be configured to apply a closing force to the jaws and thereby apply a clip to tissue positioned within the jaws. Accordingly, the longitudinal cam load force can correspond to the amount of force being imparted upon the jaws of the clip applier. The displacement stroke can correspond to the distance that the cam of the camming assembly has been translated. The profile of the cam force applied by the surgical clip applier as a function of the distance by which the cam has been translated is a controllable parameter that can be tailored to different clip applier assemblies (e.g., as shown in FIGS. 69A and 69B) and/or different surgical clip types. In various aspects, this controllable parameter can be automatically selected by a control system 8111 for the surgical instrument and/or manually selected by a user. In this example, the control circuit 1210 has received 8352 a first datum from the surgical instrument identifying the surgical instrument as a clip applier, received 8454 a second datum identifying the consumable as a particular type of surgical clip, determined 8456 that the particular surgical clip type is associated with a particular cam force profile, and then controlled 8458 the clip applier according to the determined force profiles, as shown by the various lines 8080, 8082, 8084, 8086. The first line 8080 can correspond to the force profile determined 8356 by the control circuit 1210 for a first clip applier type (e.g., the jaw assembly 8051a illustrated in FIG. 69A) and first surgical clip type (e.g., a Ti-6Al-4V clip). The second line 8082 can correspond to the force profile determined 8356 by the control circuit 1210 for a first clip applier type and a second surgical clip type (e.g., a Ti-3AV/2.5V clip). The third line 8084 can correspond to the force profile determined 8356 by the control circuit 1210 for a first clip applier type and a third surgical clip type (e.g., a Ti-CP clip). The fourth line 8086 can correspond to the force profile determined 8356 by the control circuit 1210 for a second clip applier type (e.g., the jaw assembly 8051b illustrated in FIG. 69B) and a third surgical clip type.

Figure 75:
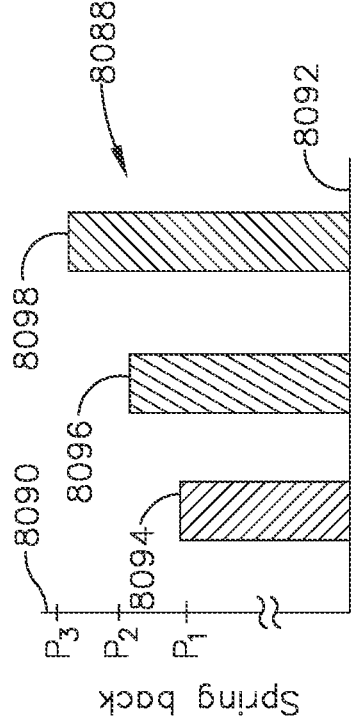
FIG. 75 illustrates a graph depicting spring back properties for various type of surgical clips, in accordance with at least one aspect of the present disclosure.

It can be desirable to utilize applied force profiles that are tailored to the types of clip appliers and surgical clips being utilized because different types of clip appliers apply forces in different ways and different types of surgical clips have different mechanical properties. Some examples of different mechanical properties are illustrated in the tables 8040, 8050 of FIGS. 63 and 64. Another mechanical property for which surgical clips can differ is the degree to which the surgical clips spring back in response to applied forces, which can in turn affect the degree or amount of force that one would wish to apply to the surgical clips to have them maintained in a desired configuration. For example, FIG. 75 illustrates a graph 8088 depicting the relationship between the spring back, represented by the vertical axis 8090, for different surgical clip types, represented by the horizontal axis 8092. The spring back can correspond to the percentage or degree to which a surgical clip will return relative to its initial position in response to a set force, for example. As can be seen from the graph 8088, a first surgical clip type 8094 has a spring back of $P_1$, a second surgical clip type 8096 has a spring back of $P_2$, and a third surgical clip type 8098 has a spring back of $P_3$. Therefore, it would be desirable for a control circuit 1210 executing the process 8350 illustrated in FIG. 72 to read which surgical clip type has been loaded into the clip applier and then adjust the applied force profile, at least based in part on the spring-back characteristic of a detected clip type.

In one aspect, a control system 8111 for a surgical instrument 8002 can be configured to automatically implement operational settings of the surgical instrument 8002 that are customized for a particular user. For example, the control system 8111 can execute the process 8400 illustrated in FIG. 76. Accordingly, the control circuit 1210 receives 8402 a first datum from a first RFID tag associated with a device or surgical instrument and receives 8404 a second datum from a second RFID tag associated with a user (e.g., from a user identifier 8010 as illustrated in FIG. 61) via one or more RFID scanners such as, for example, RFID scanners 8008 (FIG. 55A) to which the control circuit 1210 is coupled. The data received from the instrument or device can indicate, for example, the serial number of the device, the device type, and/or characteristics or parameters associated with the device. The data received from the user identifier 8010 can indicate, for example, the identity or title of the user.

Accordingly, the control circuit 1210 determines 8406 an operational setting for the surgical instrument that is associated with the user. The control circuit 1210 can determine 8406 the user setting by retrieving the relevant user setting(s) (e.g., from the memory 1212). As noted above, the user settings can be manually set by the user at a computer system or automatically learned by the surgical system through situational awareness. In one aspect, the determined operational setting can be selected from a range for the parameter. The user can manually select a value or the surgical system can learn the user's preference within the parameter range, for example. Accordingly, the control circuit 1210 can control the surgical instrument according to the operational setting associated with the user.

Figures 77, 78, 79:
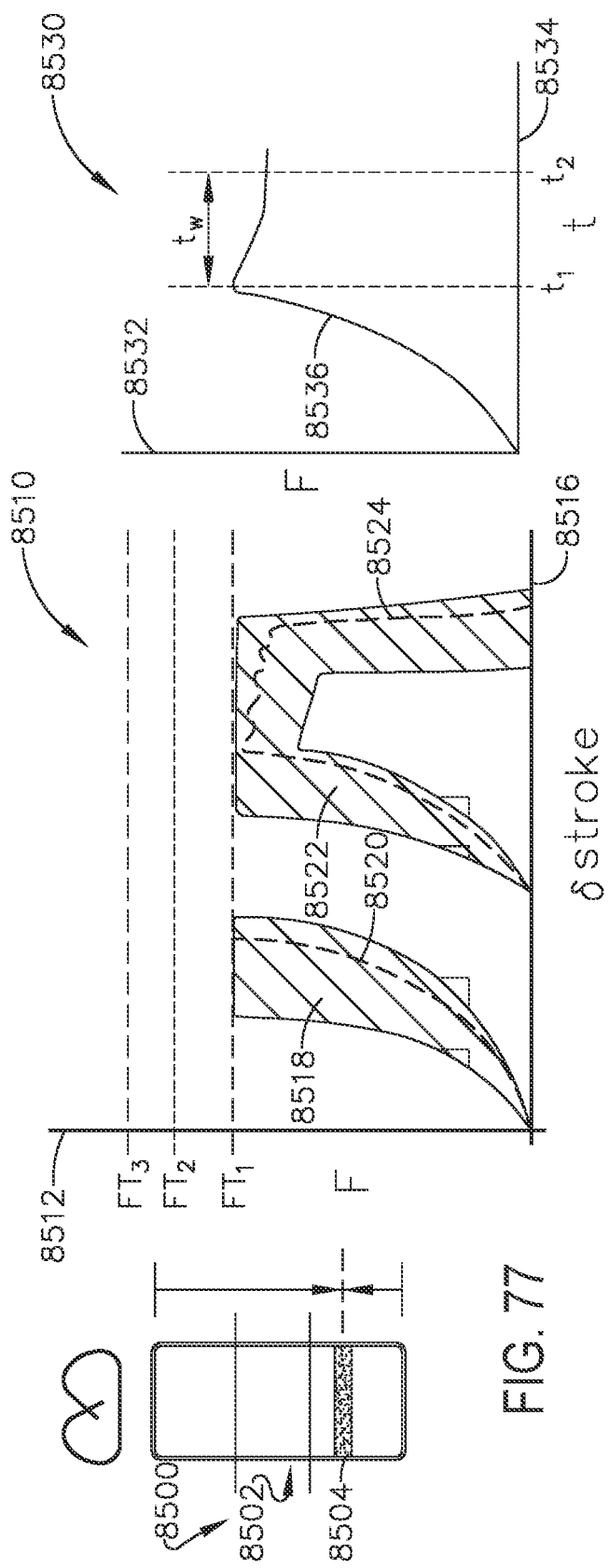
FIG. 77 illustrates a graphical user interface including a staple height widget, in accordance with at least one aspect of the present disclosure.
FIG. 78 illustrates a graph depicting force relative to displacement stroke for a surgical stapler firing as controlled by a control system, in accordance with at least one aspect of the present disclosure.
FIG. 79 illustrates a graph depicting force relative to time for a surgical stapler firing as controlled by a control system, in accordance with at least one aspect of the present disclosure.

Various prophetic implementations of the process 8350 of FIG. 72 are illustrated in connection with FIGS. 77-79. For example, FIG. 77 illustrates a staple height widget or icon 8500 that is displayable on a graphical user interface. The staple height or degree of deformation applied by a surgical stapler to deployed staples is a controllable parameter. The graphical user interface can be displayed on, for example, a device/instrument display 11237 or a hub display 11215. The staple height widget 8500 can include a range icon 8502 to indicate a suggested selection range for the staple height and a selection icon 8504 indicating the actual staple height that has been selected for the surgical stapler. In various aspects, the staple height widget 8500 can be manually manipulated by a user of the surgical stapler and/or controlled by a control system 8111 of the surgical stapler. In this example, the control circuit 1210 has received 8402 a first datum from the surgical instrument identifying the surgical instrument as a surgical stapler and/or from the staple cartridge identifying the cartridge type, received 8404 a second datum identifying the user, determined 8406 that the user identity is associated with a particular staple height setting for surgical staplers, and then controlled 8408 the surgical stapler to set the staple height to the defined setting indicated by the selection icon 8504.

Figure 76:
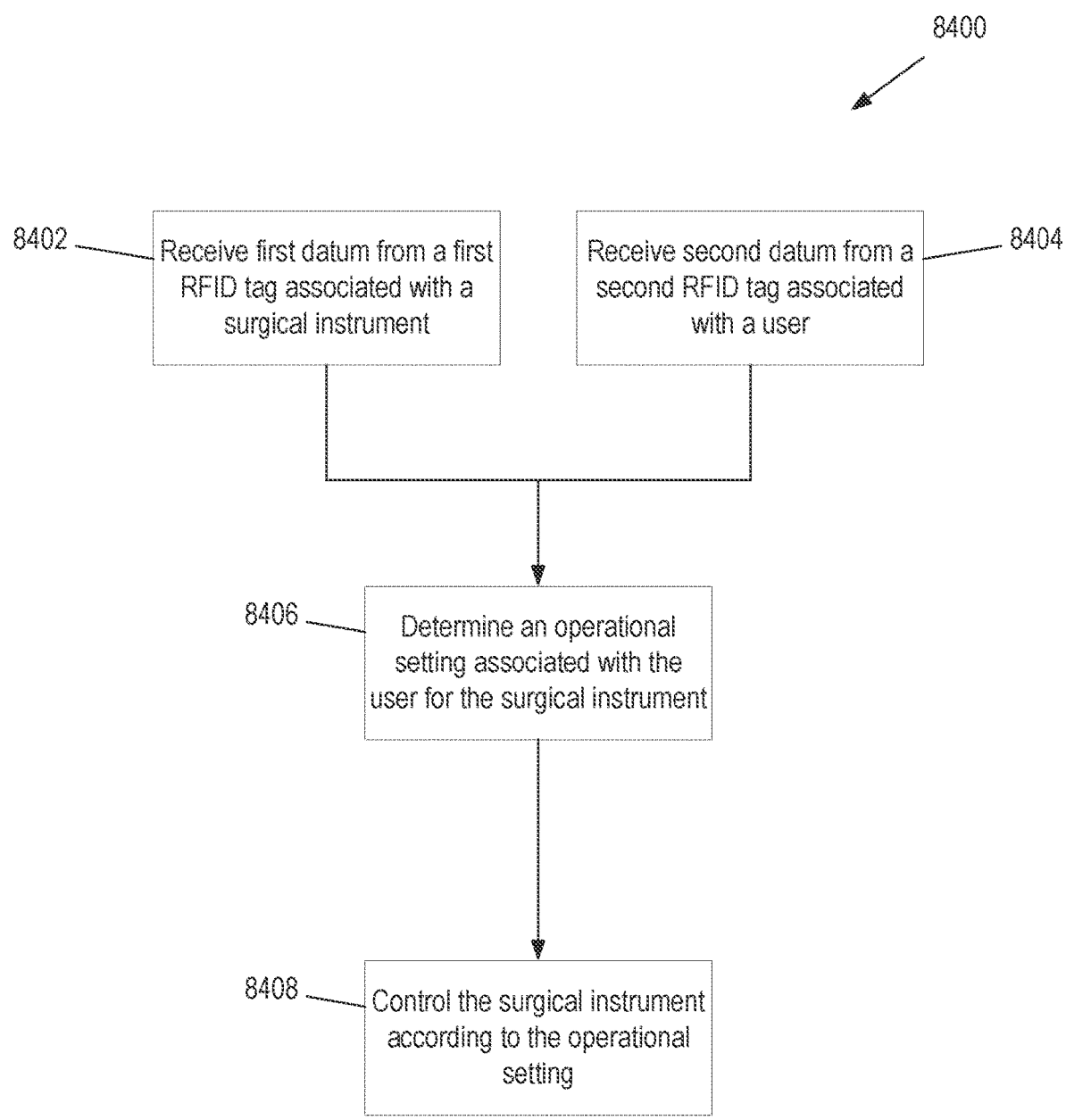
FIG. 76 illustrates a logic flow diagram of a process for determining surgical instrument operational settings tailored to a user via an RFID assembly, in accordance with at least one aspect of the present disclosure.

As another example, FIG. 78 illustrates a graph 8510 depicting the relationship between force, represented by the vertical axis 8512, and displacement stroke, represented by the horizontal axis 8516, for a prophetic firing of a surgical stapler including a control system 8111 executing the process 8400 illustrated in FIG. 76. The force represented by the vertical axis 8512 can correspond to the force experienced by or imparted upon a firing member configured to close the jaws of a surgical stapler, fire staplers, and/or cut tissue captured by the jaws. The force represented by the vertical axis 8512 can also correspond to the force load generated by a motor. The displacement stroke represented by the horizontal axis 8516 can correspond to the distance traveled by a firing member, which can be delineated into two distinct phases. In a first or closure phase, represented by the first line 8520, the firing member is driving closure of the jaws. In a second or firing phase, represented by the second line 8524, the firing member is deploying staples and cutting tissue. The speed at which the firing member is translated during the closure phase (i.e., the closure speed) and the speed at which the firing member is translated during the firing phase (i.e., the firing speed) are both controllable parameters. Further, the force threshold representing the maximum force that is permitted to be experienced by the surgical instrument before the control system 8111 halts the translation of the firing member or takes other corrective actions is likewise a controllable parameter. The force threshold can depend upon the particular surgical instrument component types that are being utilized. For example, the first force threshold $FT_1$ can represent the standard or base force limit, the second force threshold $FT_2$ can represent the force limit for a particular shaft type, and the third force threshold $FT_3$ can represent the force limit for a particular cartridge type. In various aspects, these controllable parameters can be automatically selected by a control system 8111 for the surgical instrument and/or manually selected by a user. This particular graph 8510 illustrates that the control system 8111 for the surgical instrument is executing two separate processes.

In particular, the graph 8510 demonstrates that a control circuit 1210 executing the process 8400 illustrated in FIG. 76 has received 8402 a first datum from the surgical instrument identifying the surgical instrument as a surgical stapler, received 8404 a second datum identifying the user, determined 8406 that the user identity is associated with a particular surgical stapler closure speed setting selected from a permitted closure speed range 8518 and a particular surgical stapler firing speed setting selected from a permitted firing speed range 8522, and then controlled 8408 the surgical stapler to drive the firing member at the selected speeds.

Figure 71:
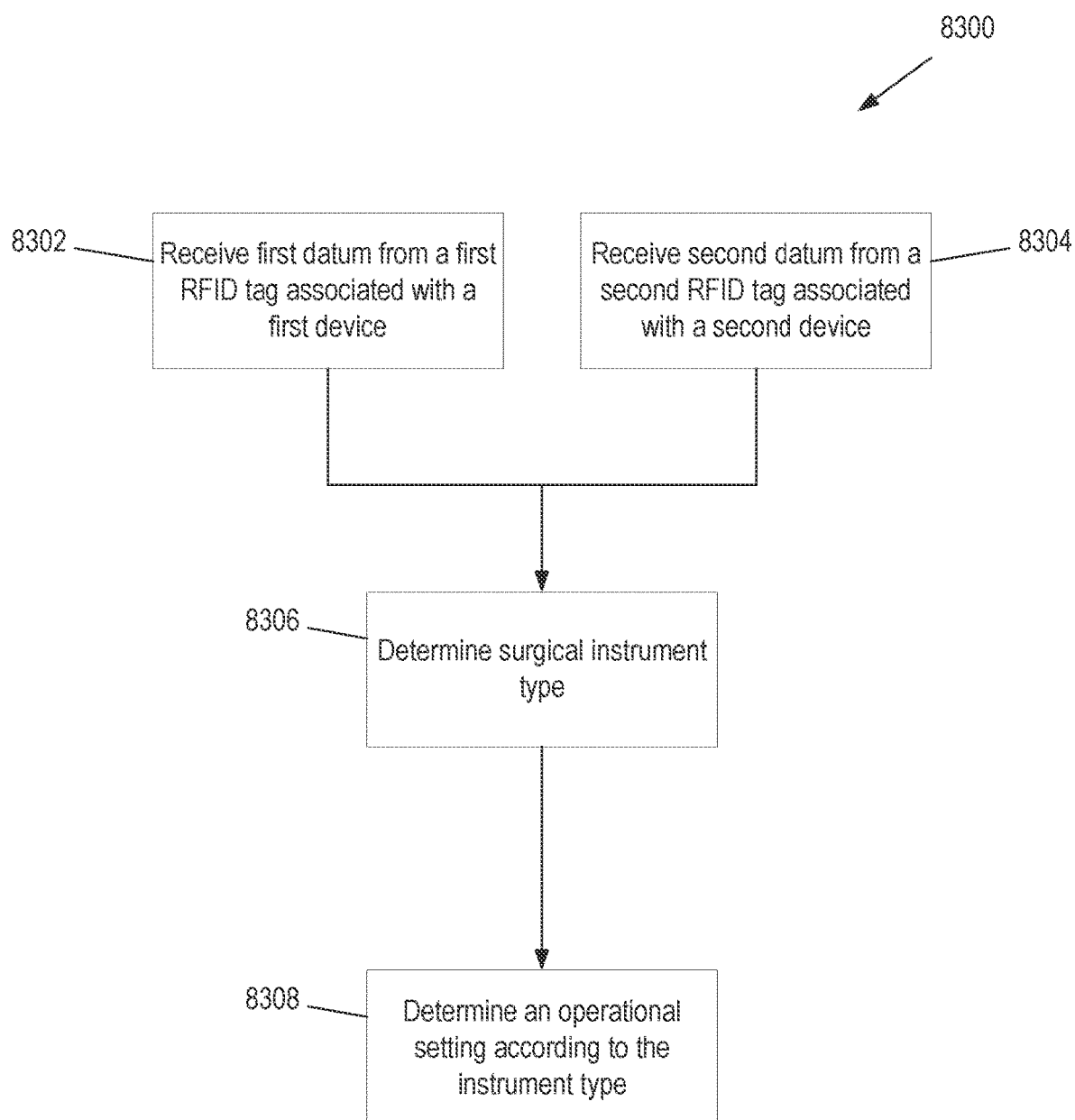
FIG. 71 illustrates a logic flow diagram of a process for determining surgical instrument operational settings via an RFID assembly, in accordance with at least one aspect of the present disclosure.

Further, the graph 8510 demonstrates that a control circuit 1210 executing the process 8300 illustrated in FIG. 71 or the process 8350 illustrated in FIG. 72 has received 8302, 8352 a first datum from the surgical instrument identifying the surgical instrument as a surgical stapler, received 8304, 8354 a second datum from the staple cartridge identifying the cartridge type, determined 8306, 8356 that the cartridge type is associated with a particular force threshold setting for the surgical stapler, and then controlled 8308, 8358 the surgical instrument to enforce the determined force threshold.

As demonstrated by FIG. 78, the various processes described herein, or any suitable portions thereof, can be utilized in conjunction with one other in any combination or arrangement for controlling a surgical instrument. Therefore, control systems 8111 implementing any combination of the described processes are intended to be within the scope of the present disclosure.

As yet another example, FIG. 79 illustrates a graph 8530 demonstrating the relationship between force, represented by the vertical axis 8532, and time, represented by the horizontal axis 8534, for a prophetic firing of a surgical stapler including a control system 8111 executing the process 8400 illustrated in FIG. 76. After clamping tissue, a surgical stapler is programmed to wait for a time period $t_w$ before cutting the clamped tissue or performing other actions. The wait time $t_w$ is a controllable parameter. In various aspects, the wait time $t_w$ can be manually selected by a user of the surgical stapler and/or controlled by a control system 8111 of the surgical stapler. In this example, the control circuit 1210 has received 8402 a first datum from the surgical instrument identifying the surgical instrument as a surgical stapler and/or from the staple cartridge identifying the cartridge type, received 8404 a second datum identifying the user, determined 8406 that the user identity is associated with a particular wait time $t_w$ setting for surgical staplers, and then controlled 8408 the surgical stapler to wait for a time period defined by the wait time $t_w$ setting, as indicated by the line 8536.

Figure 80:
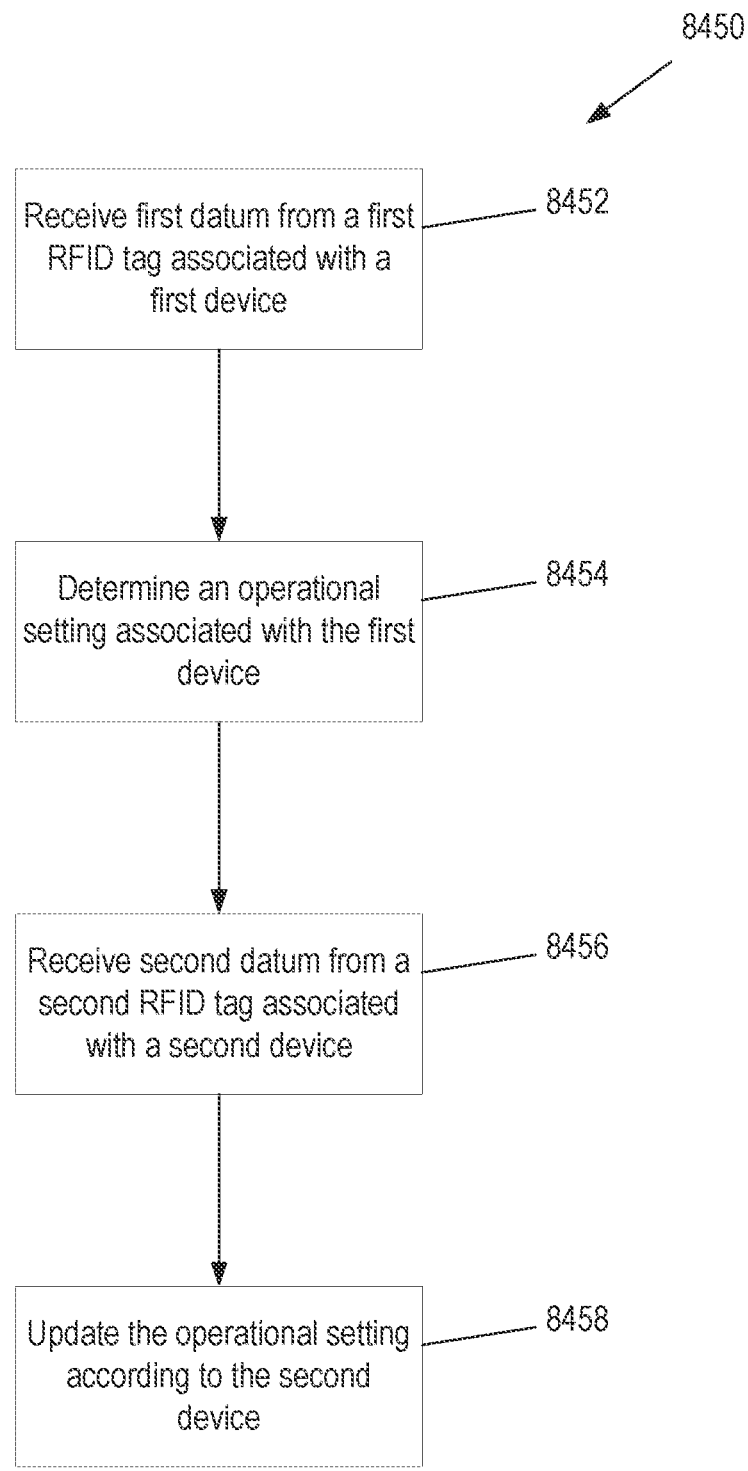
FIG. 80 illustrates a logic flow diagram of a process for successively updating an operational parameter via an RFID assembly, in accordance with at least one aspect of the present disclosure.

In one aspect, a control system 8111 for a surgical instrument 8002 can be configured to update an operational setting according to successively scanned devices. For example, the control system 8111 can execute the process 8450 illustrated in FIG. 80. Accordingly, the control circuit 1210 receives 8452 a first datum from a first RFID tag associated with a device or surgical instrument via one or more RFID scanners such as, for example, RFID scanners 8008 (FIG. 55A) to which the control circuit 1210 is coupled. Accordingly, the control circuit 1210 can determine 8454 an operational setting an operational setting based upon the scanned device. Further, the control circuit 1210 can thereafter receive 8456 a second datum from a second RFID tag associated with a second device via the RFID scanner 8008. Accordingly, the control circuit 1210 can update the determined operational setting according to the second device. For example, the control circuit 1210 can change the operational setting from a first value that is dependent on the first device to a second value that is dependent on both the first and second devices. The data received from the devices can indicate, for example, the serial number of the device, the device type, and/or characteristics or parameters associated with the device. As one example, the surgical instrument 8002 can include a trocar including an RFID scanner 8008. When a first device is inserted through the trocar, the control circuit 1210 can read the RFID tag associated with that first device and then update an operational setting associated with the surgical system based on the detection of that device. Then when a second device is inserted through the trocar, the control circuit 1210 can read the RFID tag associated with that second device and then update the operational setting accordingly. The operational setting in this example can include, for example, a generator power setting, a surgical stapler firing speed, or a counter tracking the number of device exchanges. Therefore, a control circuit 1210 executing the process 8450 can successively update operational settings as additional devices are introduced within the operating theater or surgical environment.

In one aspect, a control system 8111 for a surgical instrument 8002 can be configured to automatically update a default operational algorithm of the surgical instrument 8002 according to scanned components thereof. For example, the control system 8111 can execute a process 8700 illustrated in FIG. 81. Accordingly, the control circuit 1210 receives 8702 a first datum from a first RFID tag associated with a first device and receives 8704 a second datum from a second RFID tag associated with a second device via one or more RFID scanners such as, for example, RFID scanners 8008 (FIG. 55A) to which the control circuit 1210 is coupled. The received data can indicate, for example, the serial number of the device, the device type, and/or characteristics or parameters associated with the device. In one aspect, the RFID scanners 8008 can be positioned such that the RFID tags associated with each of the components are naturally read by the RFID scanners 8008 as a natural consequence of the assembly or utilization of the surgical instrument 8002, as described above in connection with FIGS. 61 and 62.

Furthermore, the control circuit 1210 can determine 8706 adjustments to a default control algorithm of the surgical instrument 8002 the received data. In addition, the control circuit 1210 can update 8708 the default control algorithm to an updated control algorithm based on the determined adjustments. The control algorithm can dictate how the surgical instrument 8002 itself (or a component thereof) is controlled or how a third device (e.g., a surgical generator that the surgical instrument 8002 is coupled to) is controlled.

Figure 81:
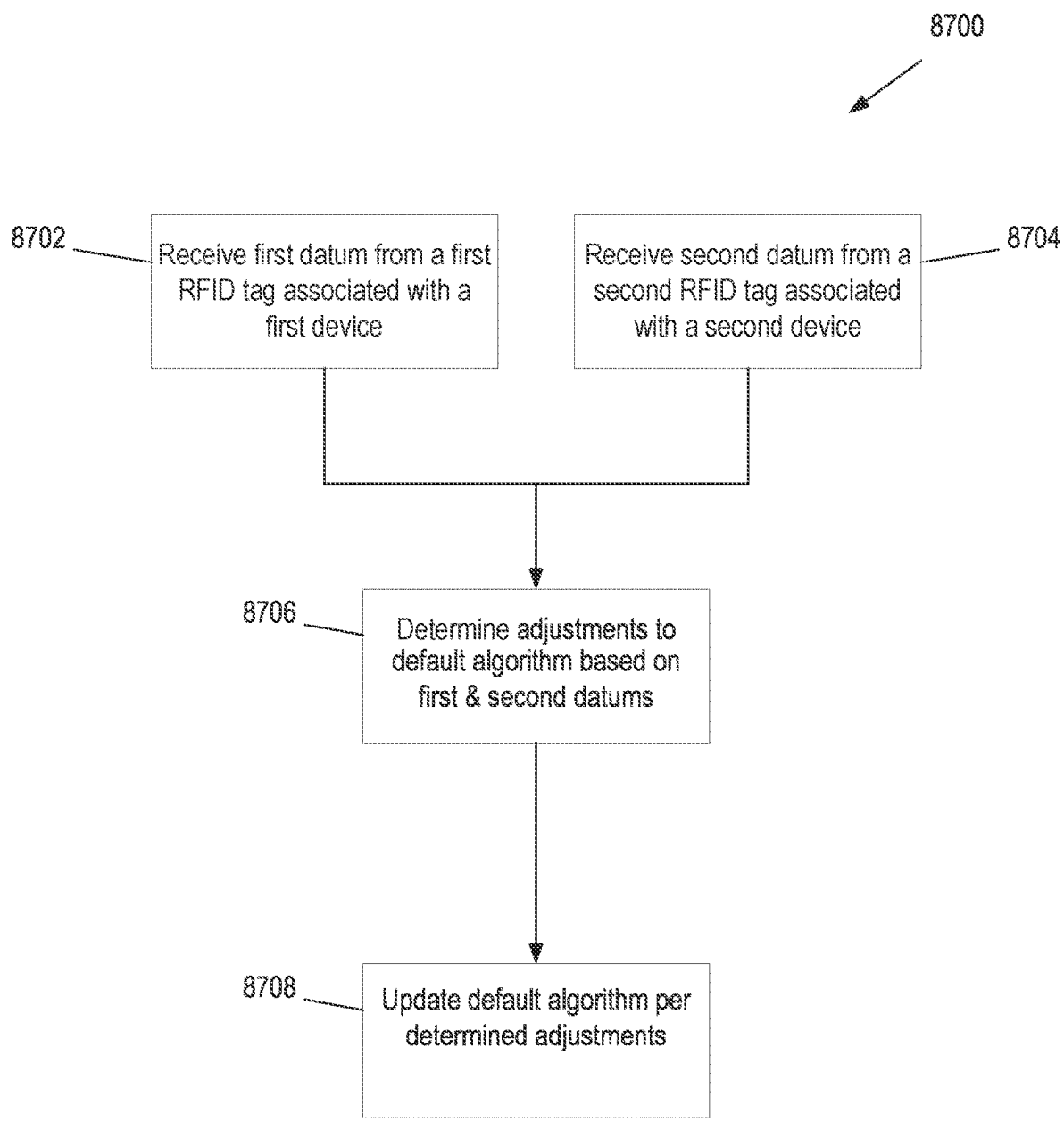
FIG. 81 illustrates a logic flow diagram of a process for updating a default operational algorithm of a surgical instrument via an RFID assembly, in accordance with at least one aspect of the present disclosure.

In one example in accordance with the process 8700 of FIG. 81, the surgical instrument 8002 is an ultrasonic surgical instrument, and the first and second devices are an ultrasonic transducer and an ultrasonic waveguide with RFID tags 8006 that store a first datum and a second datum, respectively, indicative of adjustments to a default natural frequency of the surgical instrument 8002. Ultrasonic surgical instruments are designed to operate within a defined frequency band or range (e.g. 53-57 kHz). Ultrasonic energy is used to drive a predefined displacement of an ultrasonic blade. The ultrasonic energy is transmitted from the ultrasonic transducer to the ultrasonic blade through the ultrasonic waveguide, in order to complete a desired tissue treatment function. The manufacturing process of the first and second devices can yield mass variations, material density variations, and/or assembly variations that can shift a natural frequency of ultrasonic surgical instrument and cause differences in the output displacement. Accordingly, during manufacturing each of the first and second devices can be tested to capture a natural frequency associated therewith. The RFID tags 8006 of the first device and the second device can store a first datum and a second datum, respectively, indicative of the captured natural frequencies.

Further to the above, the control circuit 1210 can be configured to determine 8706 adjustments to a default natural frequency of the surgical instrument 8002 based on the first datum and the second datum, can cause a generator or handle assembly associated with the surgical instrument 8002 to adjust the power delivered to the ultrasonic transducer to yield an updated 8708 natural frequency based on the determined adjustments. This would optimize the function and variation between devices by having the surgical instrument output tuned to the specific design and/or manufacturing parameters of its components. Additionally operating at the updated natural frequency would reduce undesirable stresses and lower opportunity of breakage. In at least one example, the control circuit 1210 can employ a lookup table of natural frequency adjustments for corresponding devices of the surgical instrument 8002, which can be identified via any suitable identification information such as, for example, a device number, type, or manufacturer transmitted.

For brevity, the various processes above are described as being executed by the control circuit 1210 illustrated in FIG. 55. However, this is a non-limiting example of a control circuit and it should be recognized that the depicted processes can be executed by circuitry that can include a variety of hardware and/or software components. As another example, the processes can be embodied as an ASIC that is configured to perform the described functions. As yet another example, the processes can be embodied as instructions stored in a memory coupled to a processor that, when executed by the processor, cause the processor or device to perform the described functions. A control circuit can include, for example, the control circuit 1210 illustrated in FIG. 55, the processor module 11232 of the surgical hub 11206 illustrated in FIGS. 43 and 54, and various other hardware and/or software components.

In various aspects, one of the first device and the second device utilized in the processes described in connection with FIGS. 65, 66, 68, 71, 81 can be a device packaging. In one example, the second device is a device packaging of the first device. In another example, the second device is a device packaging of a third device releasably couplable to the surgical instrument 8002. In at least one example, the first device is a housing assembly 8004a (FIG. 60), and the second device is a packaging of the housing assembly 8004a. In such example, the device packaging can include an RFID tag storing information about the housing assembly 8004a. The stored information can indicate whether the device packaging has been opened or tampered with, can indicate an expiration date of the packaged device, and/or can include compatibility and/or authenticity information.

During various surgical procedures, a surgical instrument comprising at least one replaceable component are used. It is important that such replaceable components be replaced with functional and/or compatible components. Various identification systems described in greater detail herein verify, among other things, a component's compatibility with the surgical instrument and/or verify an operating status of the component. For instance, a controller and/or an identification system can serve to, for example, ensure that the packaging containing the replaceable component has not been destroyed and/or tampered with, alert a clinician if a component is compatible or incompatible with the surgical instrument, alert the clinician if the replaceable component is expired, and/or alert the clinician if a recall exists for a particular manufacturing batch and/or type of the replaceable component.

The identification systems described herein can either be active systems or passive systems. In various embodiments, a combination of active and passive identification systems are used. Passive systems can include, for example, a barcode, a quick response (QR) code, and/or a radio frequency identification (RFID) tag. Passive systems do not comprise an internal power source, and the passive systems described herein require a reader and/or scanner to send a first signal, such as an interrogation signal, for example.

Passive radio frequency identification (RFID) systems communicate information by using radio frequencies. Such passive RFID systems comprise an RFID scanner and an RFID tag with no internal power source. The RFID tag is powered by electromagnetic energy transmitted from the RFID scanner. Each RFID tag comprises a chip, such as a microchip, for example, that stores information about the replaceable component and/or a surgical instrument with which the replaceable component is compatible. While the chip may only contain an identification number, in various instances, the chip can store additional information such as, for example, the manufacturing data, shipping data, and/or maintenance history. Each RFID tag comprises a radio antenna that allows the RFID tag to communicate with the RFID scanner. The radio antenna extends the range in which the RFID tag can receive signals from the RFID scanner and transmit response signals back to the RFID scanner. In a passive RFID system, the RFID scanner, which also comprises its own antenna, transmits radio signals that activate RFID tags that are positioned within a pre-determined range. The RFID scanner is configured to receive the response signals that are "bounced back" from RFID tags, allowing the RFID scanner is to capture the identification information representative of the replaceable component. In various instances, the one or more response signals comprise the same signal as the interrogation signal. In various instances, the one or more response signals comprise a modified signal from the interrogation signal. In various instances, the RFID scanner is also able to write, or encode, information directly onto the RFID tag. In any event, the RFID scanner is able to pass information about the replaceable component to a controller, such as the control system of a surgical instrument and/or a remote surgical system. The RFID scanner is configured to read multiple RFID tags at once, as the RFID tags are activated by radio signals. Additionally, in certain instances, the RFID scanner is able to update, or rewrite, information stored on an RFID tag in signal range with the RFID scanner. The updates can, for example, be transmitted to the RFID scanner from a surgical hub, or any suitable server. Various surgical hubs are described in described in U.S. patent application Ser. No. 16/209,395, titled METHOD OF HUB COMMUNICATION, and filed Dec. 4, 2018, now U.S. Patent Application Publication No. 2019/0201136, which is hereby incorporated by reference in its entirety.

Active radio frequency identification (RFID) systems also comprise an RFID tag and an RFID scanner. However, the RFID tag in an active RFID system comprises an internal power source. Active RFID systems utilize battery-powered RFID tags that are configured to continuously broadcast their own signal. One type of active RFID tag is commonly referred to as a "beacon." Such beacon RFID tags do not wait to receive a first signal from an RFID scanner. Instead, the beacon RFID tag continuously transmits its stored information. For example, the beacon can send out its information at an interval of every 3-5 seconds. Another type of active RFID tag comprises a transponder. In such systems, the RFID scanner transmits a signal first. The RFID transponder tag then sends a signal back to the RFID scanner with the relevant information. Such RFID transponder tag systems are efficient, as they conserve battery life when, for example, the RFID tag is out of range of the RFID scanner. In various instances, the active RFID tag comprises an on-board sensor to track an environmental parameter. For example, the on-board sensor can track moisture levels, temperature, and/or other data that might be relevant.

Figure 82:
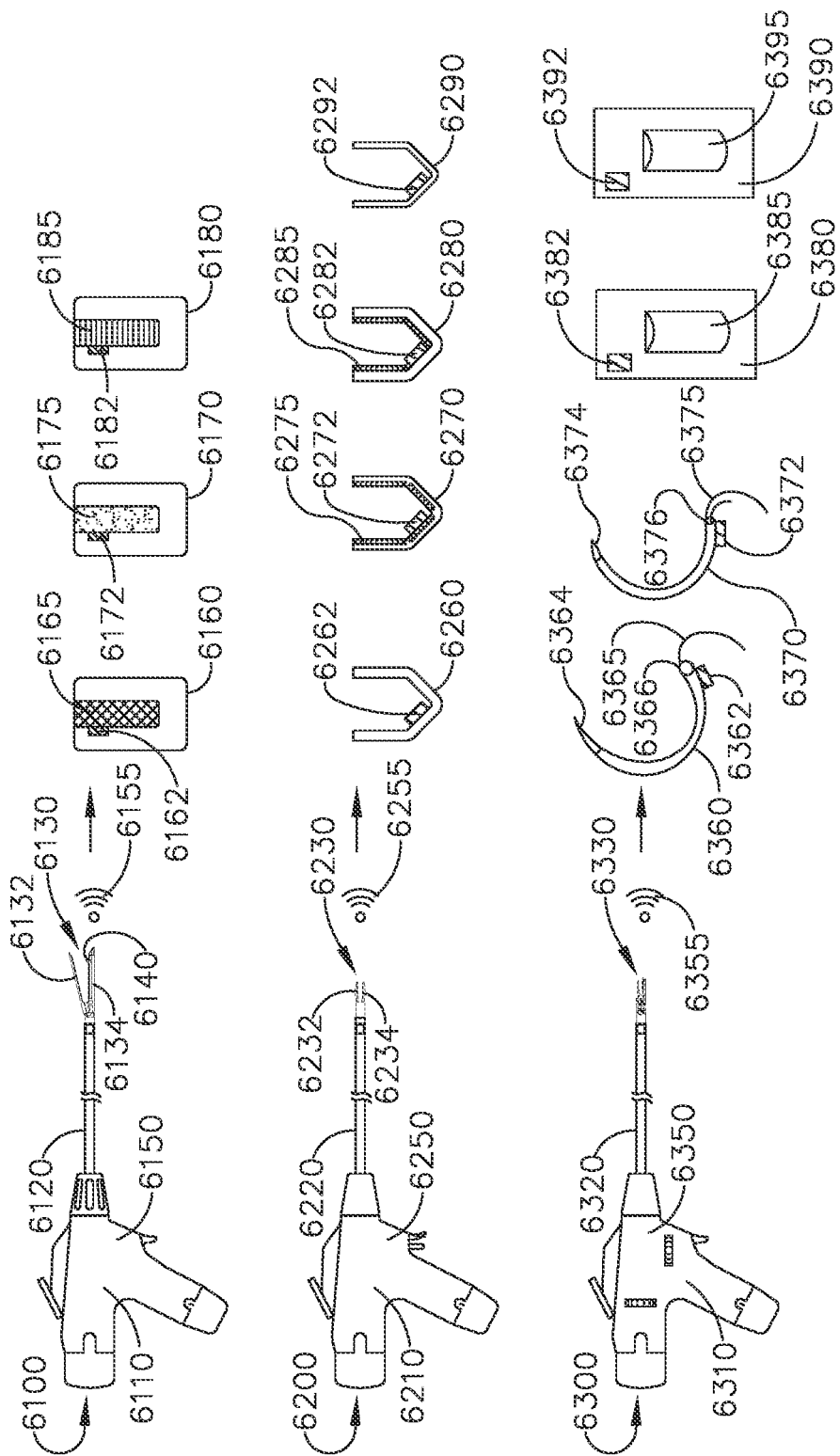
FIG. 82 is a schematic of various surgical instruments and supplemental components for use with the surgical instruments.

FIG. 82 illustrates various surgical instruments that are configured to receive various supplemental components that can be replaced during a surgical procedure. Such surgical instruments can benefit from the inclusion of at least one of the identification systems described herein, such as an RFID system. For example, a surgical stapling instrument 6100 comprises a handle 6110, an elongate shaft 6120 extending from the handle 6110, and an end effector 6130 extending from the elongate shaft 6120. The end effector 6130 comprises a first jaw 6132 and a second jaw 6134, wherein the second jaw 6134 is configured to receive a replaceable staple cartridge 6140. During a particular surgical procedure, a clinician may want to attach various supplemental components to the end effector 6130. Such supplemental components, or adjunct materials, are used to reinforce the staples and/or supplement the function of the staples. For example, a buttress, or tissue thickness compensator, 6165 may be attached to the first jaw 6132 and/or the second jaw 6134 to accommodate for varying tissue thicknesses. The addition of the buttress 6165 to the end effector 6130 can assist in forming a uniform staple line on the patient tissue, for example. In an effort to facilitate attachment of the buttress 6165 to the end effector 6130 and/or for storage, the buttress 6165 can be supported on a mounting member 6160. In various instances, the clinician can attach a layer of hemostatic agent 6175 to the first jaw 6132 and/or the second jaw 6134 of the end effector 6130 to promote rapid blood coagulation, among other things. The layer of hemostatic agent 6175 can improve the seal created by the staples, for example. In an effort to facilitate attachment of the layer of hemostatic agent 6175 to the end effector 6130 and/or for storage, the layer of hemostatic agent 6175 can be supported on a mounting member 6170. In various instances, the clinician can attach a layer of adhesive 6185 to the first jaw 6132 and/or the second jaw 6134 of the end effector 6130 to promote healing of the treated tissue and/or enhance the connection between two layers of tissue, among other things. The layer of adhesive 6185 can improve the seal created by the staples, for example. In an effort to facilitate attachment of the layer of adhesive can be supported on a mounting member 6180.

As described in greater detail herein, a first RFID tag 6162 is positioned on the mounting member 6160. The first RFID tag 6162 comprises stored information, wherein the stored information comprises data that identifies a characteristic of the buttress 6165 supported on the mounting member 6160. A second RFID tag 6172 is positioned on the mounting member 6170. The second RFID tag 6172 comprises stored information, wherein the stored information comprises data that identifies a characteristic of the layer of hemostatic agent 6175 supported on the mounting member 6170. A third RFID tag 6182 is positioned on the mounting member 6180. The third RFID tag 6182 comprises stored information, wherein the stored information comprises data that identifies a characteristic of the layer of adhesive 6185 supported on the mounting member 6180. The surgical stapling instrument 6100 further comprises an RFID scanner 6150. As discussed in greater detail herein, the RFID scanner 6150 can be positioned in any suitable location on the surgical instrument 6100 that allows the RFID scanner 6150 to communicate with the first RFID tag 6162, the second RFID tag 6172, and/or the third RFID tag 6182 as the supplemental component is being attached and/or after the supplemental component is attached to the end effector 6130.

A surgical clip applier 6200 comprises a handle 6210, an elongate shaft 6220 extending from the handle 6210, and an end effector 6230 extending from the elongate shaft 6220. The end effector 6230 comprises a first jaw 6232 and a second jaw 6234, wherein at least one of the first jaw 6232 and the second jaw 6234 is movable relative to one another during a clip crimping stroke. During a particular surgical procedure, a clinician may want to attach various supplemental components to the end effector 6230. For example, a clip 6260 comprising a first thickness may be loaded into the surgical clip applier 6200. The clip 6260 may be loaded individually into the surgical clip applier 6200 and/or the clip 6260 may be loaded into the surgical clip applier 6200 as a part of a clip cartridge. The attachment of the clip 6260 to the surgical clip applier 6200 can be beneficial when the patient tissue is thick and/or dense, for example. In various instances, the clinician can attach a clip 6290 comprising a second thickness to the surgical clip applier 6200. In various instances, the second thickness of the clip 6290 is smaller than the first thickness of the clip 6260. The attachment of the clip 6290 to the surgical clip applier 6200 can be beneficial when the patient tissue is thin and/or delicate, for example. In various instances, the clinician can attach a clip 6270 comprising a plurality of projections 6275 to the surgical clip applier 6200. The projections 6275 of the clip 6270 can serve to enhance the grip between the clip 6270 and the patient tissue and/or maintain the position of a crimped clip 6270 on the patient tissue, among other things. As shown on clip 6270, the projections 6275 may be attached to a thin clip. Utilization of the projections 6275 on the thin clip is beneficial when the patient tissue is thin and/or delicate, for example. In various instances, the clinician can attach a clip 6280 comprising a plurality of projections 6285 to the surgical clip applier 6200. The projections 6285 of the clip 6280 can serve to enhance the grip between the clip 6280 and the patient tissue and/or maintain the position of a crimped clip 6280 on the patient tissue, among other things. As shown on clip 6280, the projections 6285 may be attached to a thick clip. Utilization of the projections 6285 on the thick clip is beneficial when the patient tissue is thick and/or dense, for example.

As described in greater detail herein, a first RFID tag 6262 is positioned on the first clip 6260. The first RFID tag 6162 comprises stored information, wherein the stored information comprises data that identifies a characteristic of the clip 6260. A second RFID tag 6272 is positioned on the second clip 6270. The second RFID tag 6272 comprises stored information, wherein the stored information comprises data that identifies a characteristic of the second clip 6270. A third RFID tag 6282 is positioned on the third clip 6280. The third RFID tag 6282 comprises stored information, wherein the stored information comprises data that identifies a characteristic of the third clip 6280. A fourth RFID tag 6292 is positioned on the fourth clip 6290. The fourth RFID tag 6292 comprises stored information, wherein the stored information comprises data that identifies a characteristic of the fourth clip 6290. The surgical clip applier 6200 further comprises an RFID scanner 6250. As discussed in greater detail herein, the RFID scanner 6250 can be positioned in any suitable location on the surgical instrument 6200 that allows the RFID scanner 6250 to communicate with the first RFID tag 6262, the second RFID tag 6272, the third RFID tag 6282, and/or the fourth RFID tag 6292 as the supplemental component is being and/or after the supplemental component is attached to the suturing device 6200.

A surgical suturing device 6300 comprises a handle 6310, an elongate shaft 6320 extending from the handle 6310, and an end effector 6330 extending from the elongate shaft 6320. The end effector 6330 comprises a needle track configured to receive a portion of a replaceable needle. During a particular surgical procedure, a clinician may want to attach various supplemental components to the end effector 6330. Different knot tying mechanisms and/or different suture termination elements can be used to finish a line of sutures instead of tying a knot laparoscopically. For example, a needle 6360 comprising a first thickness may be loaded into the end effector 6330. The needle 6360 comprises a first end 6364 and a second end 6366. The first end 6364 comprises a pointed tip that comprises a first degree of sharpness. The second end 6366 comprises a suturing material 6365 attached thereto. The attachment of the shaft needle 6360 to the end effector 6330 can be beneficial when the patient tissue is thick and/or dense, for example. In various instances, the clinician can attach a needle 6370 comprising a second thickness to the end effector 6330. In various instances, the second thickness of the clip 6370 is smaller than the first thickness of the clip 6360. The clip 6370 further comprises a first end 6374 comprising a pointed tip that comprises a second degree of sharpness. In various instances, the second degree of sharpness of the clip 6370 is less than the first degree of sharpness of the clip 6360. The second end 6376 comprises a suturing material 6375 attached thereto. The attachment of the needle 6370 to the end effector 6330 can be beneficial when the patient tissue is thin and/or delicate, for example. In various instances, the clinician can select a particular suturing material to be attached to the replaceable needle. For example, a first suturing material 6385 can be made of a first material, comprise a first length, and/or comprise a first thickness. The first suturing material 6385 can be stored in a first packaging 6380 prior to attachment to a replaceable needle. A second suturing material 6395 can be made of a second material, comprise a second length, and/or comprise a second thickness. The second suturing material 6395 can be stored in a second packaging 6390 prior to attachment to a replaceable needle.

As described in greater detail herein, a first RFID tag 6362 is positioned on the first replaceable needle 6360. The first RFID tag 6362 comprises stored information, wherein the stored information comprises data that identifies a characteristic of the replaceable needle 6360 and/or the suturing material 6365 attached thereto. A second RFID tag 6372 is positioned on the second replaceable needle 6370. The second RFID tag 6372 comprises stored information, wherein the stored information comprises data that identifies a characteristic of the second replaceable needle 6370 and/or the suturing material 6375 attached thereto. A third RFID tag 6382 is positioned on the packaging 6380 of the third suturing material 6385. The third RFID tag 6382 comprises stored information, wherein the stored information comprises data that identifies a characteristic of the third suturing material 6385. A fourth RFID tag 6392 is positioned on the packaging 6390 of the fourth suturing material 6395. The fourth RFID tag 6392 comprises stored information, wherein the stored information comprises data that identifies a characteristic of the fourth suturing material 6390. The surgical suturing device 6300 further comprises an RFID scanner 6350. As discussed in greater detail herein, the RFID scanner 6350 can be positioned in any suitable location on the surgical instrument 6300 that allows the RFID scanner 6350 to communicate with the first RFID tag 6362 and/or the second RFID tag 6372 as one of the replaceable needles 6360, 6370 is being positioned and/or after the replaceable needle is positioned within the needle track of the end effector 6330 and/or to communicate with the third RFID tag 6382 and/or the fourth RFID tag 6392 when the packaging 6380, 6390 is brought within a pre-defined distance from the RFID scanner 6300.

Supplemental components, such as, for example, the buttress 6165, the hemostatic agent 6175, and/or the adhesive 6185, are contained within a sealed packaging after being manufactured until the packaging in opened in the operating room. In various instances, the supplemental component is supported on a mounting member within the packaging, for example, to facilitate storage and/or facilitate attachment of the supplemental component to the surgical instrument. Various forms of packaging include, for example, peel-pouches, woven and/or non-woven material wrappers, and rigid containers.

Figure 83:
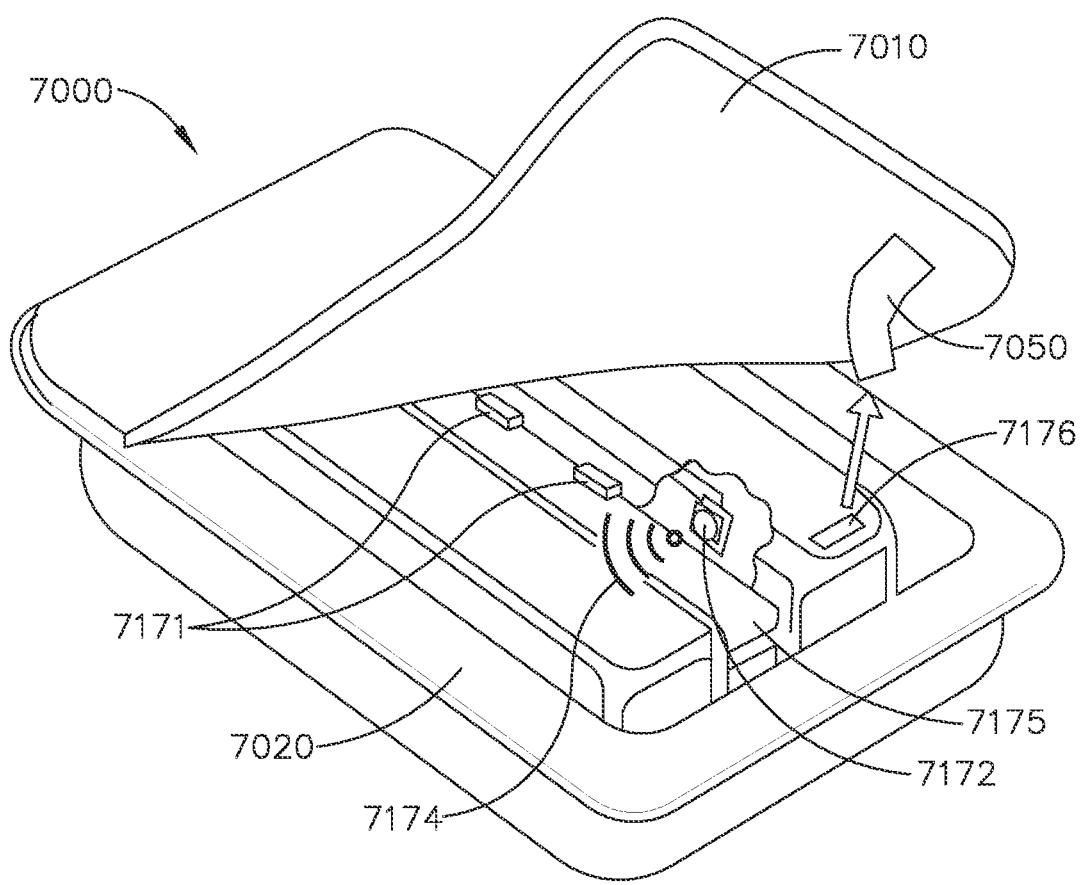
FIG. 83 is a perspective view of a packaging, wherein the packaging comprises an identifying characteristic of the supplemental component contained therein.

FIG. 83 depicts an example of a sealed packaging 7000. The depicted packaging 7000 is a peel-pouch. The packaging 7000 comprises a first layer 7010 and a second layer 7020. The first layer 7010 and the second layer 7020 form a protective barrier around a layer of hemostatic agent 7175, which is configured to be attached to a surgical staple cartridge. The layer of hemostatic agent 7175 is supported on a mounting member 7170 prior to the attachment of the layer of hemostatic agent 7175 to a surgical instrument. The mounting member 7170 comprises retention members 7171 configured to receive a portion of the layer of hemostatic agent 7175 and to, for example, facilitate alignment of the layer of hemostatic agent 7175. An adhesive bonds the first layer 7010 and the second layer 7020 together to form an airtight and/or fluid-tight seal and/or pouch around the layer of hemostatic agent 7175. The adhesive forms a seal without creases, wrinkles, and/or gaps. The seal created by the adhesive prevents contaminants from coming into contact with the layer of hemostatic agent 7175 and/or prevents components of the layer of hemostatic agent 7175 from being misplaced, for example. In various instances, the hemostatic agent 7175 is hermetically sealed within the packaging 7000. In various instances, the packaging 7000 provides a completely fluid-tight and airtight seal.

The first layer 7010 and the second layer 7020 are comprised of a material such as, for example, paper with a laminated inner surface. The laminated inner surface provides a barrier to prevent contaminants from entering the sealed portion of the packaging 7000. In various instances, the first layer 7010 and the second layer 7020 are comprised of plastic. The first layer 7010 and the second layer 7020 can be comprised of a material with a particular degree of transparency to allow a clinician, for example, to observe the contents of the packaging 7000 prior to breaking the seal. The above being said, any suitable material and/or combinations of materials can be used for the first layer 7010 and/or the second layer 7020. The first layer 7010 comprises a first portion positioned outside of the seal, and the second layer 7020 comprises a second portion positioned outside of the seal. The clinician can expose the sealed layer of hemostatic agent 7175 by holding the first portion and the second portion in separate hands and pulling the first portion in a direction away from the second layer 7020, although any suitable opening method can be used.

FIG. 83 depicts an RFID system 7500 integrated with the packaging 7000. The RFID system 7500 comprises an RFID tag 7172 and an insulator 7050. The RFID tag 7172 comprises a chip, such as a microchip, for example, that stores information about the packaging 7000 and/or the contents of the packaging 7000. In various instances, the chip comprises an identification number. Such an identification number can be assigned to the chip that can communicate the chip's existence to an RFID scanner. In various instances, the chip comprises additional information such as, for example, manufacturing data, shipping data, and/or compatibility data. The RFID tag 7172 further comprises a radio antenna 7173 configured to facilitate communication between the RFID tag 7172 and the RFID scanner.

The insulator 7050 is attached to the first layer 7010 of the packaging 7000, while the RFID tag 7172 is attached to a mounting member 7170 supporting the layer of hemostatic agent 7175. When the packaging 7000 is in a sealed configuration, the insulator 7050 is affixed to, or otherwise connected to an integrated battery 7176 of the RFID tag 7172. The integrated battery 7176 is activated when the packaging 7000 is opened. Prior to the packaging 7000 being opened, the interface between the insulator 7050 and the integrated battery 7176 prevents the integrated battery 7176 from providing power to the RFID tag 7172. In such instances, the RFID tag 7172 is unable to emit a signal. When a clinician breaks the seal of the packaging 7000 by peeling the first layer 7010 away from the second layer 7020, the insulator 7050 is disconnected, or otherwise disassociated, from the integrated battery 7176 of the RFID tag 7172. Upon disassociation of the insulator 7050 from the integrated battery 7176, the circuit between the integrated battery 7176 and the RFID tag 7172 is closed, and the RFID tag 7172 is energized. As shown in FIG. 83, the RFID tag 7172 begins emitting a signal 7174 upon being energized. The RFID tag 7172 is configured to emit the signal 7174 at any appropriate frequency and/or for any appropriate duration. For example, the RFID tag 7172 can continuously emit the signal 7174 or the RFID tag 7172 can emit the signal 7174 every 3-5 seconds. The signal 7174 comprises some, or all, of the information stored on the chip of the RFID tag 7172. In various instances, the signal 7174 may serve to alert a surgical instrument that the packaging 7000 has been tampered with during shipping and/or storage or simply that the packaging 7000 has been unsealed, for example.

Figure 85:
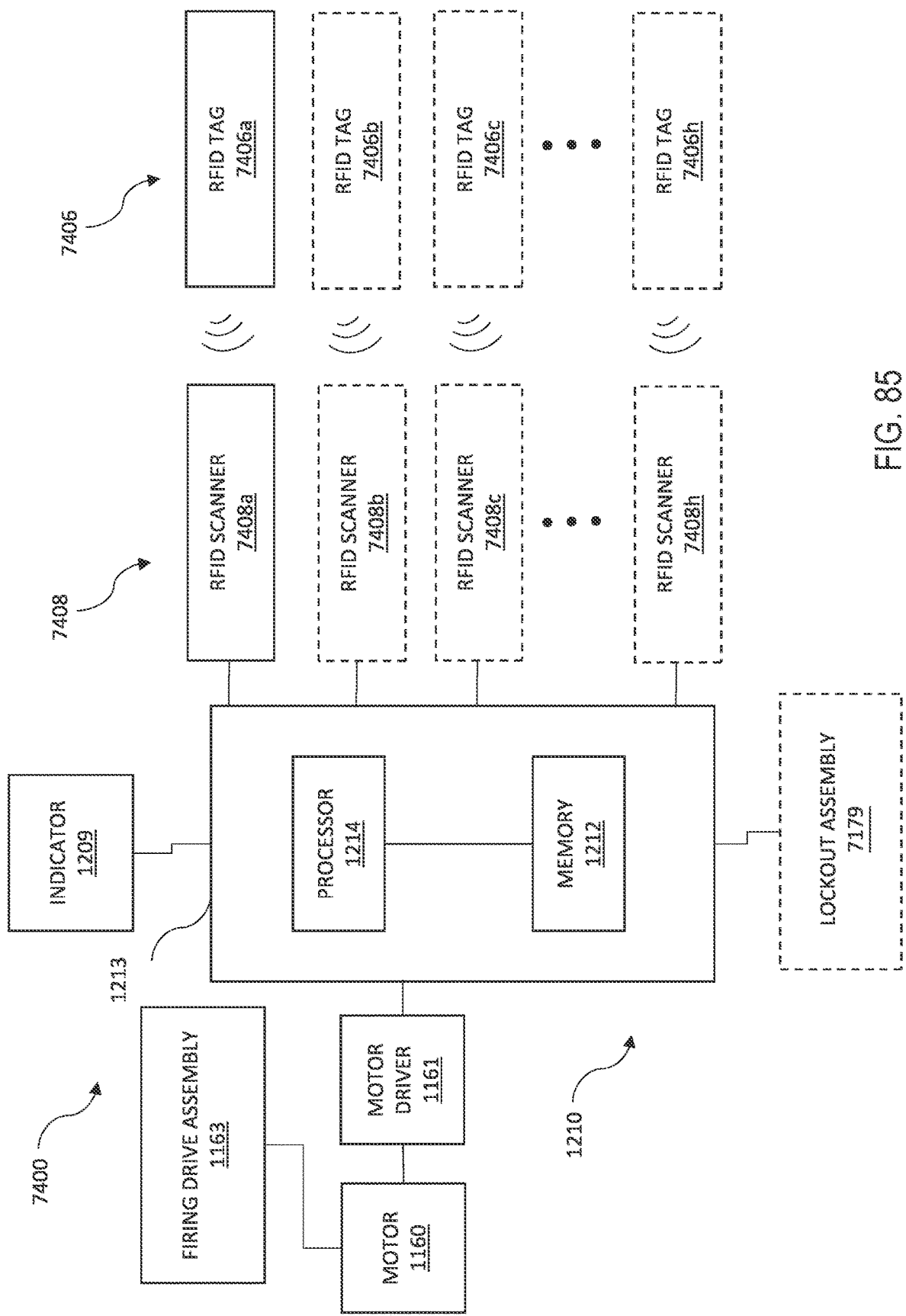
FIG. 85 is a representation of an RFID system for use with the surgical instruments disclosed herein.

FIG. 85 illustrates a block diagram of an RFID system and/or control system 7400 of the surgical stapling instrument and/or tool 7100; however the control system 7400 can be adapted for use with alternative surgical instruments and/or tools, such as the surgical clip applier 7200 and/or the surgical suturing device 7300 described in greater detail herein. The control system 7400 includes a control circuit 1210 that can be integrated with the RFID scanner, such as RFID scanner 7408*a* or can be coupled to, but positioned separately from, the RFID scanner 7408*a*. The control circuit 1210 can be configured to receive input from the RFID scanner 7408*a* indicative of the information stored in the RFID tag 7406*a* about the supplemental component 7175 and/or information about the packaging 7000 of the supplemental component 7175. In various instances, the RFID system 7400 comprises more than one RFID scanner 7408*b-h* and/or more than one RFID tag 7406*b-h*. The RFID scanners 7408*a-h* are communicably coupled to the control circuit 1210 can receive data from the RFID scanners 7408*a-h* and then take various actions based upon the read data, as are described below.

In at least one example, the control circuit 1210 includes a microcontroller 1213 that has a processor 1214 and a storage medium such as, for example, a memory 1212. The memory 1212 stores program instructions for performing various processes such as, for example, identity verification. The program instructions, when executed by the processor 1214, cause the processor 1214 to verify the identity of the packaging 7000 and/or the supplemental component 7175 by comparing the identification information received from the RFID tag(s) 7406*a-h* to identification information stored in the memory 1212 in the form of an identity database or look-up table, for example. In various examples, the memory 1212 comprises a local memory of the instrument 7100. In other examples, identity databases or tables and/or compatibility databases or tables can be downloaded from a remote server. In various aspects, the instrument 7100 may transmit the information received from RFID tag(s) 7406*a-* 7406*h* to a remote server that stores the databases or tables for performing the identity and/or compatibility checks remotely.

The RFID tag 7172 is configured to communicate with an RFID scanner. Once the insulator 7050 has been removed, the integrated battery 7176 of the RFID tag 7172 allows the RFID tag 7172 to emit the signal 7174 prior to receiving a first signal, such as an interrogation signal, from the RFID scanner. The RFID scanner comprises a scanner antenna configured to transmit and/or receive radio signals 7174 from the RFID tag 7172. In various instances, the RFID scanner comprises reading and writing capabilities. The RFID scanner is configured to pass the collected information from the RFID tag 7172 to a controller of the surgical instrument for further interpretation. In various instances, the controller is configured to determine if the supplemental component is compatible with the particular surgical instrument. In various instances, the controller is configured to activate a lockout assembly 7179 to prevent the surgical instrument from performing a function with the firing drive assembly 1163 such as, for example, a staple firing stroke, a suture firing stroke, and/or a clip crimping stroke if the controller determines that the supplemental component is not compatible with the particular surgical instrument and/or for use during the particular surgical procedure. Various lockout assemblies are described in greater detail in U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, the disclosures of which are incorporated by reference herein in their entireties. The RFID scanner is positioned within a pre-determined range of the RFID tag 7172 that allows for the RFID scanner to be able to receive the emitted signal 7174 transmitted by the RFID tag 7172. Depending on the application, the RFID scanner can be positioned on a surgical instrument, on the contents of the packaging, and/or remotely located on a console, such as a remote surgical system in communication with the surgical instrument. Additionally, the controller can be located in any suitable location, such as, for example, the surgical instrument or on a remote console.

In various instances, the tag antenna of the RFID tag 7172 is destroyed and/or is otherwise rendered inoperable as the packaging 7000 is opened and/or after the packaging 7000 is opened. The RFID tag 7172 is unable to transmit and/or receive communication and/or signals from an RFID scanner when the tag antenna is inoperable. In such instances, the RFID scanner is configured to receive a first signal from the RFID tag 7172 before the packaging is opened. Once the RFID scanner receives the first signal, the controller of the surgical instrument is configured to authenticate the packaging 7000 and the contents of the packaging 7000. If the RFID scanner does not receive the first signal from the RFID tag 7172, the controller is configured to prevent the surgical instrument from performing a function with the firing drive assembly 1163. The failure of the RFID scanner to receive the first signal is indicative of a tampered packaging and/or an inauthentic packaging, among other things. In various instances, the tag antenna is still operable after the packaging 7000 is opened; however, the communication range of the tag antenna is diminished. In such instances, the diminished communication range prevents the RFID tag 7172 from receiving and/or transmitting communication to the RFID scanner.

In various instances, a switch is positioned between the RFID tag 7172 and the power source. The insulator 7050 biases the switch open when the packaging 7000 is in a sealed configuration, and the power source is unable to supply power to the RFID tag 7172. In such circumstances, the RFID tag 7172 is unable to communicate with the RFID scanner. When the packaging 7000 in an unsealed configuration, the insulator 7050 is disassociated from the RFID tag 7172, and the switch is closed. In such circumstances, the power source is able to supply power to the RFID tag 7172, and the RFID tag 7172 is able to communicate with the RFID scanner.

In various instances, an RFID system comprising an RFID tag mounted to the second layer 7020 of the packaging 7000 can be used. Further to the above, the RFID tag comprises an internal power source positioned on the second layer 7020 of the packaging 7000. An insulator, similar to the insulator 7050, is attached to the packaging 7000 and, when the packaging 7000 is opened, the RFID tag on the second layer 7020 is activated. The insulator is attached to, or otherwise associated with, the first layer 7010 of the packaging 7000. When the packaging 7000 is in a sealed configuration, the insulator 7050 is attached to, or otherwise connected to, the RFID tag on the second layer 7020 of the packaging 7000 and holds open the circuit between the integrated power source and the RFID tag. The interface between the insulator 7050 and the RFID tag prevents the power source from activating the RFID tag, and the RFID tag is unable to emit a signal. When a clinician breaks the seal of the packaging 7000 by peeling away the first layer 7010, for example, the insulator 7050 is disconnected, or otherwise disassociated, from the RFID tag and the circuit between the power source and the RFID tag is closed. At such point, the RFID tag is energized and begins to emit a signal.

In various instances, the RFID system 7500 further comprises a transponder. The transponder receives a first communication from an RFID scanner. In various instances, the first communication from the RFID scanner energizes the transponder to a degree sufficient for the transponder to communicate with the RFID tag. In various instances, the transponder is energized prior to receiving the first communication from the RFID scanner. In any event, the transponder is configured to automatically transmit a signal to the RFID tag upon hearing, or otherwise receiving, the first communication from the RFID scanner. The power source of the RFID tag energizes the RFID tag upon receiving the signal from the transponder, and the RFID tag is able to respond to the communication transmitted by the RFID scanner. The transponder serves to, among other things, preserve the battery life of the RFID tag until, for example, the RFID tag is within range of the RFID scanner.

As described in greater detail herein, it is valuable for a clinician to be able to verify the compatibility of a supplemental component for use with a particular surgical instrument and/or for use during a particular surgical procedure. For various reasons, it can be also be meaningful for a clinician to be able to ensure that the supplemental component has not been previously used and/or tampered with. The clinician may also want to confirm, for example, that the supplemental component is not contaminated, that the supplemental component is intact, and/or that the supplemental component comprises an acceptable composition and/or dimension.

Figure 84:
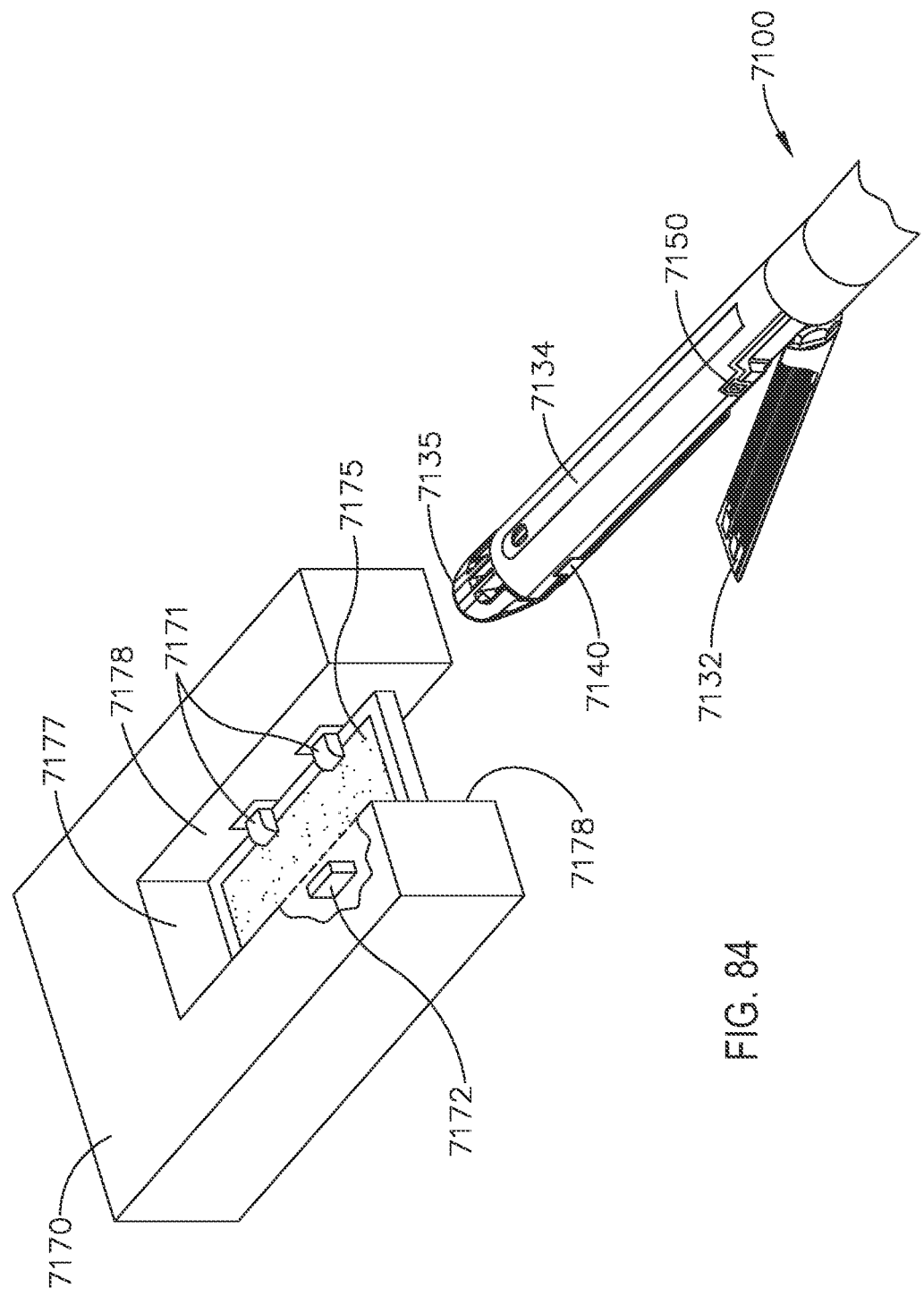
FIG. 84 is a partial cross-sectional view of a surgical stapling instrument system comprising a mounting member and a supplemental component, wherein the mounting member comprises an RFID tag.

FIG. 84 illustrates a portion of a surgical stapling instrument 7100. As discussed in greater detail elsewhere herein, the surgical stapling instrument 7100 comprises an end effector 7130 extending from an elongate shaft 7120 of the surgical stapling instrument 7100. The end effector 7130 comprises a first jaw 7132, wherein the first jaw 7132 is an anvil. The first jaw 7132 comprises a plurality of staple forming pockets. The end effector 7130 further comprises a second jaw 7134 comprising a channel configured to receive a replaceable staple cartridge 7140. The replaceable staple cartridge 7140 comprises a cartridge body and a plurality of staples removably stored within the cartridge body. The plurality of staples are driven out of the cartridge body during a staple firing stroke 1163. In an effort to, for example, promote rapid blood coagulation, of patient tissue affected during the staple firing and tissue cutting stroke 1163, the clinician can attach a layer of hemostatic agent 7175 to the end effector 7130 prior to performing the staple firing stroke 1163. In various instances, the layer of hemostatic agent 7175 is attached to a deck surface of the cartridge body. In various instances, the layer of hemostatic agent 7175 is attached to a tissue-supporting surface of the anvil. In any event, the layer of hemostatic agent 7175 is in contact with the patient tissue during and/or after the staple firing stroke 1163.

As discussed above, the layer of hemostatic agent 7175 is sealed within a packaging prior to attachment to the surgical instrument. Within the packaging, the layer of hemostatic agent 7175 is part of a mounting assembly configured to facilitate storage and attachment of the layer of hemostatic agent 7175. The mounting assembly comprises a mounting member 7170. In various instances, the mounting member 7170 provides a physical barrier between the layers of the packaging and the hemostatic agent 7175 and prevents the layers of the packaging from coming into contact with the hemostatic agent 7175. For example, the mounting member 7170 prevents the layer of hemostatic agent 7175 from sticking and/or otherwise adhering to one or both of the layers of the packaging. The layer of hemostatic agent 7175 is positioned between an opening within the mounting member 7170 defined by sidewalls 7177, 7188 of the mounting member 7170. The mounting member 7170 comprises retention members 7171 that receive a portion of the layer of hemostatic agent 7175. The retention members 7171 maintain the alignment of the layer of hemostatic agent 7175 and secure the layer of hemostatic agent 7175 to the mounting member 7170. The mounting member 7170 also provides a surface for the clinician to hold when aligning the layer of hemostatic agent 7175 for attachment to the end effector 7130 of the surgical instrument. The surface provided by the mounting member 7170 allows a clinician to attach the layer of hemostatic agent 7175 to the end effector 7130 without having to touch or otherwise contact the layer of hemostatic agent 7175.

The mounting member 7170 further comprises an RFID tag 7172. The RFID tag 7172 comprises a chip, such as a microchip, for example, that stores information about the mounting member 7170 and/or the layer of hemostatic agent 7175. In various instances, the set of stored information stored on the RFID chip comprises data that identifies the type of supplemental component the mounting member 7170 is supporting. In the depicted embodiment, the mounting member 7170 is supporting a layer of hemostatic agent 7175. However, the mounting member 7170 can support any suitable form of supplemental component such as, for example, a tissue thickness compensator and/or an adhesive. As shown in FIG. 81, the RFID tag 7172 is mounted to a sidewall 7178 of the mounting member 7170. However, the RFID tag 7172 can be embedded within and/or attached to the mounting member 7170 by any suitable method. In various instances, the RFID tag 7172 can be positioned on the layer of hemostatic agent 7175.

The RFID tag 7172 in the mounting member 7170 provides a lockout 7179 for the surgical instrument. The surgical instrument will not perform a function with the firing drive assembly 1163, such as a staple firing stroke and/or a jaw closure stroke, for example, if the information stored on the RFID tag 7172 is not received by a controller of the surgical instrument. In various instances, the surgical instrument will not perform the function with the firing drive assembly 1163 when the RFID tag 7172 is still in communication with an RFID scanner 7150 after the layer of hemostatic agent 7175 has been attached to the end effector 7130. Such a lockout 7179 prevents the surgical instrument from performing the function with the firing drive assembly 1163 when the mounting member 7170 is still attached to the layer of hemostatic agent 7175 and/or the layer of hemostatic agent 7175 has been inappropriately attached to the end effector 7130.

As mentioned in greater detail herein, the surgical stapling instrument 7100 comprises an RFID scanner 7150 configured to communicate with nearby RFID tags. The RFID scanner 7150 comprises a scanner antenna configured to transmit radio signals. The radio signals activate RFID tags that are positioned within a pre-determined range of the RFID scanner 7150. The RFID scanner 7150 then receives one or more response signals that are "bounced back" from the RFID tag(s). In various instances, the one or more response signals comprise the same signal as the interrogation signal. In various instances, the one or more response signals comprise a modified signal from the interrogation signal. In various instances, the RFID scanner 7150 comprises reading and writing capabilities. The RFID scanner 7150 is then able to pass the collected information from the RFID tag to a controller for further interpretation. The controller can be positioned in the surgical instrument, the remote console, or in any suitable location. The RFID scanner 7150 and/or the controller can comprise a stored set of information that corresponds to surgical stapling assemblies that are compatible with a particular surgical instrument and/or for use during a particular surgical procedure.

More specifically, the surgical system comprises an RFID scanner 7150 configured to interact with the RFID tag 7172 attached to the mounting member 7170. The RFID scanner 7150 can be present in various locations. For example, the RFID scanner 7150 can be retained by the staple cartridge 7140. In various instances, the RFID scanner is powered by the battery and/or power source of the surgical instrument. In the depicted embodiment, the RFID scanner 7150 is positioned on the second jaw 7134 of the end effector 7130; however, the RFID scanner 7150 can be located in an alternative location within the surgical system and/or any other suitable location that would allow for communication between the RFID tag 7172 and the RFID scanner 7150 when the mounting member 7170 is within a pre-determined range of the end effector 7130. The RFID scanner 7150 and/or the RFID tag 7172 are powered such that the signal(s) they emit can only be detected within a limited radius. That said, as the mounting member 7170 is removed from the layer of hemostatic agent 7175 after attaching the layer of hemostatic agent 7175 to the end effector 7130, the RFID tag 7172 is unable to communicate with the RFID scanner 7150.

In various instances, the end effector 7130 comprises an RFID scanner positioned on a distal end of the end effector 7130. An RFID tag is retained by a back wall 7177 of the mounting member 7170. During proper attachment of the supplemental component 7175 to the end effector 7130, the distal end of the end effector 7130 is brought close to, aligned with, and/or brought into contact with the back wall 7177 of the mounting member 7170. In various instances, the communication range of the RFID scanner spans a distance that only encompasses the RFID tag of the back wall 7177 of the mounting member 7170 when the end effector 7130 is brought close to and/or brought into contact with the back wall 7177. Such a communication range allows the RFID tag to communicate with the RFID scanner only when the supplemental component 7175 is fully aligned with the end effector 7130. The communication between the RFID tag and the RFID scanner can alert a clinician that the supplemental component 7175 is fully aligned with the end effector 7130 and a function with the firing drive assembly 1163 of the surgical instrument can be performed. If the RFID scanner does not receive a communication from the RFID tag, the supplemental component 7175 may be misaligned and/or not fully attached to the end effector 7130, for example, which can lead to the formation of a non-uniform staple line, for example. In various instances, the controller of the surgical instrument prevents the surgical instrument from performing a function with the firing drive assembly 1163, such as a staple firing stroke, for example. In various instances, if the RFID scanner continues to receive communication from the RFID tag when the clinician believes the supplemental component 7175 is attached to the end effector, the controller is configured to prevent the function with the firing drive assembly 1163 of the surgical instrument. The continued communication indicates that the mounting member 7170 is still attached to the supplemental component 7175. In such circumstances, the loss of communication indicates that the mounting member 7170 has been removed and/or moved out of communication distance from the end effector 7130 and/or the supplemental component 7175.

If the mounting member 7170 does not comprise an RFID tag and/or the RFID tag 7172 comprises information that is not compatible with the surgical instrument, the supplemental component verification system of the surgical instrument will be unable to permit the surgical instrument to perform a function with the firing drive assembly 1163, such as the staple firing stroke or the jaw closure stroke. If the RFID scanner 7150 receives a response to an interrogation signal that is not found within a stored set of compatible supplemental components, the controller of the surgical instrument is programmed to communicate an error to the clinician. Likewise, if the RFID scanner 7150 does not receive a response to the interrogation signal, the controller of the surgical instrument is programmed to communicate an error to the clinician. In various instances, the detection of an error by the controller can render the surgical instrument inoperable for use with that particular supplemental component. In various instances, a detected error can prevent the surgical instrument from performing a staple firing stroke, jaw closure stroke, and/or tissue cutting stroke. In various instances, the surgical instrument further comprises a manual override that can be activated to allow a clinician to override any system lockout 7179 and utilize operational functions of the surgical instrument in an emergency. As discussed above, the controller is configured to alert the clinician that an error has been detected by way of an indicator 1209. Such an alert and/or indication 1209 can be communicated through various forms of feedback, including, for example, haptic, acoustic, and/or visual feedback. In at least one instance, the feedback comprises audio feedback, and the surgical instrument can comprise a speaker which emits a sound, such as a beep, for example, when an error is detected. In certain instances, the feedback comprises visual feedback and the surgical instrument can comprise a light emitting diode (LED), for example, which flashes when an error is detected. In various instances, the feedback comprises haptic feedback and the surgical instrument can comprise an electric motor 1160 comprising an eccentric element which vibrates when an error is detected. The alert can be specific or generic. For example, the alert can specifically state that the RFID tag 7172 on the mounting member 7170 is unable to be detected, or the alert can specifically state that the RFID tag 7172 comprises information representative of an incompatible and/or defective supplemental component 7175.

In various instances, the controller can be configured to select and/or modify various operational parameters based on the identification of the layer of hemostatic agent 7175 using the information stored on the RFID tag 7172. Such an identification can include the material the layer of hemostatic agent 7175 is comprised of and/or the thickness of the layer of hemostatic agent 7175, among other things. After identification of the layer of hemostatic agent 7175, the controller is configured to permit the surgical instrument to perform the desired function with the firing drive assembly 1163 using the modified operational parameters.

Figure 86:
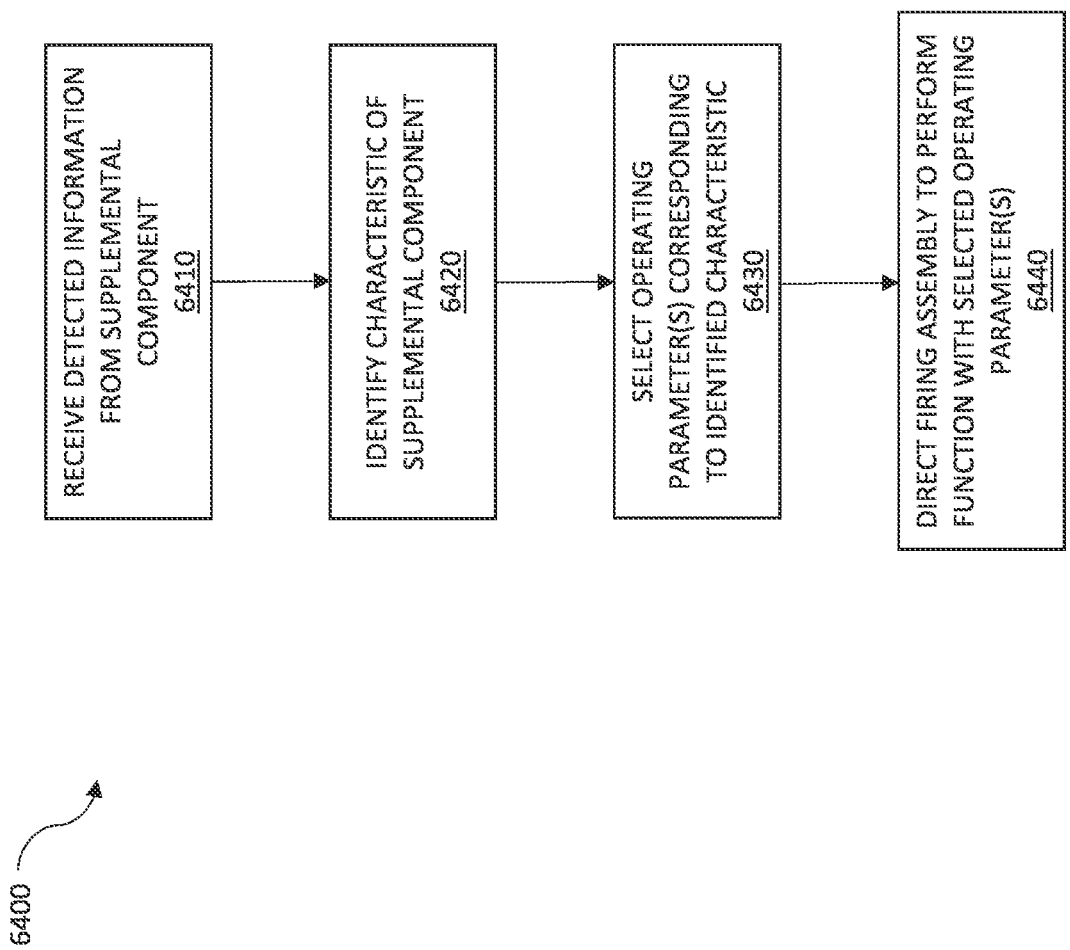
FIG. 86 is a flowchart representative of a process of a controller for modifying at least one operational parameter based on an identified supplemental component.

For example, FIG. 86 depicts an exemplary process 6400 of the control circuit 1210. As discussed above, the control circuit 1210 is configured to receive 6410 the information stored on the RFID tag 7172 corresponding to the supplemental component, such as the layer of hemostatic agent 7175. Using the received information, the control circuit 1210 is configured to identify 6420 a characteristic of the supplemental component 7175 using the received information. The control circuit 1210 is configured to select 6430 one or more appropriate operating parameters 6430 that correspond to the identified characteristic of the supplemental component 7175. The control circuit 1210 is configured to direct 6440 the firing assembly to perform a function, such as a staple firing stroke, with the selected operating parameter(s).

In various instances, and as discussed above, the RFID tag 7172 can comprise an integrated power source and become activated upon the opening of the packaging 7000. In such instances, the RFID tag 7172 can continuously transmit the stored set of information, and the RFID tag 7172 does not need to wait for an interrogation signal from the RFID scanner 7300 to transmit the stored set of information.

Figure 87:
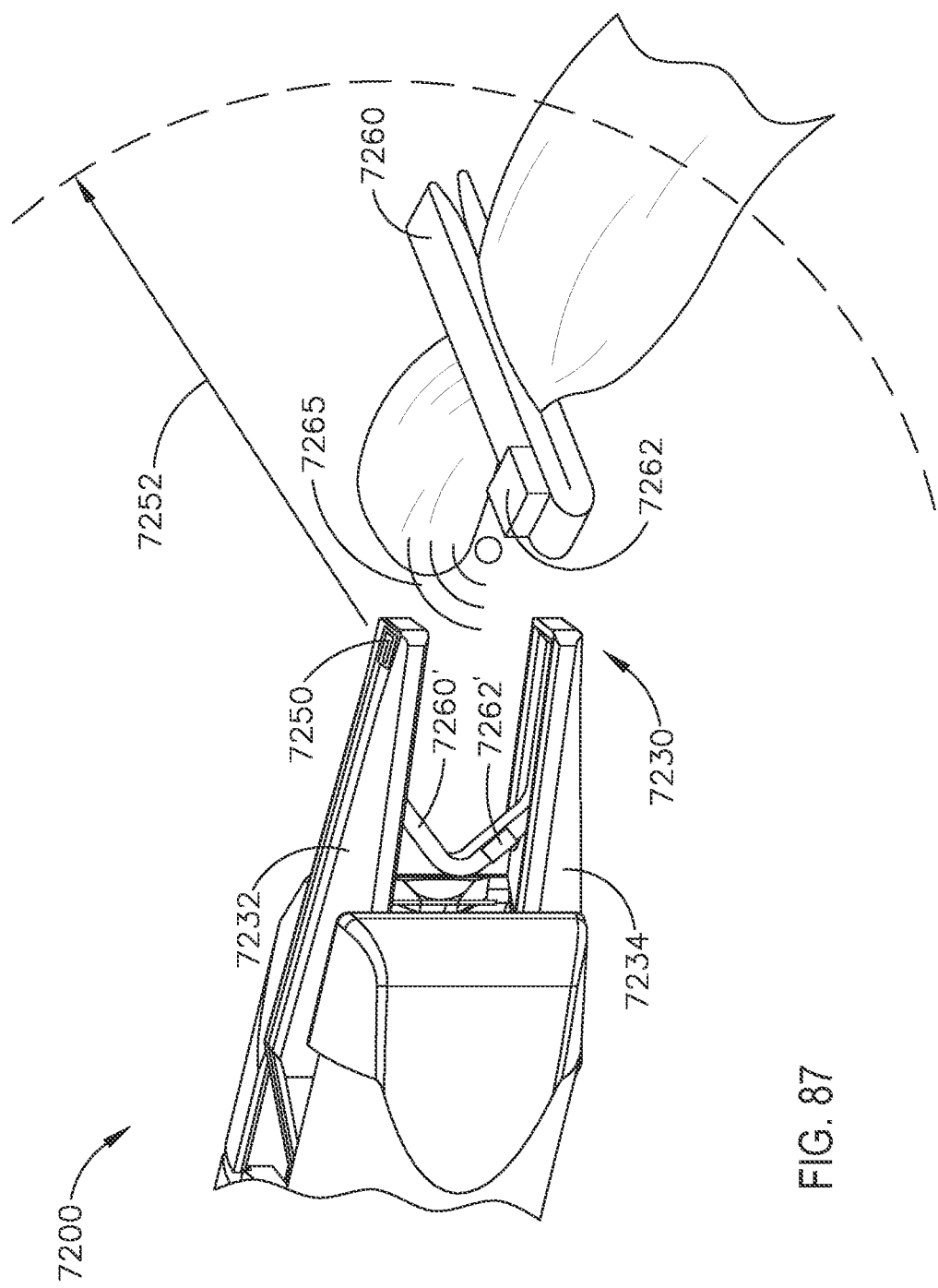
FIG. 87 is a partial perspective view of a surgical clip applier comprising an RFID system.

FIG. 87 illustrates a portion of a surgical clip applier 7200. As discussed in greater detail herein, the surgical clip applier 7200 comprises an end effector 7230. The end effector 7230 comprises a first jaw 7232 and a second jaw 7234. At least one of the first jaw and the second jaw are movable toward one another during a crimping stroke. The surgical clip applier 7200 further comprises at least one clip. In various instances, the surgical clip applier 7200 is configured to receive a cartridge comprising a plurality of clips. In other instances, the surgical slip applier 7200 is configured to receive one clip at a time. Each clip is configured to be crimped around patient tissue T one at a time during the crimping strokes.

The surgical clip applier 7200 is configured to receive a clip cartridge comprising a first clip 7260 and a second clip 7260'. The first clip 7260 comprises a first RFID tag 7262. The first RFID tag 7262 comprises a chip, such as a microchip, for example, that stores information about the surgical clip applier 7200, the first clip 7260, and/or the cartridge attached to the surgical clip applier 7200. In various instances, the set of information stored on the RFID chip comprises data that identifies the type of clip 7260 and/or clip cartridge attached to the surgical instrument 7200. As shown in FIG. 87, the first RFID tag 7262 is mounted to an outer surface of the first clip 7260. The first RFID tag 7262 is positioned on the outer surface of the first clip 7260 so that the first RFID tag 7262 is not in contact with patient tissue T when the first clip 7260 is crimped. Such placement can minimize damage and/or trauma to the patient tissue T, for example. The first RFID tag 7262 is positioned on a portion of the first clip 7260 that is not bent during the crimping stroke. Such placement avoids damaging the first RFID tag 7262 during the crimping stroke, for example. That said, the first RFID tag 7262 can be embedded within and/or attached to the first clip 7260 by any suitable method and/or at any suitable location.

The first RFID tag 7262 on the first clip 7260 provides a lockout for the surgical instrument, such as lockout 7179, for example. The clip applier will not perform a function with the firing drive assembly 1163, such as the crimping stroke on the first clip 7260, for example, if the information stored on the first RFID tag 7262 is not received by a controller of the surgical instrument. In various instances, the surgical instrument will not perform the function with the firing drive assembly 1163 when the first RFID tag 7262 is still in communication with an RFID scanner 7250 after the crimping stroke has been performed on the first clip 7260. As described in greater detail herein, the continued communication between the first RFID tag 7262 and the RFID scanner 7250 after the crimping stroke has been performed on the first clip 7260 indicates, among other things, that the clip applier is positioned too close to the formed first clip 7260. In various instances, the clip applier can alert a clinician of the detected location of the clip applier with respect to the formed first clip 7260 to prevent the clip applier from applying clips too close together, for example.

Figure 88:
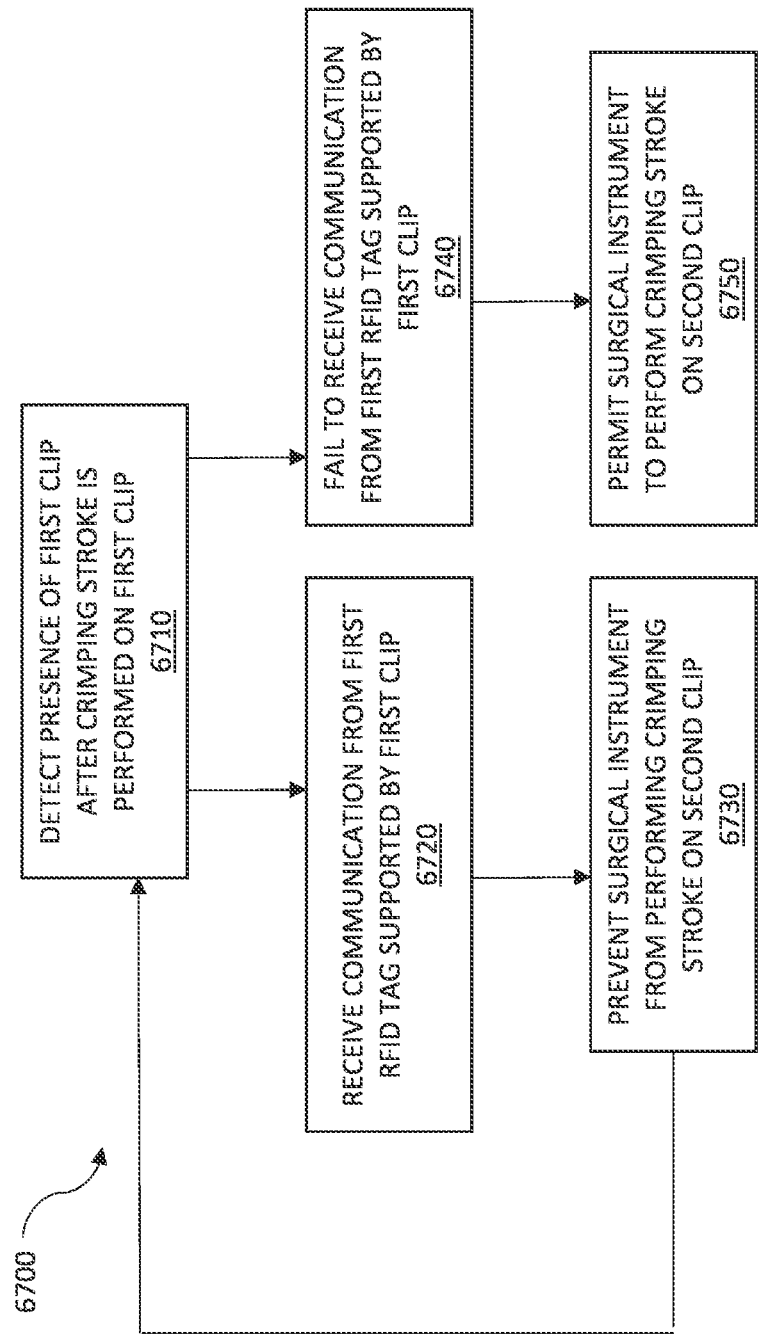
FIG. 88 is a flowchart representative of a process of a controller for controlling the performance of a crimping stroke based on the detection of an RFID tag.

For example, a process 6700 of the control circuit 1210 is depicted in FIG. 88. The control circuit 1210 is configured to detect 6710 the presence of a first clip after a crimping stroke is performed on the first clip. If the controller, through an RFID scanner, receives 6720 a communication and/or signal from the first RFID tag supported by the first clip, the controller is configured to prevent 6730 the surgical instrument 7200 from performing a crimping stroke on a second clip. If the controller, through the RFID scanner, fails to receive 6740 a communication and/or signal from the first RFID tag supported by the first clip, the controller is configured to permit 6750 the surgical instrument 7200 to perform the crimping stroke on the second clip.

Figure 89:
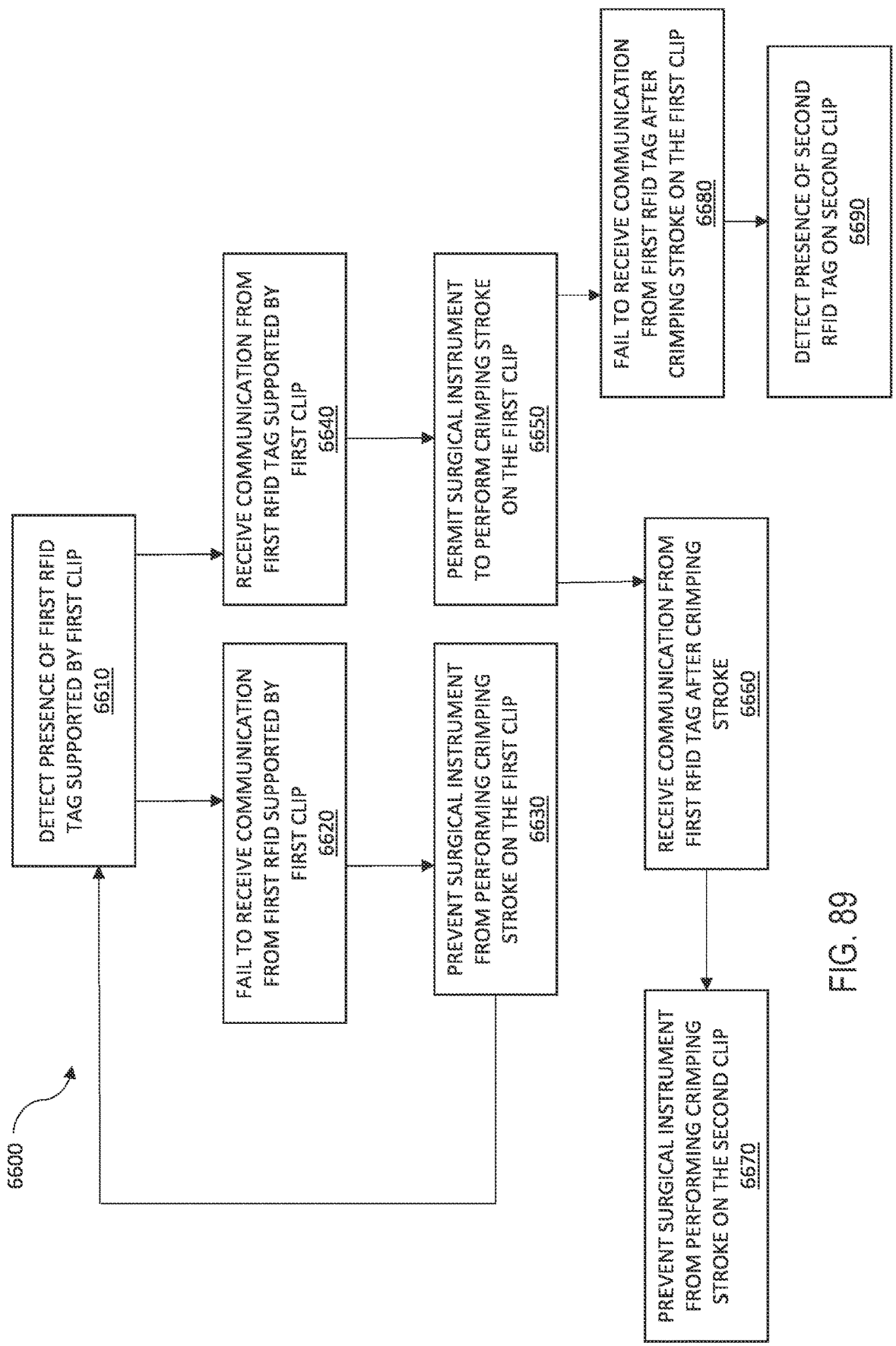
FIG. 89 is a flowchart representative of a process of a controller for controlling the performance of a crimping stroke based on the monitoring of multiple RFID tags.

An additional process 6600 of the control circuit 1210 is depicted in FIG. 89. The control circuit 1210 is configured to detect the presence of a first RFID tag supported by a first clip 6610. If the control circuit 1210 fails to receive a communication from the first RFID tag 6620, through an RFID scanner, the controller is configured to prevent the surgical instrument 7200 from performing a function 6630, such as a crimping stroke, on the first clip. The control circuit 1210 continues to detect the presence of the first RFID tag 6610 until the controller receives a communication from the first RFID tag 6640. Upon receiving the communication from the first RFID tag 6640, through the RFID scanner, the control circuit 1210 is configured to permit the surgical instrument 7200 to perform a crimping stroke on the first clip. After the crimping stroke is performed on the first clip, if the controller continues to receive communication from the first RFID tag 6660, the controller is configured to prevent the surgical instrument 7200 from performing a crimping stroke on a second clip 6670. After the crimping stroke is performed on the first clip, if the controller no longer receives communication from the first RFID tag 6680, the controller is configured to permit the surgical instrument 7200 to perform the crimping stroke on the second clip 6690.

As mentioned in greater detail herein, the surgical clip applier 7200 comprises an RFID scanner 7250 configured to communicate with nearby RFID tags. The RFID scanner 7250 comprises a scanner antenna configured to transmit radio signals. The radio signals activate RFID tags that are positioned within a pre-determined range of the RFID scanner 7250. The RFID scanner 7250 then receives one or more response signals that are "bounced back" from the RFID tag(s). In various instances, the one or more response signals comprise the same signal as the interrogation signal. In various instances, the one or more response signals comprise a modified signal from the interrogation signal. In various instances, the RFID scanner 7250 comprises reading and writing capabilities. The RFID scanner 7250 is then able to pass the collected information from the RFID tag to a controller for further interpretation. The controller can be positioned in the surgical instrument 7200, the remote console, or in any suitable location. The RFID scanner 7250 and/or the controller can comprise a stored set of compatibility information that corresponds to clip cartridges and/or clips that are compatible with a particular surgical instrument and/or for use during a particular surgical procedure.

More specifically, the surgical system 7200 comprises an RFID scanner 7250 configured to interact with the RFID tag 7262 attached to the first clip 7262. The RFID scanner 7250 can be present in various locations. In the depicted embodiment, the RFID scanner 7250 is positioned on the second jaw 7234 of the end effector 7230; however, the RFID scanner 7250 can be located in an alternative location within the surgical system 7200 and/or any other suitable location that would allow for communication between the first RFID tag 7262 and the RFID scanner 7250. The RFID scanner 7250 and/or the first RFID tag 7262 are powered such that the signal(s) they emit can only be detected within a communication range 7252 defined by a limited radius. That said, as the surgical clip applier 7200 is moved away from the patient tissue T where the first clip 7260 was applied, the first RFID tag 7262 is unable to communicate with the RFID scanner 7250. In such circumstances, the RFID tag 7262 moves outside of the communication range 7252 of the RFID scanner 7250. The RFID tag 7262 is unable to transmit and/or receive signals from the RFID scanner 7250 when the RFID tag 7262 is positioned outside of the communication range 7252.

If the first clip 7260 does not comprise an RFID tag and/or the first RFID tag 7262 comprises information that is not compatible with the surgical instrument 7200, the supplemental component verification system of the surgical instrument 7200 will be unable to permit the surgical instrument to perform a function with the firing drive assembly 1163, such as the crimping stroke. If the RFID scanner 7250 receives a response to an interrogation signal that is not found within a stored set of compatible supplemental components, the controller of the surgical instrument is programmed to communicate an error to the clinician. Likewise, if the RFID scanner 7250 does not receive a response to the interrogation signal, the controller of the surgical instrument is programmed to communicate an error to the clinician. In various instances, the detection of an error by the controller can render the surgical instrument inoperable for use with that particular clip cartridge and/or clip 7260. In various instances, a detected error can prevent the surgical instrument from performing a clip applying and/or crimping stroke. In various instances, the surgical instrument further comprises a manual override that can be activated to allow a clinician to override any system lockout 7179 and utilize operational functions of the surgical instrument in an emergency. As discussed above, the controller is configured to use an indicator 1209 to alert the clinician that an error has been detected. Such an alert can be communicated through various forms of feedback, including, for example, haptic, acoustic, and/or visual feedback. The alert can be specific or generic. For example, the alert can specifically state that the first RFID tag 7262 on the first clip 7260 is unable to be detected, or the alert can specifically state that the first RFID tag 7262 comprises information representative of an incompatible and/or defective clip cartridge and/or clip 7260.

Figure 90:
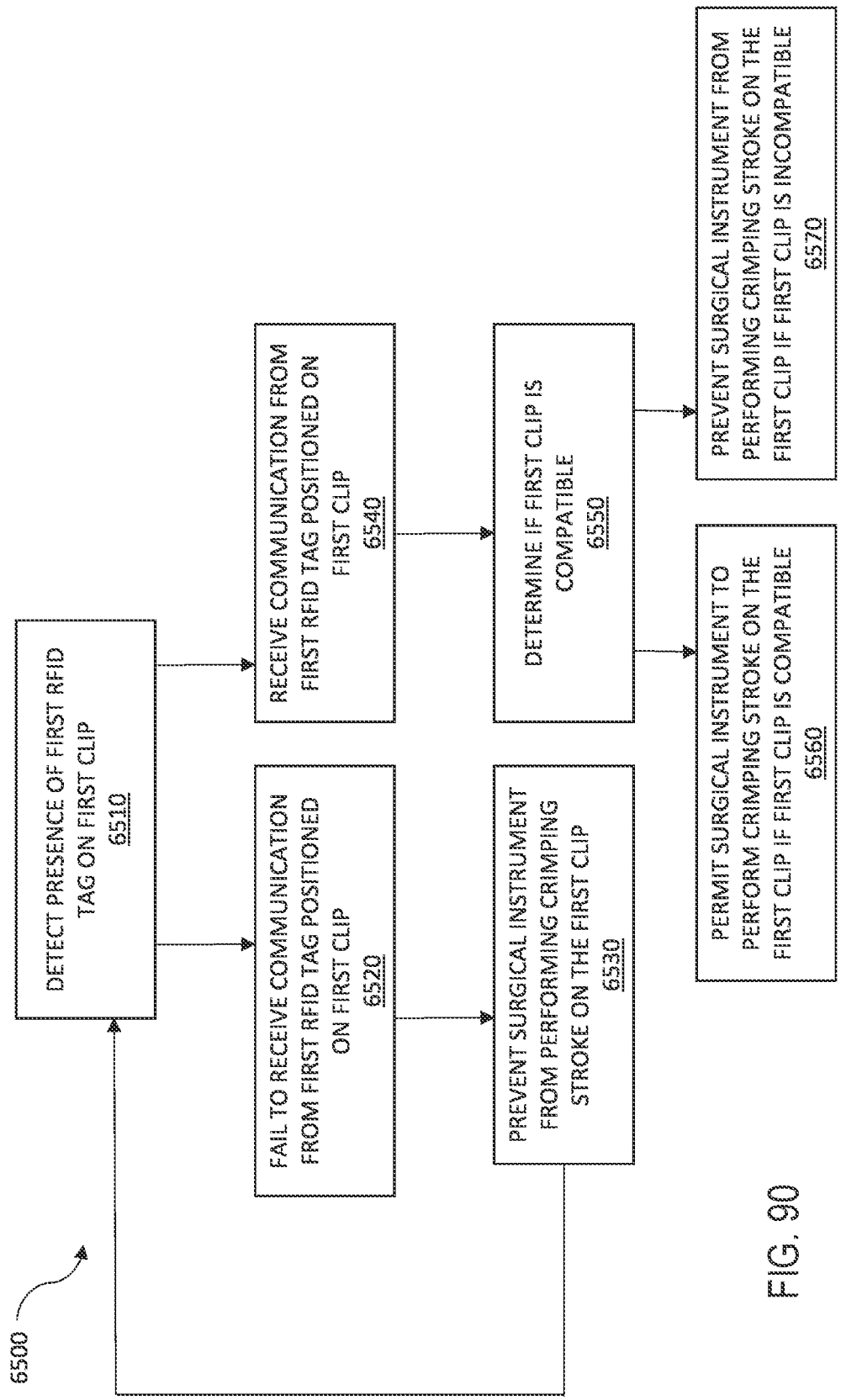
FIG. 90 is a flowchart representative of a process of a controller for detecting the compatibility of an attached clip.

For example, a process 6500 of the control circuit 1210 to determine authenticity and/or compatibility of the clips and/or the clip cartridge attached to the surgical instrument 7200 is depicted in FIG. 90. In instances where each clip comprises an RFID tag, the control circuit 1210 is configured to detect the presence of the first RFID tag supported by the first clip 6510 through an RFID scanner. If the RFID scanner fails to receive a communication from the first RFID tag, the RFID scanner is unable to pass along the communication to the control circuit 1210. In such instances, the control circuit 1210 fails to receive the information stored on the first RFID tag 6520, and the control circuit 1210 prevents the surgical instrument 7200 from performing a crimping stroke on the first clip 6530. The failure for the RFID scanner to detect the first RFID tag can arise from various scenarios such as an inauthentic clip, a defective clip, and/or an improperly aligned clip, among other things. If the RFID scanner receives a communication from the first RFID tag, the RFID scanner is configured to communicate the received information to the control circuit 1210. The control circuit 1210 determines if the first clip is compatible 6550 for use with the surgical instrument 7200 and/or during the surgical procedure. If the control circuit 1210 determines that the first clip is compatible for use, the control circuit 1210 permits the surgical instrument 7200 to perform a function 6560, such as a crimping stroke, on the first clip. If the control circuit 1210 determines that the first clip is incompatible for use, the control circuit 1210 prevents the surgical instrument 7200 from performing the function 6570.

In various instances, the controller can modify various operational parameters based on the identification of the clip cartridge and/or clip 7260 using the information stored on the first RFID tag 7262. Such an identification can include the material the first clip 7260 is comprised of, the number of clips 7260 remaining in the clip cartridge, the size of the clips 7260, and/or the thickness of the first clip 7260, among other things. After identification of the first clip 7260, the controller is configured to permit the surgical instrument to perform the desired function with the firing drive assembly 1163 using the modified operational parameters.

As discussed above, the RFID scanner 7250 comprises a communication range 7252 that spans a distance D from the RFID scanner 7250. When the first RFID tag 7262 on the first clip 7260 is located a distance away from the RFID scanner 7250 that is less than the distance D, the RFID scanner 7250 is able to transmit signals to and receive signals 7265 from the first RFID tag 7262. As discussed above, the surgical clip applier 7200 depicted in FIG. 87 further comprises the second clip 7260' comprising a second RFID tag 7260'. The second RFID tag 7260' comprises an RFID chip and a tag antenna, and the second RFID tag 7260' is similar in function and structure to the first RFID tag 7260. When the RFID scanner 7250 receives signals from both the first RFID tag 7260 and the second RFID tag 7260', the controller of the surgical clip applier 7200 is configured to alert the clinician. Such an alert can notify the clinician that the surgical clip applier 7200 is about to crimp the second clip 7260' in a location that is too close to the first formed clip 7260, for example. The controller can then prevent the clip applier 7200 from performing a crimping stroke on the second clip 7260' until the RFID scanner 7250 is unable to send and/or receive communications and/or signals from the first RFID tag 7262 on the first clip 7260.

In various instances, the information stored on the first RFID tag 7262 is a first serial number that is specific to the first clip 7260 and the information stored on the second RFID tag 7262' is a second serial number that is specific to the second clip 7260'. Based on the information received by the RFID scanner 7250, the controller is able to monitor each individual clip 7260, 7260' for compatibility with the surgical clip applier 7200 and/or authenticity, for example. In various instances, the controller is further able to maintain a count of the number of clips remaining in the loaded clip cartridge. In such instances, the controller is configured to alert the clinician of the number of clips remaining in the clip cartridge so that the clinician can prepare a new clip cartridge for attachment to the clip applier 7200.

Figure 91:
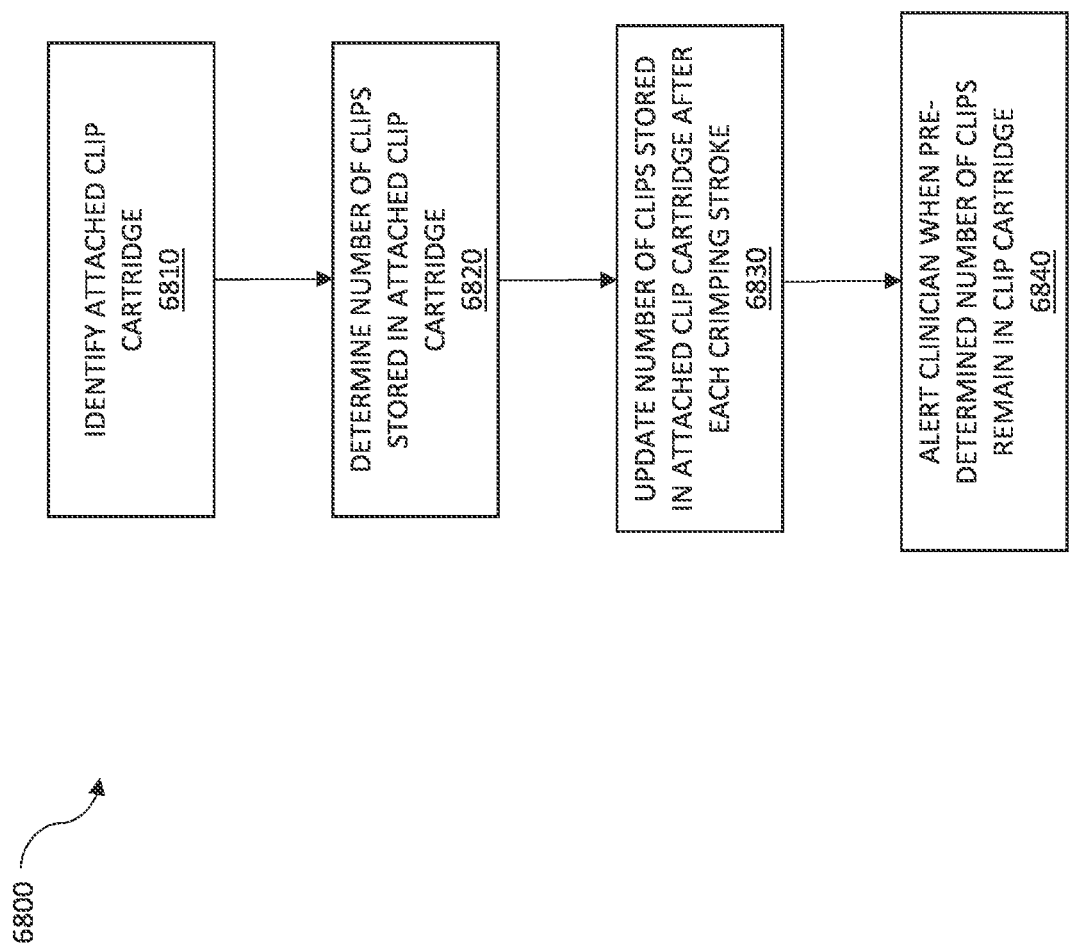
FIG. 91 is a flowchart representative of a process of a controller for monitoring the number of clips remaining in a clip cartridge.

For example, a process 6800 of the control circuit 1210 is depicted in FIG. 91. The control circuit 1210 is configured to identify a characteristic of a clip cartridge 6810 attached to the surgical instrument 7200. Using the identified characteristic, the control circuit 1210 is configured to determine a number 6820 of clips stored and/or remaining in the clip cartridge. The control circuit 1210 is configured to update the count of the number of clips 6830 stored and/or remaining in the clip cartridge after each crimping stroke. The control circuit 1210 is further configured to alert a clinician 6840 when a pre-determined number of clips remain in the clip cartridge. For example, the clinician can be alerted when only one clip remains in the clip cartridge. In various instances, the clinician can be continuously alerted of the clip count.

In various instances, individual surgical clip appliers, such as the clip appliers 6200 and 7200, are configured to be interchangeably used with various configurations of clips and/or clip cartridges. For example, clips can comprise different dimensions, different strengths, different harnesses, and/or different material compositions. Furthermore, the end effector 6230 can be removably attached to the elongate shaft 6220 to allow different end effector configurations to be attached to the clip applier 6200. Such modularity requires the controller of the clip applier to implement different operational parameters for each type of attached clip, attached clip cartridge, and/or attached end effector.

The surgical clip applier 7200 further comprises an electric motor 1160 and a driver 1161 configured to control the operation of the motor 1160 including the flow of electrical energy from a power source. The controller varies and/or modifies parameters of the electric motor 1160 through a motor control program. The motor control program is configured to determine the appropriate operational parameters based on the information received by the RFID scanner. The motor control program can compare the information received from the RFID tag to a look-up table and/or database stored within a memory, such as the memory 1212. Such a look-up table and/or database can comprise recommended operational parameters for the motor control program to implement based on the detected attached components. Operational parameters that can be adjusted based on the identification of the identified replaceable components comprise the overall motor rate, the loading force applied to a clip by the jaws of the end effector during a crimping stroke, the duration of the crimping stroke, the rate of crimping, and/or the duration the jaws of the end effector are held in a closed configuration upon completion of the crimping stroke, for example. Such operational parameters should be changed based on the attached clip to ensure proper clip closing without severing patient tissue, for example.

In various instances, the motor control program is configured to set a maximum load threshold based on the information received from the RFID tag positioned on the attached clip and/or clip cartridge. In such instances, the motor control program prevents the clip applier 7200 from performing a crimping stroke by blocking the power source's ability to supply power to the electric motor 1160 when the maximum load threshold is exceeded. In various instances, the motor control program is configured to prevent the clip applier 7200 from performing functions 1163 when other thresholds are exceeded, such as handling loads and/or elongate shaft twist loads, among others. The motor control program can implement prevent the power source from providing power to the electric motor 1160 after the crimping stroke is completed but before the jaws of the end effector are opened. Such a pause in suppling power to the motor 1160 allows the jaws to hold the crimped clip in place for a predetermined amount of time. In various instances, the clip applier 7200 comprises a locking member that holds the jaw in the closed configuration when power is no longer being supplied to the motor 1160. Such a locking member prevents the jaws from returning to the open configuration when power is no longer being supplied to the motor 1160. In various instances, the motor control program is configured to cause the power source to supply a minimum amount of power to the motor 1160 after the crimping stroke is completed, wherein the minimum amount of power is sufficient to keep the jaws in the closed configuration.

The ability for the end effector 7230 to be interchangeably attached to the elongate shaft of the clip applier 7200 requires the instrument controller to vary and/or otherwise adjust the length an advancing member must be translated to separate an individual clip from the clips stored within a clip cartridge to a crimping position, for example. The controller is configured to account for the differences in distance between the first jaw and the second jaw of the modular end effector 7330 to appropriately crimp the clips. The operational parameters should also be modified based on the attached clip to compensate for the spring back and/or other responses of the clip based on the material composition of the clip and the patient tissue, for example. The ability for the controller of the clip applier 7200 to determine the identification of the clip material and/or size, the clip cartridge side and configuration, and/or the end effector configuration and/or capabilities allows the control system to appropriately adapt by setting maximum threshold limits and/or the rates and/or speeds of performing a crimping stroke, among other things.

Figure 92:
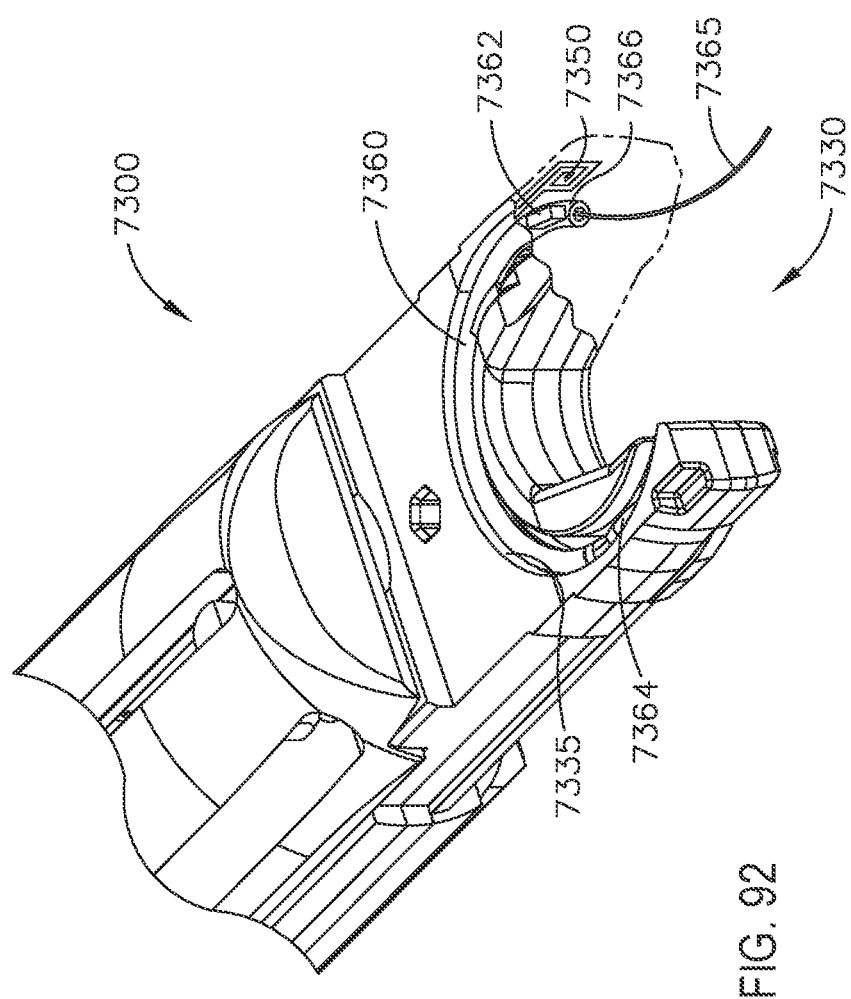
FIG. 92 is a partial perspective view of a surgical suturing device comprising an RFID system.

FIG. 92 illustrates a portion of a surgical suturing device 7300. As discussed in greater detail herein, the surgical suturing device 7300 comprises an end effector 7330. The end effector 7330 comprises a needle track 7335 configured to guide a replaceable needle 7360. The replaceable needle 7360 comprises a first end 7364 comprising a pointed tip configured to pierce through patient tissue. The replaceable needle 7360 comprises a second end 7366, wherein the second end 7366 comprises suturing material 7365 attached thereto. The replaceable needle 7360 is guided by the needle track 7335 and actuated by a firing drive through a firing stroke.

As discussed above, the needle track 7335 of the end effector 7330 is configured to receive a replaceable needle 7360. The replaceable needle 7360 comprises an RFID tag 7362. The RFID tag 7362 comprises a chip, such as a microchip, for example, that stores information about the surgical suturing device 7300, the replaceable needle 7360, and/or the suturing material 7365 attached to the replaceable needle 7360. In various instances, the set of information stored on the RFID chip comprises data that identifies the size of the needle 7360 positioned in the needle track 7335, the material the needle 7360 is comprised of, and/or the material the suturing material 7365 is comprised of. As shown in FIG. 92, the RFID tag 7362 is molded within the replaceable needle 7362. The RFID tag 7362 is molded within the replaceable needle 7362 to allow the needle 7362 to travel through the needle track 7335 uninterrupted, for example. Furthermore, the RFID tag 7362 is molded within the replaceable needle 7362 to allow the needle 7362 to travel through the patient tissue T in a smooth path. In other words, the RFID tag 7362 does not get stuck during the firing stroke and/or require an additional force to fire the replaceable needle through the patient tissue and/or the needle track 7335 during the firing stroke. That said, the RFID tag 7362 can be embedded within and/or attached to the replaceable needle 7360 by any suitable method and/or at any suitable location.

The RFID tag 7362 on the replaceable needle 7360 provides a lockout 7179 for the surgical instrument 7300. The suturing device 7300 will not perform a function with the firing drive assembly 1163, such as the needle firing stroke, for example, if the information stored on the RFID tag 7362 is not received by a controller of the surgical instrument. As mentioned in greater detail herein, the surgical suturing device 7300 comprises an RFID scanner 7350 configured to communicate with nearby RFID tags. The RFID scanner 7350 comprises a scanner antenna configured to transmit radio signals. The radio signals activate RFID tags that are positioned within a pre-determined range of the RFID scanner 7350. The RFID scanner 7350 then receives one or more response signals that are "bounced back" from the RFID tag(s). In various instances, the one or more response signals comprise the same signal as the interrogation signal. In various instances, the one or more response signals comprise a modified signal from the interrogation signal. In various instances, the RFID scanner 7350 comprises reading and writing capabilities. The RFID scanner 7350 is then able to pass the collected information from the RFID tag to a controller for further interpretation. The controller can be positioned in the surgical instrument 7300, the remote console, or in any suitable location. The RFID scanner 7350 and/or the controller can comprise a stored set of compatibility information that corresponds to replaceable needles and/or suturing materials that are compatible with a particular surgical instrument and/or for use during a particular surgical procedure.

More specifically, the surgical system 7300 comprises an RFID scanner 7350 configured to interact with the RFID tag 7362 attached to the replaceable needle 7360. The RFID scanner 7350 can be present in various locations. In the depicted embodiment, the RFID scanner 7350 is positioned on a distal end of the of the end effector 7330. More specifically, the RFID scanner 7350 is positioned at a first end of the needle track 7335 adjacent the second end 7366 of the replaceable needle 7360 when the replaceable needle 7360 is appropriately positioned in the needle track 7335; however, the RFID scanner 7350 can be located in an alternative location within the surgical system 7300 and/or any other suitable location that would allow for communication between the RFID tag 7362 and the RFID scanner 7350. The RFID scanner 7350 and/or the RFID tag 7362 are powered such that the signal(s) they emit can only be detected within a limited radius.

If the replaceable needle 7360 does not comprise an RFID tag and/or the RFID tag 7362 comprises information that is not compatible with the surgical instrument 7300, the supplemental component verification system and/or the controller of the surgical instrument 7300 will be prevent the surgical instrument from performing a function with the firing drive assembly 1163, such as the firing stroke. If the RFID scanner 7350 receives a response to an interrogation signal that is not found within a stored set of compatible supplemental components, the controller of the surgical instrument is programmed to communicate an error to the clinician. Likewise, if the RFID scanner 7350 does not receive a response to the interrogation signal, the controller of the surgical instrument is programmed to communicate an error to the clinician. In various instances, the detection of an error by the controller can render the surgical instrument inoperable for use with that particular replaceable needle 7360. In various instances, a detected error can prevent the surgical instrument from performing a firing stroke. In various instances, the surgical instrument further comprises a manual override that can be activated to allow a clinician to override any system lockout 7179 and utilize operational functions of the surgical instrument in an emergency. As discussed above, the controller is configured to alert the clinician that an error has been detected through an indicator 1209. Such an alert can be communicated through various forms of feedback, including, for example, haptic, acoustic, and/or visual feedback. The alert can be specific or generic. For example, the alert can specifically state that the RFID tag 7362 on the replaceable needle 7360 is unable to be detected, or the alert can specifically state that the RFID tag 7362 comprises information representative of an incompatible and/or defective needle 7360 and/or suturing material 7365.

In various instances, the controller can modify various operational parameters based on the identification of the replaceable needle 7360 and/or the suturing material 7365 using the information stored on the RFID tag 7362. Such an identification can include the material the needle 7360 and/or the suturing material 7365 is comprised of, the length of the suturing material 7365, and/or the thickness of the replaceable needle 7360 and/or the suturing material 7365, among other things. After identification of a characteristic of the replaceable needle 7360, the controller is configured to permit the surgical instrument to perform the desired function with the firing drive assembly 1163 using the modified operational parameters.

Figure 93:
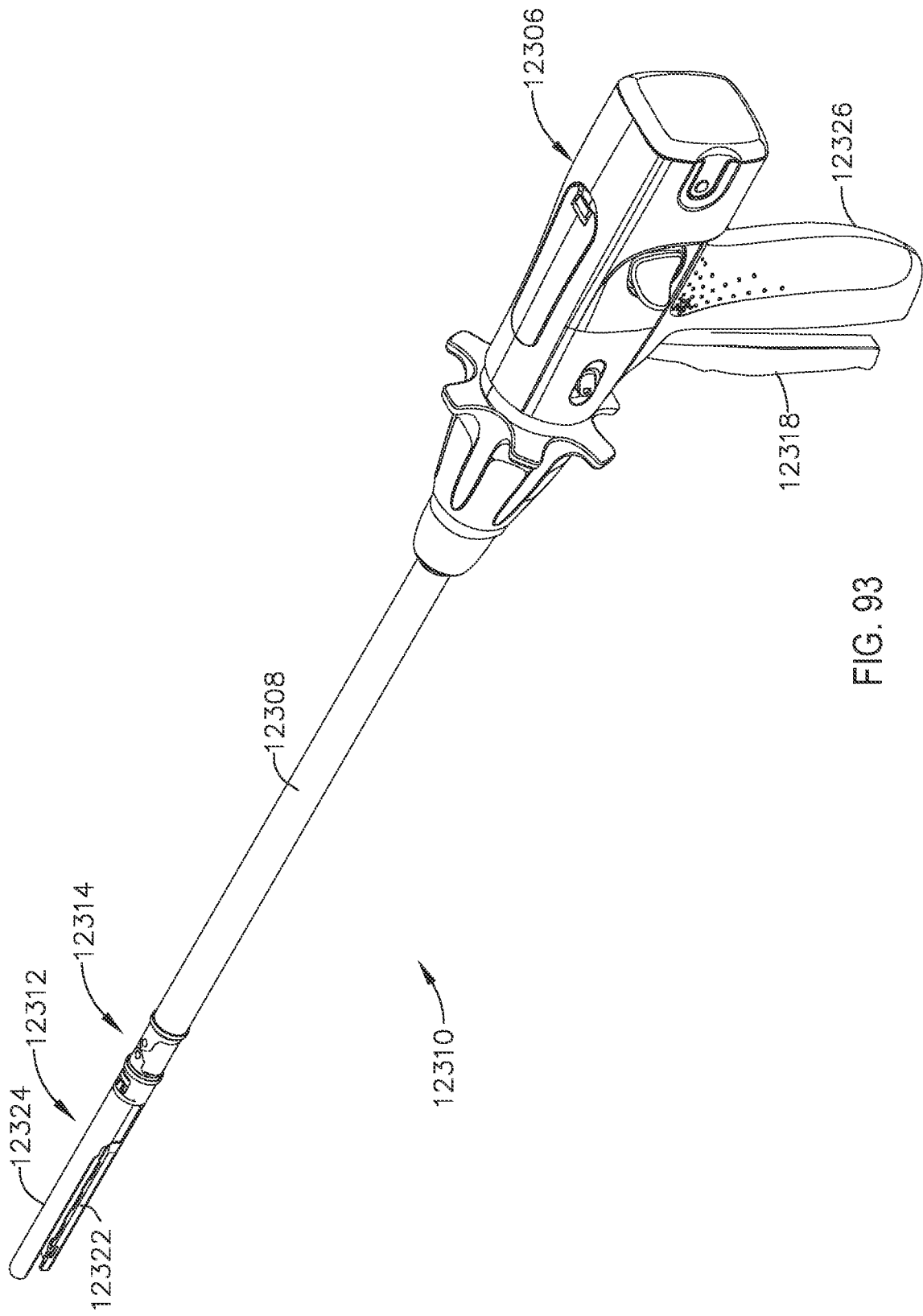
FIG. 93 is a perspective view of a surgical instrument comprising a handle, a shaft, and an articulatable end effector.
Figure 94:
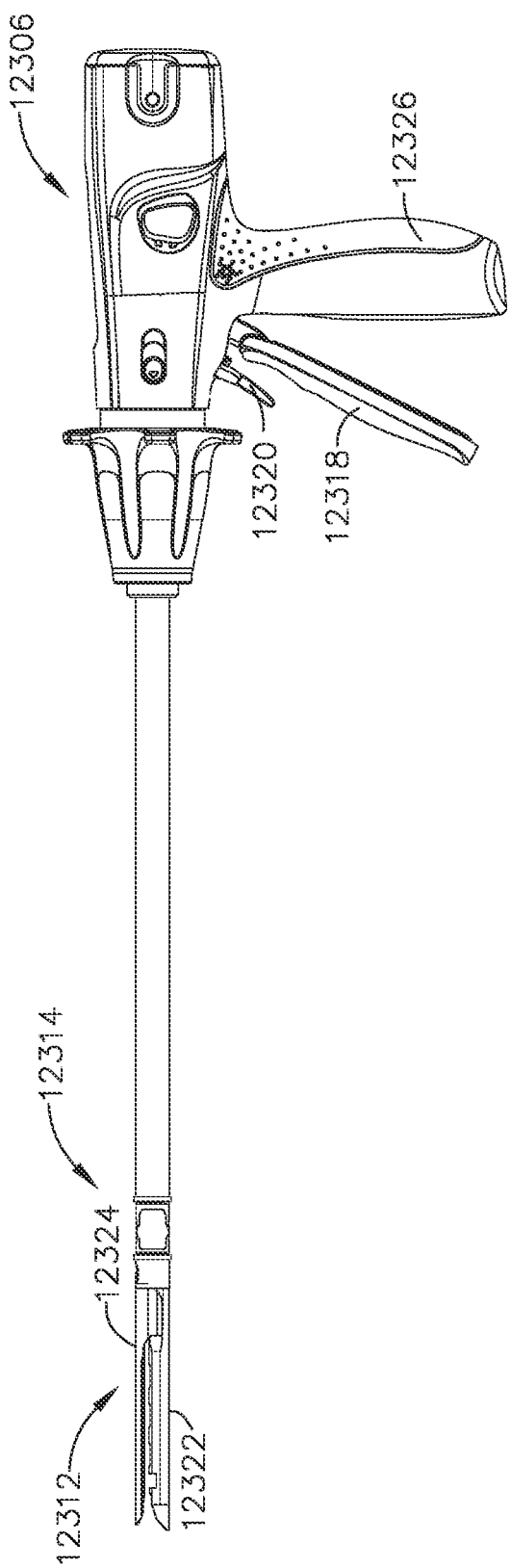
FIG. 94 is a side view of the surgical instrument of FIG. 93.

The embodiments disclosed herein are configured for use with surgical clip appliers and systems such as those disclosed in U.S. patent application Ser. No. 14/200,111, now U.S. Pat. No. 9,629,629, entitled CONTROL SYSTEMS FOR SURGICAL INSTRUMENTS, which is incorporated in its entirety herein. FIGS. 93 and 94 depict a motor-driven surgical cutting and fastening instrument 12310. This illustrated embodiment depicts an endoscopic instrument and, in general, the instrument 12310 is described herein as an endoscopic surgical cutting and fastening instrument; however, it should be noted that the invention is not so limited and that, according to other embodiments, any instrument disclosed herein may comprise a non-endoscopic surgical cutting and fastening instrument. The surgical instrument 12310 depicted in FIGS. 93 and 94 comprises a handle 12306, a shaft 12308, and an end effector 12312 connected to the shaft 12308. In various embodiments, the end effector 12312 can be articulated relative to the shaft 12308 about an articulation joint 12314. Various means for articulating the end effector 12312 and/or means for permitting the end effector 12312 to articulate relative to the shaft 12308 are disclosed in U.S. Pat. No. 7,753,245, entitled SURGICAL STAPLING INSTRUMENTS, which issued on Jul. 13, 2010, and U.S. Pat. No. 7,670,334, entitled SURGICAL INSTRUMENT HAVING AN ARTICULATING END EFFECTOR, which issued on Mar. 2, 2010, the entire disclosures of which are incorporated by reference herein. Various other means for articulating the end effector 12312 are discussed in greater detail below. Similar to the above, the end effector 12312 is configured to act as a surgical stapler for clamping, severing, and/or stapling tissue, although, in other embodiments, different types of end effectors may be used, such as end effectors for other types of surgical devices, graspers, cutters, staplers, clip appliers, access devices, drug/gene therapy devices, ultrasound, RF and/or laser devices, etc. Several RF devices may be found in U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL CUTTING AND FASTENING INSTRUMENT HAVING RF ELECTRODES, filed Feb. 14, 2008, the entire disclosures of which are incorporated by reference in their entireties.

The end effector 12312 can include, among other things, a staple channel 12322 and a pivotally translatable clamping member, such as an anvil 12324, for example. The handle 12306 of the instrument 12310 may include a closure trigger 12318 and a firing trigger 12320 for actuating the end effector 12312. It will be appreciated that instruments having end effectors directed to different surgical tasks may have different numbers or types of triggers or other suitable controls for operating the end effector 12312. The handle 12306 can include a downwardly extending pistol grip 12326 toward which the closure trigger 12318 is pivotally drawn by the clinician to cause clamping or closing of the anvil 12324 toward the staple channel 12322 of the end effector 12312 to thereby clamp tissue positioned between the anvil 12324 and channel 12322. In other embodiments, different types of clamping members in addition to or lieu of the anvil 12324 could be used. The handle 12306 can further include a lock which can be configured to releasably hold the closure trigger 12318 in its closed position. More details regarding embodiments of an exemplary closure system for closing (or clamping) the anvil 12324 of the end effector 12312 by retracting the closure trigger 12318 are provided in U.S. Pat. No. 7,000,818, entitled SURGICAL STAPLING INSTRUMENT HAVING SEPARATE DISTINCT CLOSING AND FIRING SYSTEMS, which issued on Feb. 21, 2006, U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008, and U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008, the entire disclosures of which are incorporated by reference herein.

Once the clinician is satisfied with the positioning of the end effector 12312, the clinician may draw back the closure trigger 12318 to its fully closed, locked position proximate to the pistol grip 12326. The firing trigger 12320 may then be actuated, or fired. In at least one such embodiment, the firing trigger 12320 can be farther outboard of the closure trigger 12318 wherein the closure of the closure trigger 12318 can move, or rotate, the firing trigger 12320 toward the pistol grip 12326 so that the firing trigger 12320 can be reached by the operator using one hand. Thereafter, the operator may pivotally draw the firing trigger 12320 toward the pistol grip 12312 to cause the stapling and severing of clamped tissue in the end effector 12312. Thereafter, the firing trigger 12320 can be returned to its unactuated, or unfired, position after the clinician relaxes or releases the force being applied to the firing trigger 12320. A release button on the handle 12306, when depressed, may release the locked closure trigger 12318. The release button may be implemented in various forms such as, for example, those disclosed in published U.S. Patent Application Publication No. 2007/0175955, entitled SURGICAL CUTTING AND FASTENING INSTRUMENT WITH CLOSURE TRIGGER LOCKING MECHANISM, which was filed on Jan. 31, 2006, the entire disclosure of which is incorporated herein by reference in its entirety.

Further to the above, the end effector 12312 may include a cutting instrument, such as knife, for example, for cutting tissue clamped in the end effector 12312 when the firing trigger 12320 is retracted by a user. Also further to the above, the end effector 12312 may also comprise means for fastening the tissue severed by the cutting instrument, such as staples, RF electrodes, and/or adhesives, for example. A longitudinally movable drive shaft located within the shaft 12308 of the instrument 12310 may drive/actuate the cutting instrument and the fastening means in the end effector 12312. An electric motor, located in the handle 12306 of the instrument 12310 may be used to drive the drive shaft, as described further herein. In various embodiments, the motor may be a DC brushed driving motor having a maximum rotation of, approximately, 25,000 RPM, for example. In other embodiments, the motor may include a brushless motor, a cordless motor, a synchronous motor, a stepper motor, or any other suitable electric motor. A battery (or "power source" or "power pack"), such as a Li ion battery, for example, may be provided in the pistol grip portion 12326 of the handle 12306 adjacent to the motor wherein the battery can supply electric power to the motor via a motor control circuit. According to various embodiments, a number of battery cells connected in series may be used as the power source to power the motor. In addition, the power source may be replaceable and/or rechargeable.

Figure 95:
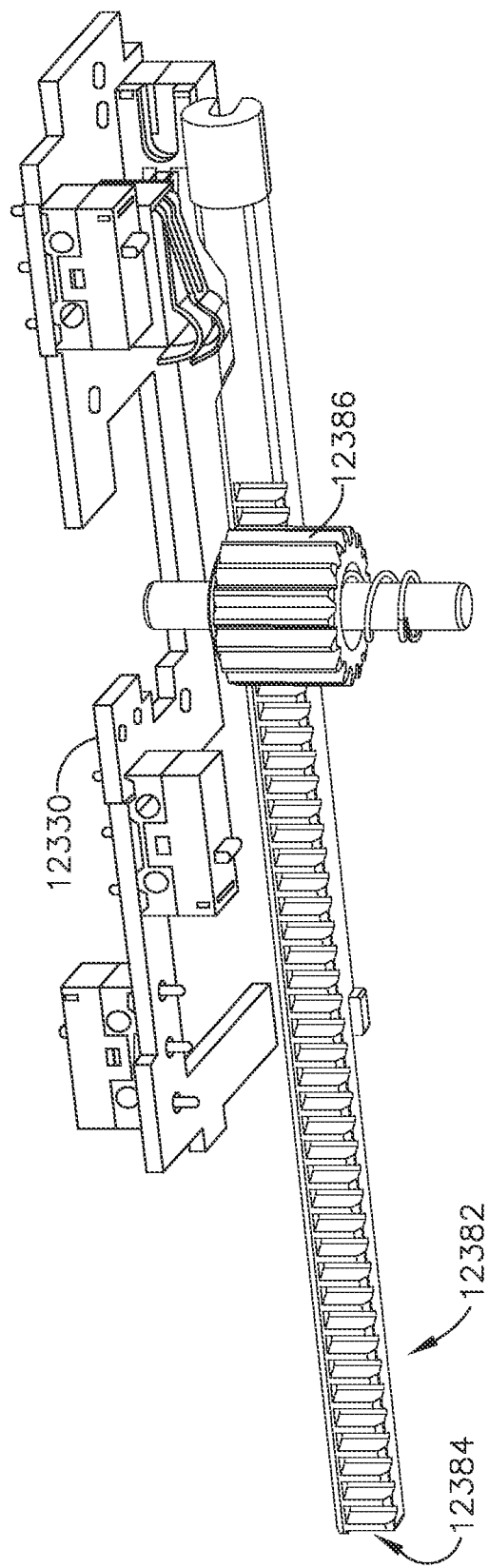
FIG. 95 is a perspective view of a firing member and a pinion gear positioned within the handle of FIG. 93.
Figure 96:
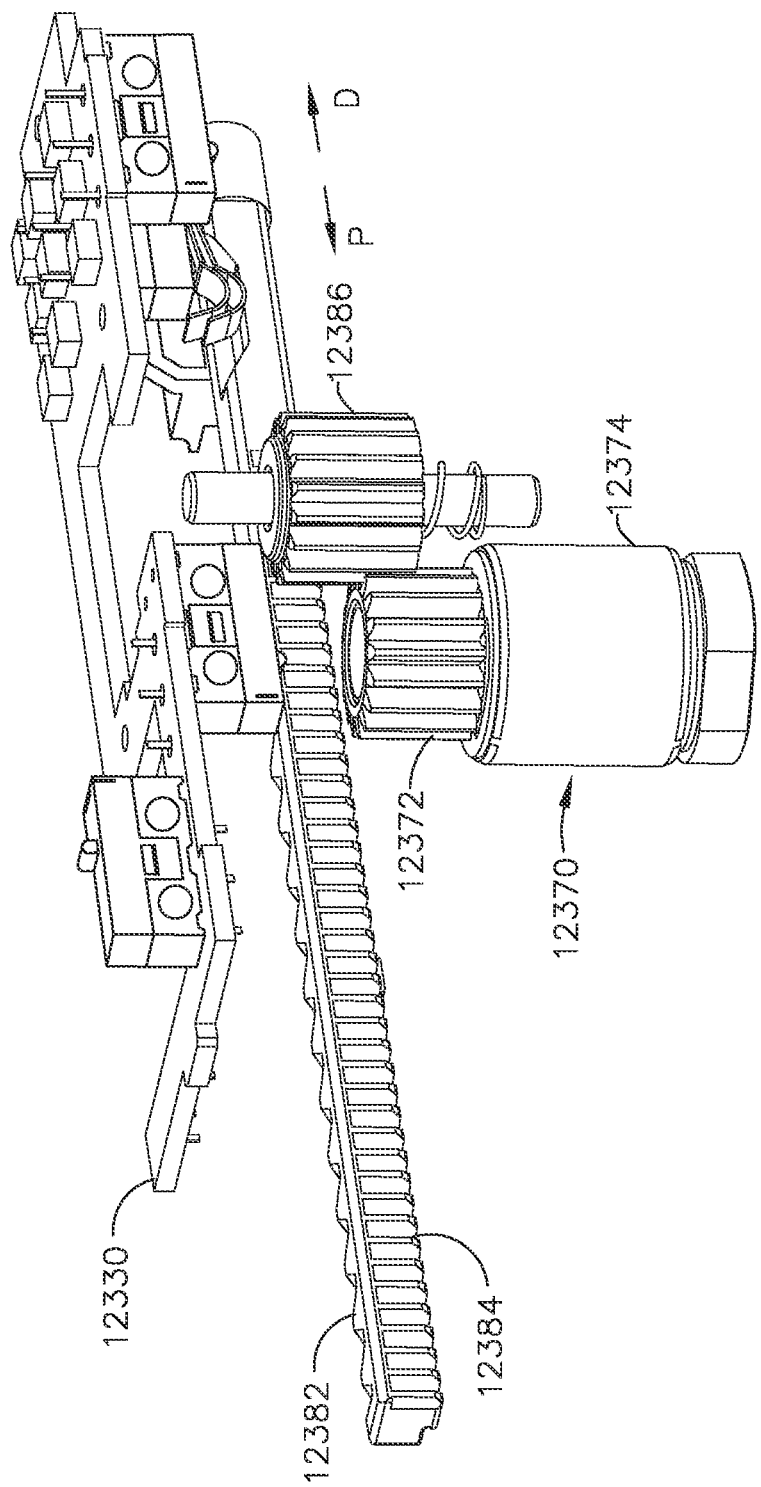
FIG. 96 is a perspective view of the firing member and the pinion gear of FIG. 95 and a gear reducer assembly operably engaged with the pinion gear.
Figure 97:
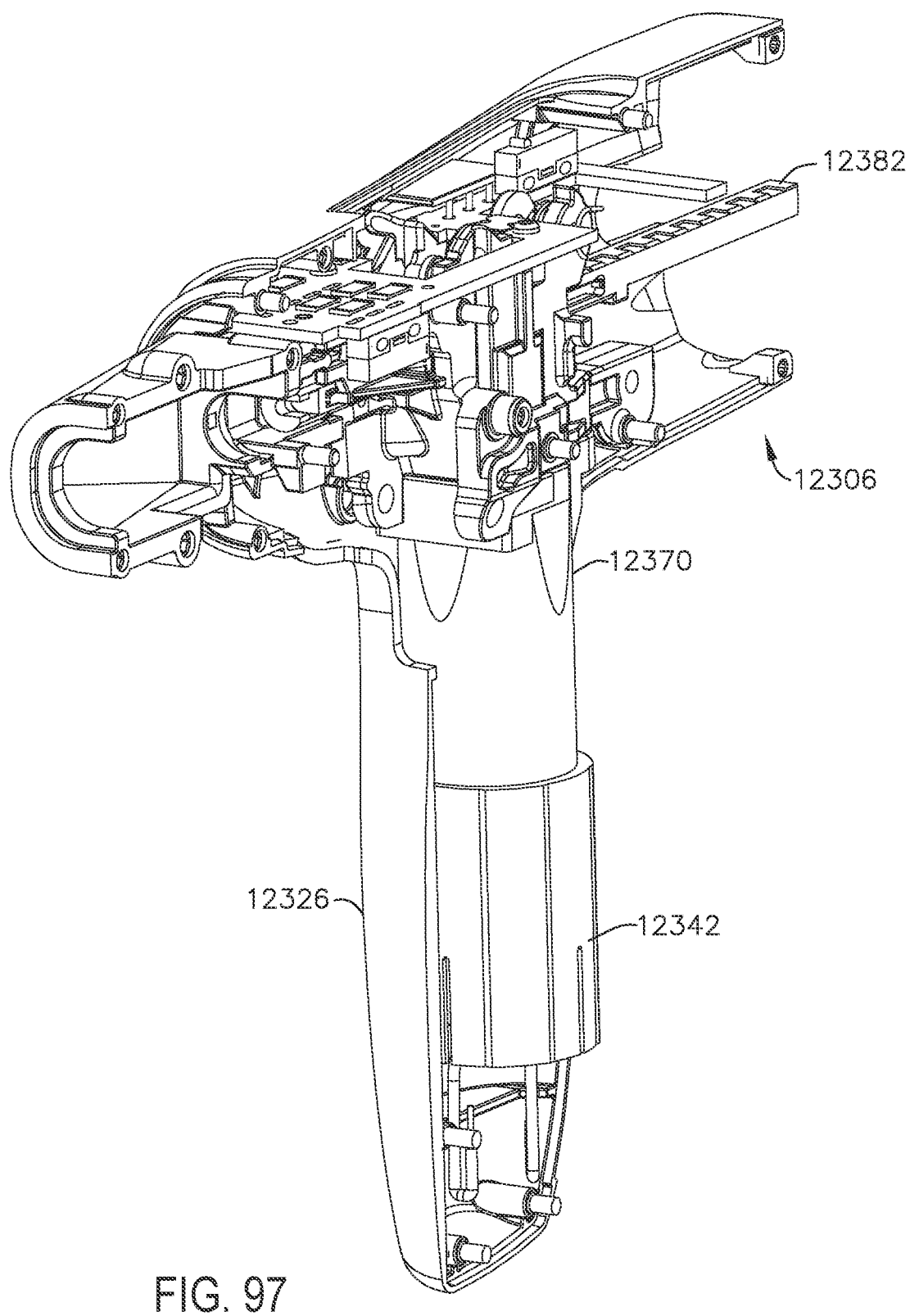
FIG. 97 is a perspective view of the handle of FIG. 93 with portions thereof removed to illustrate the firing member and the pinion gear of FIG. 95, the gear reducer assembly of FIG. 96, and an electric motor configured to drive the firing member distally and/or proximally depending on the direction in which the electric motor is turned.

As outlined above, the electric motor in the handle 12306 of the instrument 12310 can be operably engaged with the longitudinally-movable drive member positioned within the shaft 12308. Referring now to FIGS. 95-97, an electric motor 12342 can be mounted to and positioned within the pistol grip portion 12326 of the handle 12306. The electric motor 12342 can include a rotatable shaft operably coupled with a gear reducer assembly 12370 wherein the gear reducer assembly 12370 can include, among other things, a housing 12374 and an output pinion gear 12372. In certain embodiments, the output pinion gear 12372 can be directly operably engaged with a longitudinally-movable drive member 12382 or, alternatively, operably engaged with the drive member 12382 via one or more intermediate gears 12386. The intermediate gear 12386, in at least one such embodiment, can be meshingly engaged with a set, or rack, of drive teeth 12384 defined in the drive member 12382. In use, the electric motor 12342 can be drive the drive member distally, indicated by an arrow D (FIG. 90), and/or proximally, indicated by an arrow D (FIG. 91), depending on the direction in which the electric motor 12342 rotates the intermediate gear 12386. In use, a voltage polarity provided by the battery can operate the electric motor 12342 in a clockwise direction wherein the voltage polarity applied to the electric motor by the battery can be reversed in order to operate the electric motor 12342 in a counter-clockwise direction. The handle 12306 can include a switch which can be configured to reverse the polarity applied to the electric motor 12342 by the battery. The handle 12306 can also include a sensor 12330 configured to detect the position of the drive member 12382 and/or the direction in which the drive member 12382 is being moved.

Figure 106:
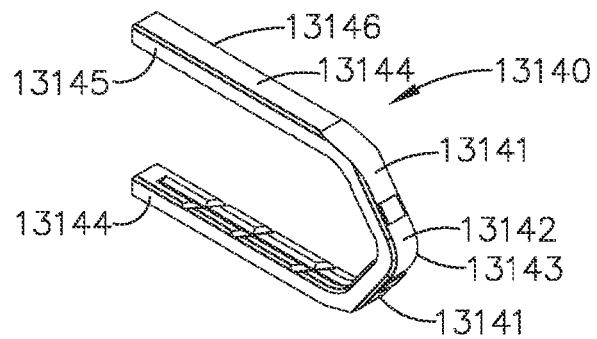
FIG. 106 is a perspective view of a clip illustrated in FIG. 99.

The embodiments disclosed herein are configured for use with surgical clip appliers and systems such as those disclosed in U.S. patent application Ser. No. 16/112,237, filed on Aug. 24, 2018, now U.S. Pat. No. 11,026,713, entitled SURGICAL CLIP APPLIER CONFIGURED TO STORE CLIPS IN A STORED STATE, which is incorporated in its entirety herein. Referring to FIG. 98, a surgical instrument, such as a clip applier 13100, for example, can be configured to apply one or more clips to tissue located within a surgical site in the patient. Generally, referring now to FIG. 106, the clip applier 13100 can be structured and arranged to position a clip 13140 relative to the tissue in order to compress the tissue within the clip 13140. The clip applier 13100 can be configured to deform the clip 13140 as illustrated in FIGS. 100 and 101, for example, and as described in greater detail further below. Each clip 13140 can comprise a base 13142 and opposing legs 13144 extending from the base 13142. The base 13142 and the legs 13144 can comprise any suitable shape and can define a substantially U-shaped configuration and/or a substantially V-shaped configuration, for example. The base 13142 can comprise angled portions 13141 which are connected together by a joint 13143. In use, the legs 13144 of the clip 13140 can be positioned on opposite sides of the tissue wherein the legs 13144 can be pushed toward one another to compress the tissue positioned between the legs 13144. The joint 13143 can be configured to permit the angled portions 13141 of the base 13142, and the legs 13144 extending therefrom, to deform inwardly. In various circumstances, the clip 13140 can be configured to yield, or deform plastically, when the clip 13140 is sufficiently compressed, although some amount of elastic deformation, or spring-back, may occur within the deformed clip 13140.

Figures 107, 108:
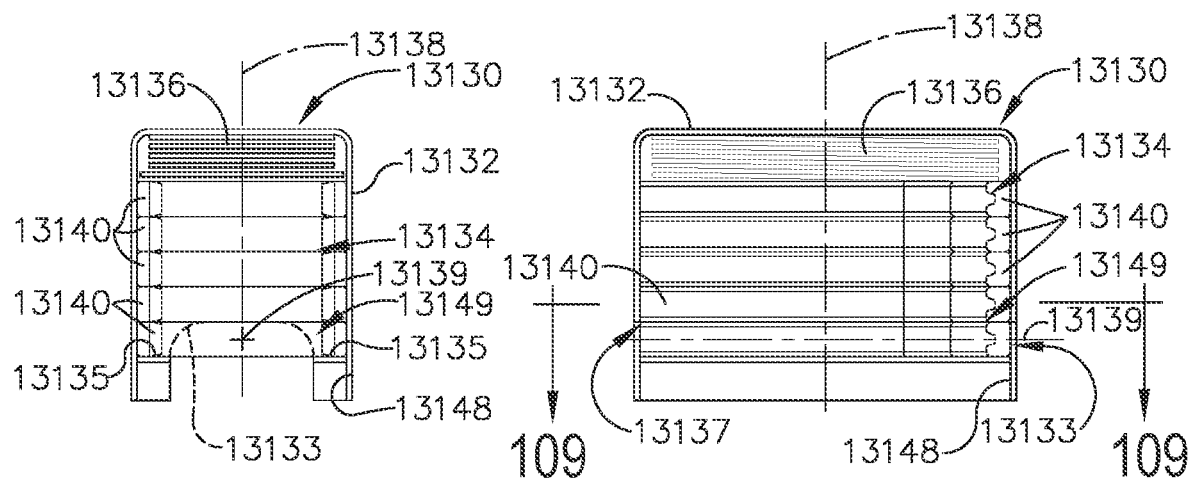
FIG. 107 is a front view of a cartridge illustrated in FIG. 99 comprising a plurality of clips with portions of the cartridge removed to illustrate the clips stored in the cartridge.
FIG. 108 is a side view of the cartridge of FIG. 107 illustrated with portions removed to illustrate the clips stored in the cartridge.
Figure 109:
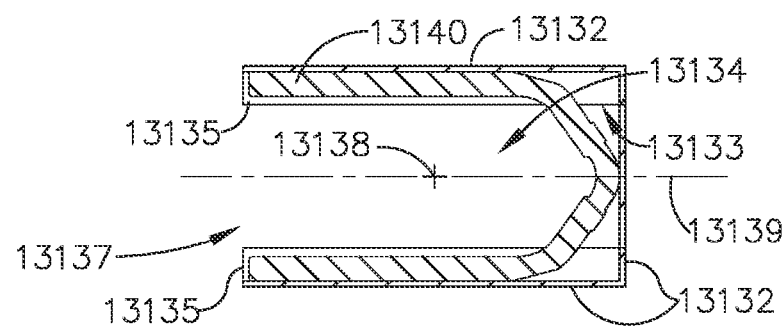
FIG. 109 is a cross-sectional plan view of the cartridge of FIG. 107 taken along line 109-109 in FIG. 108.
Figure 110:
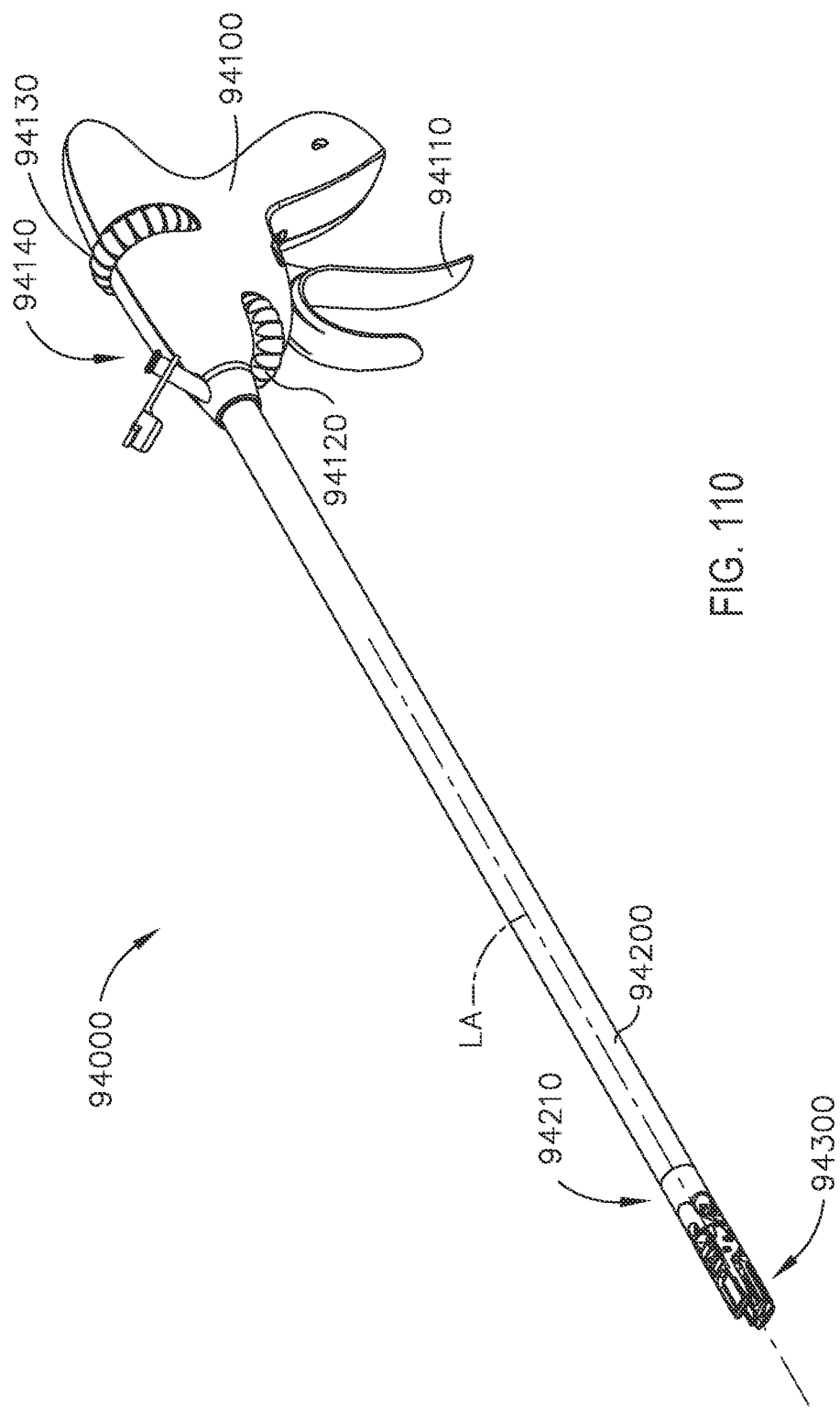
FIG. 110 is a perspective view of a surgical suturing instrument comprising a handle, a shaft, and an end effector.
Figure 111:
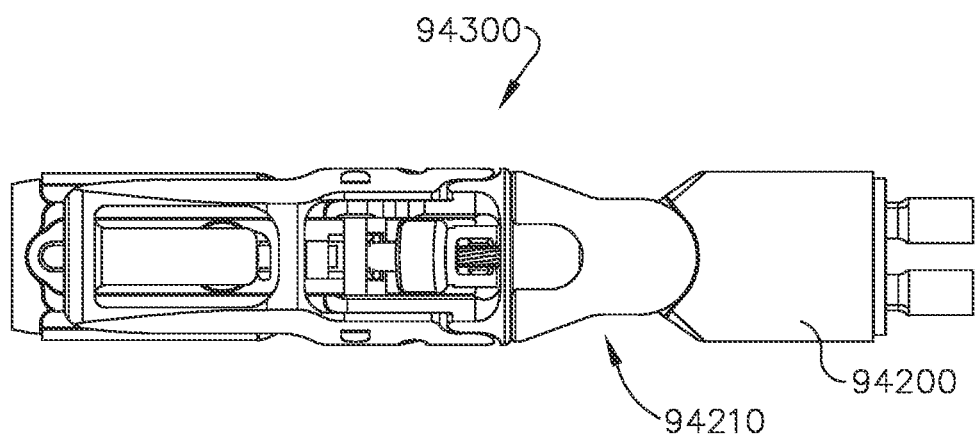
FIG. 111 is a partial plan view of the surgical suturing instrument of FIG. 110.
Figure 112:
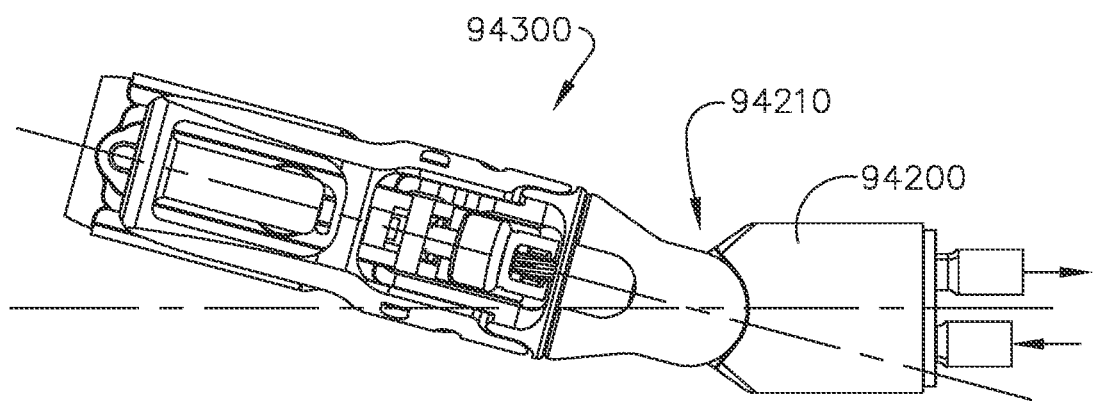
FIG. 112 is a partial plan view of the surgical suturing instrument of FIG. 110, wherein the end effector is in an articulated state.
Figure 113:
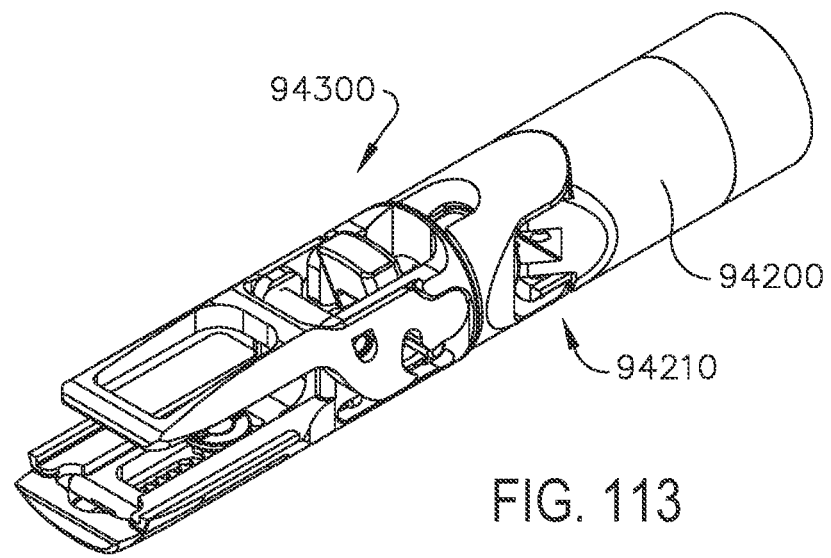
FIG. 113 is a partial perspective view of the surgical suturing instrument of FIG. 110.
Figure 114:
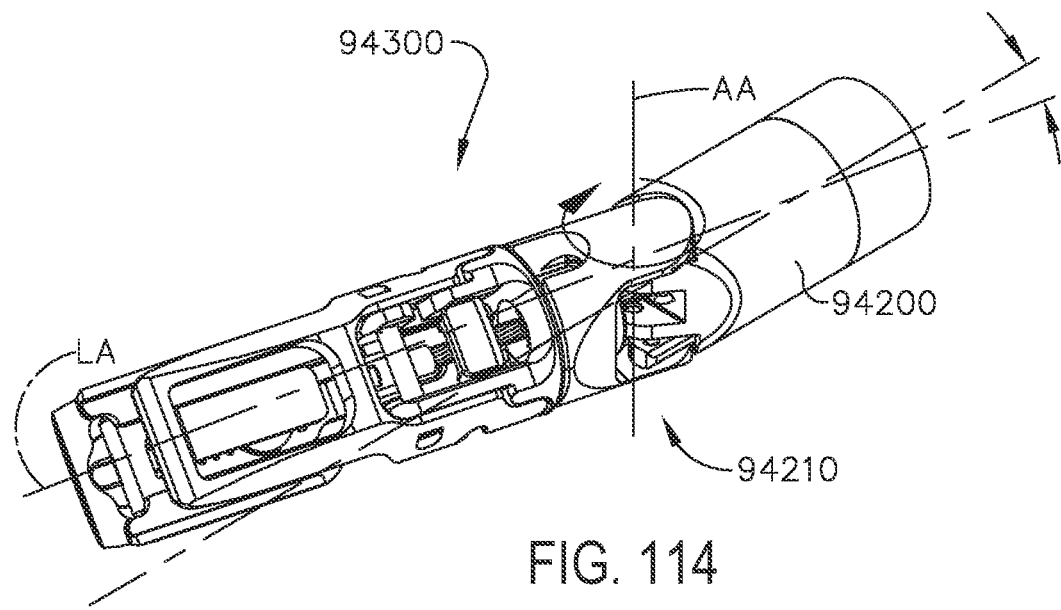
FIG. 114 is a partial perspective view of the surgical suturing instrument of FIG. 110, wherein the end effector is in an articulated and rotated state.

Referring now to FIGS. 98 and 99, the clip applier 13100 can include a shaft 13110, an end effector 13120, and a replaceable clip cartridge, or magazine, 13130. Referring to FIGS. 107-109, the clip cartridge 13130 can comprise a housing 13132 and a plurality of clips 13140 positioned within the housing 13132. The housing 13132 can define a storage chamber 13134 in which the clips 13140 can be stacked. The storage chamber 13134 can comprise sidewalls which extend around, or at least substantially around, the perimeter of the clips 13140. Referring again to FIG. 106, each clip 13140 can comprise opposing faces, such as a top face 13145 and a bottom face 13146 on opposite sides of the clip 13140 wherein, when the clips 13140 are stacked in the housing 13132, the top face 13145 of a clip 13140 can be positioned against the bottom face 13146 of an adjacent clip 13140 and wherein the bottom face 13146 of the clip 13140 can be positioned against the top face 13145 of another adjacent clip 13140. In various circumstances, the bottom faces 13146 of the clips 13140 can face downwardly toward one or more support shelves, or platforms, 13135 defined in the housing 13132 while the top faces 13145 of the clips 13140 can face upwardly away from the support shelves 13135. The top faces 13145 and the bottom faces 13146 of the clips 13140 may be identical, or at least substantially identical, in some cases, while, in other cases, the top faces 13145 and the bottom faces 13146 may be different. The stack of clips 13140 depicted in FIGS. 107-109 comprises five clips 13140, for example; however, other embodiments are envisioned in which the stack of clips 13140 can include more than five clips 13140 or less than five clips 13140. In any event, the clip cartridge 13130 can further comprise at least one biasing member, such as biasing member 13136, for example, positioned intermediate the housing 13132 and the top clip 13140 in the stack of clips 13140. As described in greater detail below, the biasing member 13136 can be configured to bias the bottom clip 13140 in the stack of clips 13140 or, more particularly, the bottom face 13146 of the bottom clip 13140, against the support shelves 13135 defined in the housing 13132. The biasing member 13136 can comprise a spring, and/or any suitable compressed elastic element, for example, which can be configured to apply a biasing force to the clips 13140, or at least apply a biasing force to the top clip 13140 which is transmitted downwardly through the stack of clips 13140.

When a clip 13140 is positioned against the support shelves 13135 as described above, the clip 13140 can be supported in a firing position in which the clip 13140 can be advanced and ejected from the cartridge 13130. In various circumstances, the support shelves 13135 can define at least a portion of a firing chamber 13149 in which the clips 13140 can be sequentially positioned in the firing position. In some cases, the firing chamber 13149 can be entirely defined within the cartridge 13130 or, in other cases, the firing chamber 13149 can be defined within and/or between the shaft 13110 and the cartridge 13130. In any event, as described in greater detail further below, the clip applier 13100 can comprise a firing drive which can advance a firing member into the cartridge 13130 and push the clip 13140 from its firing position positioned against the support shelves 13135 to a fired position in which it is received within the end effector 13120 of the clip applier 13100. Referring primarily to FIGS. 107-109, the housing 13132 of the cartridge 13130 can comprise a proximal opening, or window, 13133 which can be aligned, or at least substantially aligned, with the support shelves 13135 such that the firing member can enter into the cartridge 13130 through the proximal opening 13133 and advance a clip 13140 distally out of the cartridge 13130. In at least one such embodiment, the housing 13132 can further comprise a distal, or discharge, opening, or window, 13137 which is also aligned with the support shelves 13135 such that the clip 13140 can be advanced, or fired, distally along a firing axis 13139 extending through the proximal opening 13133, the firing chamber 13149, and the distal opening 13137, for example.

In order to advance a clip 13140 out of the cartridge 13130, further to the above, the firing member of the firing drive can be advanced into to the cartridge housing 13132 and, in various circumstances, into the firing chamber 13149. As disclosed in greater detail further below, the firing member can pass entirely through the cartridge 13130 in order to advance the clip 13140 into its fired position within the end effector 13120. After the clip 13140 positioned in the firing chamber 13149 has been advanced distally by the firing member, as outlined above, the firing member can be retracted sufficiently such that the biasing member 13136 can position another clip 13140 against the support shelves 13135. In various circumstances, the biasing member 13136 can bias a clip 13140 against the firing member while the firing member is positioned within the housing 13132. Such a clip 13140 can be referred to as a queued clip. After the firing member has been sufficiently retracted and slid out from underneath the queued clip 13140, the biasing member 13136 can then bias the clip 13140 against the support shelves 13135 where it is staged for the next stroke of the reciprocating firing member. Referring primarily to FIGS. 109 and 107-109, the cartridge 13130 can be configured to supply the clips 13140 to the firing chamber 13149 along a predetermined path, such as supply axis 13138, for example. The supply axis 13138 can be transverse to the firing axis 13139 such that the clips 13140 are fed into the firing chamber 13149 in a direction which is different than the direction in which the firing member passes through the firing chamber 13149. In at least one such embodiment, the supply axis 13138 can be perpendicular, or at least substantially perpendicular, to the firing axis 13139, for example.

Referring again to FIG. 109, the shaft 13110 can comprise a cartridge, or magazine, aperture 13131 which can be sized and configured to receive a clip cartridge 13130, for example, therein. The cartridge aperture 13131 can be sized and configured such that the housing 13132 of the cartridge 13130 is closely received within the cartridge aperture 13131. The sidewalls which define the cartridge aperture 13131 can limit, or at least substantially limit, the lateral movement of the cartridge 13130 relative to the shaft 13110. The shaft 13110 and/or the cartridge 13130 can further comprise one or more locks which can be configured to releasably hold the cartridge 13130 in the cartridge aperture 13131. As illustrated in FIG. 99, the cartridge 13130 can be loaded into the cartridge aperture 13131 along an axis which is, in at least one embodiment, parallel to or collinear with the supply axis 13138. As also illustrated in FIG. 99, the shaft 13110 can further comprise a pad or seat 13118 extending from the sidewall 13111 of the shaft 13110 wherein the pad 13118 can be configured to be received within and/or engaged with the housing 13132 of the cartridge 13130. The pad 13118 can be sized and configured to be closely received within a recess 13148 defined in the cartridge housing such that the pad 13118 can limit, or at least substantially limit, the lateral movement of the cartridge 13130 relative to the shaft 13110. The pad 13118 can be sized and configured to align the cartridge 13130 within the shaft 13110 and/or support the cartridge housing 13132.

Once the clip cartridge 13130 has been positioned and seated within the shaft aperture 13131, referring now to FIGS. 102 and 103, a firing drive 13160 of the clip applier 13100 can be actuated to advance the clips 13140 from the clip cartridge 13130 as described above. The firing drive 13160 can comprise a rotary drive input such as a drive screw 13161, for example, and a displaceable firing nut 13163 operably engaged with the drive screw 13161. The drive screw 13161 can comprise at least one drive thread 13162 which can be threadably engaged with a threaded aperture extending through the firing nut 13163. In various embodiments, the clip applier 13100 can further include an electric motor, for example, operably coupled with the drive screw 13161. In various instances, the drive screw 13161 can be operably coupled with the motor of a surgical instrument system comprising a hand-held instrument or a robotic arm, for example. In any event, the movement of the firing nut 13163 within the shaft 13110 can be constrained such that the firing nut 13163 moves along a longitudinal axis 13164 when the drive screw 13161 is rotated about the longitudinal axis 13164 by the motor. For instance, when the drive screw 13161 is rotated in a first direction by the motor, the drive screw 13161 can advance the firing nut 13163 distally toward the end effector 13120, as illustrated in FIG. 103. When the drive screw 13161 is rotated in a direction opposite the first direction by the motor, the drive screw 13161 can retract the firing nut 13163 proximally away from the end effector 13120. The shaft 13110 can comprise one or more bearings which can be configured to rotatably support the drive screw 13161. For instance, a bearing 13159 can be configured to rotatably support the distal end of the drive screw 13161, for example, as illustrated in FIGS. 21 and 22.

The firing drive 13160 can further comprise a firing member 13165 extending from the firing nut 13163 which can be advanced distally and retracted proximally with the firing nut 13163, as described in greater detail further below. Upon comparing FIGS. 102 and 103, the reader will note that the firing nut 13163 and the firing member 13165 have been advanced from a proximal, unfired position, illustrated in FIG. 102, to a distal, fired position, illustrated in FIG. 103, in which the firing member 13165 has advanced a clip 13140 from the clip cartridge 13130 into the end effector 13120. Referring primarily to FIG. 102, the clip cartridge 13130 is illustrated as comprising a plurality of clips 13140 stored therein wherein one of the clips 13140 is positioned in a firing position, as described above. As illustrated in FIGS. 102 and 103, the firing member 13165 can include a distal portion 13166 which can be advanced into the staple cartridge 13130 along a firing axis 13167 and engage the clip 13140 positioned in the firing position when the firing member 13165 and the firing nut 13163 are advanced distally. In some cases, the firing member 13165 can comprise a linear member while, in other cases, the distal end 13166 of the firing member 13165 can extend upwardly from the firing member 13165, for example. Further to the above, the firing member 13165 can advance the clip 13140 distally out of the clip cartridge 13130 along the firing axis 13167 and into a receiving cavity 13122 defined in the end effector 13120.

In various cases, the firing member 13165 can be attached to and extend distally from the firing nut 13163 while, in other cases, the firing member 13165 and the firing nut 13163 can be operably connected to one another by a firing actuator 13168. The firing actuator 13168 can be pivotably mounted to the firing member 13165 at a pivot 13169 and can include a distal arm 13170a and a proximal arm 13170b which can be engaged with a longitudinal slot 13113 defined in the housing 13112 of the shaft 13110. In at least one such embodiment, each of the arms 13170a, 13170b can include a projection, such as projections 13171a and 13171b, respectively, extending therefrom which can be configured to slide within the longitudinal slot 13113. Further to the above, the firing nut 13163 can further include a firing pin 13172 extending therefrom which can be configured to engage the distal arm 13170a in order to advance the actuator 13168 and the firing member 13165 distally, as described above. In use, referring again to the progression illustrated in FIGS. 102 and 103, the firing nut 13163 can be advanced distally by the drive screw 13161 wherein the firing pin 13172, which is positioned intermediate the distal arm 13170a and the proximal arm 13170b, can contact the distal arm 13170a and drive the actuator 13168 and the firing member 13165 distally. As the actuator 13168 is advanced distally, the actuator 13168 may be prevented from rotating about the pivot pin 13169 as one or both of the projections 13171a and 13171b sliding in the shaft slot 13113 can be prevented from being moved laterally relative to the longitudinal shaft slot 13113 until the actuator 13168 reaches the position illustrated in FIG. 103.

Once a clip 13140 has been positioned within the receiving cavity 13122, further to the above, the clip 13140 can be deformed by a crimping drive 13180, for example. Referring now to FIGS. 100 and 101, the end effector 13120 of the clip applier 13100 can further comprise a first jaw 13123a and a second jaw 13123b wherein the first jaw 13123a and the second jaw 13123b can at least partially define the receiving chamber 13122. As illustrated in FIGS. 100 and 101, the first jaw 13123*a* can comprise a first channel 13124*a* and the second jaw 13123*b* can comprise a second channel 13124*b* which can each be configured to receive and support at least a portion of a clip 13140 therein. The first jaw 13123*a* can be pivotably coupled to a frame 13111 of the shaft 13110 by a pin 13125*a* and the second jaw 13123*b* can be pivotably coupled to the frame 13111 by a pin 13125*b*. In use, the crimping drive 13180 can be configured to rotate the first jaw 13123*a* toward the second jaw 13123*b* and/or rotate the second jaw 13123*b* toward the first jaw 13123*a* in order to compress the clip 13140 positioned therebetween. In at least one such embodiment, the crimping drive 13180 can comprise a cam actuator 13181 which can be configured to engage a first cam surface 13126*a* defined on the first jaw 13123*a* and a second cam surface 13126*b* on the second jaw 13123*b* in order to pivot the first jaw 13123*a* and the second jaw 13123*b* toward one another. The cam actuator 13181 can comprise a collar which at least partially surrounds the first jaw 13123*a* and the second jaw 13123*b*. In at least one such embodiment, the collar can comprise an inner cam surface 13182 which can be contoured to contact the cam surfaces 13126*a*, 13126*b* of the jaws 13123*a*, 13123*b* and drive them inwardly toward one another. In various circumstances, the clip 13140 positioned within the receiving chamber 13122 defined in the end effector 13120 can be positioned relative to tissue before the crimping drive 13180 is actuated. In some circumstances, the crimping drive 13180 can be at least partially actuated prior to positioning the clip 13140 relative to the tissue in order to at least partially compress the clip 13140. In certain instances, the clip 13140 and the receiving chamber 13122 can be sized and configured such that the clip 13140 can be biased or flexed inwardly when the end effector 13120 is in its unactuated state, as illustrated in FIG. 100. In various instances, the crimping first jaw 13123*a* and the second jaw 13123*b* can be actuated to elastically crimp and/or permanently crimp the clip 13140 positioned therebetween.

Figure 104:
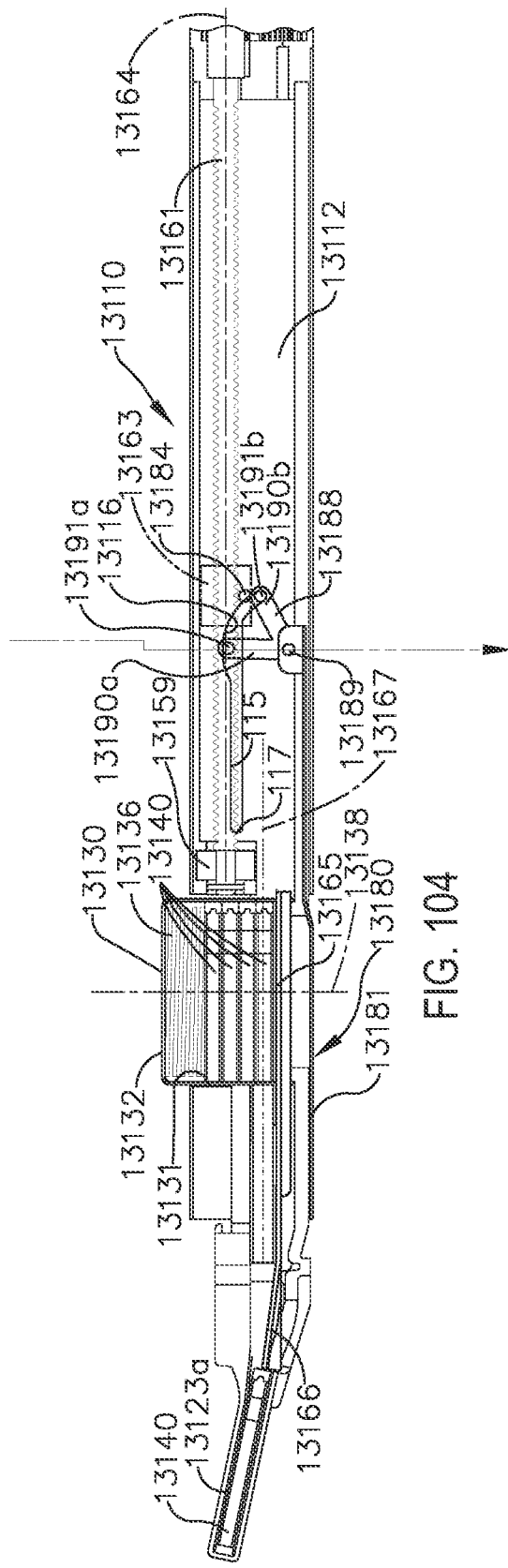
FIG. 104 is a cross-sectional view of the end effector of FIG. 99 illustrating the firing drive coming into engagement with the crimping drive.
Figure 105:
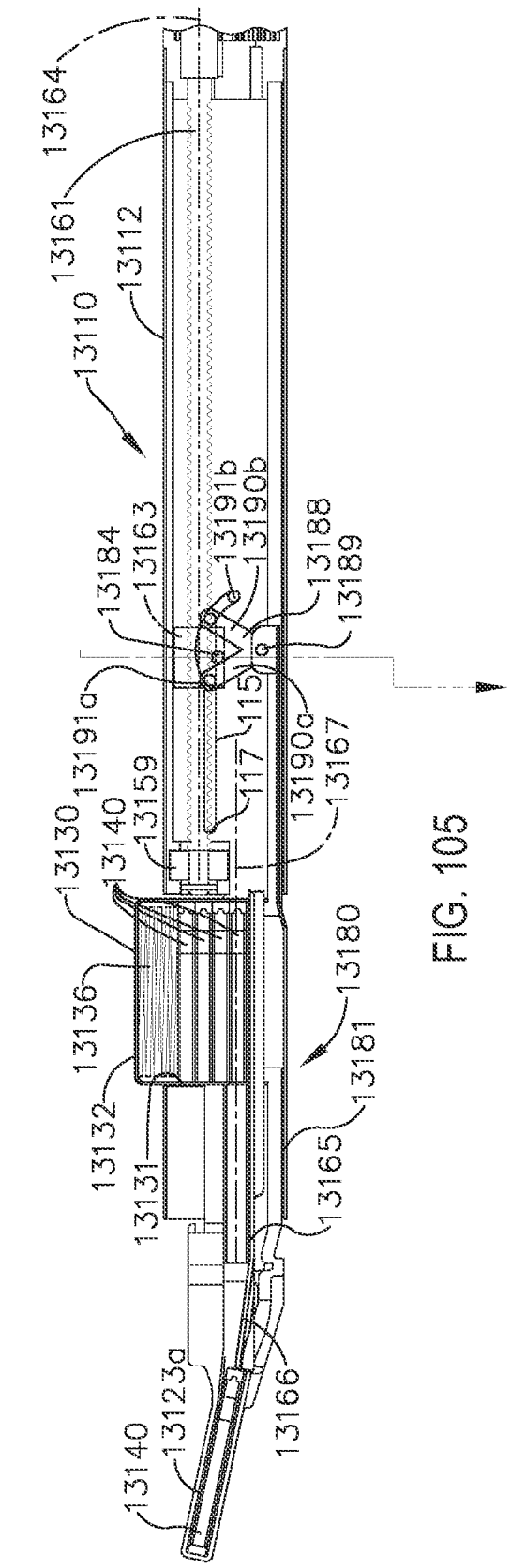
FIG. 105 is a cross-sectional view of the end effector of FIG. 99 illustrating the crimping drive in an at least partially fired condition.

Further to the above, the firing nut 13163 can be configured to actuate the crimping drive 13180. More particularly, referring now to FIG. 104, the crimping drive 13180 can comprise a crimping actuator 13188 operably coupled with the cam actuator 13181 wherein the crimping actuator 13188 can be selectively engaged by the firing nut 13163 as the firing nut 13163 is advanced distally as described above. In at least one such embodiment, the firing nut 13163 can further comprise a second firing pin, such as firing pin 13184, for example, extending therefrom which can be configured to engage the crimping actuator 13188 as the firing nut 13163 is advancing the firing actuator 13168. Referring again to FIG. 104, the crimping actuator 13188 is positioned in an unactuated position and, when the firing nut 13163 is advanced sufficiently to engage a distal arm 13190*a* of the crimping actuator 13188, the firing nut 13163 can rotate the crimping actuator 13188 upwardly into an actuated position as illustrated in FIG. 105. As also illustrated in FIG. 105, the distal arm 13190*a* and a proximal arm 13190*b* can each comprise a projection, such as projections 13191*a* and 13191*b*, respectively, extending therefrom which can be positioned within a second longitudinal slot defined in shaft 13110, such as slot 13115, for example. As the crimping actuator 13188 is rotated upwardly from its unactuated position about a pivot 13189, the projections 13191*a* and 13191*b* can move from the proximal curved end 13116 of the longitudinal slot 13115 into a portion of the longitudinal slot 13115 which is substantially linear. Similar to the above, the sidewalls of the longitudinal slot 13115 can be configured to confine the movement of the crimping actuator 13188 along a longitudinal path and can be configured to limit or prevent the rotation of the crimping actuator 13188 once the crimping actuator 13188 has been rotated upwardly into an at least partially actuated position, as discussed above. As the reader will understand, the firing pin 13172 of the firing drive 13160 and the firing pin 13184 of the crimping drive 13180 both extend from the firing nut 13163. For the sake of expediency and demonstration, the firing pins 13172 and 13184 are illustrated as extending from the same side of the firing nut 13163; however, it is envisioned that the firing pin 13172 can extend from a first lateral side of the firing nut 13163 while the firing pin 13184 can extend from the other lateral side of the firing nut 13163. In such circumstances, the firing actuator 13168 can be positioned alongside the first lateral side of the drive screw 13161 and the crimping actuator 13188 can be positioned alongside the opposite lateral side of the drive screw 13161. Correspondingly, the longitudinal slot 13113 can be defined in a first lateral side of the shaft housing 13112 while the longitudinal slot 13115 can be defined in the opposite lateral side of the shaft housing 13112.

Further to the above, the cam actuator 13181 can be operably coupled with crimping actuator 13188 such that, when the crimping actuator 13188 is advanced distally by the firing nut 13163, the cam actuator 13181 can be advanced distally, as illustrated in FIG. 105, until the distal projection 13191*a* extending from the distal arm 13190*a* reaches the distal end 13117 of the longitudinal slot 13115. In such a distal position, the cam actuator 13181 may be in a fully advanced position and the clip 13140 positioned within the receiving chamber 13122 can be in a fully deformed or crimped configuration. Thereafter, the cam actuator 13181 can be retracted and the end effector 13120 can be reopened. More particularly, the drive screw 13161 can be rotated in an opposite direction in order to move the firing nut 13163 proximally and retract the cam actuator 13181 wherein, in certain instances, the end effector 13120 can further include a biasing member which can be configured to bias the first jaw 13123 and the second jaw 13123*b* from the closed, or fired, position illustrated in FIG. 101 into the open, or unfired, position illustrated in FIG. 100.

The embodiments disclosed herein are configured for use with surgical suturing instruments and systems such as those disclosed in U.S. patent application Ser. No. 16/112,168, filed on Aug. 24, 2018, now U.S. Patent Application Publication No. 2019/0125336, entitled SURGICAL SUTURING INSTRUMENT COMPRISING A NON-CIRCULAR NEEDLE, U.S. patent application Ser. No. 13/832,786, now U.S. Pat. No. 9,398,905, entitled CIRCULAR NEEDLE APPLIER WITH OFFSET NEEDLE AND CARRIER TRACKS; U.S. patent application Ser. No. 14/721,244, now U.S. Pat. No. 10,022,120, entitled SURGICAL NEEDLE WITH RECESSED FEATURES; and U.S. patent application Ser. No. 14/740,724, now U.S. Pat. No. 9,888,914, entitled SUTURING INSTRUMENT WITH MOTORIZED NEEDLE DRIVE, which are incorporated by reference in their entireties herein. The embodiments discussed herein are also usable with the instruments, systems, and methods disclosed in U.S. patent application Ser. No. 15/908,021, entitled SURGICAL INSTRUMENT WITH REMOTE RELEASE, filed on Feb. 28, 2018, U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT, filed on Feb. 28, 2018, now U.S. Pat. No. 10,736,616, U.S. patent application Ser. No. 15/908,040, entitled SURGICAL INSTRUMENT WITH ROTARY DRIVE SELECTIVELY ACTUATING MULTIPLE END EFFECTOR FUNCTIONS, filed on Feb. 28, 2018, now U.S. Patent Application Publication No. 2018/0245337, U.S. patent application Ser. No. 15/908,057, entitled SURGICAL INSTRUMENT WITH ROTARY DRIVE SELECTIVELY ACTUATING MULTIPLE END EFFECTOR FUNCTIONS, filed on Feb. 28, 2018, now U.S. Patent Application Publication No. 2019/0125384, U.S. patent application Ser. No. 15/908,058, entitled SURGICAL INSTRUMENT WITH MODULAR POWER SOURCES, filed on Feb. 28, 2018, now U.S. Patent Application Publication No. 2019/0125324, and U.S. patent application Ser. No. 15/908,143, entitled SURGICAL INSTRUMENT WITH SENSOR AND/OR CONTROL SYSTEMS, filed on Feb. 28, 2018, now U.S. Pat. No. 10,932,804, which are incorporated in their entireties herein. Generally, these surgical suturing instruments comprise, among other things, a shaft, an end effector attached to the shaft, and drive systems positioned within the shaft to transfer motion from a source motion to the end effector. The motion source can comprise a manually driven actuator, an electric motor, and/or a robotic surgical system. The end effector comprises a body portion, a needle track defined within the body portion, and a needle driver configured to drive a needle through a rotational firing stroke. The needle is configured to be guided through its rotational firing stroke within the body portion by the needle track. In various instances, the needle driver is similar to that of a ratchet system. In at least one instance, the needle driver is configured to drive the needle through a first half of the rotational firing stroke which places the needle in a hand-off position—a position where a tissue-puncturing end of the needle has passed through the target tissue and reentered the body portion of the end effector. At such point, the needle driver can be returned to its original position to pick up the tissue-puncturing end of the needle and drive the needle through a second half of its rotational firing stroke. Once the needle driver pulls the needle through the second half of its rotational firing stroke, the needle driver is then returned to its original unfired position to grab the needle for another rotational firing stroke. The drive systems can be driven by one or more motors and/or manual drive actuation systems. The needle comprises suturing material, such as thread, for example, attached thereto. The suturing material is configured to be pulled through tissue as the needle is advanced through its rotational firing stroke to seal the tissue and/or attached the tissue to another structure, for example.

FIGS. 110-114 depict a surgical suturing instrument 94000 configured to suture the tissue of a patient. The surgical suturing instrument 94000 comprises a handle 94100, a shaft 94200 extending distally from the handle 94100, and an end effector 94300 attached to the shaft 94200 by way of an articulation joint 94210. The handle 94100 comprises a firing trigger 94110 configured to actuate a firing drive of the surgical suturing instrument 94000, a first rotational actuator 94120 configured to articulate the end effector 94300 about an articulation axis AA defined by the articulation joint 94210, and a second rotational actuator 94130 configured to rotate the end effector 94300 about a longitudinal axis LA defined by the end effector 94300. The surgical suturing instrument 94000 further comprises a flush port 94140. Examples of surgical suturing devices, systems, and methods are disclosed in U.S. patent application Ser. No. 13/832,786, now U.S. Pat. No. 9,398,905, entitled CIRCULAR NEEDLE APPLIER WITH OFFSET NEEDLE AND CARRIER TRACKS; U.S. patent application Ser. No. 14/721,244, now U.S. Pat. No. 10,022,120, entitled SURGICAL NEEDLE WITH RECESSED FEATURES; and U.S. patent application Ser. No. 14/740,724, now U.S. Pat. No. 9,888,914, entitled SUTURING INSTRUMENT WITH MOTORIZED NEEDLE DRIVE, which are incorporated by reference in their entireties herein.

Figure 115:
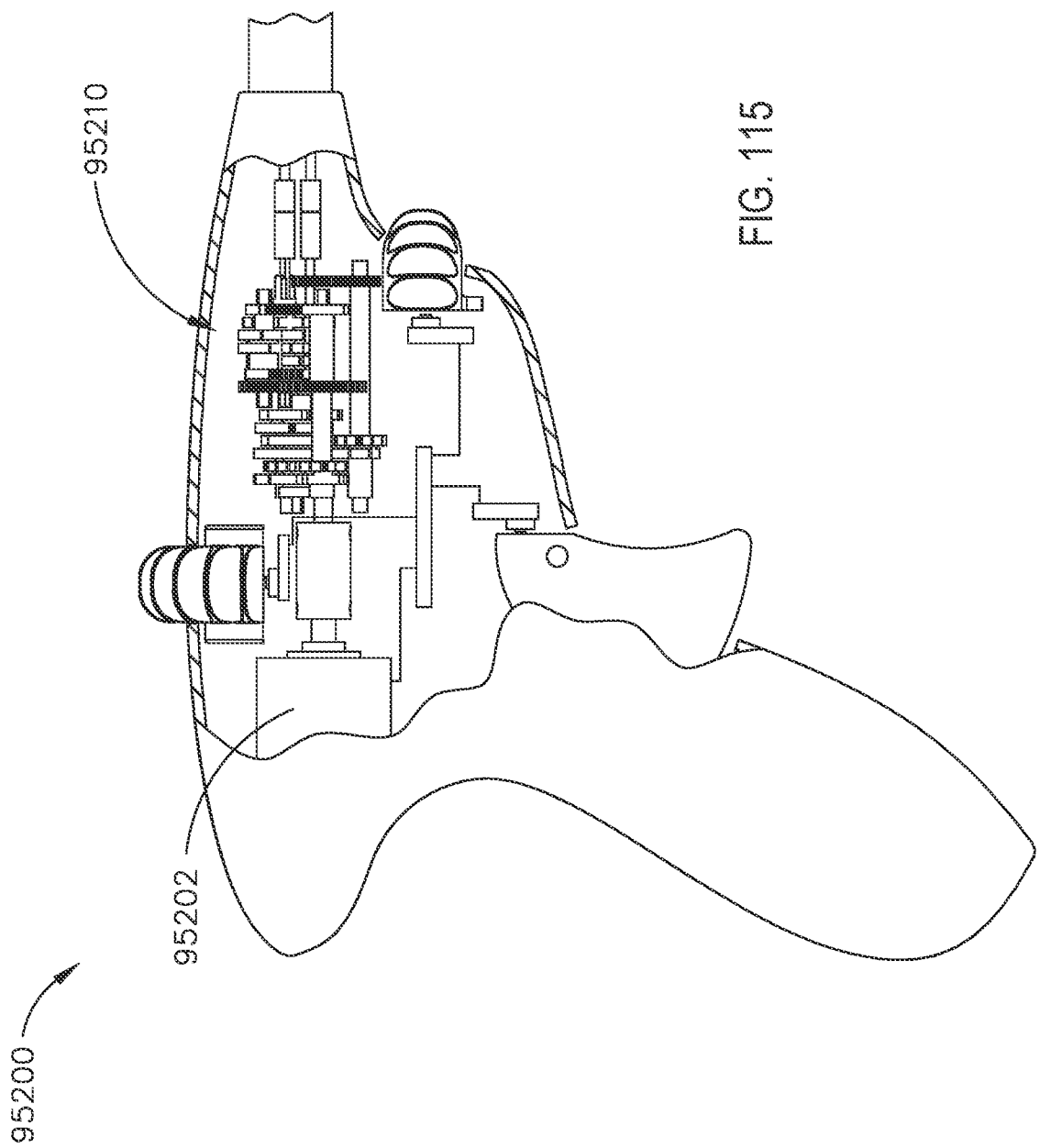
FIG. 115 is a perspective view of a surgical suturing instrument handle comprising a motor.

FIG. 115 depicts a handle assembly 95200 that is operable for use a surgical suturing instrument. The handle assembly 95200 is connected to a proximal end of a shaft. The handle assembly 95200 includes a motor 95202 and a transmission assembly 95210. The motor 95202 is configured to actuate a needle of a surgical suturing end effector by way of a needle driver, articulate the end effector, and rotate the end effector by way of the transmission assembly 95210. The transmission assembly 95210 is shifted between three states by a double acting solenoid, for example, so as to allow the motor 95202 to be used to actuate a needle of a surgical suturing end effector, articulate the end effector, and/or rotate the end effector. In at least one embodiment, the handle assembly 95200 could take the form of a robotic interface or a housing comprising gears, pulleys, and/or servomechanisms, for example. Such an arrangement could be used with a robotic surgical system.

Figure 116:
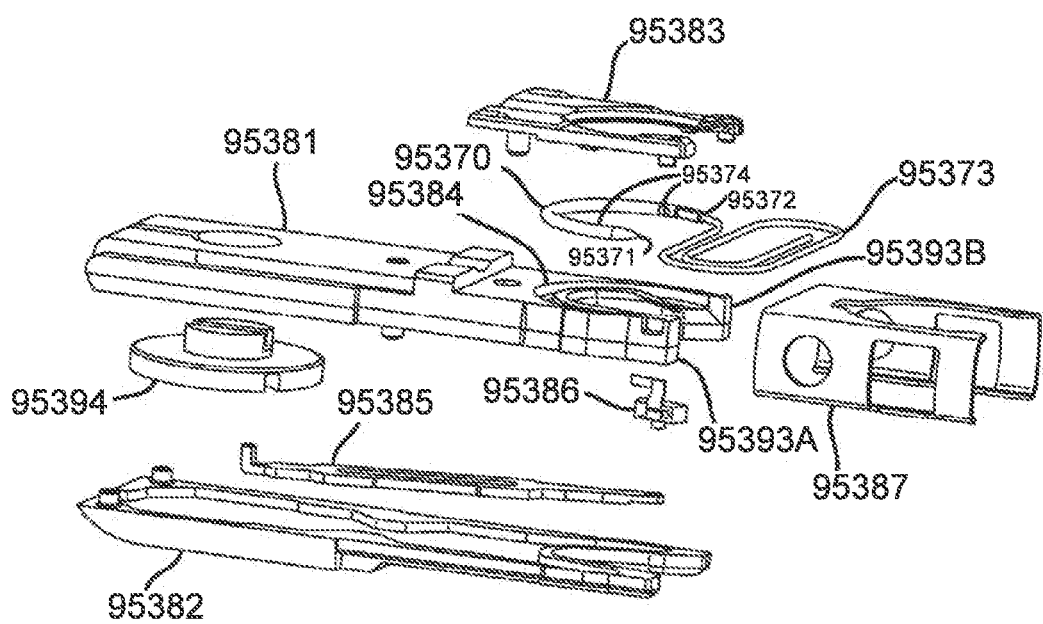
FIG. 116 is an exploded view of a suturing cartridge for use with a surgical suturing system.

FIG. 116 depicts a suturing cartridge 93590 comprising a lower body 93581, an upper body 93582, and a needle cover 93583. The cartridge 93590 further comprises a drive system comprising a needle driver 93586, a rotary input 93594, and a link 93585 connecting the needle driver 93586 and the rotary input 93594. The needle driver 93586, rotary input 93594, and link 93585 are captured between the lower body 93581 and the upper body 93582. The needle driver 93586, the link 93585, and the rotary input 93594 are configured to be actuated to drive a needle 93570 through a needle firing stroke by way of a motor-driven system, a manually-driven handheld system, and/or a robotic system, for example. The lower and upper bodies 93581, 93582 are attached to one another using any suitable technique, such as, for example, welds, pins, adhesives, and/or the like to form the cartridge body. The needle 93570 comprises a leading end 93571 configured to puncture tissue, a trailing end 93572, and a length of suture 93573 extending from and attached to the trailing end 93572. The needle 93570 is configured to rotate in a circular path defined by a needle track 93584. The needle track 93584 is defined in the cartridge body. The needle 93570 is configured to exit one of a first arm 95393A and a second arm 95393B of the cartridge body and enter the other of the first arm 95393A and the second arm 95393B during a needle firing stroke. Recessed features 93574 are provided to so that the needle driver 93586 can engage and drive the needle 93570 through the needle firing stroke in a ratchet-like motion. The needle 93570 is positioned between the needle track 93584 and the needle cover 93583. The suturing cartridge 93590 further comprises a cage 93587 that is configured to slide over the cartridge body to attach the needle cover 93583 to the lower body 93581.

Various aspects of the subject matter described herein are set out in the following numbered examples:

Example 1—A method of operating a surgical assembly, the method comprising receiving a first input from a first RFID scanner indicative of a first information stored in a first RFID chip of a first modular component of the surgical assembly, receiving a second input from a second RFID scanner indicative of a second information stored in a second RFID chip of a second modular component of the surgical assembly, determining an operational parameter of a motor of the surgical assembly based on the first input and the second input, and causing the motor to effect a tissue treatment motion of the first modular component.

Example 2—The method of Example 1, wherein the first modular component is an end effector.

Example 3—The method of Example 2, wherein the second modular component is a shaft releasably couplable to the end effector.

Example 4—The method of any one of Examples 1-3, wherein the first information is indicative of a staple cartridge size, and wherein the second information is indicative of a shaft profile.

Example 5—The method of any one of Examples 1-4, wherein the operational parameter of the motor is a velocity threshold.

Example 6—The method of any one of Examples 1-4, wherein the operational parameter of the motor is a current threshold.

Example 7—The method of any one of Examples 1-4, wherein the operational parameter of the motor is a load threshold.

Example 8—The method of any one of Examples 1-7, further comprising accessing a database to determine the operational parameter of the motor of the surgical assembly.

Example 9—The method of Example 8, wherein the database tethers the operational parameter of the motor to the first information and the second information.

Example 10—A method of operating a surgical assembly, the method comprising receiving a first input from a first RFID scanner indicative of a first information stored in a first RFID chip of an anvil of the surgical assembly, receiving a second input from a second RFID scanner indicative of a second information stored in a second RFID chip of a staple cartridge of the surgical assembly, and assessing compatibility of the anvil with the staple cartridge based on the first input and the second input.

Example 11—The method of Example 10, further comprising alerting a user of the surgical assembly regarding the compatibility of the anvil with the staple cartridge.

Example 12—The method of Examples 10 or 11, further comprising activating a lockout assembly of the surgical assembly if it is determined that the anvil is not compatible with the staple cartridge.

Example 13—The method of any one of Examples 10-12, further comprising accessing a database to assess compatibility of the anvil with the staple cartridge.

Example 14—The method of Example 13, wherein the database tethers an operational parameter of a motor to the first information and the second information.

Example 15—A method of operating a surgical assembly, the method comprising receiving a first input from a first RFID scanner indicative of a first information stored in a first RFID chip of a first modular component of the surgical assembly, receiving a second input from a second RFID scanner indicative of a second information stored in a second RFID chip of a second modular component of the surgical assembly, determining an operational parameter of a third component of the surgical assembly based on the first input and the second input, and adjusting a tissue treatment motion of the first modular component based on the operational parameter.

Example 16—The method of Example 15, wherein the first modular component is an end effector.

Example 17—The method of Example 16, wherein the second modular component is a shaft releasably couplable to the end effector.

Example 18—The method of any one of Examples 15-17, wherein the first information is indicative of a staple cartridge size, and wherein the second information is indicative of a shaft profile.

Example 19—The method of any one of Examples 15-18, wherein the operational parameter is a motor velocity threshold.

Example 20—The method of any one of Examples 15-18, wherein the operational parameter is a motor current threshold.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

In various aspects, a microcontroller of control circuit in accordance with the present disclosure may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHZ, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the housing portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical system, comprising:
    a surgical instrument;
    a first component coupleable to the surgical instrument, wherein the first component comprises a first RFID tag storing first data;
    a second component coupleable to the surgical instrument, wherein the second component comprises a second RFID tag storing second data; and
    a control circuit, to:
        receive the first data based on the first component being coupled to the surgical instrument;
        receive the second data based on the second component being coupled to the surgical instrument; and determine an operational setting of the surgical instrument based on the received first data and the received second data.

2. The surgical system of claim 1, wherein the control circuit is further to determine a compatibility between the first component and the second component.

3. The surgical system of claim 1, wherein the surgical instrument comprises an RFID scanner to:
interrogate the first RFID tag based on the first component being coupled to the surgical instrument to receive the first data;
interrogate the second RFID tag based on the second component being coupled to the surgical instrument to receive the second data; and
communicate the received first data and the received second data to the control circuit.

4. The surgical system of claim 1, wherein the first component comprises a battery, and wherein the second component comprises a motor.

5. The surgical system of claim 4, wherein the operational setting corresponds to an amount of power to apply to the motor from the battery.

6. The surgical system of claim 1, wherein the first component comprises a motor, and wherein the second component comprises a staple cartridge.

7. The surgical system of claim 6, wherein the operational setting corresponds to a force to apply to a knife by the motor.

8. A surgical system, comprising:
a surgical instrument, comprising:
a housing;
a first component operably coupleable to the housing, wherein the first component comprises a first storage medium storing first data;
a second component operably coupleable to the housing, wherein the second component comprises a second storage medium storing second data; and
a control circuit, to:
receive the first data based on the first component being operably coupled to the housing;
receive the second data based on the second component being operably coupled to the housing; and
set an operational parameter of the surgical instrument based on the received first data and the received second data.

9. The surgical system of claim 8, wherein the control circuit is further to determine a compatibility between the first component and the second component.

10. The surgical system of claim 8, wherein the surgical instrument comprises a scanner to:
interrogate the first storage medium based on the first component being coupled to the housing to receive the first data;
interrogate the second storage medium based on the second component being coupled to the housing to receive the second data; and
communicate the received first data and the received second data to the control circuit.

11. The surgical system of claim 8, wherein the first component comprises a battery, and wherein the second component comprises a motor.

12. The surgical system of claim 11, wherein the operational parameter corresponds to an amount of power to apply to the motor from the battery.

13. The surgical system of claim 8, wherein the first component comprises a motor, and wherein the second component comprises a staple cartridge.

14. The surgical system of claim 13, wherein the operational parameter corresponds to a force to apply to a knife by the motor.

15. A surgical system, comprising:
a surgical instrument, comprising:
a first component comprising a first RFID tag storing first data; and
a second component operably coupleable to the first component, wherein the second component comprises a second RFID tag storing second data; and
a control circuit, to:
receive the first data;
receive the second data; and
determine an operational setting of the surgical instrument based on the received first data and the received second data.

16. The surgical system of claim 15, further comprising an RFID scanner to:
interrogate the first RFID tag to receive the first data;
interrogate the second RFID tag to receive the second data; and
communicate the received first data and the received second data to the control circuit.

17. The surgical system of claim 15, wherein the first component comprises a battery, and wherein the second component comprises a motor.

18. The surgical system of claim 17, wherein the operational setting corresponds to an amount of power to apply to the motor from the battery.

19. The surgical system of claim 15, wherein the first component comprises a motor, and wherein the second component comprises a staple cartridge.

20. The surgical system of claim 19, wherein the operational setting corresponds to a force to apply to a knife by the motor.

* * * * *